(12) United States Patent
Tamura et al.

(10) Patent No.: US 9,980,948 B2
(45) Date of Patent: May 29, 2018

(54) AZAINDOLE DERIVATIVE HAVING AMPK-ACTIVATING ACTIVITY

(71) Applicant: Shionogi & Co., Ltd., Osaka-shi (JP)

(72) Inventors: Yuusuke Tamura, Toyonaka (JP); Yu Hinata, Toyonaka (JP); Eiichi Kojima, Toyonaka (JP); Hiroki Ozasa, Toyonaka (JP)

(73) Assignee: SHIONOGI & CO., LTD., Osaka-shi (JP)

( * ) Notice: Subject to any disclaimer, the term of this patent is extended or adjusted under 35 U.S.C. 154(b) by 0 days. days.

(21) Appl. No.: 15/505,772

(22) PCT Filed: Aug. 26, 2015

(86) PCT No.: PCT/JP2015/073947
§ 371 (c)(1),
(2) Date: Feb. 22, 2017

(87) PCT Pub. No.: WO2016/031842
PCT Pub. Date: Mar. 3, 2016

(65) Prior Publication Data
US 2017/0273955 A1    Sep. 28, 2017

(30) Foreign Application Priority Data

Aug. 27, 2014 (JP) ................... 2014-172192
Jan. 22, 2015 (JP) ................... 2015-009894
Mar. 31, 2015 (JP) ................... 2015-072597

(51) Int. Cl.
*C07D 401/02*    (2006.01)
*C07D 401/10*    (2006.01)
(Continued)

(52) U.S. Cl.
CPC ............ *A61K 31/437* (2013.01); *A61K 31/03* (2013.01); *A61K 31/10* (2013.01); *A61K 31/343* (2013.01);
(Continued)

(58) Field of Classification Search
CPC .. C07D 401/02; C07D 401/10; C07D 401/14; A61K 31/437; A61K 31/4353
(Continued)

(56) References Cited

U.S. PATENT DOCUMENTS

2010/0009992 A1    1/2010    Birnberg et al.
2012/0172333 A1    7/2012    Mirguet
(Continued)

FOREIGN PATENT DOCUMENTS

JP    2011-511008 A    4/2011
JP    2013-504537 A    2/2013
(Continued)

OTHER PUBLICATIONS

International Search Report dated Oct. 20, 2015 in PCT/JP2015/073947 filed Aug. 26, 2015.
(Continued)

*Primary Examiner* — Niloofar Rahmani
(74) *Attorney, Agent, or Firm* — Oblon, McClelland, Maier & Neustadt, L.L.P.

(57) ABSTRACT

Disclosed is a compound which is useful as an AMPK activator.

A compound represented by formula:

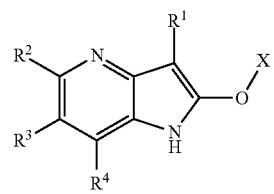

or its pharmaceutically acceptable salt,
wherein
X is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;

$R^2$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, or the like;

$R^3$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, or the like; and $R^4$ is hydrogen, halogen, hydroxy, cyano, nitro, carboxy, substituted or unsubstituted alkyl, substituted or unsubstituted alkenyl, substituted or unsubstituted alkynyl, or the like.

25 Claims, No Drawings

(51) Int. Cl.

| | | |
|---|---|---|
| C07D 401/14 | (2006.01) | |
| A61K 31/437 | (2006.01) | |
| A61K 31/4353 | (2006.01) | |
| A61K 31/444 | (2006.01) | |
| A61K 31/5377 | (2006.01) | |
| C07D 471/04 | (2006.01) | |
| C07D 519/00 | (2006.01) | |
| A61K 31/03 | (2006.01) | |
| A61K 31/10 | (2006.01) | |
| A61K 31/343 | (2006.01) | |

(52) U.S. Cl.
CPC ........ *A61K 31/444* (2013.01); *A61K 31/5377* (2013.01); *C07D 471/04* (2013.01); *C07D 519/00* (2013.01)

(58) Field of Classification Search
USPC .................................. 546/121; 514/300, 303
See application file for complete search history.

(56) References Cited

U.S. PATENT DOCUMENTS

| | | |
|---|---|---|
| 2012/0302576 A1 | 11/2012 | Birnberg et al. |
| 2013/0184240 A1 | 7/2013 | Tonogaki et al. |
| 2014/0194420 A1 | 7/2014 | Kojima et al. |
| 2015/0203450 A1 | 7/2015 | Tamura et al. |

FOREIGN PATENT DOCUMENTS

| | | |
|---|---|---|
| WO | 2009/100130 A1 | 8/2009 |
| WO | 2010/036613 A1 | 4/2010 |
| WO | 2010/047982 A1 | 4/2010 |
| WO | 2010/051176 A1 | 5/2010 |
| WO | 2010/051206 A1 | 5/2010 |
| WO | 2011/029855 A1 | 3/2011 |
| WO | 2011/106273 A1 | 9/2011 |
| WO | 2012/033149 A1 | 3/2012 |
| WO | 2012/116145 A1 | 8/2012 |
| WO | 2013/0011932 A1 | 1/2013 |
| WO | 2013/153479 A2 | 10/2013 |
| WO | 2014/031441 A1 | 2/2014 |
| WO | 2014/031445 A1 | 2/2014 |
| WO | 2014/031465 A1 | 2/2014 |
| WO | 2014/031468 A1 | 2/2014 |
| WO | 2014/031515 A1 | 2/2014 |
| WO | 2014/031517 A1 | 2/2014 |
| WO | 2014/069426 A1 | 5/2014 |
| WO | WO 2014/069426 A1 | 5/2014 |
| WO | 2014/128549 A1 | 8/2014 |
| WO | 2014/133008 A1 | 9/2014 |
| WO | 2014/139388 A1 | 9/2014 |
| WO | 2014/140704 A1 | 9/2014 |
| WO | 2015/007669 A1 | 1/2015 |
| WO | 2015/063011 A1 | 5/2015 |
| WO | 2016/001224 A1 | 1/2016 |
| WO | 2016/023789 A1 | 2/2016 |

OTHER PUBLICATIONS

Zhang, Bei B. et al., "AMPK: An Emerging Drug Target for Diabetes and the Metabolic Syndrome," Cell Metabolism, vol. 9, Issue 5, May 6, 2009, pp. 407-416.

Mirguet, Olivier et al., "Discovery of Pyridones as Oral AMPK Direct Activators," ACS Medicinal Chemistry Letters, vol. 4, Issue 7, 2013, pp. 632-636.

Supplementary European Search Report dated Dec. 20, 2017 in Patent Application No. 15836862.9, citing document AO therein, 7 pages.

AZAINDOLE DERIVATIVE HAVING AMPK-ACTIVATING ACTIVITY

FIELD OF THE INVENTION

The present invention relates to a compound which has an activating effect on adenosine monophosphate-activated protein kinase (hereinafter referred to as AMPK) and is useful as a medicine.

BACKGROUND ART

AMPK is a serine-threonine kinase, which is activated by AMP, and has three subunits, α, β and γ. In each subunit, there exist multiple isoforms (α1, α2, β1, β2, γ1, γ2 and γ3).

AMPK is involved in various physiological functions, such as suppression of gluconeogenesis and inhibition of fatty acid synthesis in liver and incorporation of sugars and an increase in fatty acid oxidation in skeletal muscles, as an energy sensor in living organisms, and has attracted attention as a target molecule of a therapeutic agent for diabetes. Therefore, an AMPK activator is expected to be effective in the treatment of diabetes as an insulin resistance improving drug, which has an insulin independent hypoglycemic effect and a lipid improving effect (Non-Patent Document 1).

Patent Documents 1 to 16, 19, and 20 disclose a variety of compounds having an AMPK activating effect. However, azaindole derivatives like the compounds of the present invention are not disclosed in any of the documents.

Patent Document 17 describes the compounds shown below, as compounds having an AMPK activating effect.

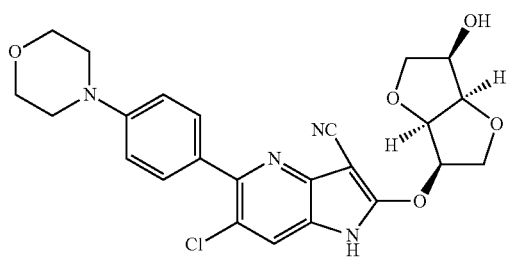

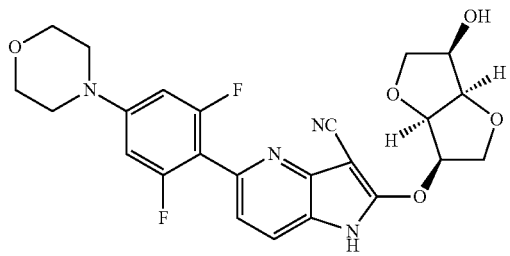

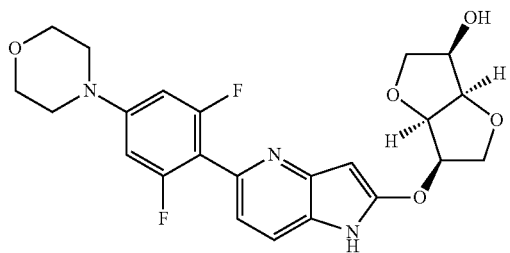

-continued

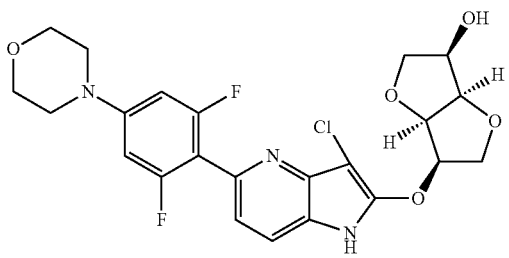

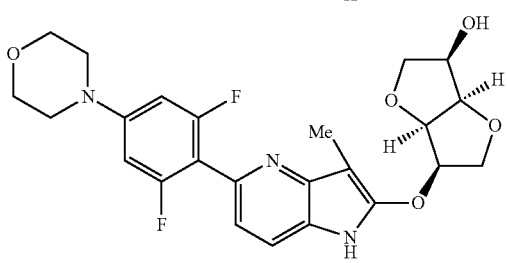

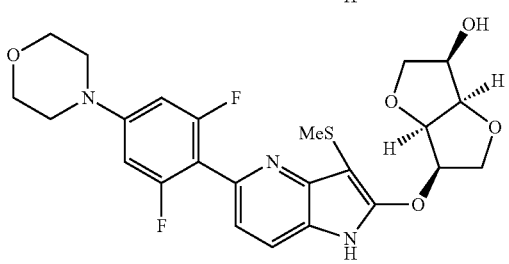

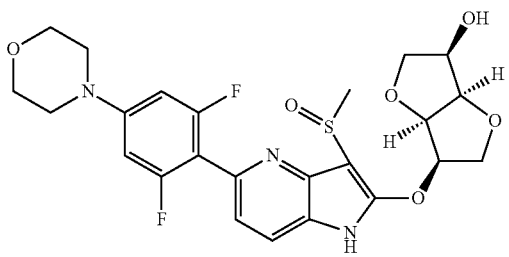

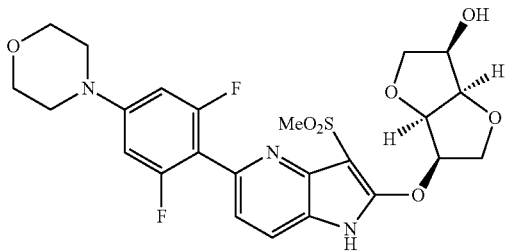

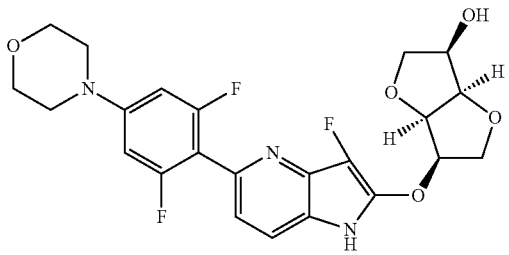

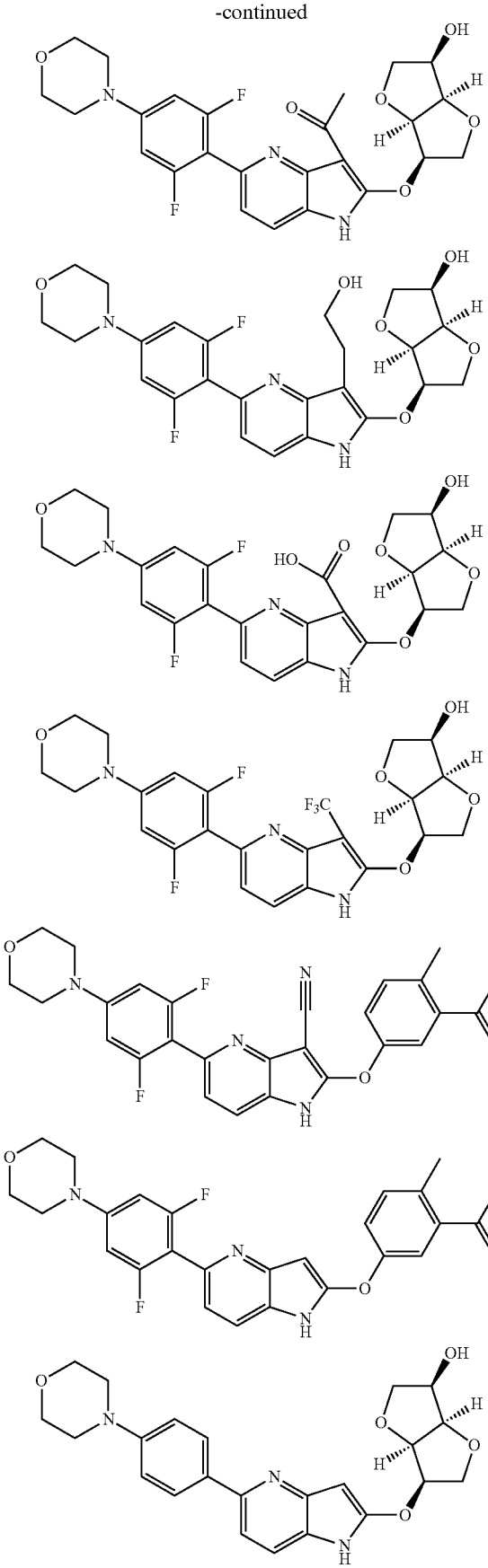
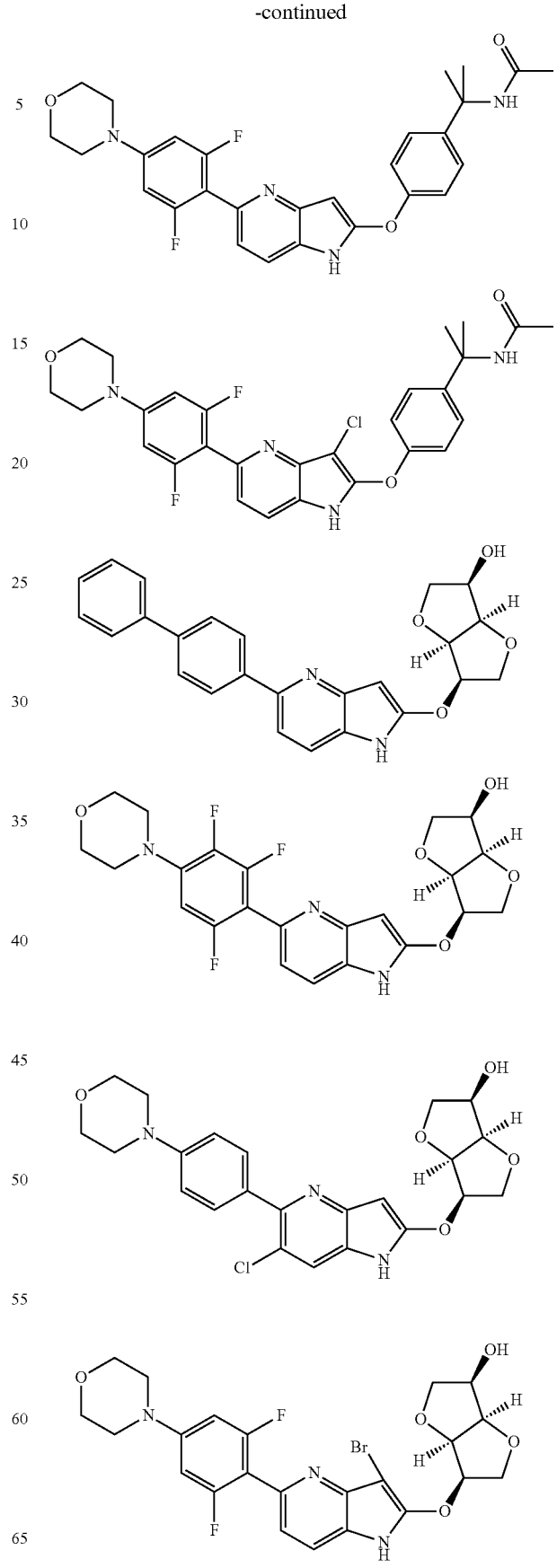

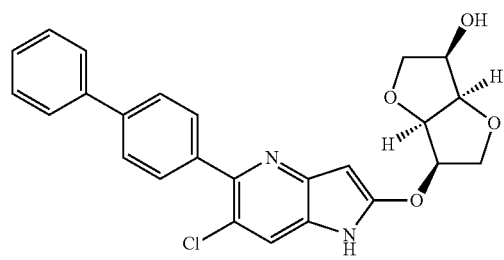
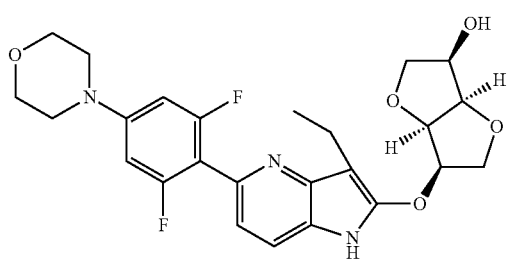
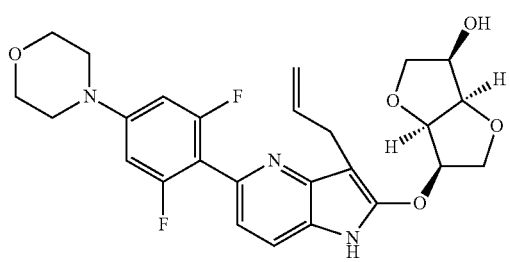
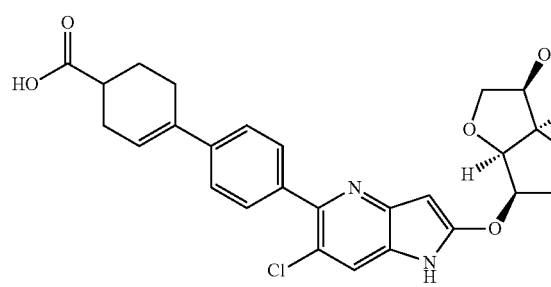
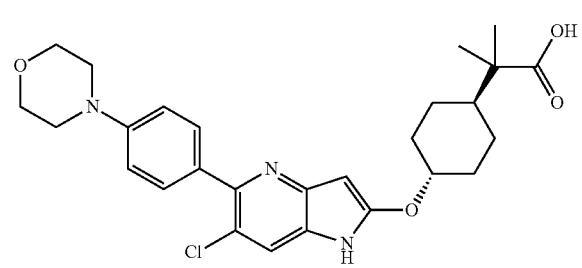
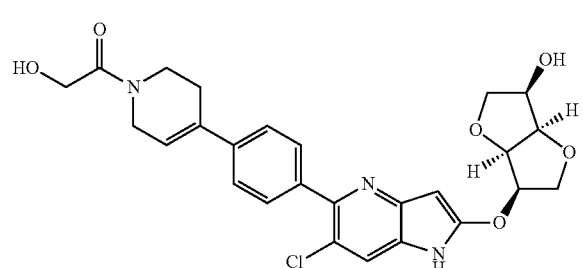
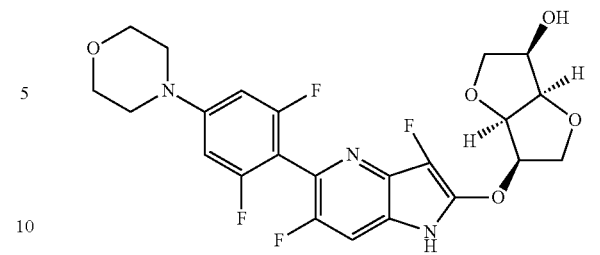

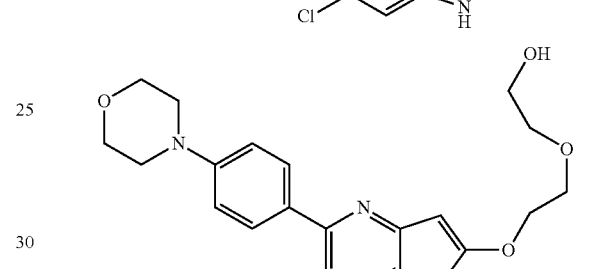
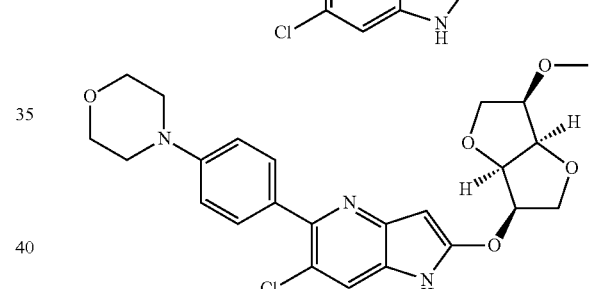
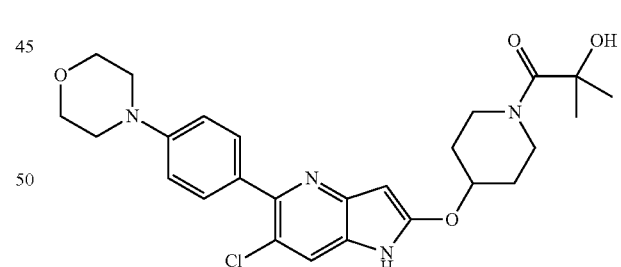
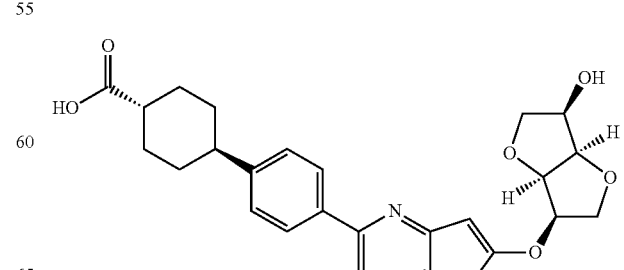

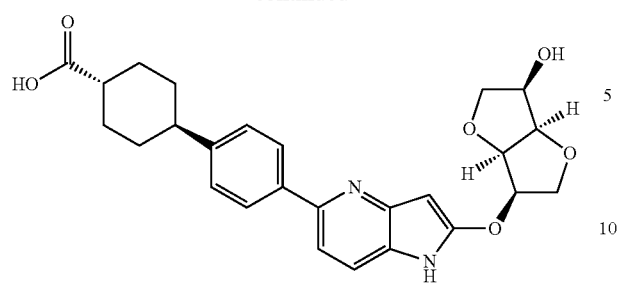
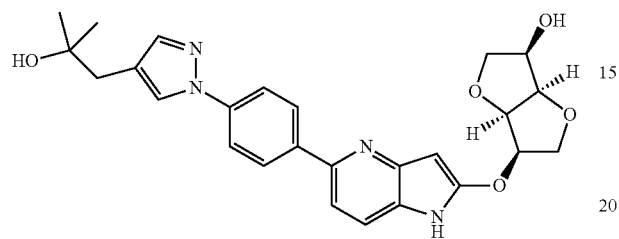
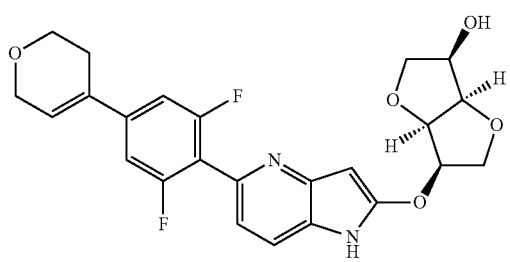
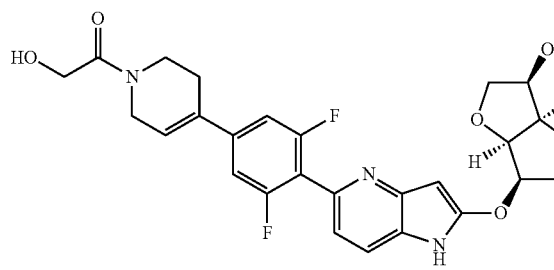
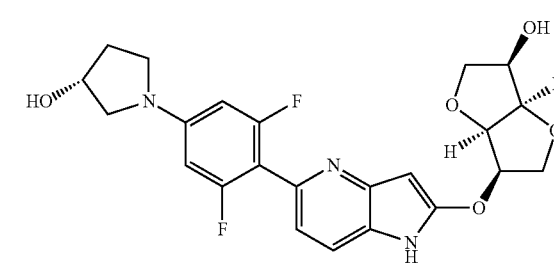
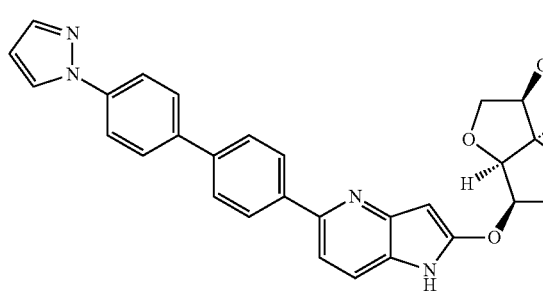
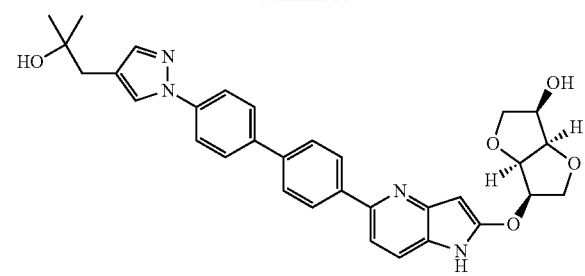
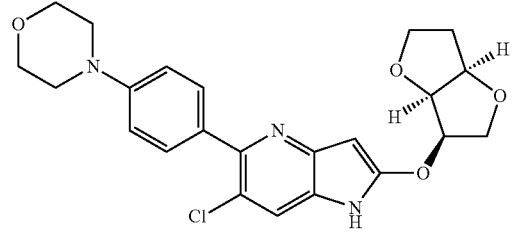
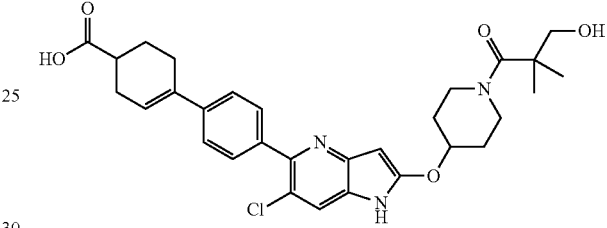
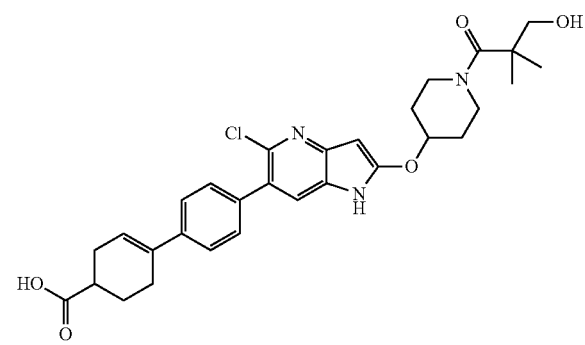
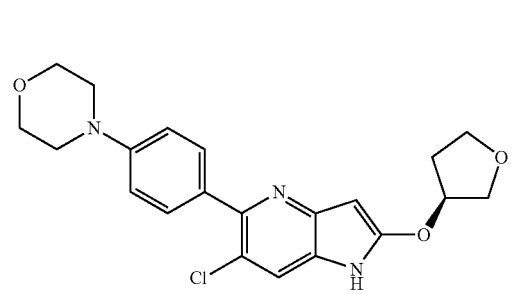
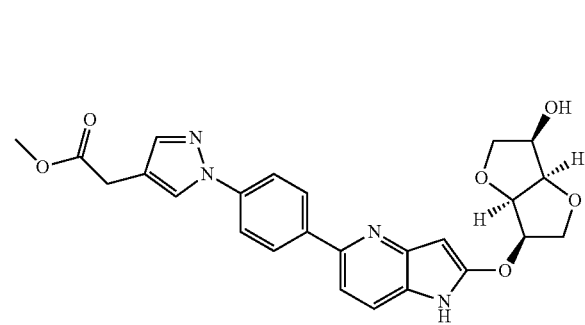

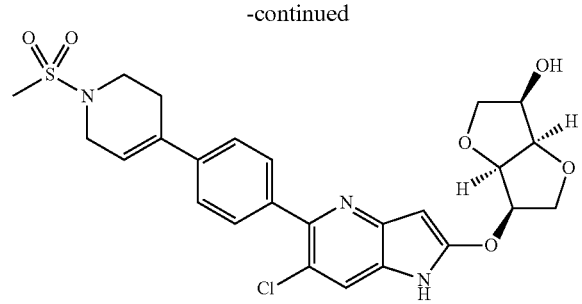
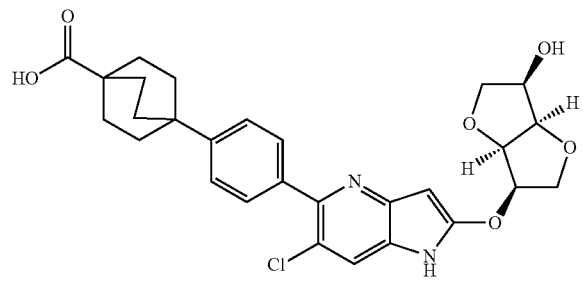
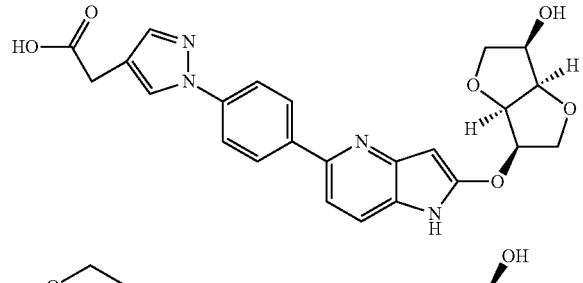
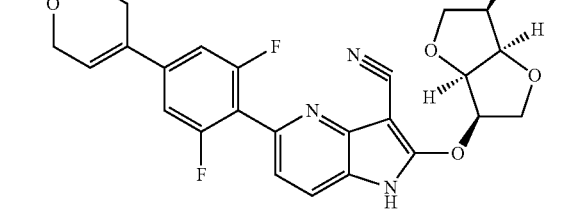
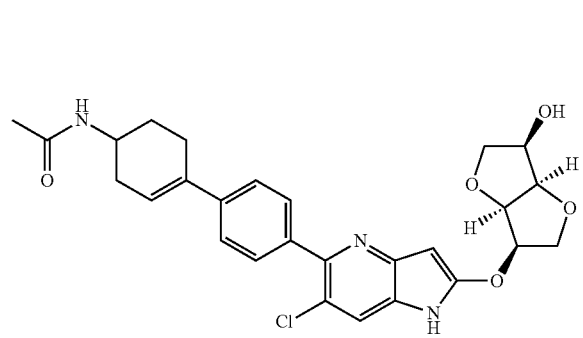
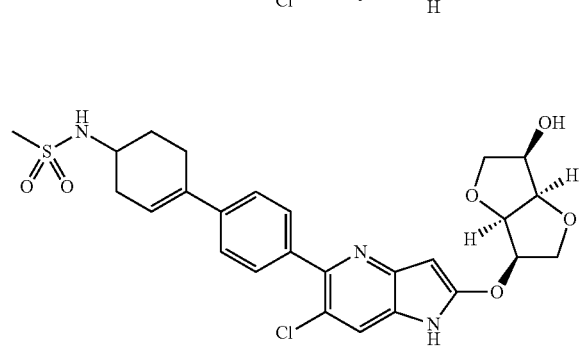
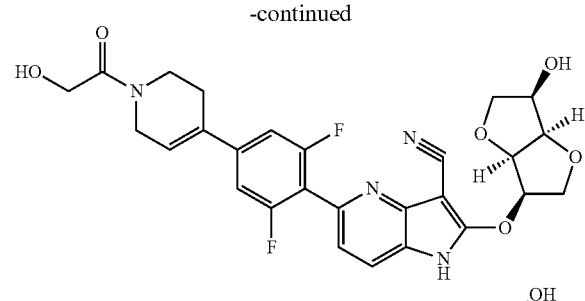
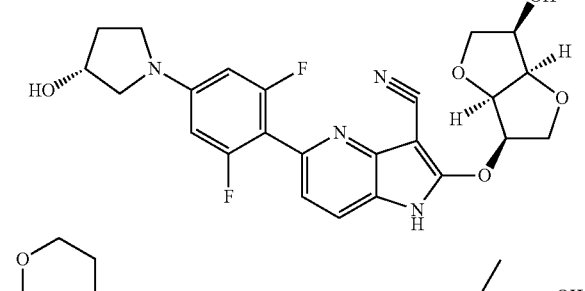
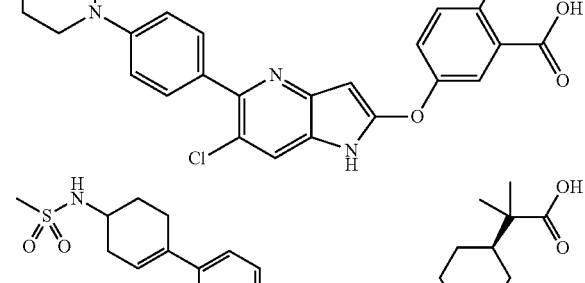
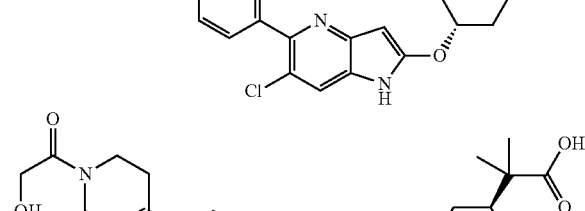
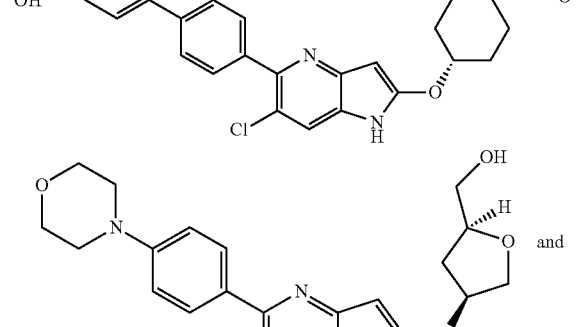
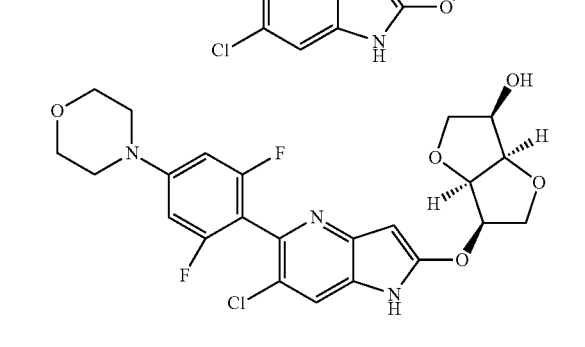

Patent Document 18 describes the compounds shown below, as compounds having an AMPK activating effect.
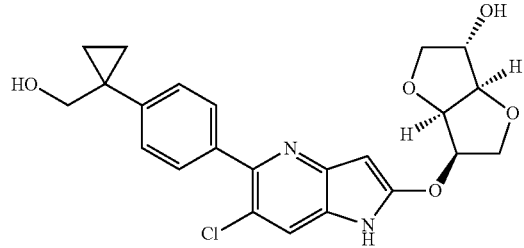
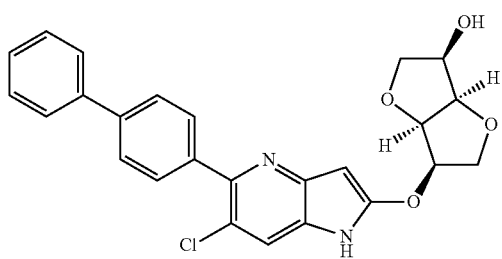
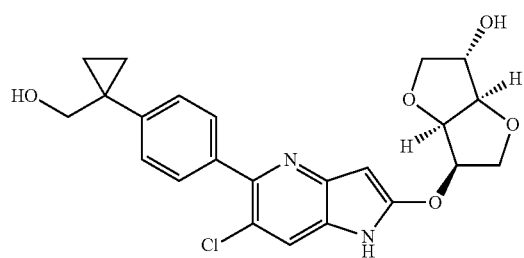
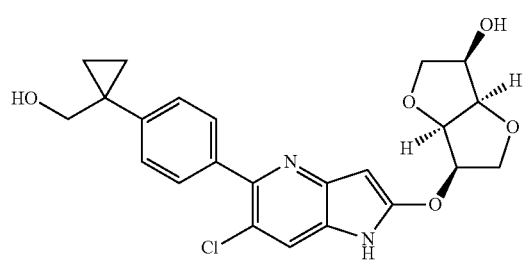
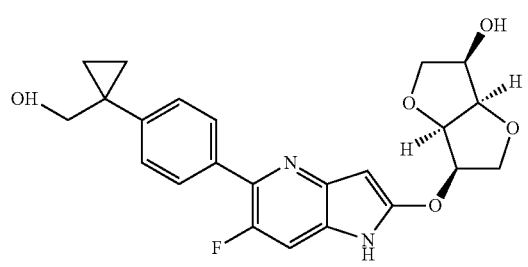
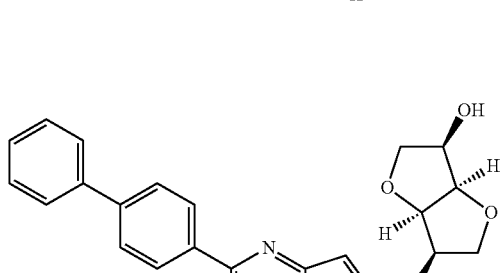
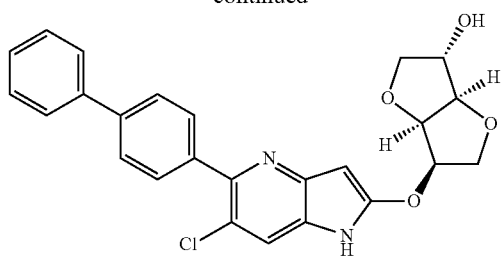
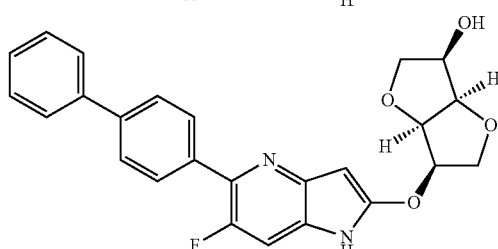
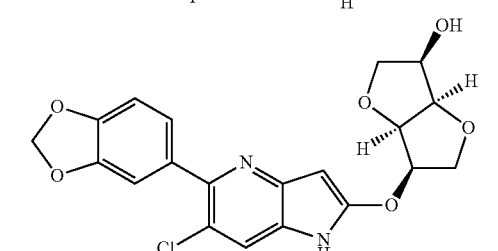
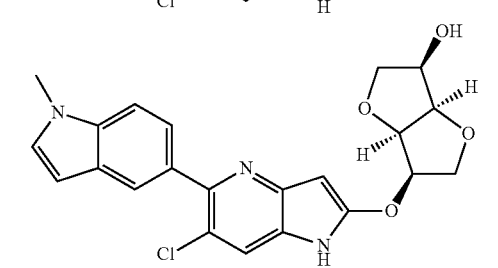
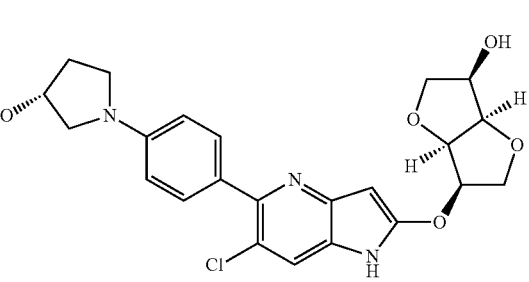
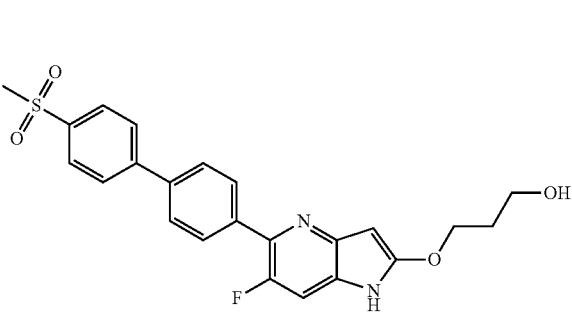

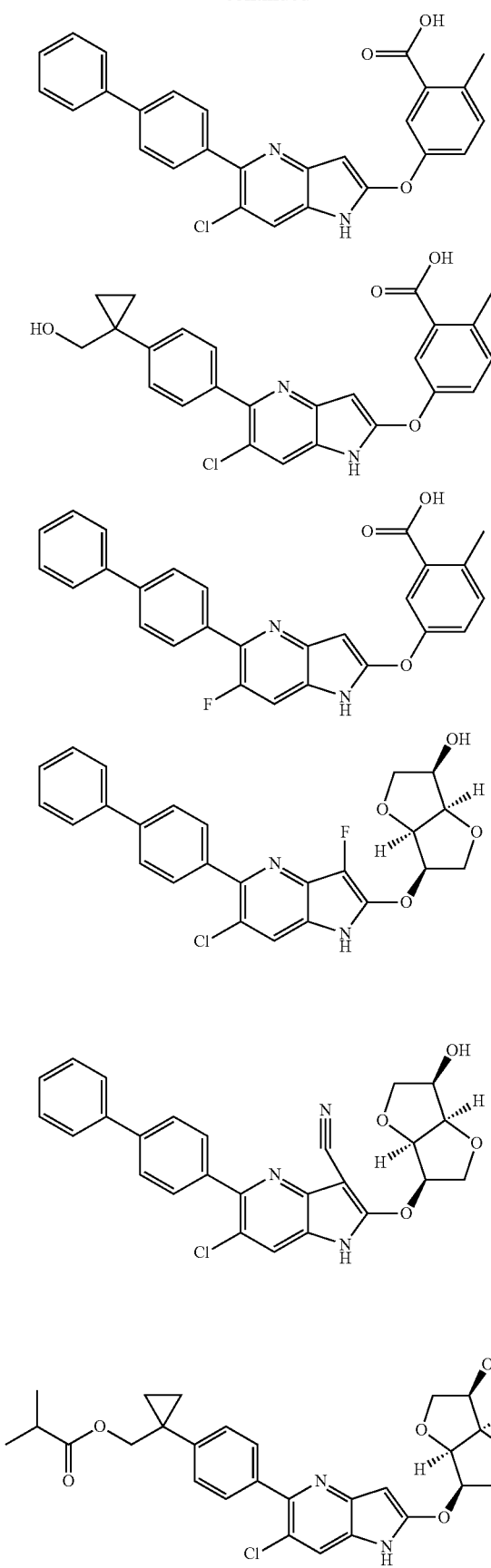
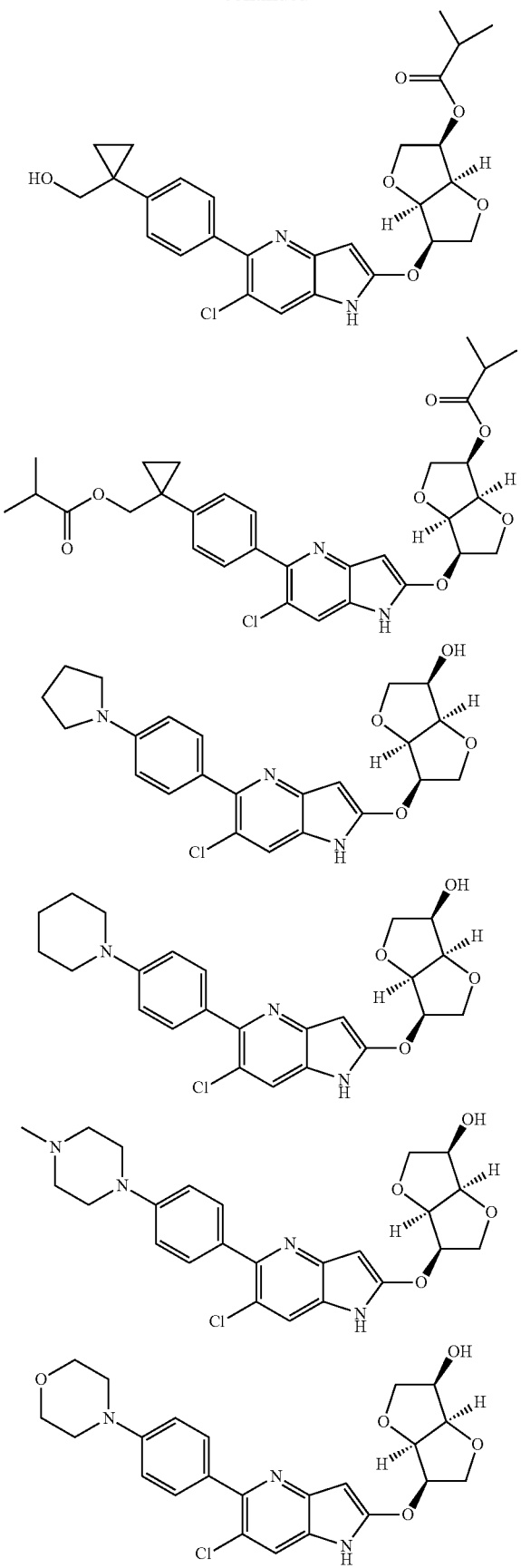

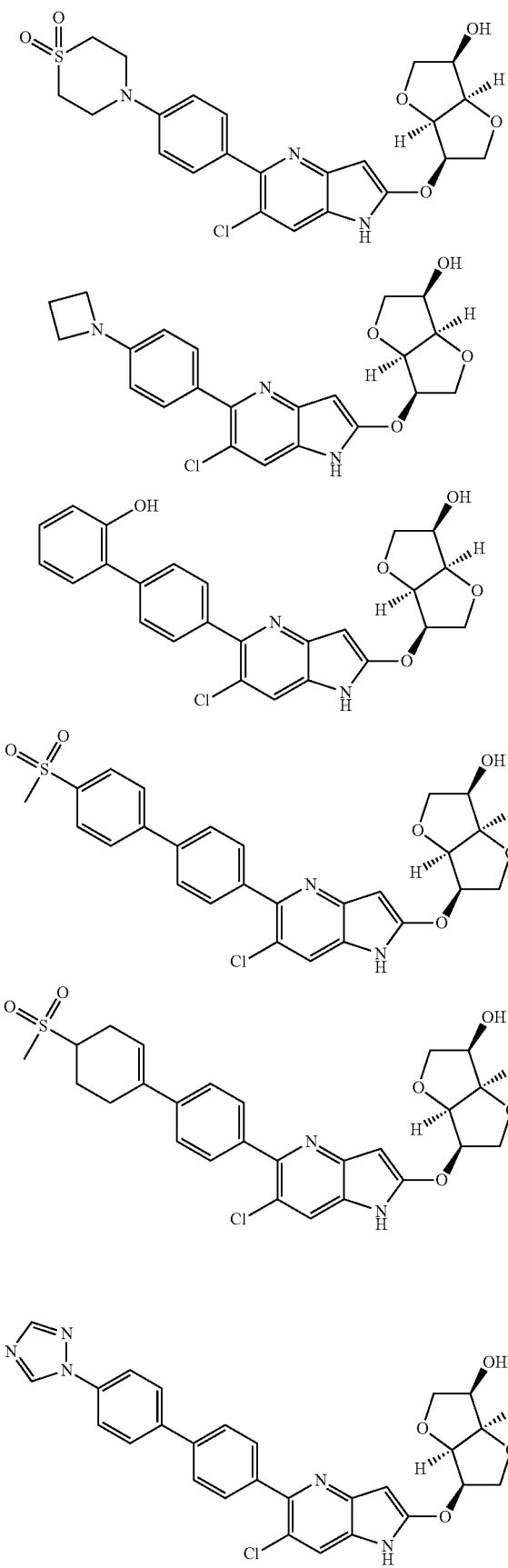
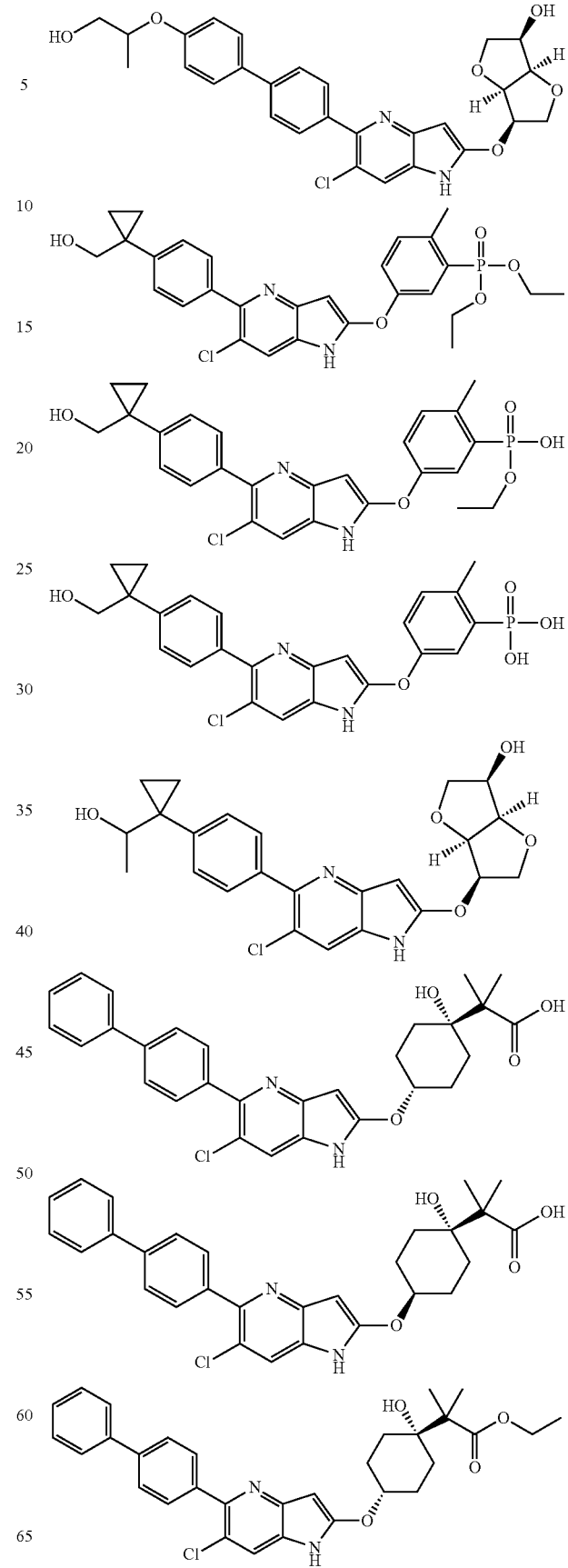

17
-continued
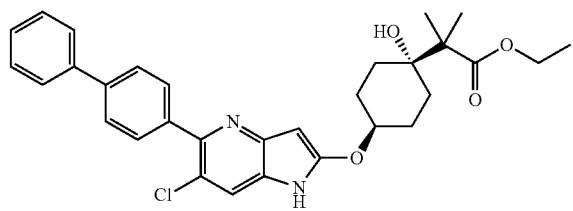
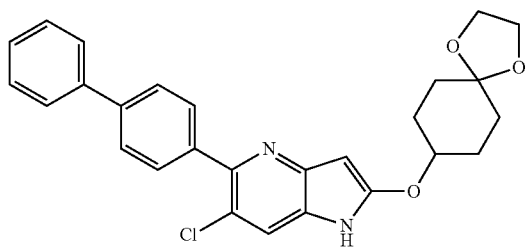
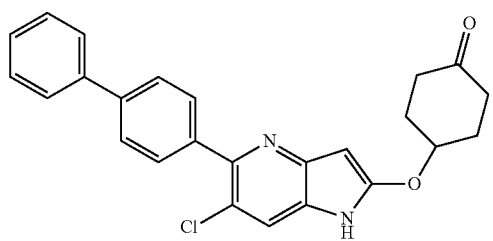
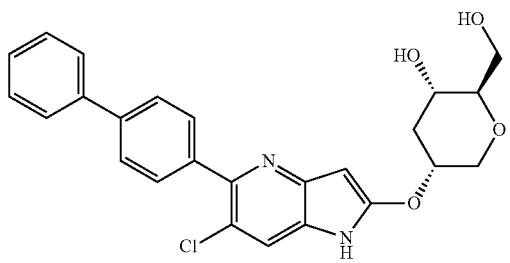
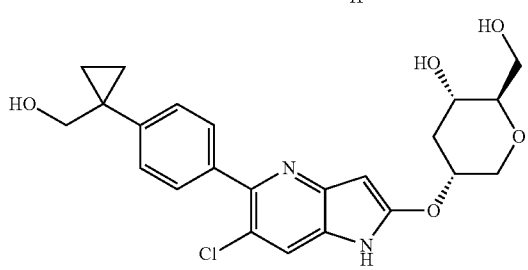
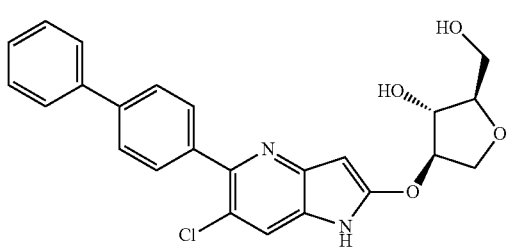
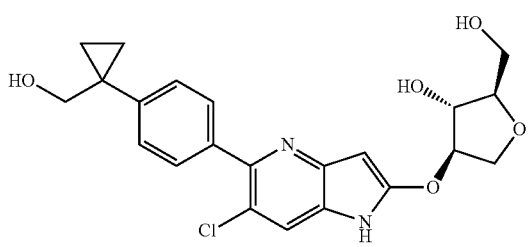
18
-continued
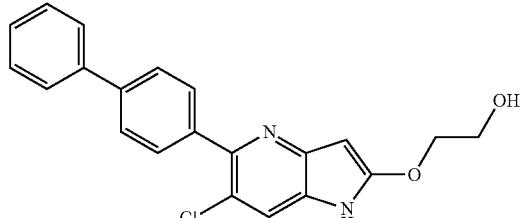
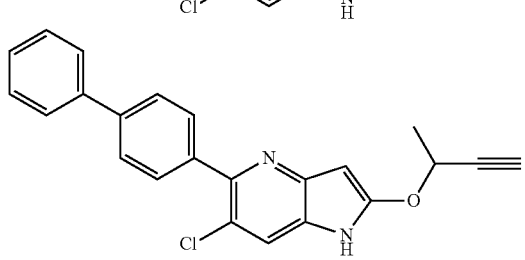
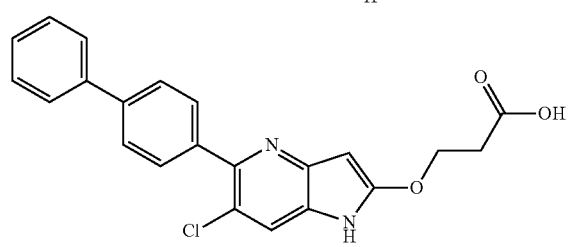
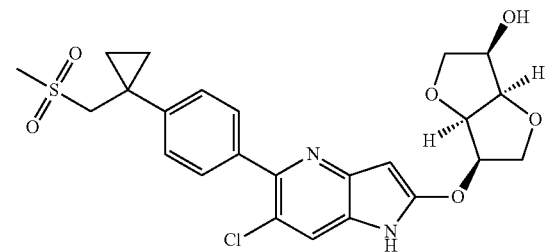
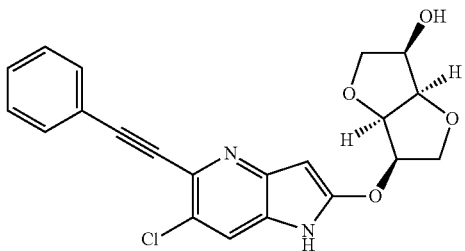
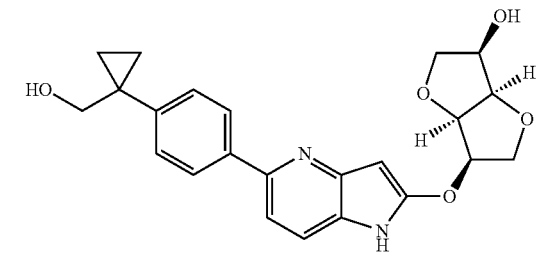
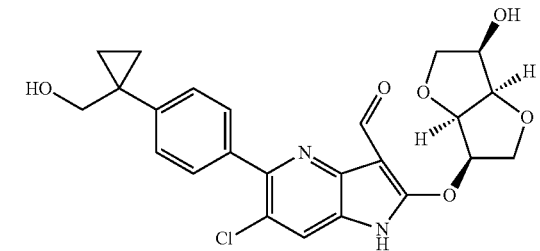

-continued

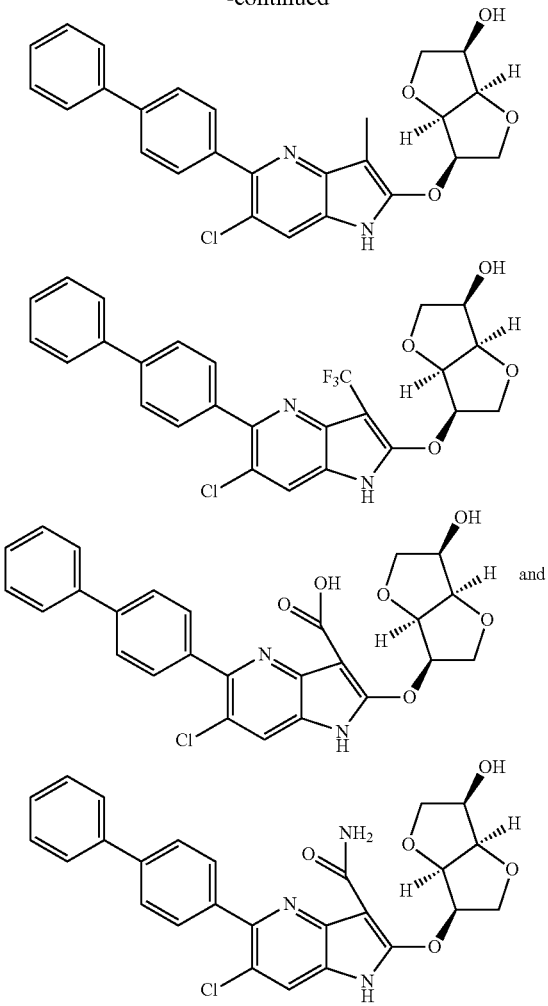

PRIOR ART DOCUMENT

Patent Document

Patent Document 1: WO 2010/036613
Patent Document 2: WO 2010/047982
Patent Document 3: WO 2010/051176
Patent Document 4: WO 2010/051206
Patent Document 5: WO 2011/106273
Patent Document 6: WO 2012/116145
Patent Document 7: WO 2012/033149
Patent Document 8: WO 2013/011932
Patent Document 9: WO 2014/069426
Patent Document 10: WO 2014/031441
Patent Document 11: WO 2014/031445
Patent Document 12: WO 2014/031468
Patent Document 13: WO 2014/031517
Patent Document 14: WO 2014/031465
Patent Document 15: WO 2014/031515
Patent Document 16: WO 2009/100130
Patent Document 17: WO 2014/133008
Patent Document 18: WO 2014/139388
Patent Document 19: WO 2015/007669
Patent Document 20: WO 2015/063011

Non-Patent Document

Non-Patent Document 1: Cell Metabolism Vol. 9, Issue 5, 407-416, 2009

DISCLOSURE OF INVENTION

Problems to be Solved by the Invention

An object of the present invention is to provide an excellent AMPK activator.

Means for Solving the Problem

As a result of intensive research, the present inventors succeeded in synthesizing an excellent compound having an AMPK activating effect.
The present invention relates to the following.
(1)
A compound represented by formula (I):

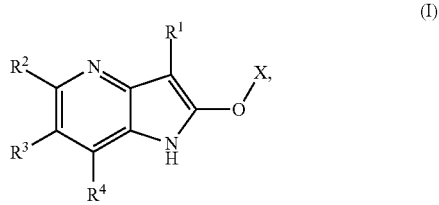

(I)

or its pharmaceutically acceptable salt,
wherein
X is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^2$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^3$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^4$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that compounds shown below are excluded:

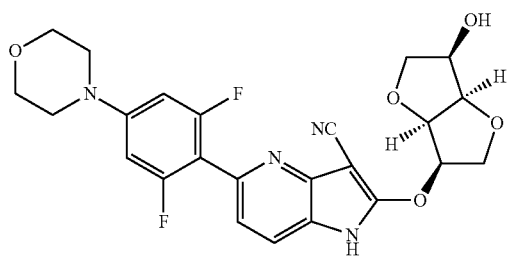

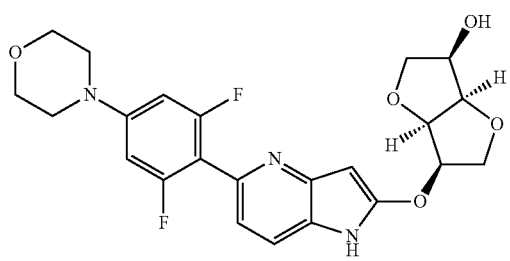

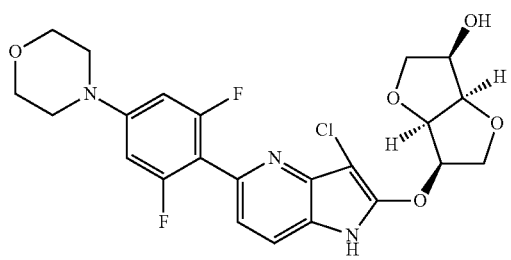

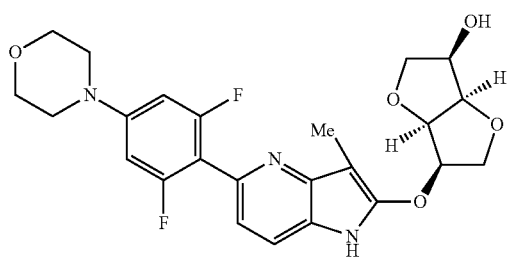


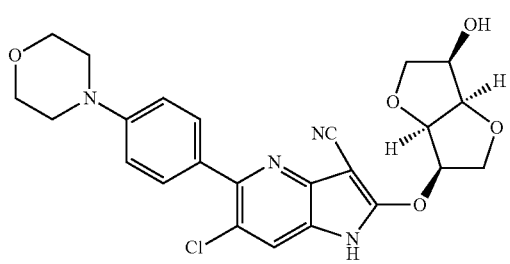

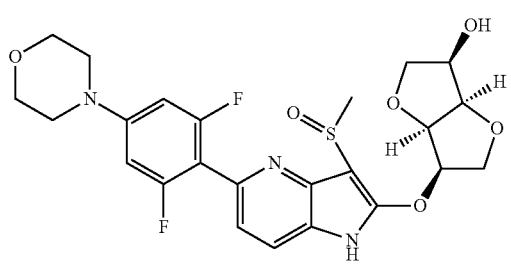

-continued
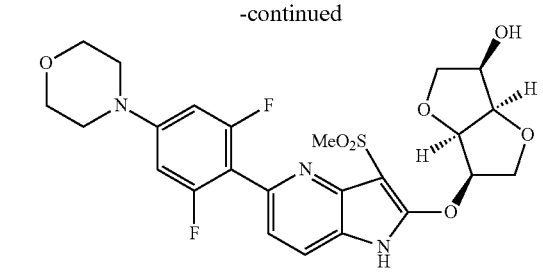
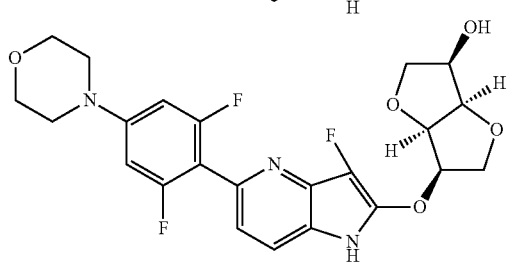
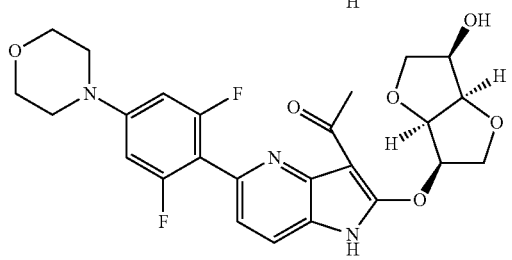
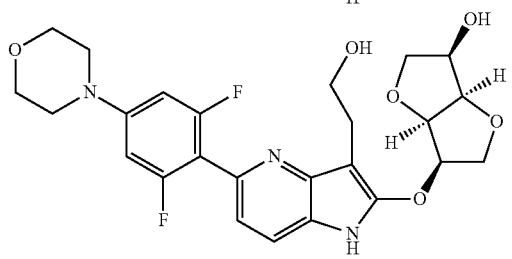
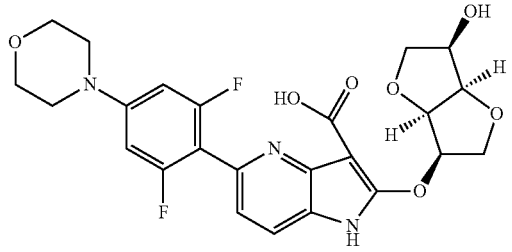
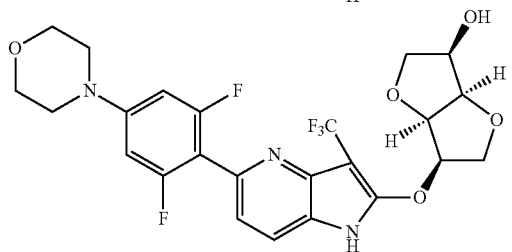
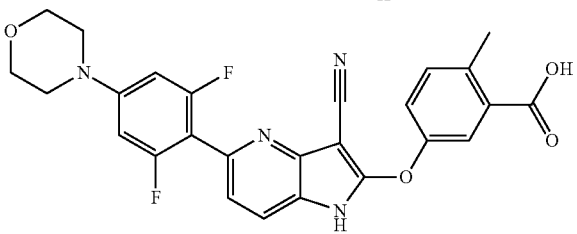
-continued
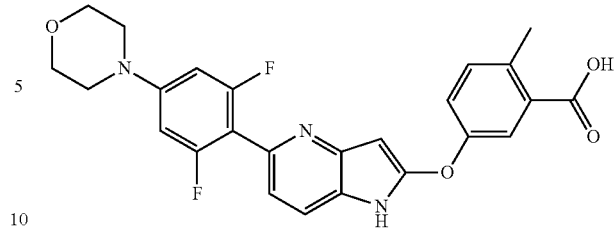
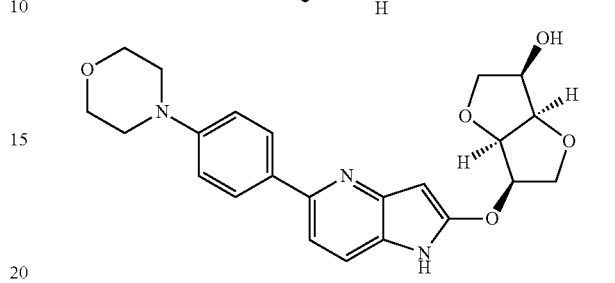
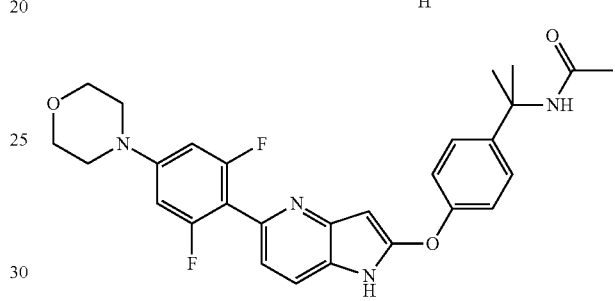
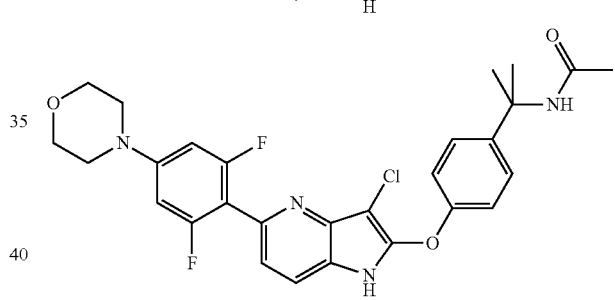
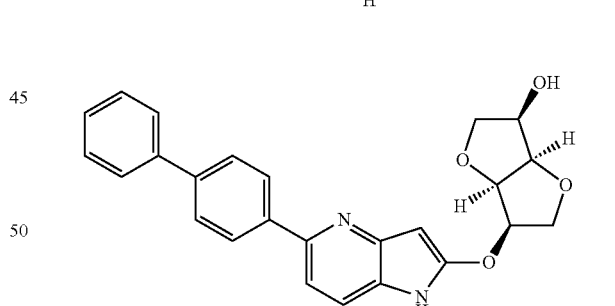
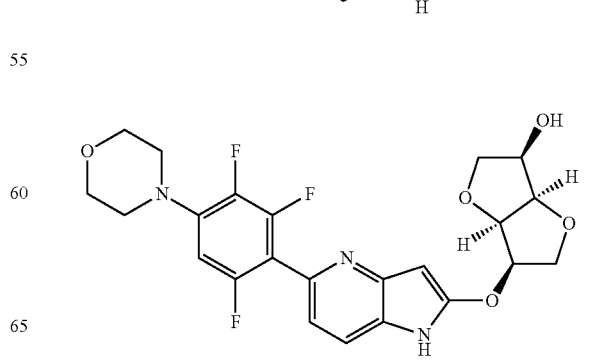

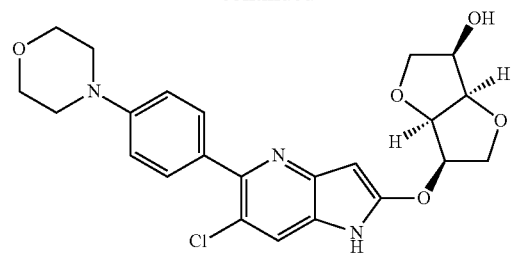
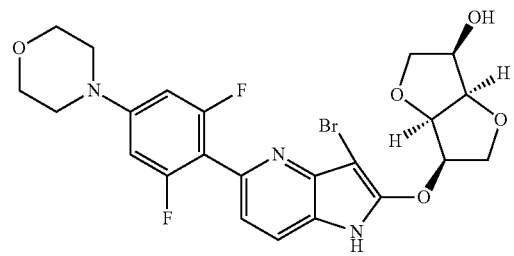
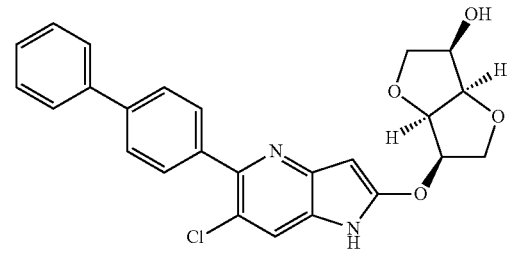
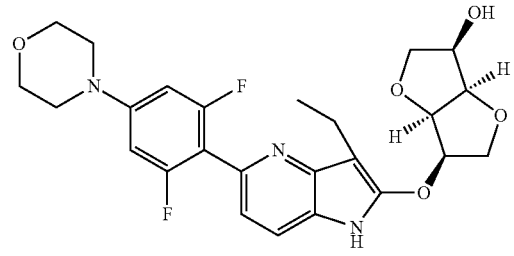
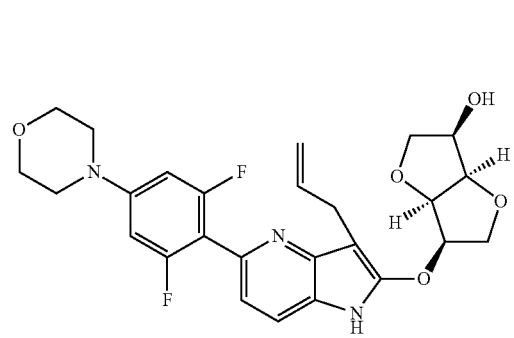
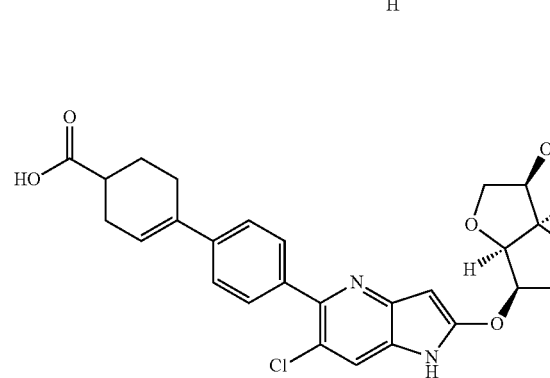
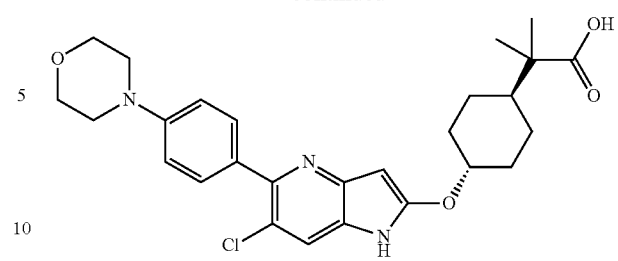
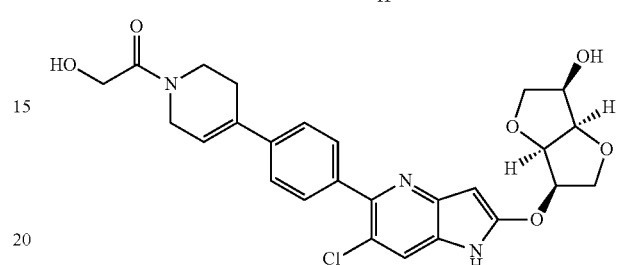
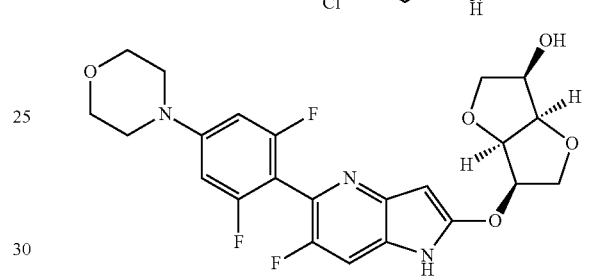
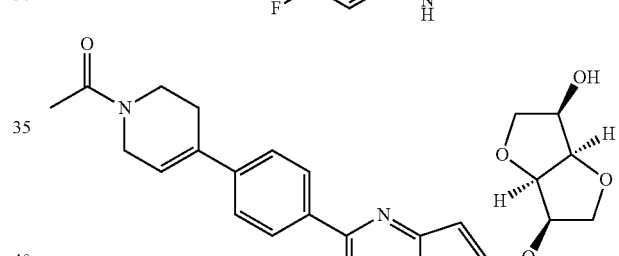
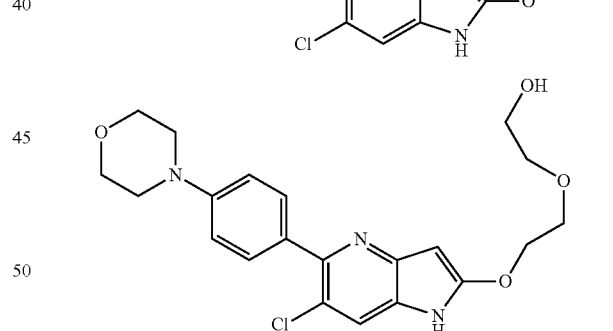
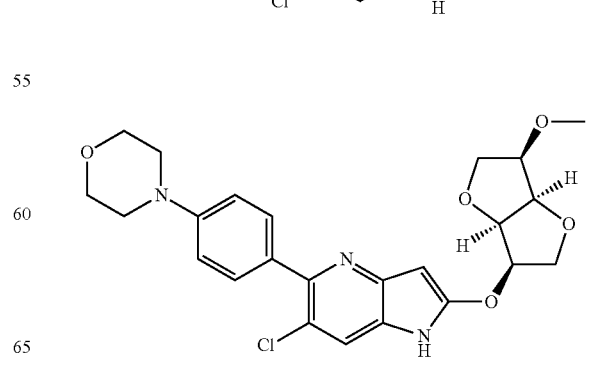

27
-continued
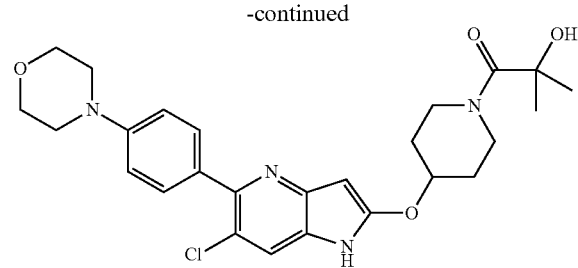
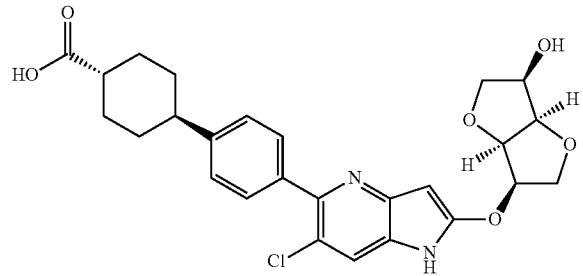
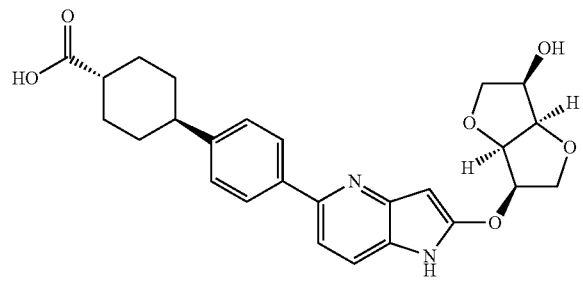
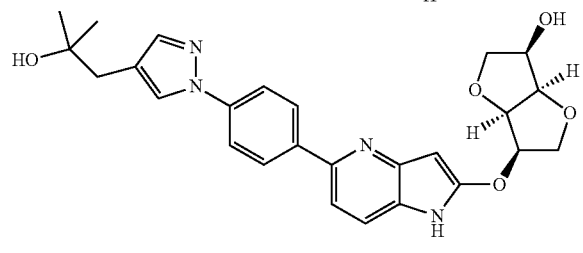
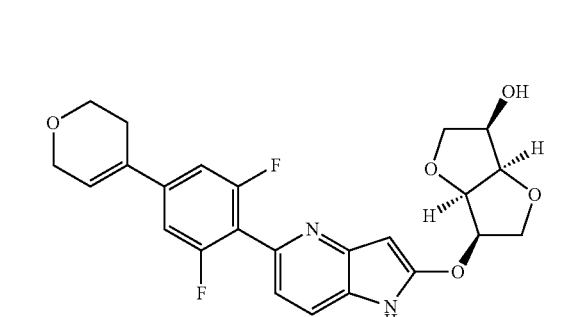
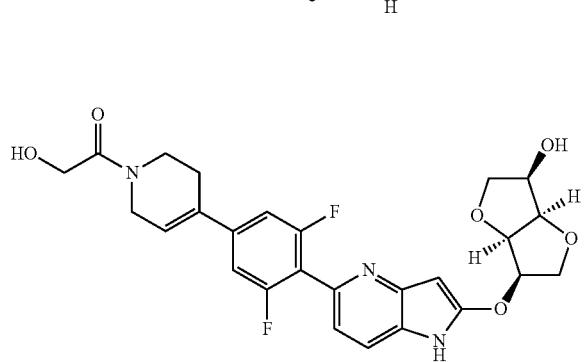
28
-continued
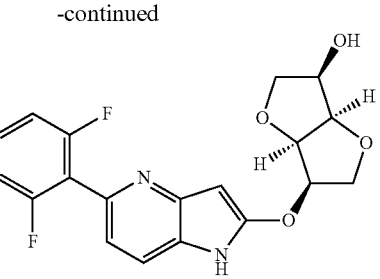
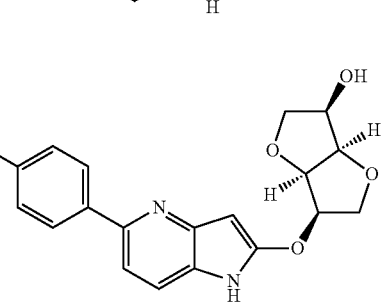
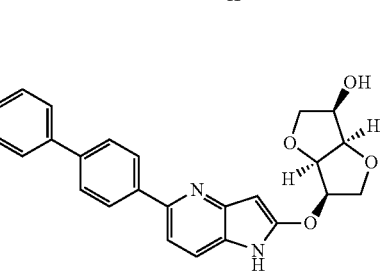
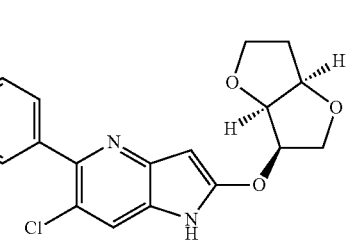
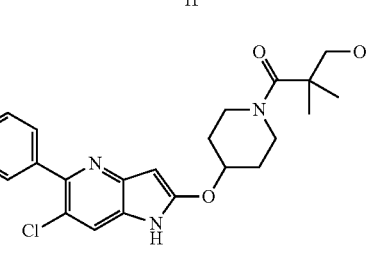
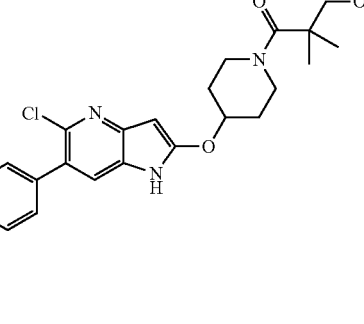

29
-continued
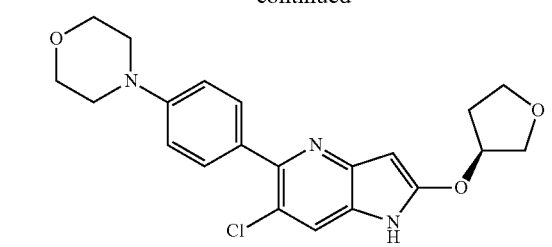
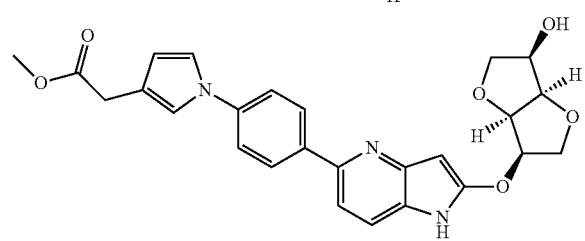
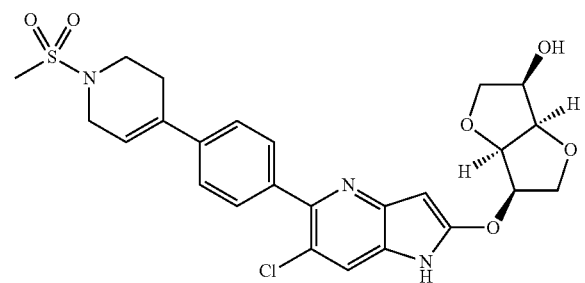
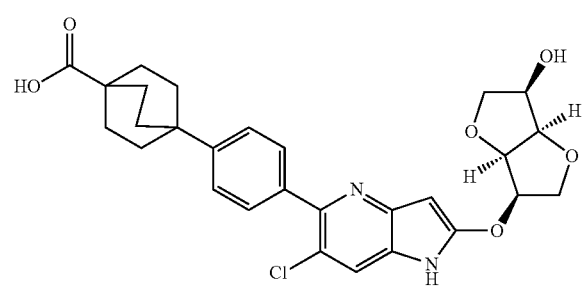
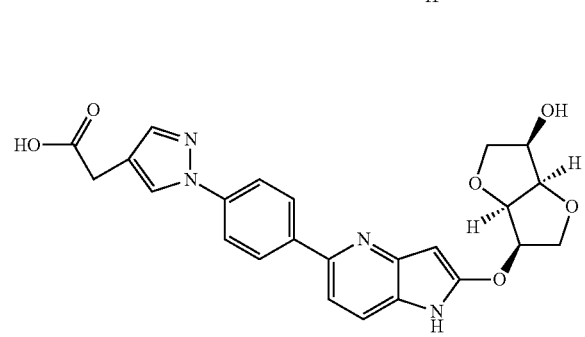
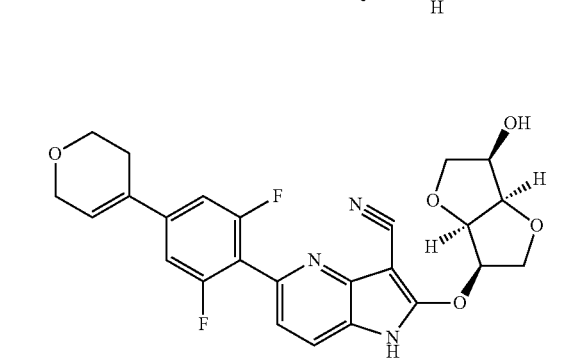
30
-continued
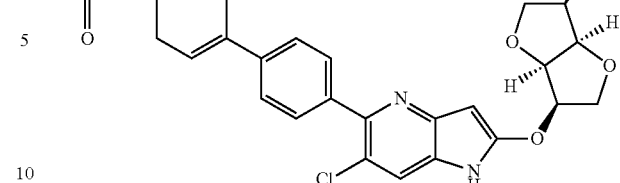
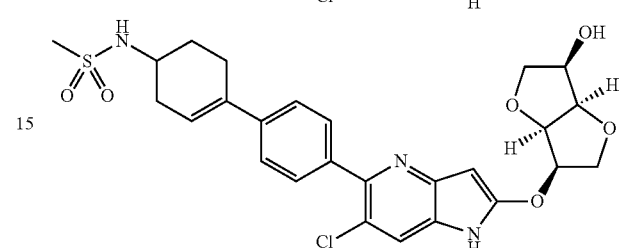
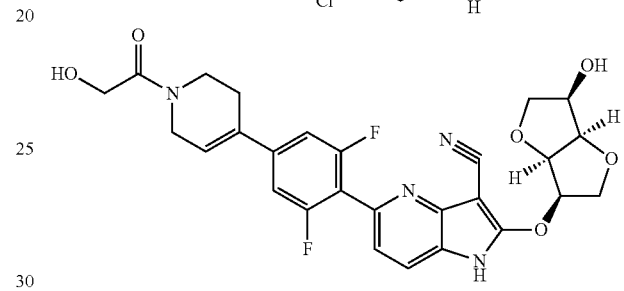
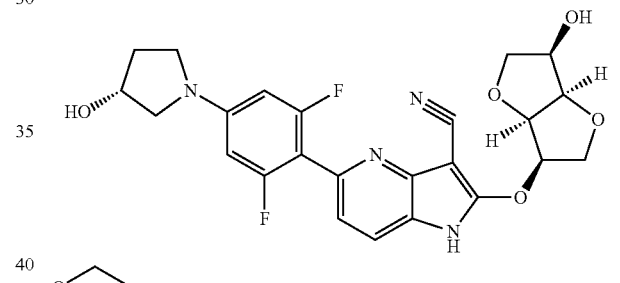
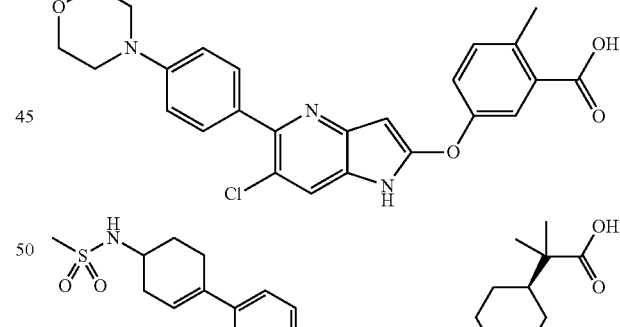
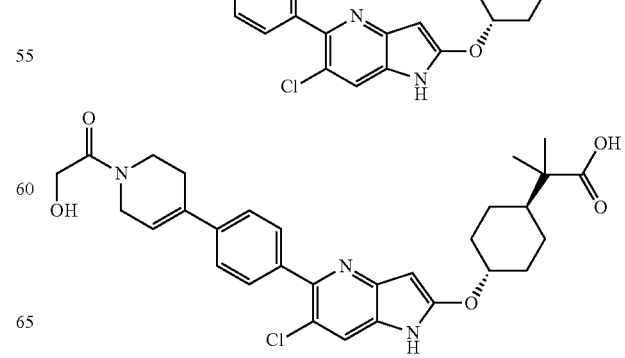

31
-continued
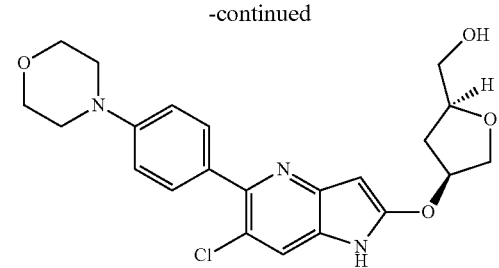
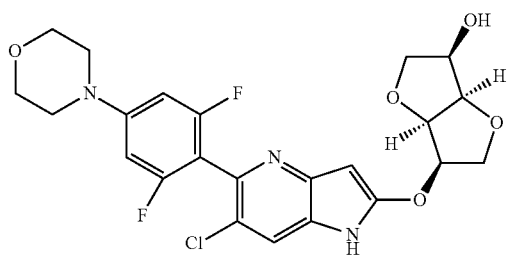 [SMILES: O[C@@H]1CO[C@H]2[C@@H]1OC[C@H]2Oc1cc2nc(-c3c(F)cc(N4CCOCC4)cc3F)c(Cl)cc2[nH]1]
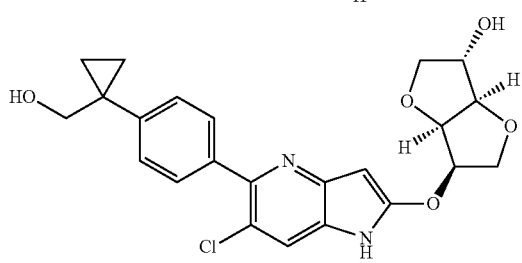
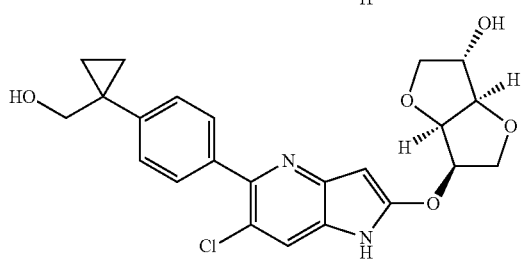
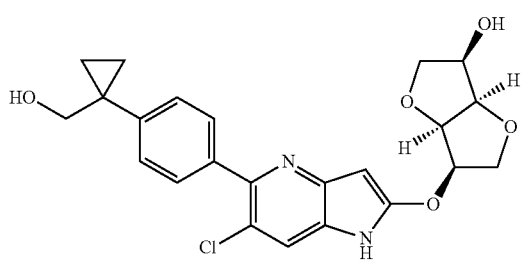
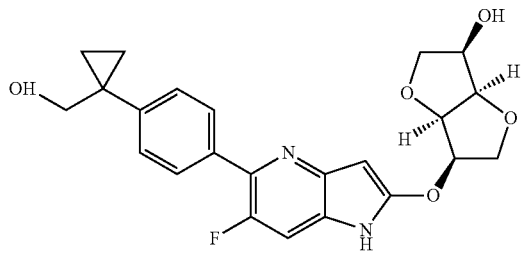
32
-continued
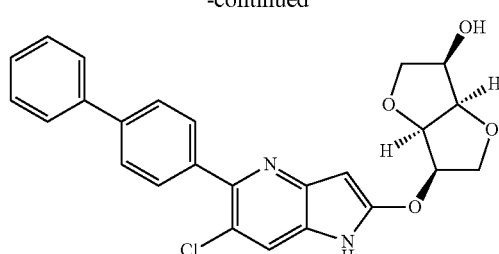
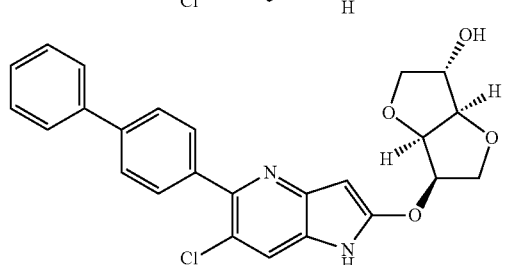
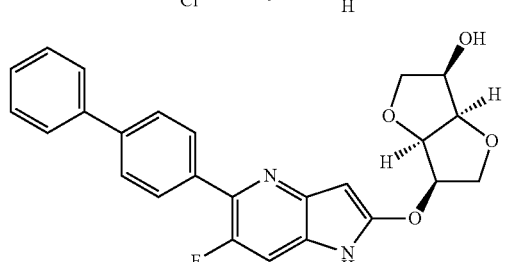
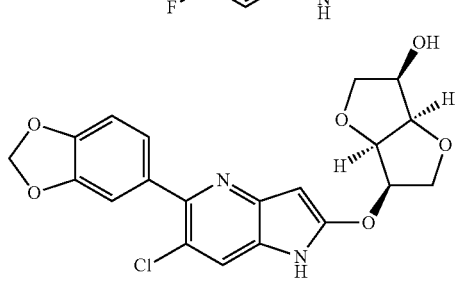
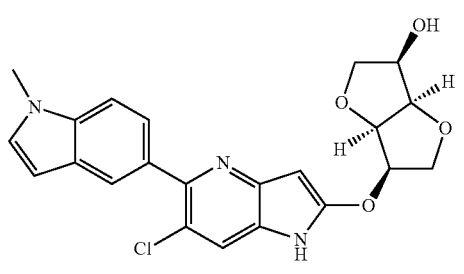
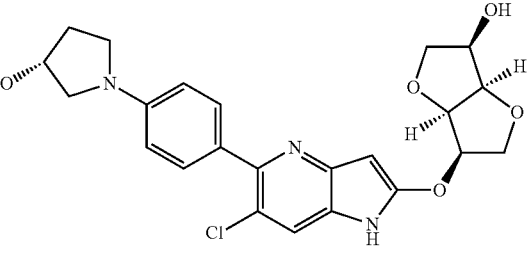

33
-continued
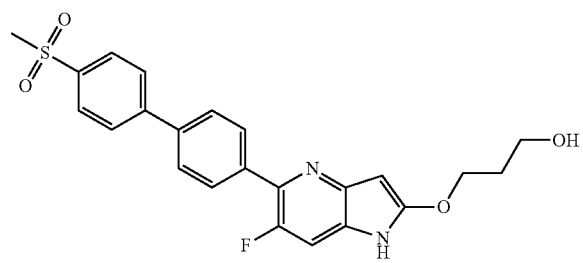
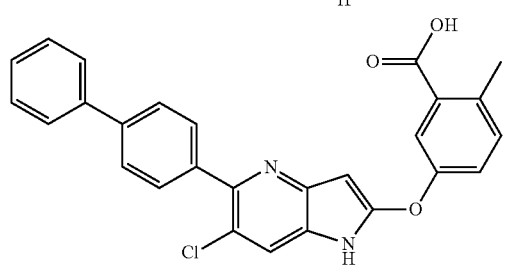
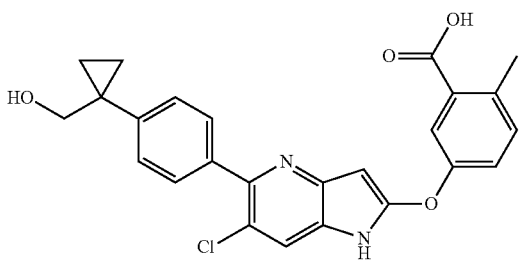
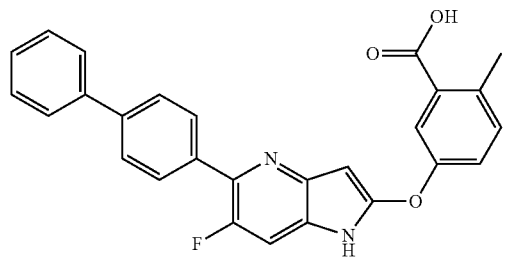
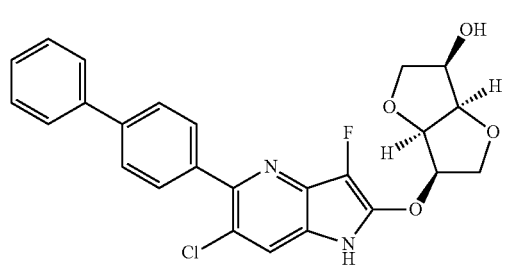
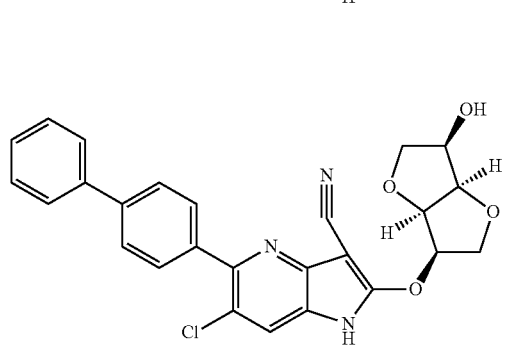
34
-continued
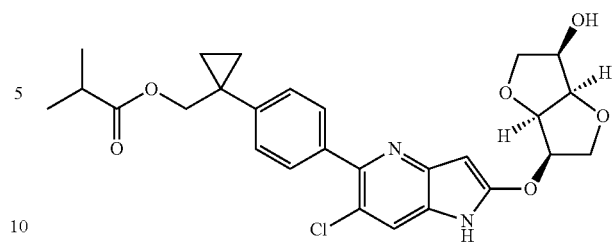
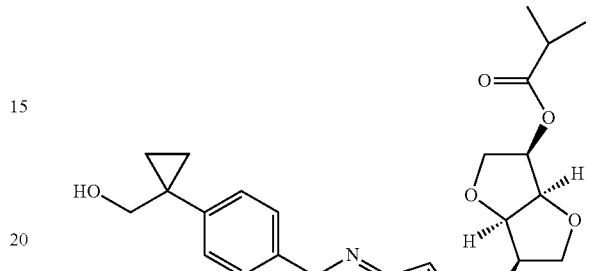
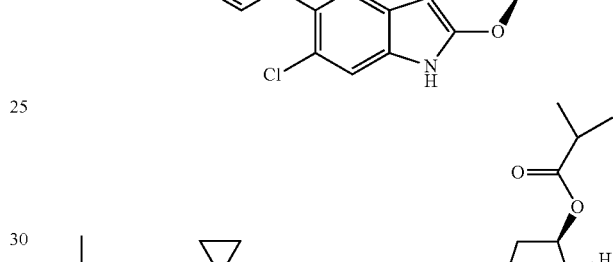
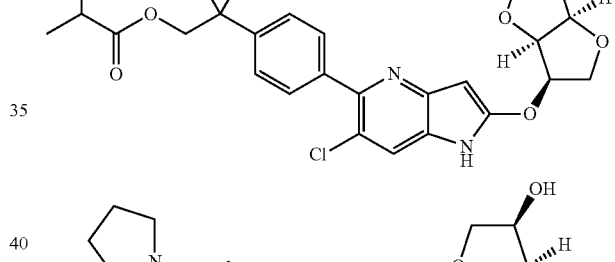
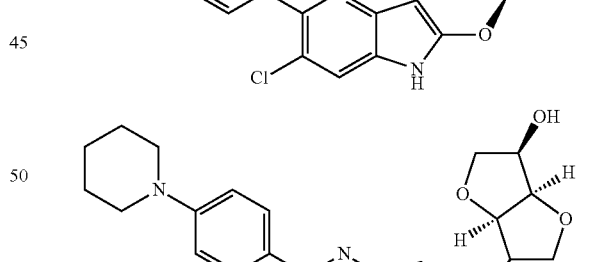
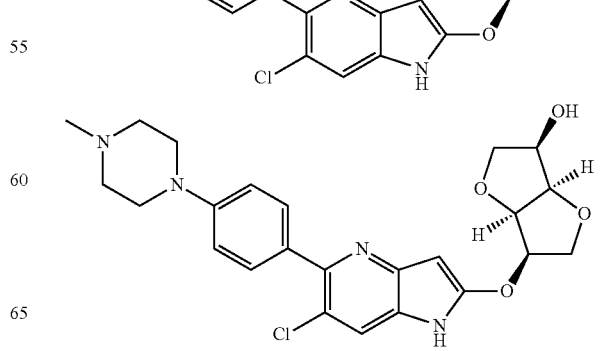

35
-continued
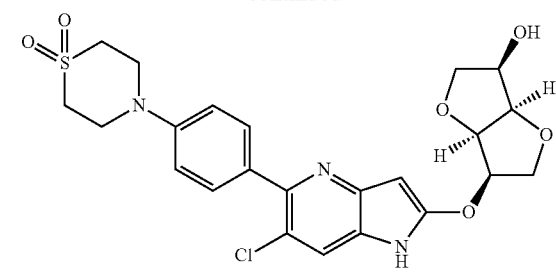
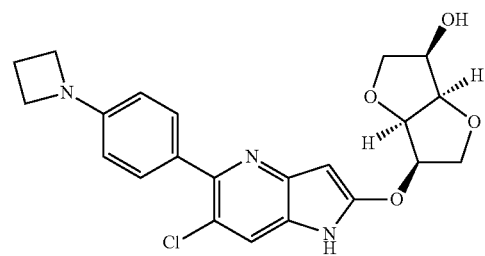
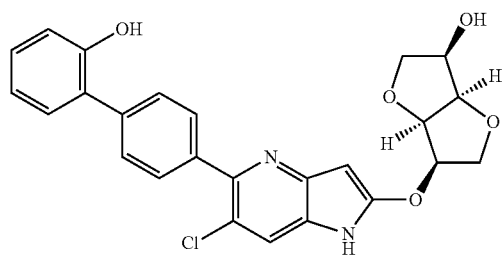
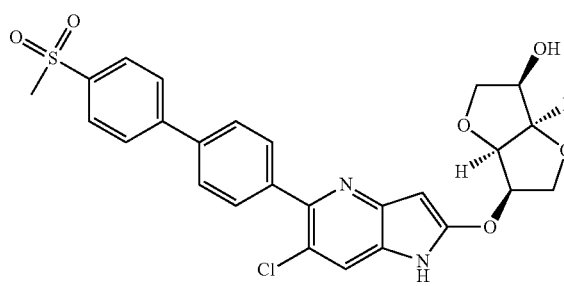
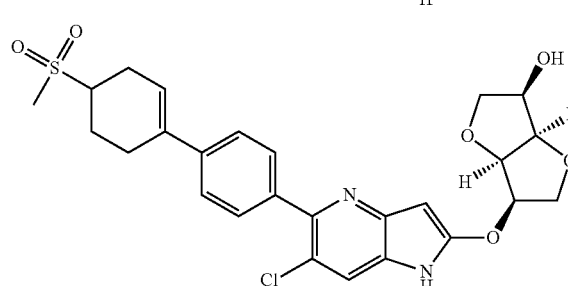
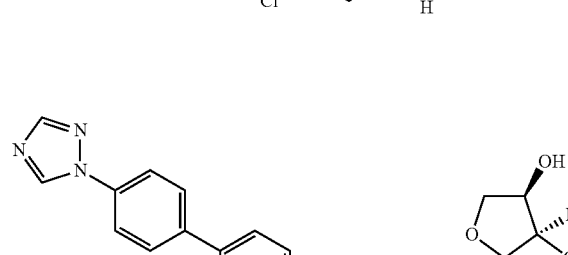
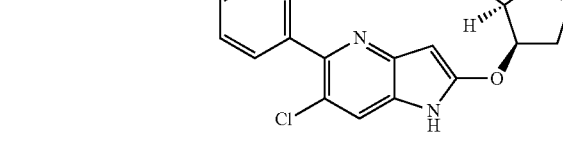
36
-continued
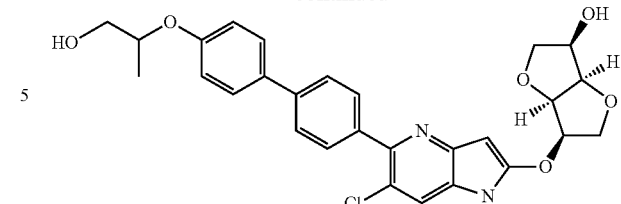
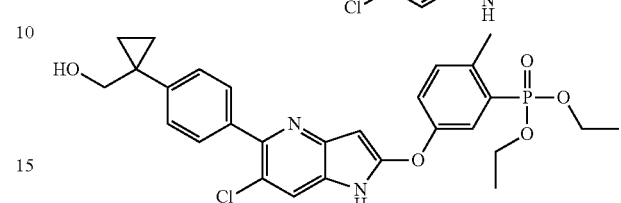
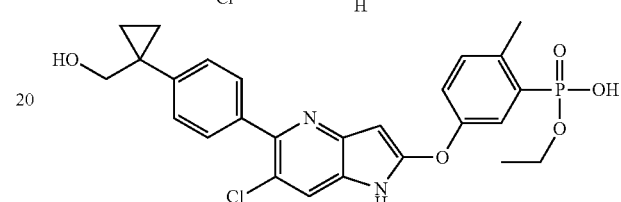
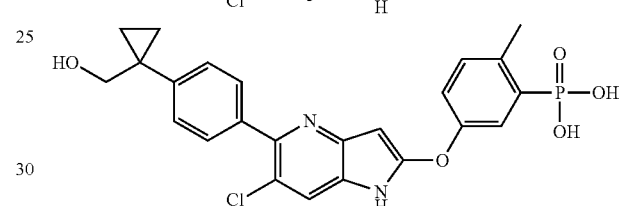
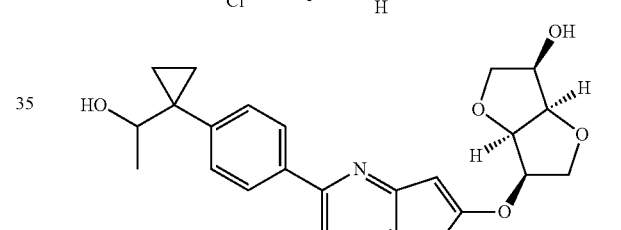
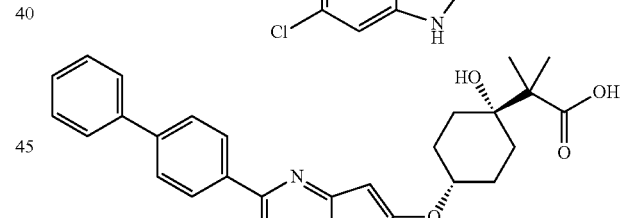
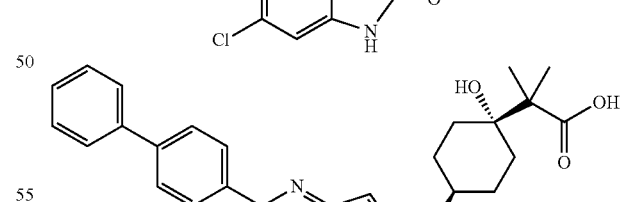
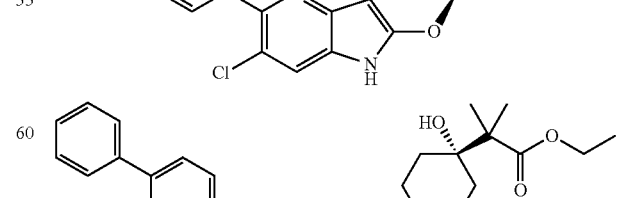

37
-continued
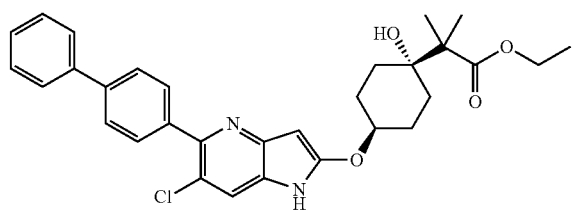
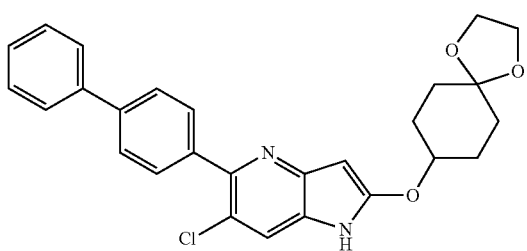
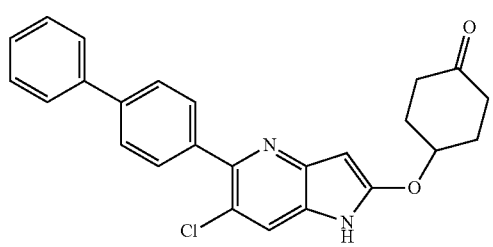
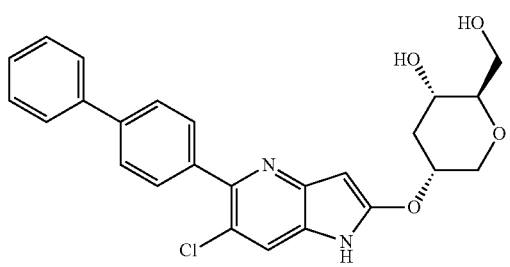
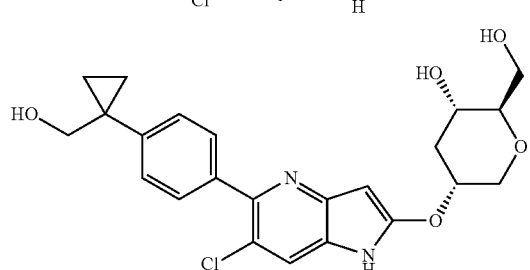
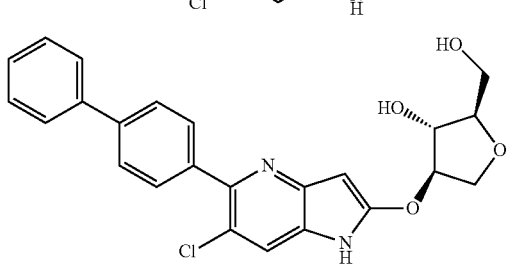
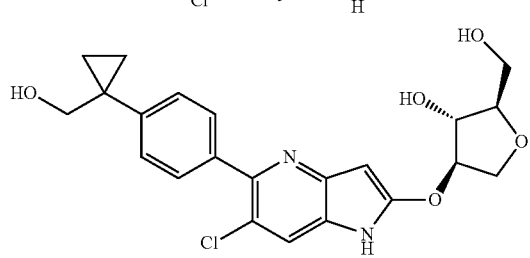
38
-continued
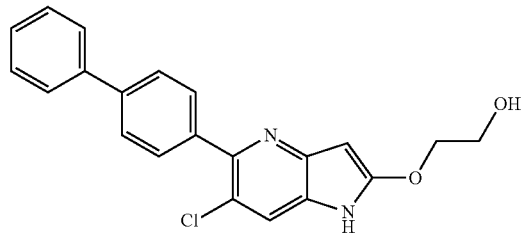
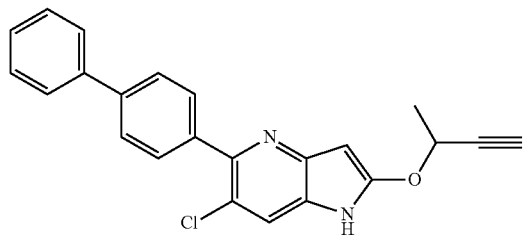
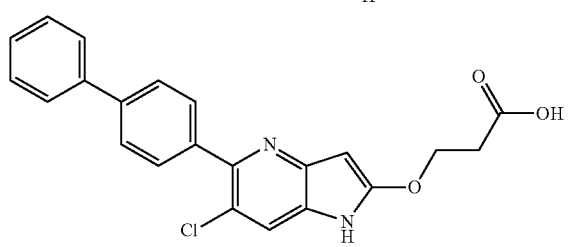
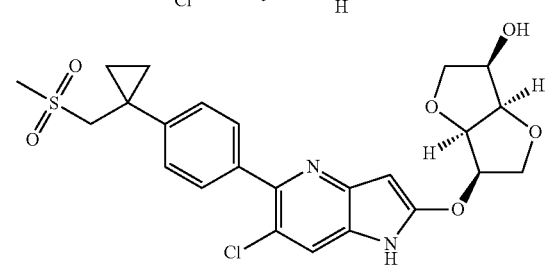
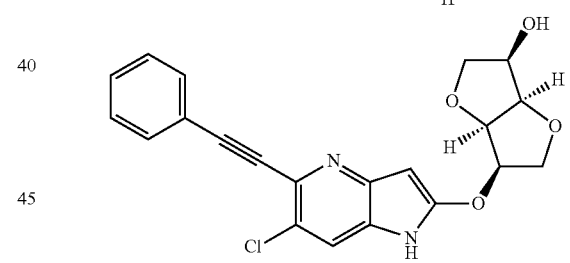
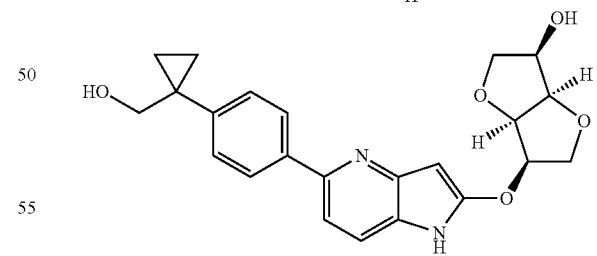
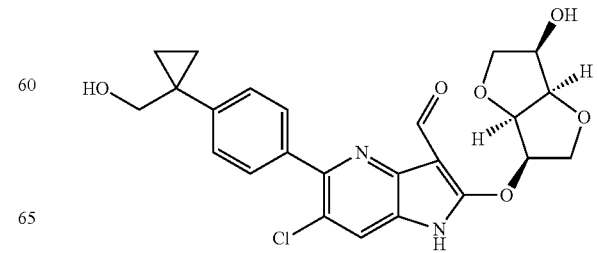

-continued

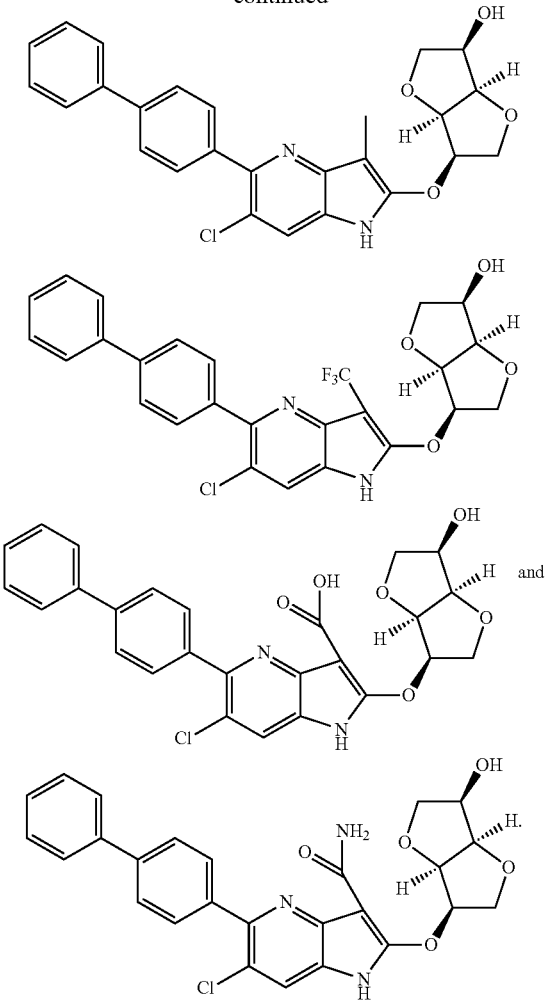

(2) The compound according to the above (1), or its pharmaceutically acceptable salt, wherein $R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl.

(3) The compound according to the above (1) or (2), or its pharmaceutically acceptable salt, wherein $R^1$ is hydrogen, halogen, or cyano.

(4) The compound according to the above (1), or its pharmaceutically acceptable salt, wherein $R^1$ is hydrogen and $R^3$ is fluoro, cyano, or substituted or unsubstituted alkyl.

(5) The compound according to the above (1), or its pharmaceutically acceptable salt, wherein $R^1$ is fluoro and $R^3$ is chloro, or $R^1$ is bromo and $R^3$ is chloro.

(6) The compound according to any one of the above (1) to (5), or its pharmaceutically acceptable salt, wherein $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(7) The compound according to the above (6), or its pharmaceutically acceptable salt, wherein $R^2$ is substituted or unsubstituted aryl.

(8) The compound according to the above (7), or its pharmaceutically acceptable salt, wherein $R^2$ is

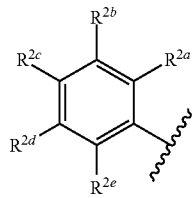

wherein $R^{2a}$, $R^{2b}$, $R^{2d}$ and $R^{2e}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^{2c}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

(9) The compound according to the above (8), or its pharmaceutically acceptable salt, wherein at least one of $R^{2a}$ or $R^{2e}$ is halogen.

(10) The compound according to the above (6), or its pharmaceutically acceptable salt, wherein $R^2$ is substituted aryl, substituted heteroaryl, substituted cycloalkyl, substituted cycloalkenyl, or substituted heterocyclyl.

(11) The compound according to the above (10), or its pharmaceutically acceptable salt, wherein $R^2$ is

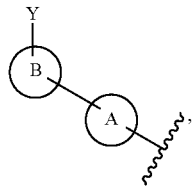

wherein
ring A is substituted aryl, substituted heteroaryl, substituted cycloalkyl, substituted cycloalkenyl, or substituted heterocyclyl, the ring A may further have (a) substituent(s) at arbitrary position(s) other than the position that is substituted with ring B;
ring B is substituted aryl, substituted heteroaryl, substituted cycloalkyl, substituted cycloalkenyl, or substituted heterocyclyl, the ring B may further have (a) substituent(s) at arbitrary position(s) other than the position that is substituted with Y and ring A;

Y is $R^SR^{S'}(O')S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$;

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;

$R^S$ and $R^{S'}$ bound to the same sulfur atom may form a substituted or unsubstituted ring together with the sulfur atom;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ together with the adjacent nitrogen atom may form a substituted or unsubstituted ring when Y is $((R^N)N=)_2S(R^S)-$;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

(12) The compound according to the above (11), or its pharmaceutically acceptable salt, wherein ring A is substituted aryl, or substituted heteroaryl.

(13) The compound according to the above (11) or (12), or its pharmaceutically acceptable salt, wherein ring B is substituted aryl, or substituted heteroaryl.

(14) The compound according to any one of the above (10) to (13), or its pharmaceutically acceptable salt, wherein Y is $R^SR^{S'}(O=)S=N-$, $(R^N)N=S(=O)(R^S)-$, or $R^OO-C(=O)-N(R^N)-$.

(15) The compound according to the above (10), or its pharmaceutically acceptable salt, wherein $R^2$ is

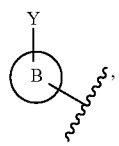

wherein ring B is substituted aryl, substituted heteroaryl, substituted cycloalkyl, substituted cycloalkenyl, or substituted heterocyclyl, the ring B may further have (a) substituent(s) other than Y;

Y is $R^SR^{S'}(O=)S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$;

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;

$R^S$ and $R^{S'}$ bound to the same sulfur atom may form a substituted or unsubstituted ring together with the sulfur atom;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ together with the adjacent nitrogen atom may form a substituted or unsubstituted ring when Y is $((R^N)N=)_2S(R^S)-$;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

(16) The compound according to the above (15), or its pharmaceutically acceptable salt, wherein ring B is substituted aryl, substituted heteroaryl, substituted cycloalkyl, or substituted heterocyclyl.

(17) The compound according to the above (15) or (16), or its pharmaceutically acceptable salt, wherein Y is $R^SR^{S'}(O=)S=N-$, $(R^N)N=S(=O)(R^S)-$, or $R^OO-C(=O)-N(R^N)-$.

(18) The compound according to any one of the above (1) to (3), (6) to (17), or its pharmaceutically acceptable salt, wherein $R^3$ is halogen, cyano, carboxy, substituted or unsubstituted alkyl, substituted or unsubstituted alkylsulfonyl, or substituted or unsubstituted carbamoyl.

(19)

The compound according to the above (18), or its pharmaceutically acceptable salt, wherein $R^3$ is fluoro, cyano, or substituted alkyl, wherein the substituent of the substituted alkyl is halogen.

(20)

The compound according to any one of the above (1) to (19), or its pharmaceutically acceptable salt,
wherein X is

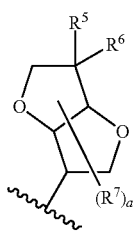

wherein $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^7$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

a is an integer from 0 to 7.

(21)

The compound according to any one of the above (1) to (20), or its pharmaceutically acceptable salt, wherein $R^4$ is hydrogen.

(22)

The compound according to any one of the above (1) to (20), or its pharmaceutically acceptable salt, wherein $R^4$ is halogen.

(23)

A pharmaceutical composition comprising the compound according to any one of the above (1) to (22), or its pharmaceutically acceptable salt.

(24)

The pharmaceutical composition according to the above (23), which has an activating effect on adenosine monophosphate-activated protein kinase.

(25)

The pharmaceutical composition according to the above (23) or (24), for the treatment and/or prevention of diabetes.

(26)

A method for preventing or treating diabetes, comprising administering the compound according to any one of the above (1) to (24), or its pharmaceutically acceptable salt.

(27)

The compound according to any one of the above (1) to (24), or its pharmaceutically acceptable salt, for the treatment and/or prevention of diabetes.

(28)

A pharmaceutical composition for oral administration, comprising a compound represented by the above formula (I), or its pharmaceutically acceptable salt.

(29)

The pharmaceutical composition according to the above (28), which is a tablet, powder, granule, capsule, pill, film, suspension, emulsion, elixir, syrup, lemonade, spirit, aromatic water, extract, decoction or tincture.

(30)

The pharmaceutical composition according to the above (29), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

(31)

A pharmaceutical composition for parenteral administration, comprising a compound represented by the above formula (I), or its pharmaceutically acceptable salt.

(32)

The pharmaceutical composition according to the above (31), for dermal, subcutaneous, intravenous, intraarterial, intramuscular, intraperitoneal, transmucosal, inhalation, transnasal, ophthalmic, inner ear or vaginal administration.

(33)

The pharmaceutical composition according to the above (31) or (32), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(34)

A pharmaceutical composition for a pediatric or geriatric patient, comprising a compound represented by the above formula (I), or its pharmaceutically acceptable salt.

(35)

A pharmaceutical composition consisting of a combination of a compound represented by the above formula (I) or its pharmaceutically acceptable salt, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, a sodium-dependent glucose transporter 2 inhibitor.

(36)

A pharmaceutical composition comprising a compound represented by the above formula (I) or its pharmaceutically acceptable salt, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, a sodium-dependent glucose transporter 2 inhibitor.

(1A)

A compound represented by formula (I):

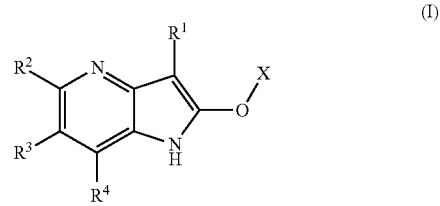

or its pharmaceutically acceptable salt, wherein

X is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

R¹ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;

R² is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

R³ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

R⁴ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that a compound wherein X is

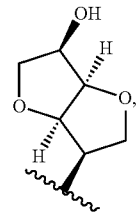 [SMILES: *[C@@H]1CO[C@H]2[C@@H]1OC[C@H]2O]

R¹ is hydrogen, R² is

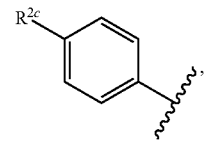

R²ᶜ is substituted or unsubstituted aryl, substituted or unsubstituted cycloalkyl, substituted or unsubstituted cycloalkenyl, or substituted or unsubstituted heterocyclyl, and R³ is chloro; and the compounds shown below are excluded:

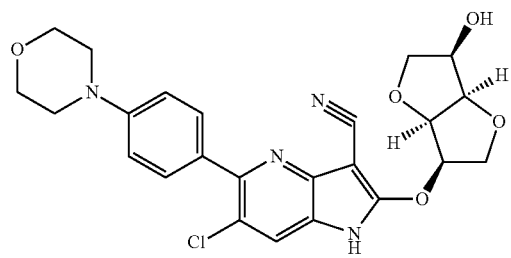

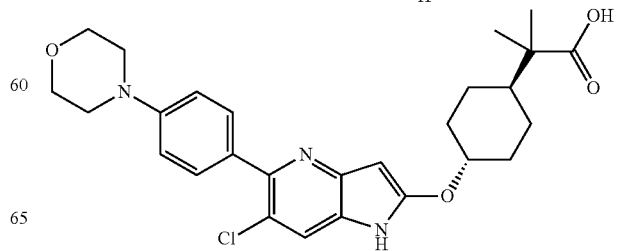

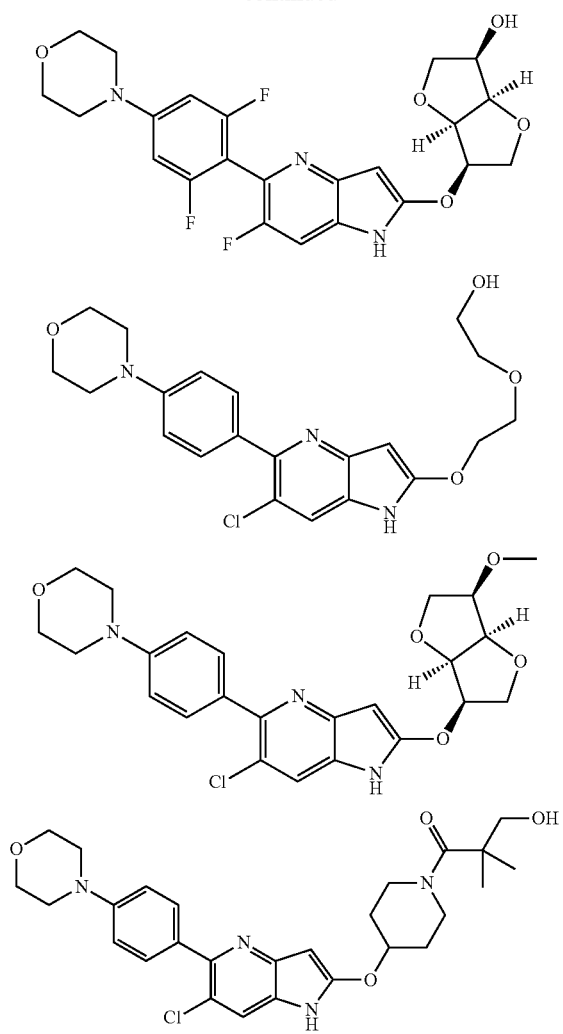
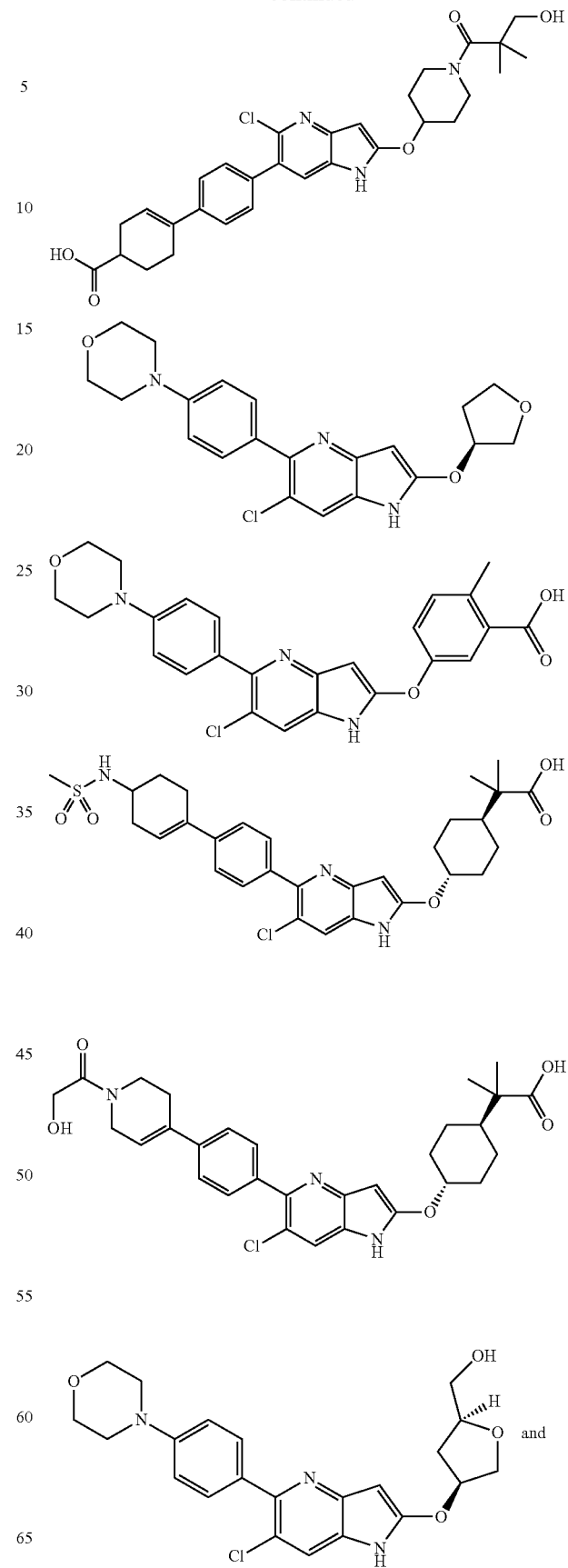

-continued

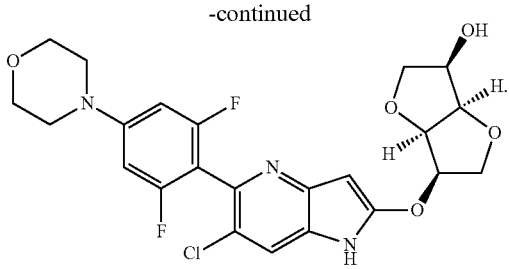

(2A)

The compound according to the above (1A), or its pharmaceutically acceptable salt, wherein is halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl.

(3A)

The compound according to the above (1A) or (2A), or its pharmaceutically acceptable salt, wherein $R^1$ is halogen or cyano.

(4A)

The compound according to the above (1A), or its pharmaceutically acceptable salt, wherein $R^1$ is hydrogen, and $R^3$ is fluoro or cyano.

(5A)

The compound according to any one of the above (1A) to (4A), or its pharmaceutically acceptable salt, wherein $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(6A)

The compound according to any one of the above (1A) to (5A), or its pharmaceutically acceptable salt, wherein $R^2$ is substituted or unsubstituted aryl.

(7A)

The compound according to the above (6A), or its pharmaceutically acceptable salt, wherein $R^2$ is

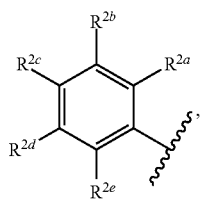

wherein $R^{2a}$, $R^{2b}$, $R^{2d}$, and $R^{2e}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^{2c}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

(8A)

The compound according to the above (7A), or its pharmaceutically acceptable salt, wherein at least one of $R^{2a}$ or $R^{2e}$ is halogen.

(9A)

The compound according to any one of the above (1A) to (8A), or its pharmaceutically acceptable salt, wherein $R^3$ is halogen, cyano, carboxy, substituted or unsubstituted alkyl, substituted or unsubstituted alkylsulfonyl, or substituted or unsubstituted carbamoyl.

(10A)

The compound according to the above (9A), or its pharmaceutically acceptable salt, wherein $R^3$ is fluoro, cyano, or substituted or unsubstituted alkyl.

(11A)

The compound according to any one of the above (1A) to (10A), or its pharmaceutically acceptable salt, wherein X is

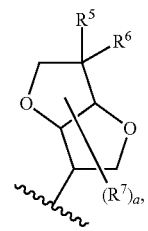

wherein $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^7$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; a is an integer from 0 to 7.

(12A)

The compound according to any one of the above (1A) to (11A), or its pharmaceutically acceptable salt, wherein $R^4$ is hydrogen.

(13A)

A pharmaceutical composition comprising the compound according to any one of the above (1A) to (12A), or its pharmaceutically acceptable salt.

(14A)

The pharmaceutical composition according to the above (13A), which has an activating effect on adenosine monophosphate-activated protein kinase.

(15A)

The pharmaceutical composition according to the above (13A) or (14A), for the treatment and/or prevention of diabetes.

(16A)
A method for preventing or treating diabetes, comprising administering the compound according to any one of the above (1A) to (14A), or its pharmaceutically acceptable salt.
(17A)
The compound according to any one of the above (1A) to (14A), or its pharmaceutically acceptable salt, for the treatment and/or prevention of diabetes.
(1B)
A compound represented by formula (I):

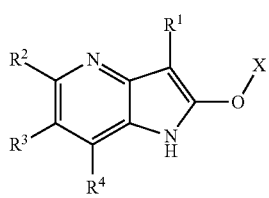

or its pharmaceutically acceptable salt,
wherein
X is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^2$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
$R^3$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
$R^4$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
with the proviso that a compound wherein X is

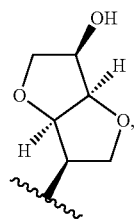 [SMILES: *[C@@H]1CO[C@H]2[C@@H]1OC[C@H]2O]

$R^1$ is hydrogen, $R^2$ is

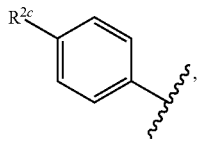

$R^{2c}$ is substituted or unsubstituted aryl, substituted or unsubstituted cycloalkyl, substituted or unsubstituted cycloalkenyl, or substituted or unsubstituted heterocyclyl, $R^3$ is chloro, and $R^4$ is hydrogen; and
the compounds shown below are excluded:
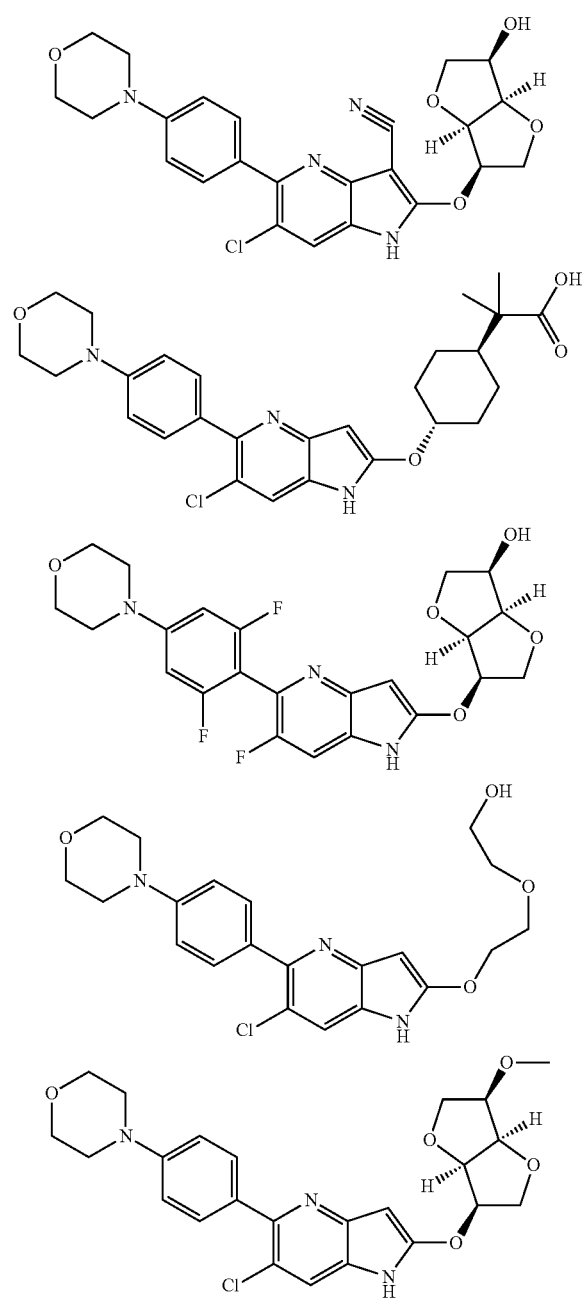
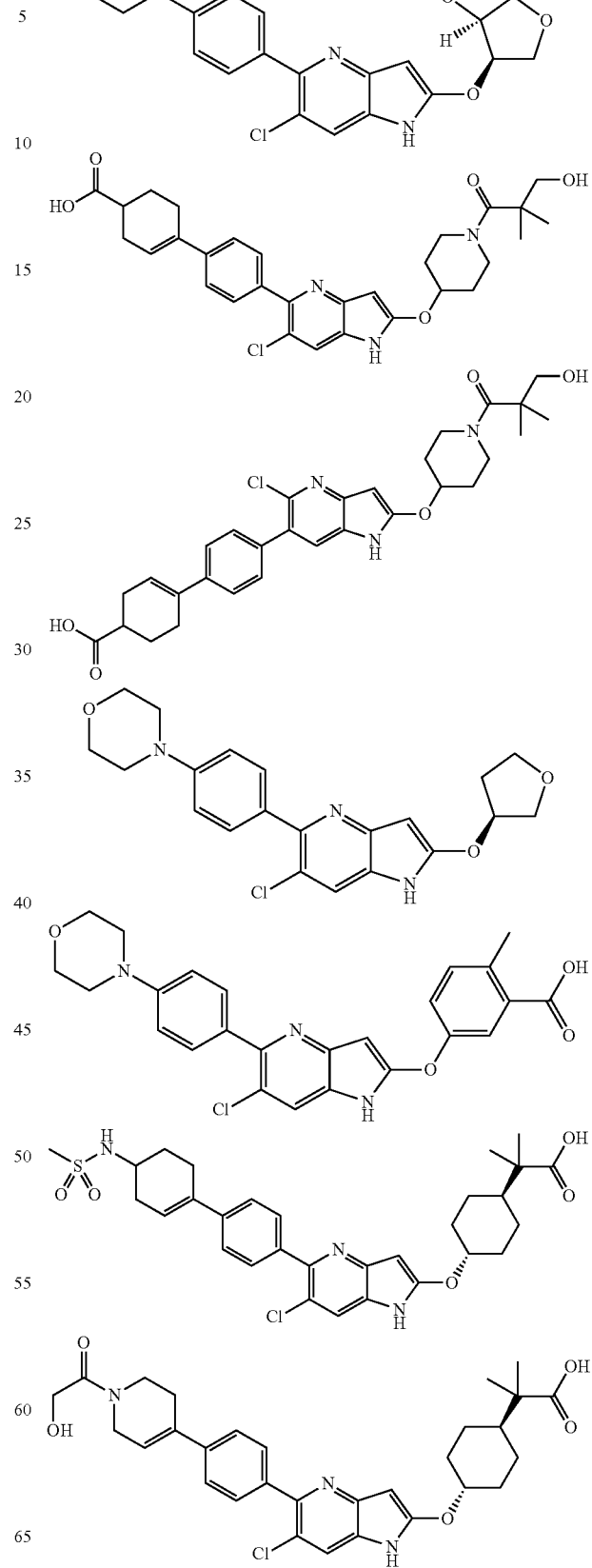

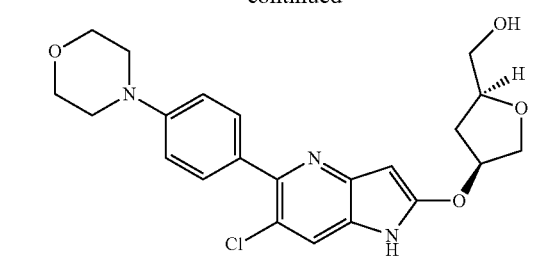
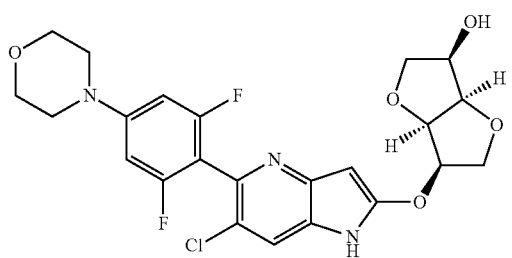
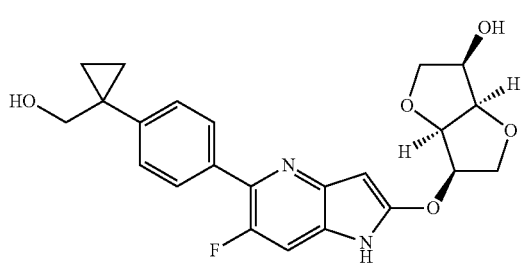
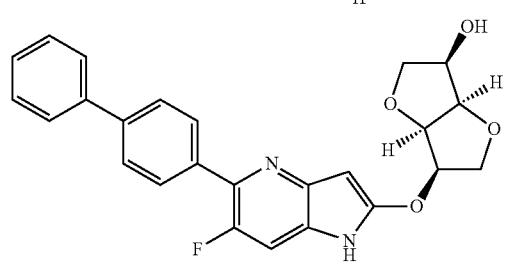
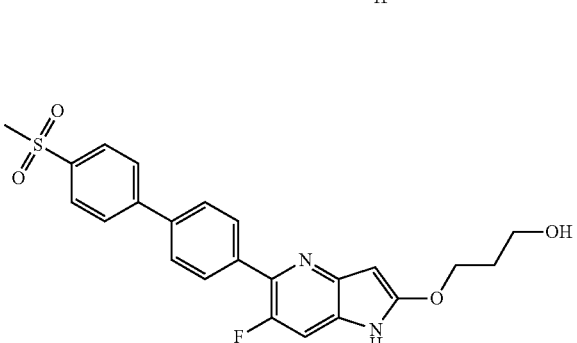
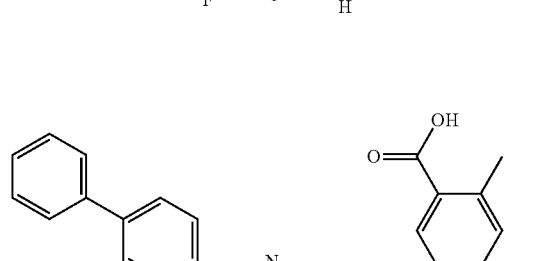
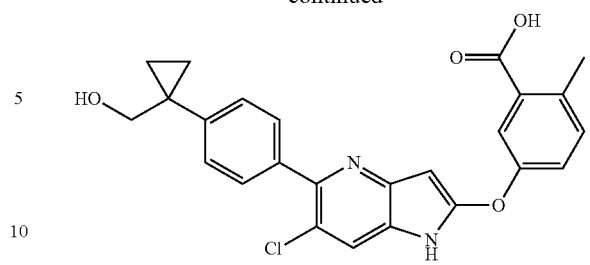
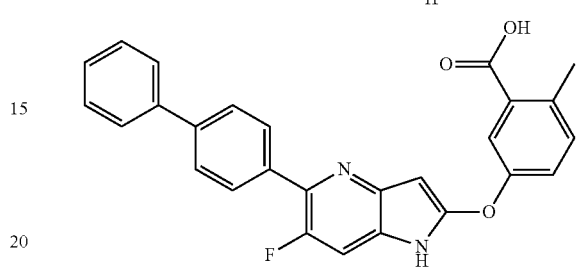
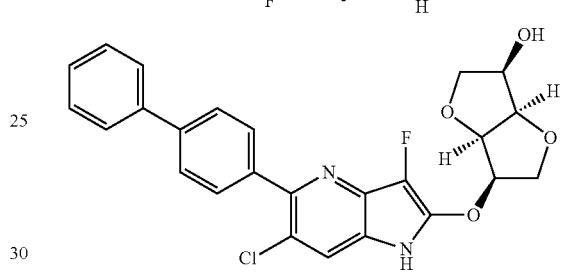
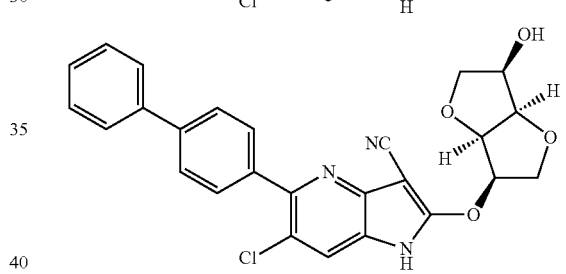
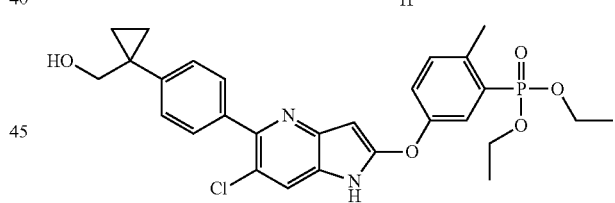
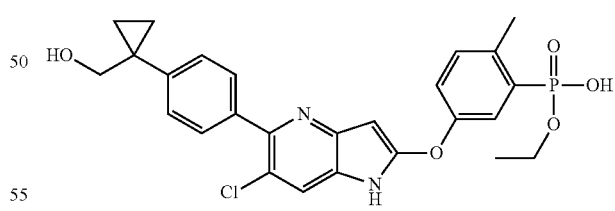
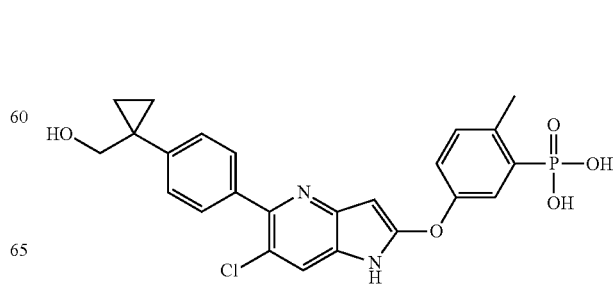

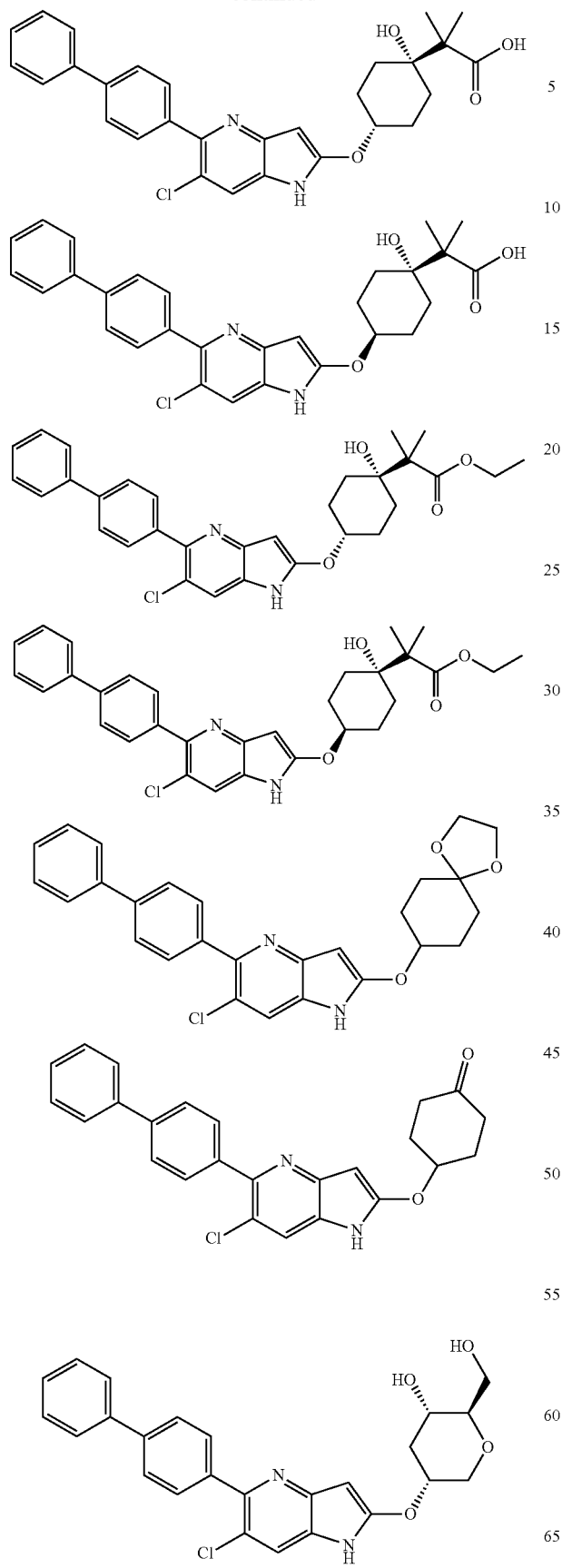
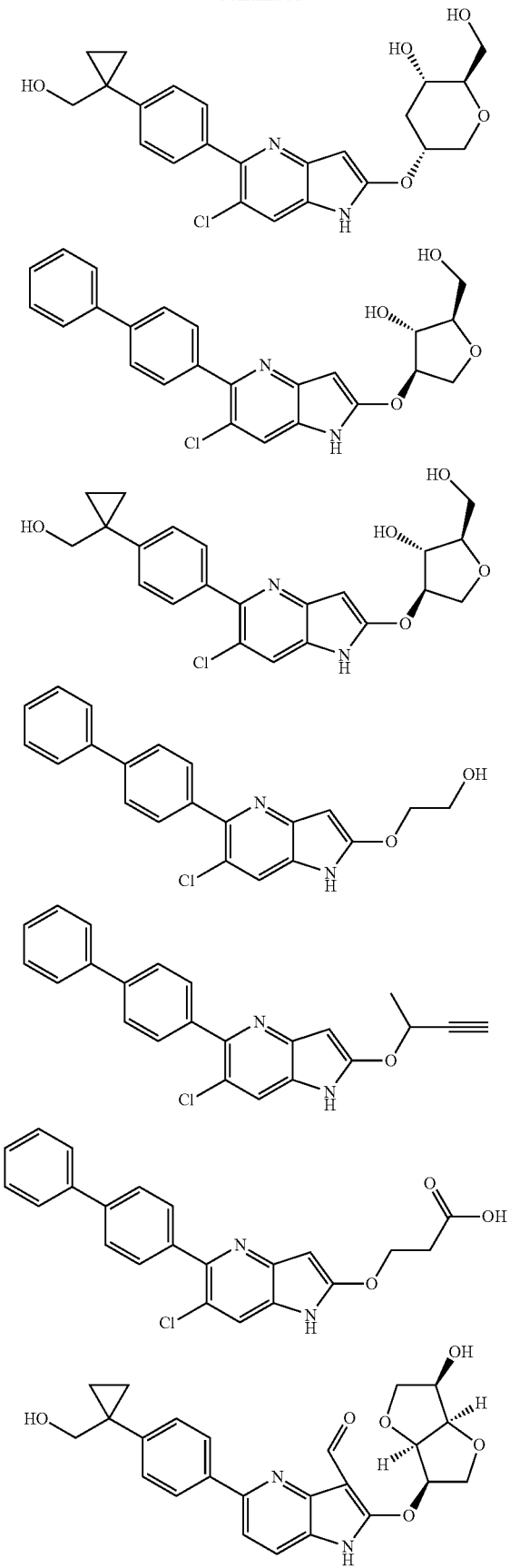

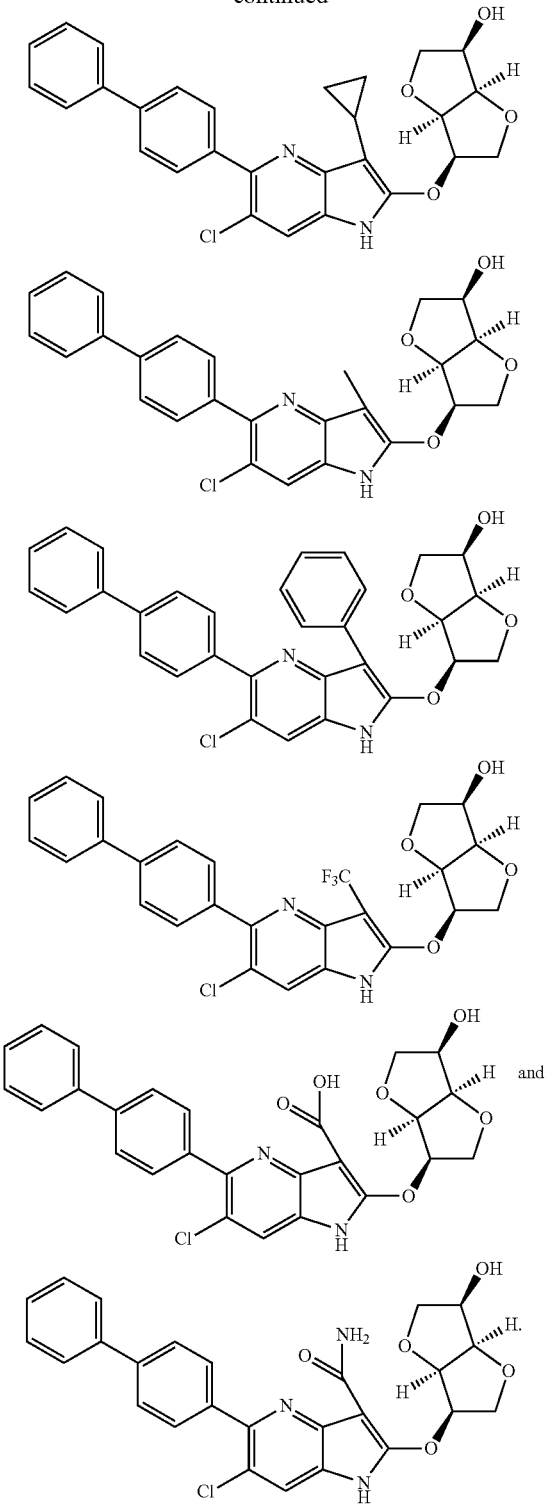

(2B)

The compound according to the above (1B), or its pharmaceutically acceptable salt, wherein $R^1$ is halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl.

(3B)

The compound according to the above (1B) or (2B), or its pharmaceutically acceptable salt, wherein $R^1$ is halogen or cyano.

(4B)

The compound according to the above (1B), or its pharmaceutically acceptable salt, wherein $R^1$ is hydrogen, and $R^3$ is fluoro or cyano.

(5B)

The compound according to the above (1B), or its pharmaceutically acceptable salt, wherein $R^1$ is fluoro and $R^3$ is chloro, or $R^1$ is bromo and $R^3$ is chloro.

(6B)

The compound according to any one of the above (1B) to (5B), or its pharmaceutically acceptable salt, wherein $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(7B)

The compound according to any one of the above (1B) to (6B), or its pharmaceutically acceptable salt, wherein $R^2$ is substituted or unsubstituted aryl.

(8B)

The compound according to the above (7B), or its pharmaceutically acceptable salt, wherein $R^2$ is

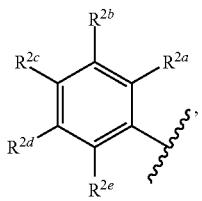

wherein $R^{2a}$, $R^{2b}$, $R^{2d}$, and $R^{2e}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^{2c}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

(9B)

The compound according to the above (8B), or its pharmaceutically acceptable salt, wherein at least one of $R^{2a}$ or $R^{2e}$ is halogen.

(10B)

The compound according to any one of the above (1B) to (9B), or its pharmaceutically acceptable salt, wherein $R^3$ is halogen, cyano, carboxy, substituted or unsubstituted alkyl, substituted or unsubstituted alkylsulfonyl, or substituted or unsubstituted carbamoyl.

(11B)

The compound according to the above (10B), or its pharmaceutically acceptable salt, wherein $R^3$ is fluoro, cyano, or substituted alkyl, wherein the substituent of the substituted alkyl is halogen.

(12B)

The compound according to any one of the above (1B) to (11B), or its pharmaceutically acceptable salt, wherein X is

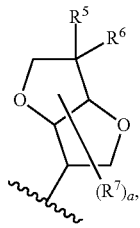

wherein $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^7$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; a is an integer from 0 to 7.

(13B)

The compound according to any one of the above (1B) to (12B), or its pharmaceutically acceptable salt, wherein $R^4$ is hydrogen.

(14B)

The compound according to any one of the above (1B) to (12B) or its pharmaceutically acceptable salt, wherein $R^4$ is halogen.

(15B)

A pharmaceutical composition comprising the compound according to any one of the above (1B) to (14B), or its pharmaceutically acceptable salt.

(16B)

The pharmaceutical composition according to the above (15B), which has an activating effect on adenosine monophosphate-activated protein kinase.

(17B)

The pharmaceutical composition according to the above (15B) or (16B), for the treatment and/or prevention of diabetes.

(18B)

A method for preventing or treating diabetes, comprising administering the compound according to any one of the above (1B) to (16B), or its pharmaceutically acceptable salt.

(19B)

The compound according to any one of the above (1B) to (16B), or its pharmaceutically acceptable salt, for the treatment and/or prevention of diabetes.

(1C)

A compound represented by formula (I):

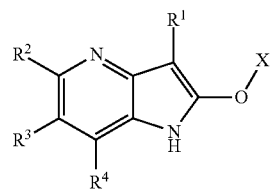

or its pharmaceutically acceptable salt,
wherein
X is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;

$R^2$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^3$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^4$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that the compounds shown below are excluded:

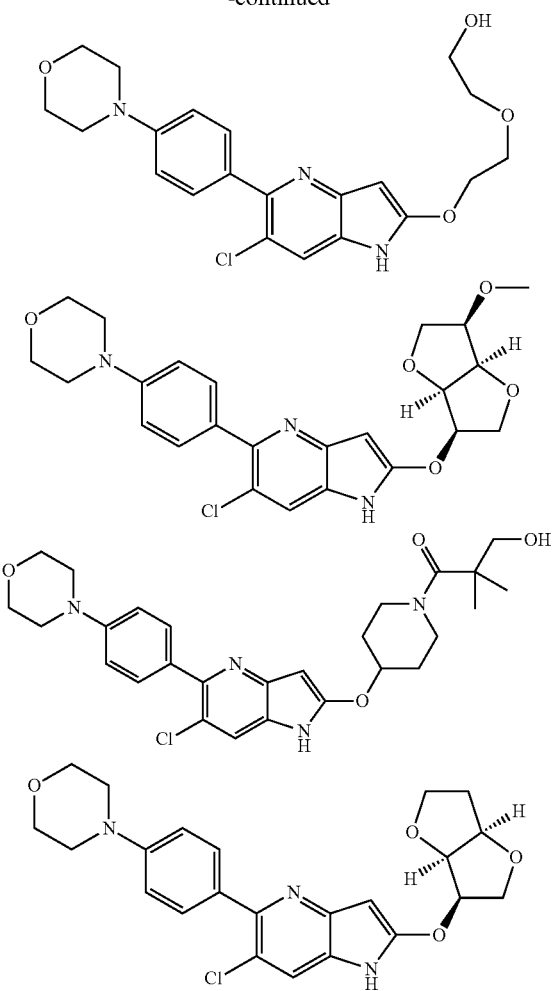

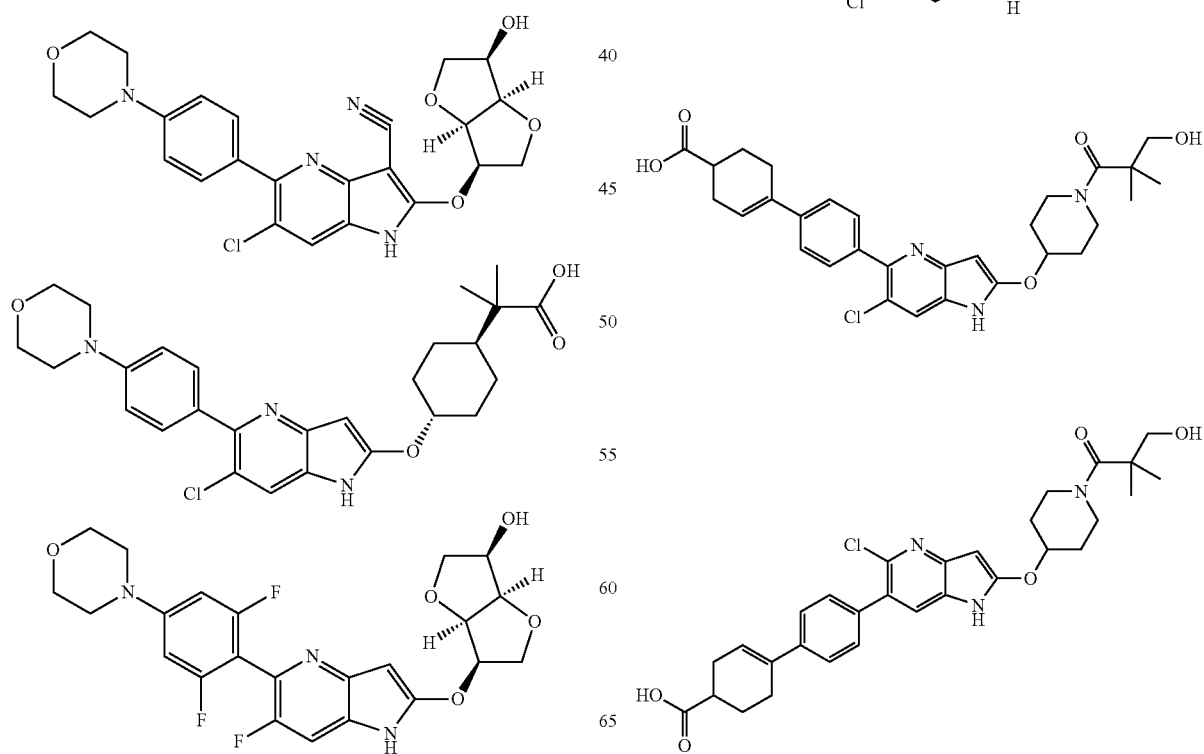

65
-continued
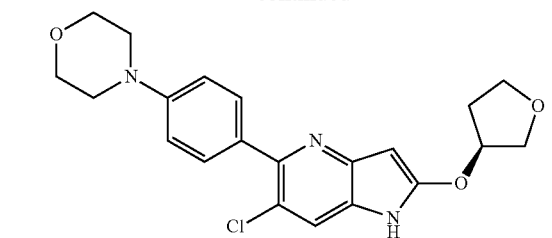
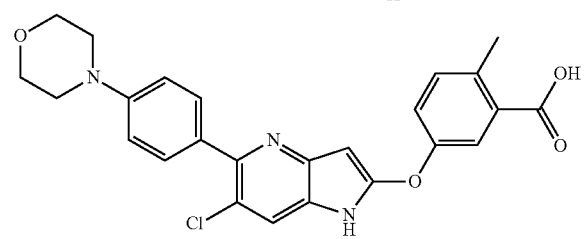
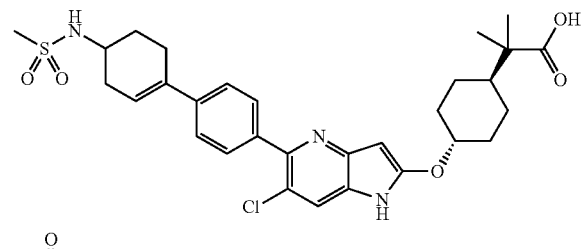
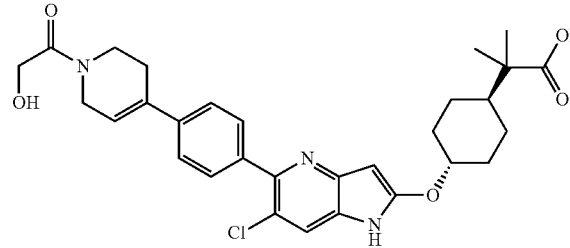
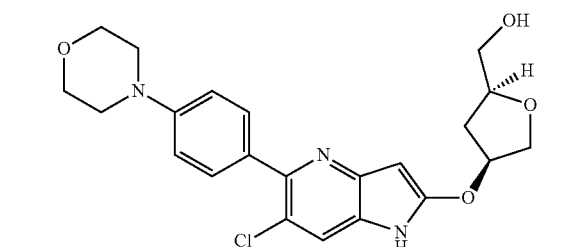
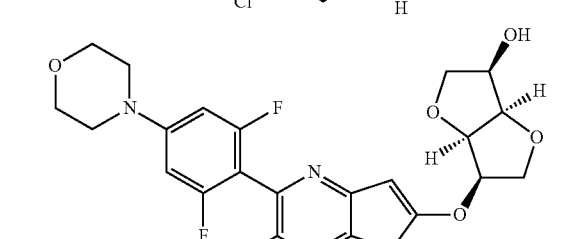
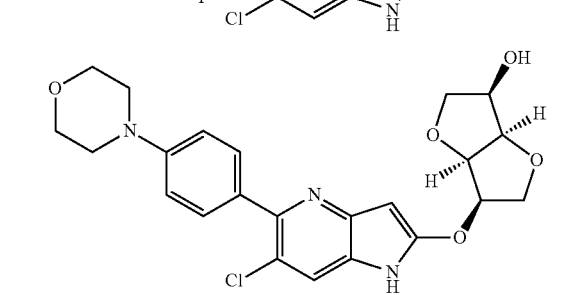
66
-continued
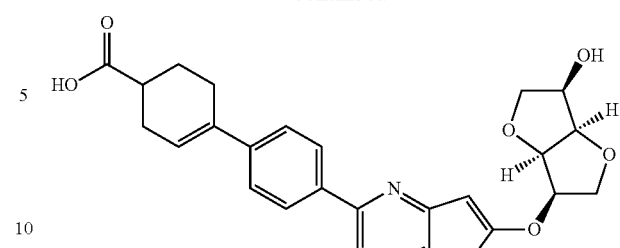
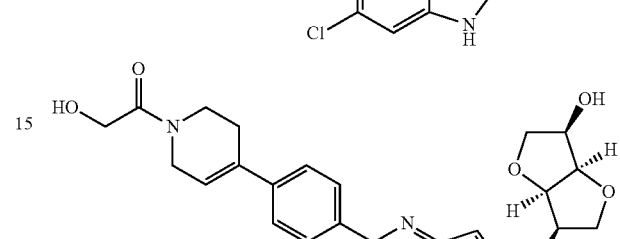
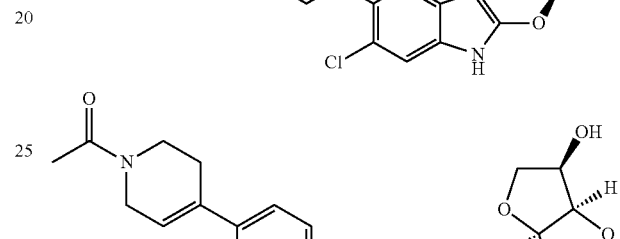
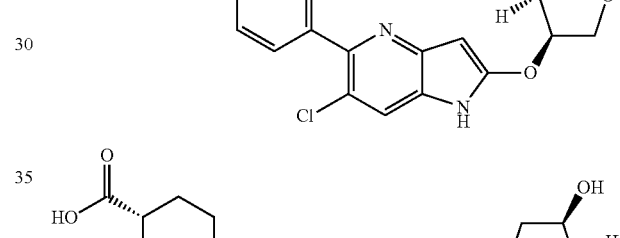
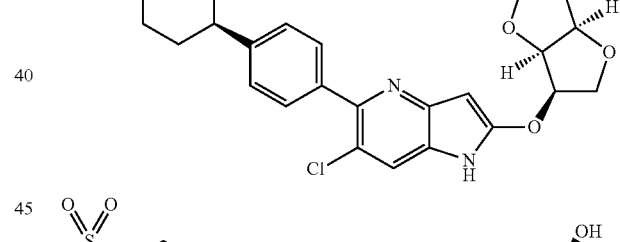
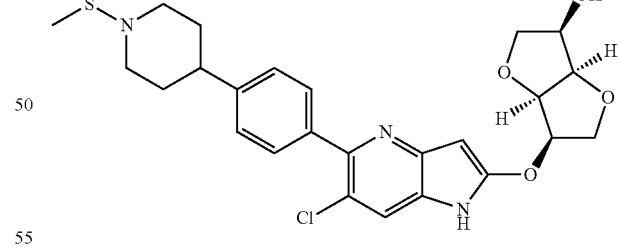
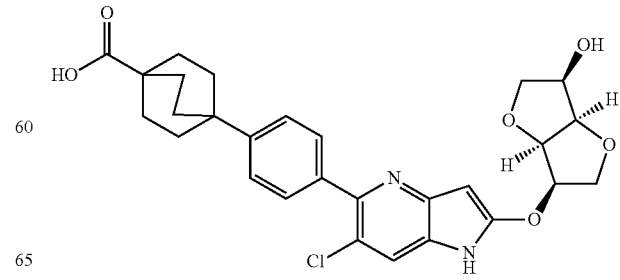

67
-continued
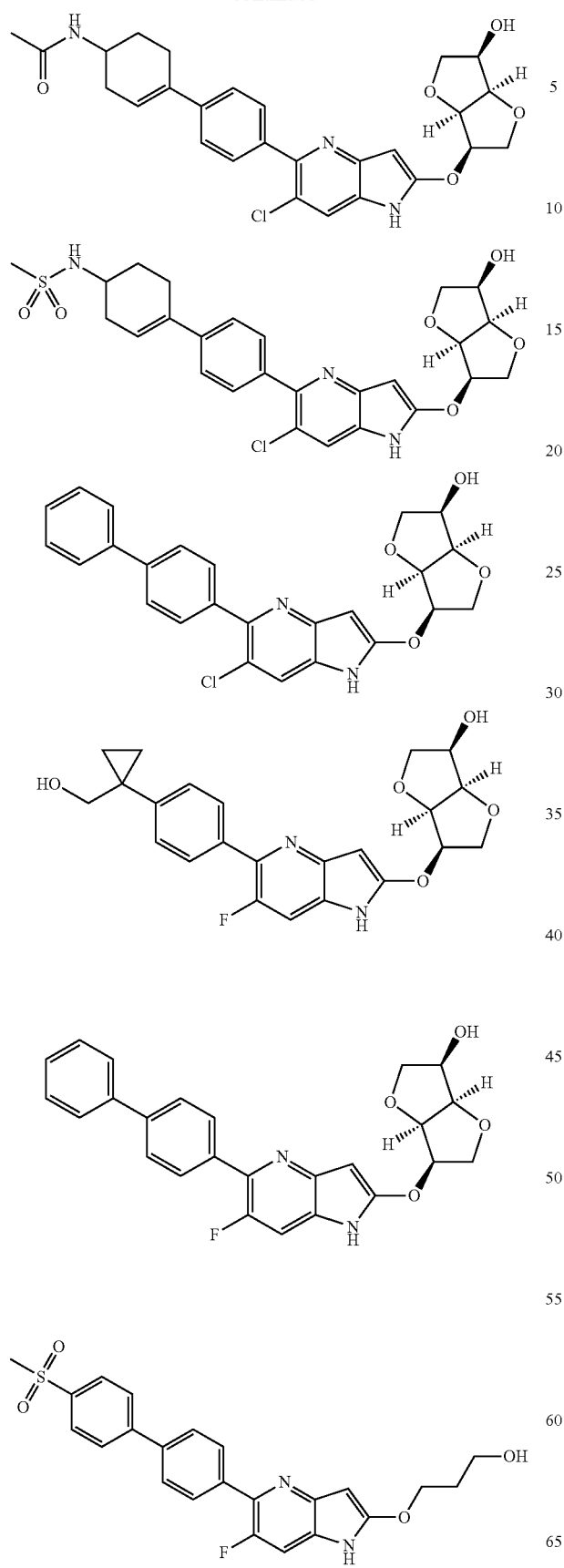
68
-continued
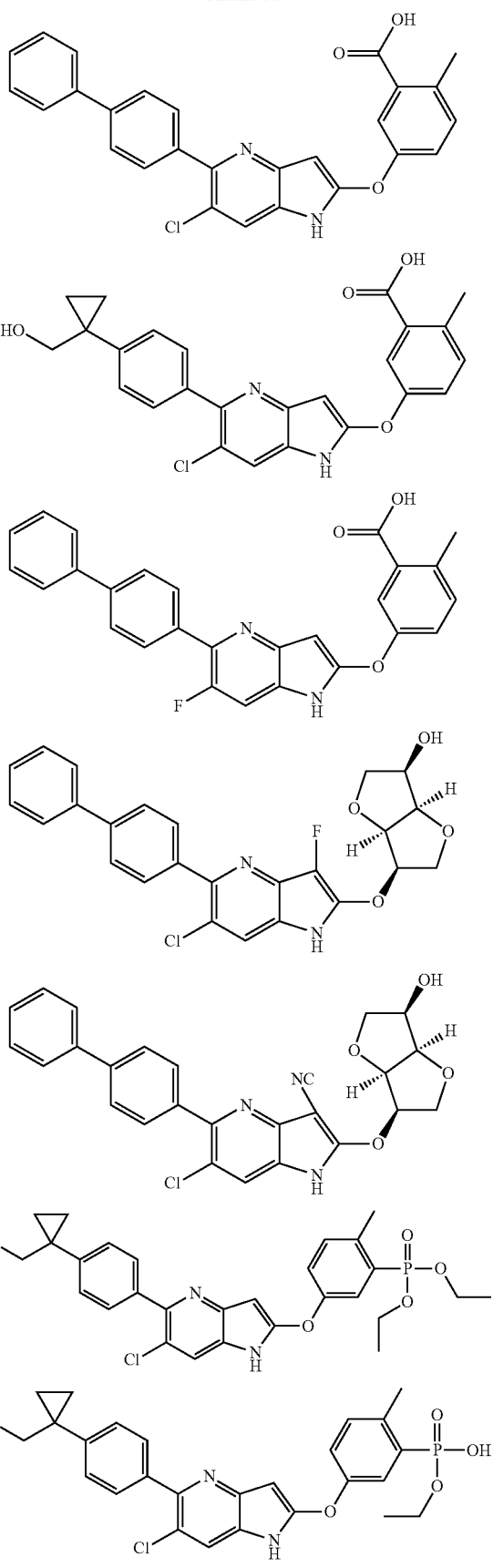

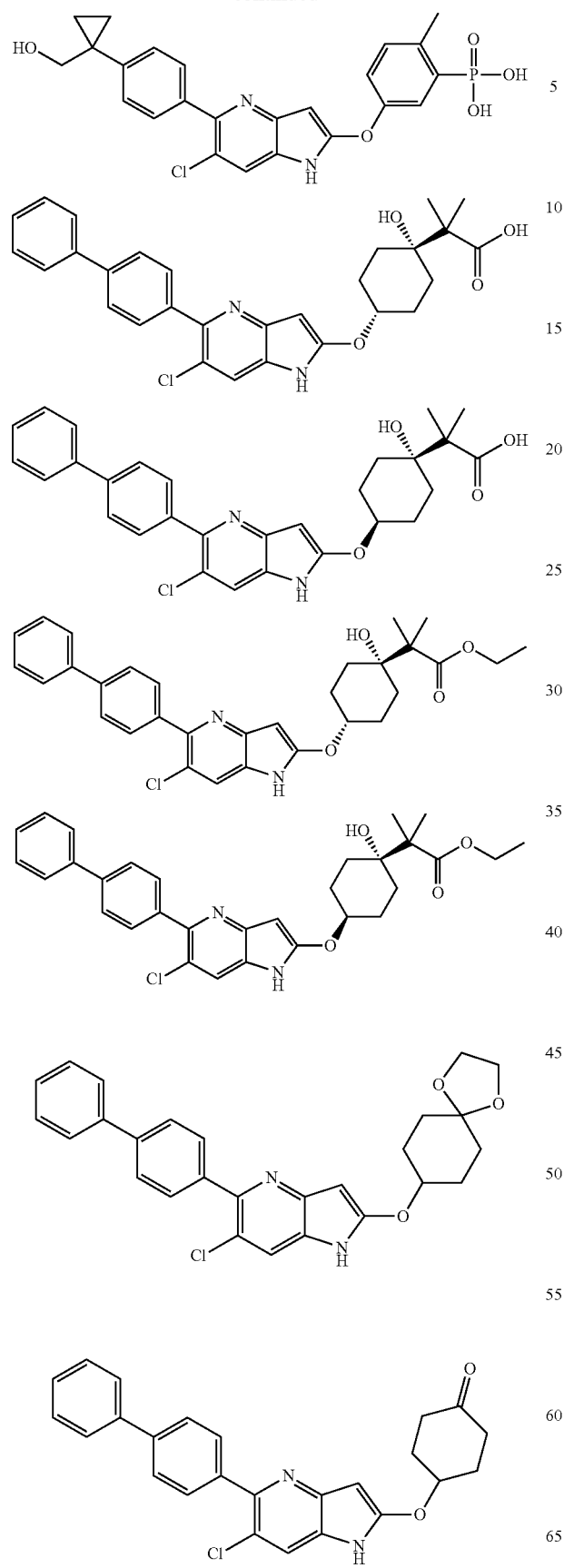
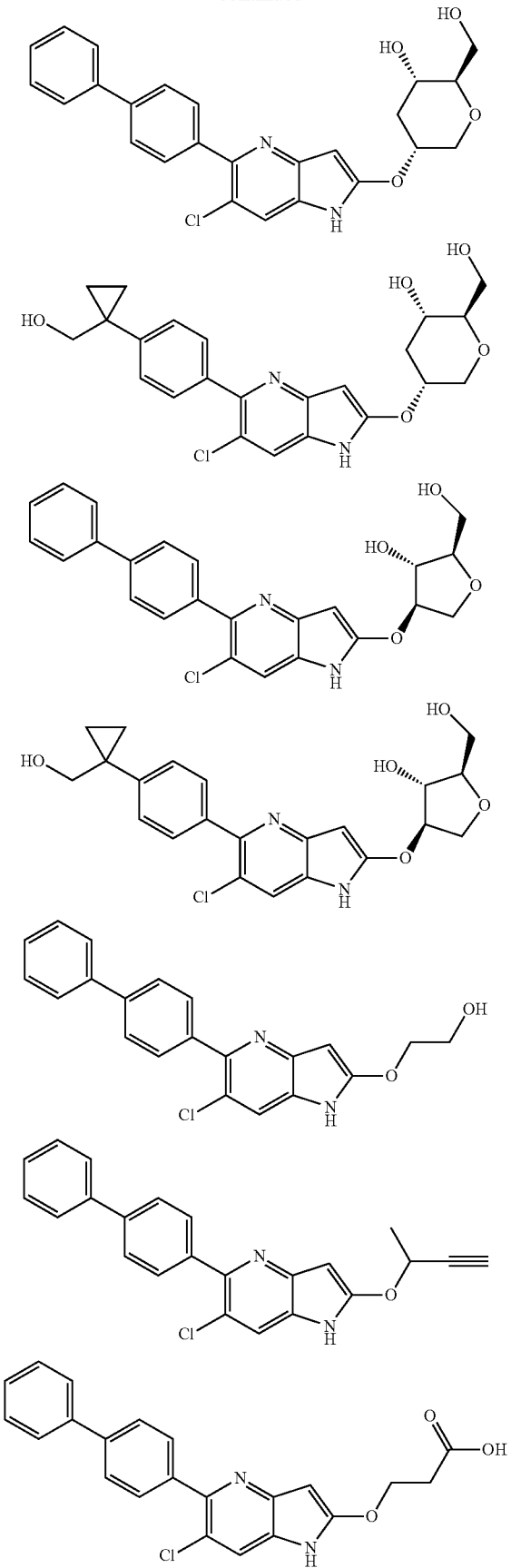

71
-continued
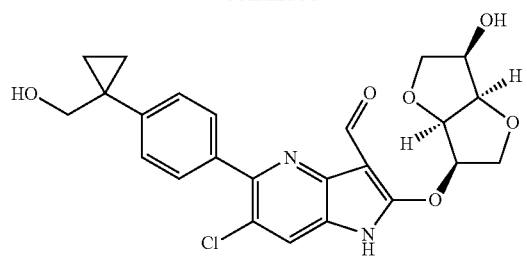
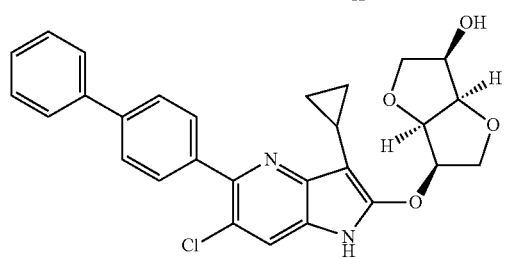
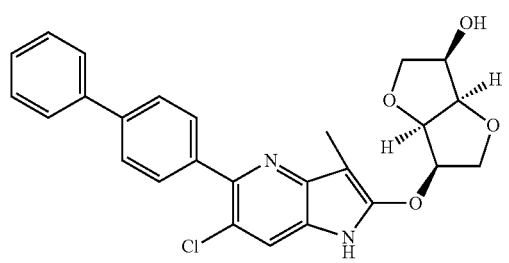
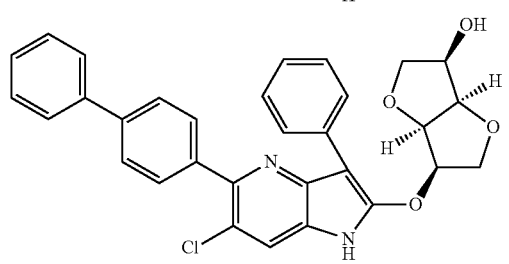
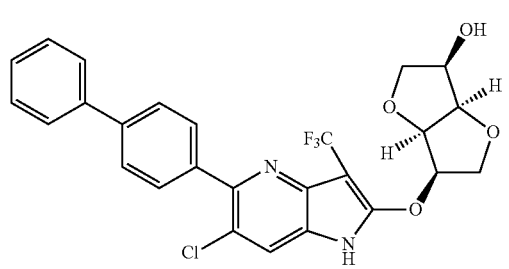
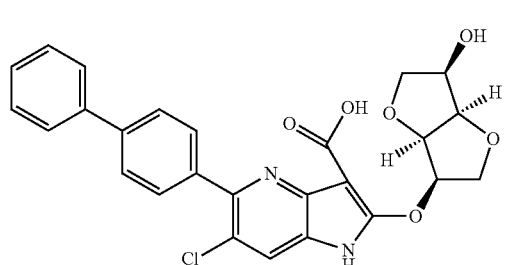
72
-continued
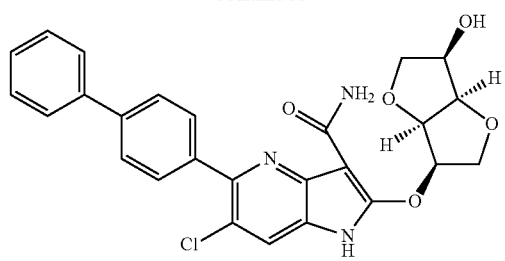
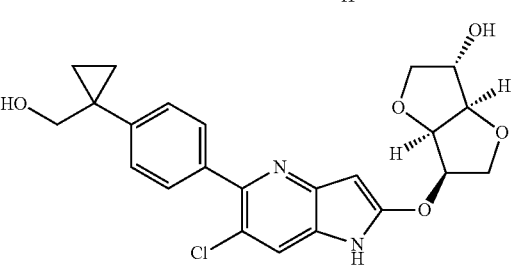
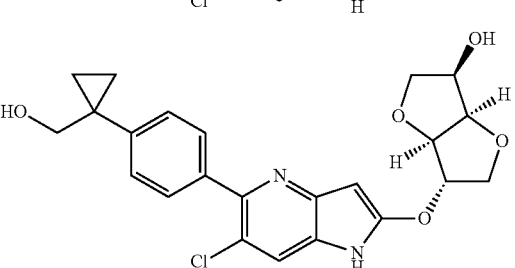
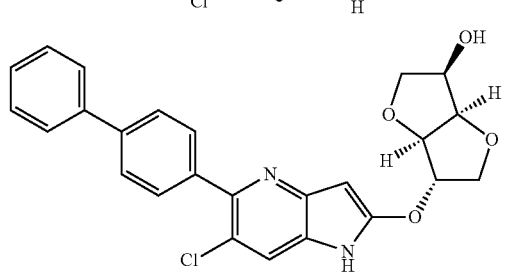
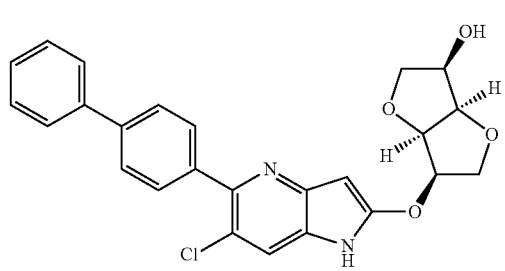
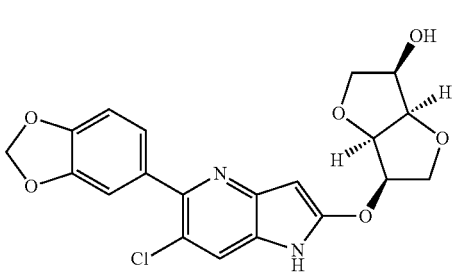

73
-continued
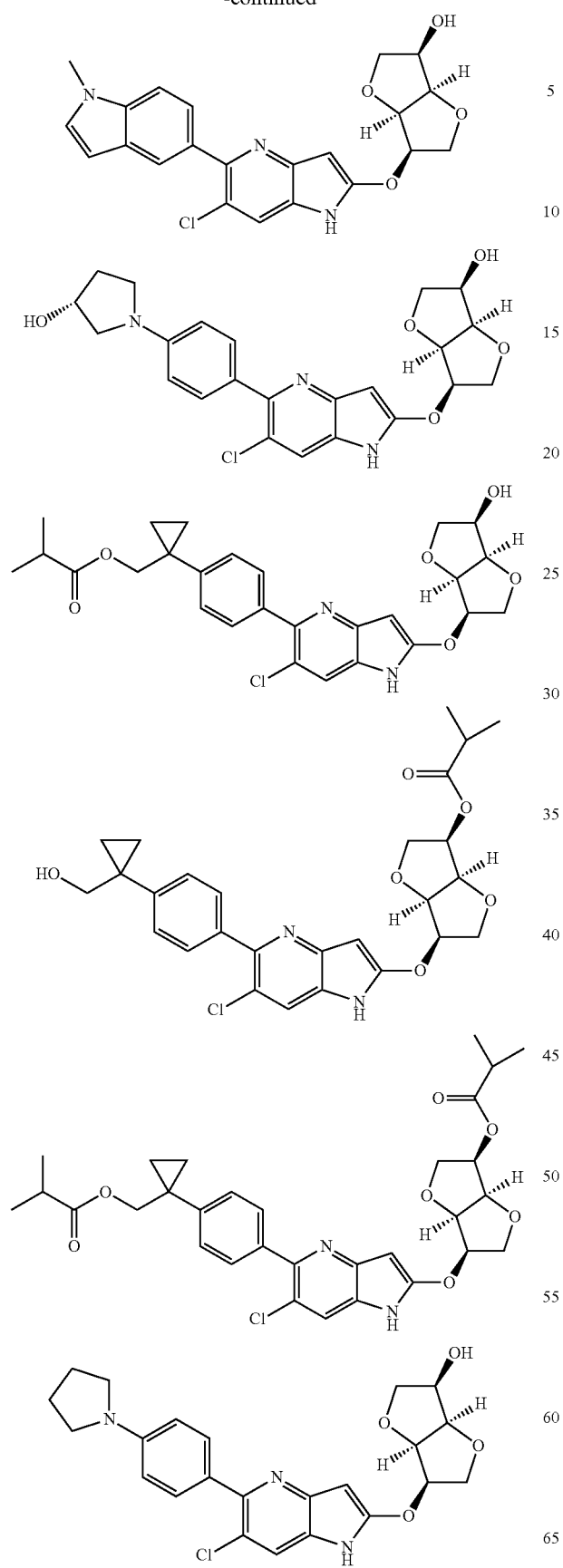
74
-continued
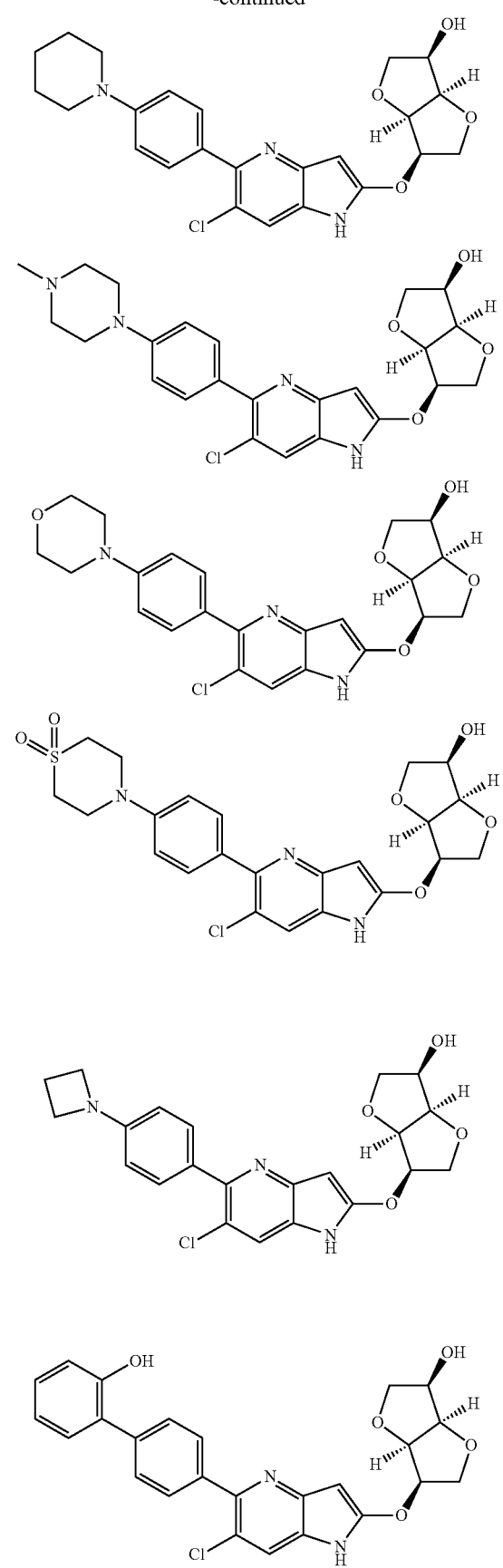

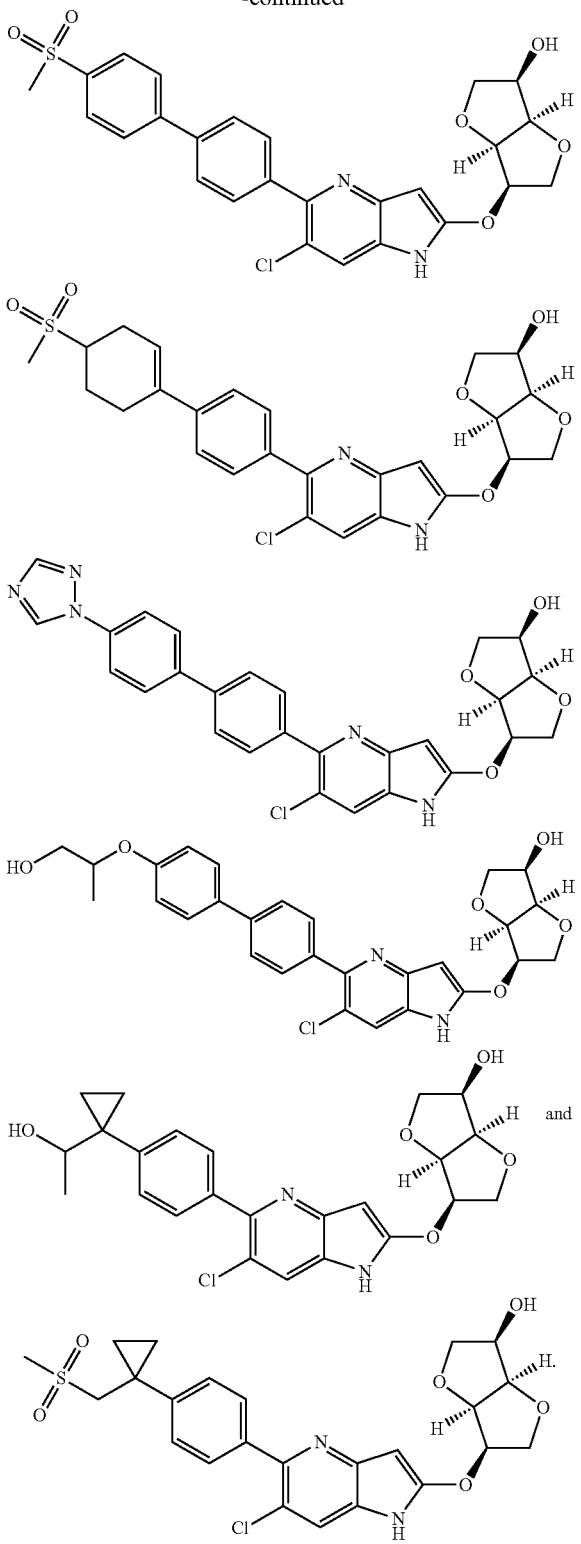

(2C) The compound according to the above (1C), or its pharmaceutically acceptable salt, wherein R¹ is halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl.

(3C) The compound according to the above (1C) or (2C), or its pharmaceutically acceptable salt, wherein R¹ is halogen or cyano.

(4C) The compound according to the above (1C), or its pharmaceutically acceptable salt, wherein R¹ is hydrogen, and R³ is fluoro or cyano.

(5C) The compound according to the above (1C), or its pharmaceutically acceptable salt, wherein R¹ is fluoro and R³ is chloro, or R¹ is bromo and R³ is chloro.

(6C) The compound according to any one of the above (1C) to (5C), or its pharmaceutically acceptable salt, wherein R² is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(7C) The compound according to any one of the above (1C) to (6C), or its pharmaceutically acceptable salt, wherein R² is substituted or unsubstituted aryl.

(8C) The compound according to the above (7C), or its pharmaceutically acceptable salt, wherein R² is

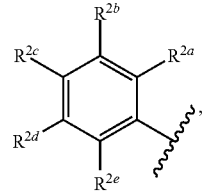

wherein $R^{2a}$, $R^{2b}$, $R^{2d}$, and $R^{2e}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^{2c}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

(9C) The compound according to the above (8C), or its pharmaceutically acceptable salt, wherein at least one of $R^{2a}$ or $R^{2e}$ is halogen.

(10C) The compound according to the above (6C), or its pharmaceutically acceptable salt, wherein R² is substituted aryl, substituted heteroaryl, substituted cycloalkyl, substituted cycloalkenyl, or substituted heterocyclyl.

(11C) The compound according to the above (10C), or its pharmaceutically acceptable salt, wherein R² is

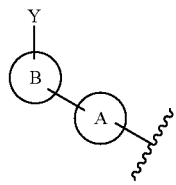

wherein
ring A is substituted aryl, substituted heteroaryl, substituted cycloalkyl, substituted cycloalkenyl, or substituted heterocyclyl, wherein the ring A may further have (a) substituent(s) at any position(s) other than the position of substitution with ring B;
ring B is substituted aryl, substituted heteroaryl, substituted cycloalkyl, substituted cycloalkenyl, or substituted heterocyclyl, wherein the ring B may further have (a) substituent(s) at any position(s) other than the positions of substitution with Y and the ring A;
Y is $R^S R^{S'}(O=)S=N-$, $R^S R^{S'}(O=)S=R^S R^{S'}(O=)S=N-C(=O)-$, $(R^N)N=S(=O)(R^S)-$, $(R^N)N=S(=O)(R^S)-R^{2f}-$, $R^S R^{S'}(R^{N'}-N=)S=N-$, or $((R^N)N=)_2 S(R^S)-$;
$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;
$R^S$ and $R^{S'}$ bound to the same sulfur atom may form a substituted or unsubstituted ring together with the sulfur atom;
$R^{2f}$ is substituted or unsubstituted alkylene;
$R^N$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;
$R^N$ together with the adjacent nitrogen atom may form a substituted or unsubstituted ring when Y is $((R^N)N=)_2 S(R^S)-$;
$R^{N'}$ is hydrogen, cyano, substituted or unsubstituted alkyl, substituted or unsubstituted cycloalkyl, substituted or unsubstituted aryl, or substituted or unsubstituted heteroaryl.

(12C)
The compound according to the above (11C), or its pharmaceutically acceptable salt, wherein the ring A is substituted aryl, or substituted heteroaryl.

(13C)
The compound according to the above (11C) or (12C), or its pharmaceutically acceptable salt, wherein the ring B is substituted aryl, or substituted heteroaryl.

(14C)
The compound according to any one of the above (10C) to (13C), or its pharmaceutically acceptable salt, wherein Y is $R^S R^{S'}(O=)S=N-$ or $(R^N)N=S(=O)(R^S)-$.

(15C)
The compound according to the above (10C), or its pharmaceutically acceptable salt, wherein $R^2$ is

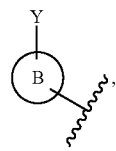

wherein
ring B is substituted aryl, substituted heteroaryl, substituted cycloalkyl, substituted cycloalkenyl, or substituted heterocyclyl, wherein the ring B may further have (a) substituent(s) other than Y;
Y is $R^S R^{S'}(O=)S=N-$, $R^S R^{S'}(O=)S=R^S R^{S'}(O=)S=N-C(=O)-$, $(R^N)N=S(=O)(R^S)-$, $(R^N)N=S(=O)(R^S)-R^{2f}-$, $R^S R^{S'}(R^{N'}-N=)S=N-$, or $((R^N)N=)_2 S(R^S)-$;
$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;
$R^S$ and $R^{S'}$ bound to the same sulfur atom may form a substituted or unsubstituted ring together with the sulfur atom;
$R^{2f}$ is substituted or unsubstituted alkylene;
$R^N$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;
$R^N$ together with the adjacent nitrogen atom may form a substituted or unsubstituted ring when Y is $((R^N)N=)_2 S(R^S)-$;
$R^{N'}$ is hydrogen, cyano, substituted or unsubstituted alkyl, substituted or unsubstituted cycloalkyl, substituted or unsubstituted aryl, or substituted or unsubstituted heteroaryl.

(16C)
The compound according to the above (15C), or its pharmaceutically acceptable salt, wherein the ring B is substituted aryl, or substituted heteroaryl.

(17C)
The compound according to any one of the above (15C) to (16C), or its pharmaceutically acceptable salt, wherein Y is $R^S R^{S'}(O=)S=N-$ or $(R^N)N=S(=O)(R^S)-$.

(18C)
The compound according to any one of the above (1C) to (17C), or its pharmaceutically acceptable salt, wherein $R^3$ is halogen, cyano, carboxy, substituted or unsubstituted alkyl, substituted or unsubstituted alkylsulfonyl, or substituted or unsubstituted carbamoyl.

(19C)
The compound according to the above (18C), or its pharmaceutically acceptable salt, wherein $R^3$ is fluoro, cyano, or substituted alkyl, wherein the substituent of the substituted alkyl is halogen.

(20C)
The compound according to any one of the above (1C) to (19C), or its pharmaceutically acceptable salt, wherein X is

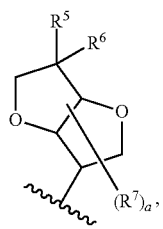

wherein $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^7$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; a is an integer from 0 to 7.
(21C)
The compound according to any one of the above (1C) to (20C), or its pharmaceutically acceptable salt, wherein $R^4$ is hydrogen.
(22C)
The compound according to any one of the above (1C) to (20C), or its pharmaceutically acceptable salt, wherein $R^4$ is halogen.
(23C)
A pharmaceutical composition comprising the compound according to any one of the above (1C) to (22C), or its pharmaceutically acceptable salt.
(24C)
The pharmaceutical composition according to the above (23C), which has an activating effect on adenosine monophosphate-activated protein kinase.
(25C)
The pharmaceutical composition according to the above (23C) or (24C), for the treatment and/or prevention of diabetes.
(26C)
A method for preventing or treating diabetes, comprising administering the compound according to any one of the above (1C) to (24C), or its pharmaceutically acceptable salt.
(27C)
The compound according to any one of the above (1C) to (24C), or its pharmaceutically acceptable salt, for the treatment and/or prevention of diabetes.

Effect of the Invention

The compound of the present invention has an AMPK activating effect, and thus a pharmaceutical composition comprising a compound of the present invention is very useful as a medicinal product, particularly, a medicine for treating and/or preventing type II diabetes, hyperglycemia, metabolic syndrome, obesity, hypercholesterolemia and/or hypertension. Further, the compound of the present invention is a compound which has usefulness as a medicine. The usefulness as a medicine herein comprises good metabolic stability, slight induction of a drug-metabolizing enzyme, slight inhibition of drug-metabolizing enzymes which metabolize other drugs, high oral absorption, low clearance, a sufficiently long half-life period to express the efficacy of a medicine, a high enzyme activity, a high maximal activation rate, a low protein binding rate, high penetration into target tissue, high solubility, high safety, an insulin resistance improving effect based on an energy consumption increase, the effect of decreasing hemoglobin $A_{1C}$ (HbA1c), the effect of improving fatty liver or the like.

MODE FOR CARRYING OUT THE INVENTION

Each term used in this description will be described below. In this description, even when each term is used individually or used with other terms, the term has the same meaning.

"Halogen" includes fluorine, chlorine, bromine, and iodine.

"Alkyl" means a C1 to C10 straight or branched alkyl group, and examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl, and the like. Preferable is a C1 to C6 or C1 to C4 alkyl, and examples thereof include methyl, ethyl, n-propyl, isopropyl, n-butyl, isobutyl, sec-butyl, tert-butyl, n-pentyl, isopentyl, neopentyl, n-hexyl, and isohexyl.

"Alkenyl" means a C2 to C8 straight or branched alkenyl having one or more double bond(s) in the above "alkyl", and examples thereof include vinyl, 1-propenyl, 2-propenyl, 1-butenyl, 2-butenyl, 3-butenyl, 1,3-butadienyl, 3-methyl-2-butenyl, and the like.

"Alkynyl" means a C2 to C8 straight or branched alkynyl having one or more triple bond(s) in the above "alkyl", and examples thereof include ethynyl, propynyl, butynyl, and the like. Furthermore, an "alkynyl" may have a double bond.

"Cycloalkyl" means a C3 to C15 cyclic saturated hydrocarbon group, and examples thereof include cyclopropyl, cyclobutyl, cyclopentyl, cyclohexyl, cycloheptyl, cyclooctyl, a bridged cyclic hydrocarbon group, a spiro hydrocarbon group, and the like. Preferable is cyclopropyl, cyclobutyl, cyclopentyl, cyclohexyl, or a bridged cyclic hydrocarbon group.

A "bridged cyclic hydrocarbon group" includes a group which is derived by removing one hydrogen from a C5 to C8 aliphatic cycle which consists of two or more rings that share two or more atoms. Specific examples include bicyclo[2.1.0]pentyl, bicyclo[2.2.1]heptyl, bicyclo[2.2.2]octyl, bicyclo[3.2.1]octyl, tricyclo[2.2.1.0]heptyl, or the like.

A "spiro hydrocarbon group" includes a group which is derived by removing one hydrogen from a cycle which consists of two hydrocarbon rings that share one carbon atom. Specific examples include spiro[3.4]octyl, or the like.

"Cycloalkenyl" means a C3 to C10 cyclic unsaturated aliphatic hydrocarbon group, and examples thereof include cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl, 3-cyclopenten-1-yl), cyclohexenyl (e.g.: 1-cyclohexen-1-yl, 2-cyclohexen-1-yl, 3-cyclohexen-1-yl), cycloheptenyl (e.g.: 1-cycloheptenyl), cyclooctenyl (e.g.: 1-cyclooctenyl), and the like. Preferable is cyclopropenyl, cyclobutenyl, cyclopentenyl, cyclohexenyl. Cycloalkenyls also include a bridged cyclic hydrocarbon group and a spiro hydrocarbon group which both have an unsaturated bond in the ring.

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, etc.). Preferable is phenyl or naphthyl (1-naphthyl, 2-naphthyl).

"Heteroaryl" means a monocyclic aromatic heterocyclic group and a fused aromatic heterocyclic group.

A "monocyclic aromatic heterocyclic group" means a group which is derived from a 5 to 8-membered aromatic ring which has one or more same or different heteroatoms optionally selected from oxygen, sulfur, and nitrogen atoms in the ring, which group may have a bond to a substituent at any substitutable position.

A "fused aromatic heterocyclic group" means a group in which a 5 to 8-membered aromatic ring which has one or more same or different heteroatoms optionally selected from oxygen, sulfur, and nitrogen atoms in the ring is fused with one to four 5 to 8-membered aromatic carbocyclic rings or another 5 to 8-membered aromatic hetero ring, which group may have a bond to a substituent at any substitutable position.

Examples of a "heteroaryl" include furyl (e.g.: 2-furyl, 3-furyl), thienyl (e.g.: 2-thienyl, 3-thienyl), pyrrolyl (e.g.: 1-pyrrolyl, 2-pyrrolyl, 3-pyrrolyl), imidazolyl (e.g.: 1-imidazolyl, 2-imidazolyl, 4-imidazolyl), pyrazolyl (e.g.: 1-pyrazolyl, 3-pyrazolyl, 4-pyrazolyl), triazolyl (e.g.: 1,2,4-triazol-1-yl, 1,2,4-triazol-3-yl, 1,2,4-triazol-4-yl), tetrazolyl (e.g.: 1-tetrazolyl, 2-tetrazolyl, 5-tetrazolyl), oxazolyl (e.g.: 2-oxazolyl, 4-oxazolyl, 5-oxazolyl), isoxazolyl (e.g.: 3-isoxazolyl, 4-isoxazolyl, 5-isoxazolyl), thiazolyl (e.g.: 2-thiazolyl, 4-thiazolyl, 5-thiazolyl), thiadiazolyl, isothiazolyl (e.g.: 3-isothiazolyl, 4-isothiazolyl, 5-isothiazolyl), pyridyl (e.g.: 2-pyridyl, 3-pyridyl, 4-pyridyl), pyridazinyl (e.g.: 3-pyridazinyl, 4-pyridazinyl), pyrimidinyl (e.g.: 2-pyrimidinyl, 4-pyrimidinyl, 5-pyrimidinyl), furazanyl (e.g.: 3-furazanyl), pyrazinyl (e.g.: 2-pyrazinyl), oxadiazolyl (e.g.: 1,3,4-oxadiazol-2-yl), benzofuryl (e.g.: 2-benzo[b]furyl, 3-benzo[b]furyl, 4-benzo[b]furyl, 5-benzo[b]furyl, 6-benzo[b]furyl, 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g.: 1-benzimidazolyl, 2-benzimidazolyl, 4-benzimidazolyl, 5-benzimidazolyl), dibenzofuryl, benzoxazolyl, benzothiazolyl, quinoxalinyl (e.g.: 2-quinoxalinyl, 5-quinoxalinyl, 6-quinoxalinyl), cinnolinyl (e.g.: 3-cinnolinyl, 4-cinnolinyl, 5-cinnolinyl, 6-cinnolinyl, 7-cinnolinyl, 8-cinnolinyl), quinazolinyl (e.g.: 2-quinazolinyl, 4-quinazolinyl, 5-quinazolinyl, 6-quinazolinyl, 7-quinazolinyl, 8-quinazolinyl), quinolyl (e.g.: 2-quinolyl, 3-quinolyl, 4-quinolyl, 5-quinolyl, 6-quinolyl, 7-quinolyl, 8-quinolyl), phthalazinyl (e.g.: 1-phthalazinyl, 5-phthalazinyl, 6-phthalazinyl), isoquinolyl (e.g.: 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g.: 2-pteridinyl, 4-pteridinyl, 6-pteridinyl, 7-pteridinyl), carbazolyl, phenanthridinyl, acridinyl (e.g.: 1-acridinyl, 2-acridinyl, 3-acridinyl, 4-acridinyl, 9-acridinyl), indolyl (e.g.: 1-indolyl, 2-indolyl, 3-indolyl, 4-indolyl, 5-indolyl, 6-indolyl, 7-indolyl), isoindolyl, phenazinyl (e.g.: 1-phenazinyl, 2-phenazinyl), phenothiazinyl (e.g.: 1-phenothiazinyl, 2-phenothiazinyl, 3-phenothiazinyl, 4-phenothiazinyl), or the like.

"Heterocyclyl" means a non-aromatic heterocyclic group, which may have a bond for substituent at any substitutable position of a ring which has at least one or more nitrogen, oxygen, or sulfur atoms in the ring, or a ring in which such ring is fused with a cycloalkane (preferably 5 to 6-membered), a benzene ring and/or a ring which has at least one or more nitrogen, oxygen, or sulfur atoms in the ring. A "non-aromatic heterocyclic group" can be saturated or unsaturated as long as it is non-aromatic. Preferable is a 5- to 8-membered ring. Examples include 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, tetrahydrofuranyl, 1,2,3,4-tetrahydroisoquinolinyl, 1,2,3,4-tetrahydroquinolinyl, 1,3-dihydro-2H-isoindol-5-yl, the following group, or the like

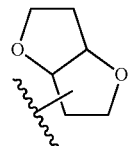

Further, examples of a "heterocyclyl" group also include a bridged group or a spiro ring forming group shown below.

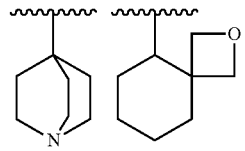

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl. The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl", and the heterocyclyl part of "heterocyclylcarbonyl" mean the above "alkyl", the above "alkenyl", the above "cycloalkyl", the above "cycloalkenyl", the above "aryl", the above "heteroaryl" and the above "heterocyclyl", respectively.

The alkyl parts of "alkylthio", "alkylsulfinyl", "alkylsulfonyl", "alkyloxycarbonyl", and "alkyloxy" mean the above "alkyl".

The aryl parts of "aryloxy", "arylthio", and "arylsulfonyl" mean the above "aryl".

The heteroaryl parts of "heteroaryloxy", "heteroarylthio", and "heteroarylsulfonyl" mean the above "heteroaryl".

The cycloalkyl parts of "cycloalkyloxy", "cycloalkylthio", and "cycloalkylsulfonyl" mean the above "cycloalkyl".

The cycloalkenyl parts of "cycloalkenyloxy", "cycloalkenylthio", and "cycloalkenylsulfonyl" mean the above "cycloalkenyl".

The heterocyclyl parts of "heterocyclyloxy", "heterocyclylthio", and "heterocyclylsulfonyl" mean the above "heterocyclyl".

Examples of substituents of a "substituted alkyl", a "substituted alkenyl", a "substituted alkynyl", a "substituted aryl", a "substituted heteroaryl", a "substituted cycloalkyl, a "substituted cycloalkenyl", a "substituted heterocyclyl", a "substituted acyl", a "substituted carbamoyl", a "substituted alkylthio", a "substituted alkylsulfinyl", a "substituted alkylsulfonyl", a "substituted alkyloxycarbonyl", a "substituted alkyloxy", a "substituted aryloxy, a "substituted heteroaryloxy", a "substituted cycloalkyloxy", a "substituted cycloalkenyloxy", a "substituted heterocyclyloxy", a "substituted arylthio", a "substituted heteroarylthio", a "substituted cycloalkylthio", a "substituted cycloalkenylthio", a "substituted heterocyclylthio", a "substituted arylsulfonyl", a "substituted heteroarylsulfonyl", a "substituted cycloalkylsulfonyl", a "substituted cycloalkenylsulfonyl", a "substituted heterocyclylsulfonyl", a "substituted sulfamoyl", a "substituted amino", a "ring formed by $R^S$ and $R^{St}$ which are bound to the same sulfur atom, together with the sulfur atom", or a "ring which $R^N$ together with the adjacent nitrogen atom forms in the case of $((R^N)N=)_2S(R^S)$—" include groups selected from the group consisting of halogen; hydroxy; carboxy; nitro; cyano;

substituted or unsubstituted alkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methyl, ethyl, isopropyl, tert-butyl, $CF_3$);

substituted or unsubstituted alkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, or substituted or unsubstituted acylamino (when substituted, substituents include hydroxy); e.g., vinyl);

substituted or unsubstituted alkynyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., ethynyl);

substituted or unsubstituted aryl (when substituted, substituents include halogen, hydroxy, carboxy, nitro, cyano, alkyl, alkenyl, alkynyl, aryl, cycloalkyl, cycloalkenyl, substituted or unsubstituted heteroaryl (when substituted, substituents include hydroxyalkyl), heterocyclyl, substituted or unsubstituted carbamoyl (when substituted, substituents include $R^SR^{St}(O=)S=$), sulfamoyl, substituted or unsubstituted amino (when substituted, substituents include alkyloxycarbonyl, or carbamoyl), substituted or unsubstituted alkyloxy (when substituted, substituents include dialkylamino), alkylsulfonyl, alkylaminosulfonyl, $R^SR^{St}(O=)S=N-$, $R^SR^{St}(O=)S=N-R^{2f}-$, $R^SR^{St}(O=)S=N-C(=O)-$, $(R^N)N=S(=O)(R^S)-$, $(R^N)N=S(=O)(R^S)-R^{2f}-$, $R^SR^{St}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$; e.g., phenyl, naphthyl);

substituted or unsubstituted cycloalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, acyl, $R^SR^{St}(O=)S=N-$, $R^SR^{St}(O=)S=N-R^{2f}-$, $R^SR^{St}(O=)S=N-C(=O)-$, $(R^N)N=S(=O)(R^S)-$, $(R^N)N=S(=O)(R^S)-R^{2f}-$, $R^SR^{St}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$; e.g., cyclopropyl, cyclobutyl);

substituted or unsubstituted cycloalkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, substituted or unsubstituted carbamoyl (when substituted, substituents include $R^SR^{St}(O=)S=$), sulfamoyl, amino, acylamino, alkylsulfonylamino, alkyloxycarbonylamino, $R^SR^{St}(O=)S=N-$, $R^SR^{St}(O=)S=N-R^{2f}-$, $R^SR^{St}(O=)S=N-C(=O)-$, $(R^N)N=S(=O)(R^S)-$, $(R^N)N=S(=O)(R^S)-R^{2f}-$, $R^SR^{St}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$; e.g., cyclopropenyl);

substituted or unsubstituted heteroaryl (when substituted, substituents include halogen, hydroxy, carboxy, nitro, cyano, substituted or unsubstituted alkyl (when substituted, substituents include hydroxy), alkenyl, alkynyl, aryl, cycloalkyl, cycloalkenyl, heteroaryl, heterocyclyl, carbamoyl, sulfamoyl, substituted or unsubstituted amino (when substituted, substituents include alkyl, acyl, alkylsulfonyl, alkylaminosulfonyl, or alkyloxycarbonyl), alkylsulfonyl, $R^SR^{St}(O=)S=N-$, $R^SR^{St}(O=)S=N-R^{2f}-$, $R^SR^{St}(O=)S=N-C(=O)-$, $(R^N)N=S(=O)(R^S)-$, $(R^N)N=S(=O)(R^S)-R^{2f}-$, $R^SR^{St}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$);

substituted or unsubstituted heterocyclyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, substituted or unsubstituted acyl (when substituted, substituents include hydroxy), aryloxy, alkylsulfonyl, alkyloxycarbonylamino, $R^SR^{St}(O=)S=N-$, $R^SR^{St}(O=)S=R^SR^{St}(O=)S=N-C(=O)-$, $(R^N)N=S(=O)(R^S)-$, $(R^N)N=S(=O)(R^S)-R^{2f}-$, $R^SR^{St}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$; e.g., morpholinyl, piperidyl, pyrrolidinyl);

substituted or unsubstituted alkyloxy (when substituted, substituents include halogen, hydroxy, carboxy, nitro, cyano, alkyl, alkenyl, alkynyl, aryl, cycloalkyl, cycloalkenyl, substituted or unsubstituted heteroaryl (when substituted, substituents include alkyl), substituted or unsubstituted heterocyclyl (when substituted, substituents include alkyl), carbamoyl, sulfamoyl, substituted or unsubstituted amino (when substituted, substituents include substituted or unsubstituted acyl (when substituted, substituents include hydroxy)), alkyloxy, alkylsulfonyl, $R^SR^{St}(O=)S=N-$, $R^SR^{St}(O=)S=N-R^{2f}-$, $R^SR^{St}(O=)S=N-C(=(R^N)N=S(=O)(R^S))-$, $(R^N)N=S(=O)(R^S)-R^{2f}-$, $R^SR^{St}(R^{N'}-N=)S=N-$, $((R^N)N=)_2S(R^S)-$, $(R^NR^{N'})N-C(=O)-O-$, $R^OO-C(=O)-N(R^N)-$, or $R^OO-C(=O)-O-$; e.g., methoxy, ethoxy);

substituted or unsubstituted alkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., vinyloxy, aryloxy);

substituted or unsubstituted aryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., phenyloxy);

substituted or unsubstituted cycloalkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

- substituted or unsubstituted cycloalkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted heteroaryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted heterocyclyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted arylalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., benzyl);
- substituted or unsubstituted amino (e.g., alkylamino (e.g., methylamino, ethylamino, dimethylamino), arylamino, cycloalkylamino, cycloalkenylamino, heteroarylamino, heterocyclylamino, acylamino (e.g., acetylamino, benzoylamino), arylalkylamino (e.g., benzylamino, tritylamino), hydroxyamino, alkyloxycarbonylamino, carbamoylamino, alkylsulfonylamino, arylsulfonylamino, cycloalkylsulfonylamino, cycloalkenylsulfonylamino, heteroarylsulfonylamino, heterocyclylsulfonylamino);
- substituted or unsubstituted carbamoyl (when substituted, substituents include halogen, hydroxy, carboxy, nitro, cyano, alkyl, alkenyl, alkynyl, aryl, cycloalkyl, cycloalkenyl, heteroaryl, or heterocyclyl; e.g., alkylcarbamoyl (e.g., methylcarbamoyl, ethylcarbamoyl, dimethylcarbamoyl, phenylethylcarbamoyl, dimethylaminoethylcarbamoyl, isopropylcarbamoyl, hydroxyethylcarbamoyl), alkylsulfonylcarbamoyl, heteroarylalkylcarbamoyl, alkyloxycarbamoyl);
- substituted or unsubstituted carbamoyloxy (when substituted, substituents include halogen, hydroxy, carboxy, nitro, cyano, alkyl, alkenyl, alkynyl, aryl, cycloalkyl, cycloalkenyl, heteroaryl, or heterocyclyl);
- substituted or unsubstituted acyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., alkylcarbonyl, arylcarbonyl, cycloalkylcarbonyl, cycloalkenylcarbonyl, heteroarylcarbonyl, heterocyclylcarbonyl, formyl, acetyl);
- substituted or unsubstituted alkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methanesulfonyl, ethanesulfonyl);
- substituted or unsubstituted arylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted cycloalkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted cycloalkenylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted heteroarylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted heterocyclylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted alkylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted arylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted cycloalkylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted cycloalkenylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted heteroarylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted heterocyclylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted sulfamoyl (when substituted, substituents include halogen, hydroxy, carboxy, nitro, cyano, alkyl, alkenyl, alkynyl, aryl, cycloalkyl, cycloalkenyl, heteroaryl, or heterocyclyl);
- substituted or unsubstituted alkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methoxycarbonyl, ethoxycarbonyl, tert-butoxycarbonyl);
- substituted or unsubstituted aryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted cycloalkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);
- substituted or unsubstituted cycloalkenyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroaryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted alkylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted arylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroarylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

nitroso;

azido;

isocyano; isocyanato; thiocyanato; isothiocyanato; mercapto;

formyloxy; haloformyl; oxalo; thioformyl; thiocarboxy; dithiocarboxy; thiocarbamoyl; sulfino; sulfo; sulfoamino; hydrazino; ureido; amidino; guanidino; phthalimido; oxo; $R^S R^{St}(O=)S=N-$; $R^S R^{St}(O=)S=N-R^{2f}-$; $R^S R^{St}(O=)S=N-C(=O)-$; $(R^N)N=S(=O)(R^S)-$; $(R^N)N=S(=O)(R^S)-R^{2f}-$; $R^S R^{St}(R^{N'}-N=)S=N-$; $((R^N)N=)_2S(R^S)-$; $(R^N R^{N'})N-C(=O)-O-$; $R^O O-C(=O)-N(R^N)-$; $R^O O-C(=O)-O-$ and the like.

The above-described substituted groups can be substituted with one to four of these substituents.

Preferred examples of substituents of a "substituted carbamoyl", a "substituted sulfamoyl", or a "substituted amino" include substituted or unsubstituted alkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methyl, ethyl, isopropyl, tert-butyl, $CF_3$);

substituted or unsubstituted alkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., vinyl);

substituted or unsubstituted aryl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., phenyl, naphthyl);

substituted or unsubstituted cycloalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., cyclopropyl, cyclobutyl);

substituted or unsubstituted cycloalkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., cyclopropenyl);

substituted or unsubstituted heteroaryl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted arylalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted alkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methoxy, ethoxy);

substituted or unsubstituted aryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., phenyloxy);

substituted or unsubstituted cycloalkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroaryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted acyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted alkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methoxycarbonyl, ethoxycarbonyl, tert-butoxycarbonyl);

substituted or unsubstituted aryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroaryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted sulfamoyl (when substituted, substituents include halogen, hydroxy, carboxy, nitro, cyano, alkyl, alkenyl, alkynyl, aryl, cycloalkyl, cycloalkenyl, heteroaryl, or heterocyclyl);

substituted or unsubstituted alkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methanesulfonyl, ethanesulfonyl);

substituted or unsubstituted arylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroarylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted carbamoyl (when substituted, substituents include halogen, hydroxy, carboxy, nitro, cyano, alkyl, alkenyl, alkynyl, aryl, cycloalkyl, cycloalkenyl, heteroaryl, or heterocyclyl);

halogen; hydroxy; carboxy; nitro; cyano; alkylsulfinyl; cycloalkylsulfinyl; cycloalkenylsulfinyl; arylsulfinyl; heteroarylsulfinyl; heterocyclylsulfinyl; amino; $R^S R^{St}(O=)S=N-$; $R^S R^{St}(O=)S=N-R^{2f}-$; $R^S R^{St}(O=)S=N-C(=O)-$; $(R^N)N=S(=O)(R^S)-$; $(R^N)N=S(=O)(R^S)-R^{2f}-$; $R^S R^{St}(R^{N'}-N=)S=N-$; $((R^N)N=)_2S(R^S)-$; $(R^N R^{N'})N-C(=O)-O-$; $R^O O-C(=O)-N(R^N)-$; $R^O O-C(=O)-O-$ and the like.

The alkyl parts of "alkylamino", "arylalkylamino", "alkyloxycarbonylamino", "alkylsulfonylamino", "alkylcarbamoyl", "alkylsulfonylcarbamoyl", "heteroarylalkylcarbamoyl", "alkyloxycarbamoyl", "arylalkyl", "dialkylamino" and "hydroxyalkyl" mean the above-described "alkyl".

The alkenyl part of "alkenyloxy" means the above-described "alkenyl".

The aryl parts of "arylalkyl", "arylamino", "arylalkylamino", "arylsulfonylamino", "aryloxycarbonyl", and "arylsulfinyl" mean the above-described "aryl".

The heteroaryl parts of "heteroarylamino", "heteroarylsulfonylamino", "heteroarylalkylcarbamoyl", "heteroaryloxycarbonyl", and "heteroarylsulfinyl" mean the above-described "heteroaryl".

The cycloalkyl parts of "cycloalkylamino", "cycloalkylsulfonylamino", "cycloalkyloxycarbonyl", and "cycloalkylsulfinyl" mean the above-described "cycloalkyl".

The cycloalkenyl parts of "cycloalkenylamino", "cycloalkenylsulfonylamino", "cycloalkenyloxycarbonyl", and "cycloalkenylsulfinyl" mean the above-described "cycloalkenyl".

The heterocyclyl parts of "heterocyclylamino", "heterocyclylsulfonylamino", "heterocyclyloxycarbonyl", and "heterocyclylsulfinyl" mean the above-described "heterocyclyl".

Among the compounds of the present invention, compounds in the following embodiments are preferred.

X is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, X is substituted or unsubstituted aryl, substituted or unsubstituted heteroaryl, substituted or unsubstituted cycloalkyl, substituted or unsubstituted cycloalkenyl, or substituted or unsubstituted heterocyclyl.

Further preferably, X is substituted or unsubstituted aryl, substituted or unsubstituted cycloalkyl, or substituted or unsubstituted heterocyclyl.

Particularly preferably, X is substituted or unsubstituted heterocyclyl. In this case, X is preferably substituted or unsubstituted monocyclic or bicyclic heterocyclyl, further preferably substituted or unsubstituted bicyclic heterocyclyl.

An example of such a bicyclic heterocyclyl is

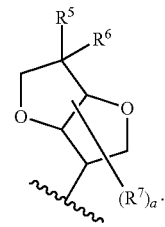

$R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, one of $R^5$ and $R^6$ is hydroxy, and the other is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Further preferably, one of $R^5$ and $R^6$ is hydroxy, and the other is hydrogen, or substituted or unsubstituted alkyl.

Particularly preferably, one of $R^5$ and $R^6$ is hydroxy, and the other is hydrogen.

$R^7$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

$R^7$ can be present at any position at which it can be substituted on the ring.

a is an integer from 0 to 7. Preferably, a is an integer of 0 to 4. Further preferably, a is 0 or 1. Particularly preferably, a is 0.

$R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl.

Preferably, $R^1$ is hydrogen, halogen, or cyano.

Further preferably, $R^1$ is hydrogen.

$R^2$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

Preferably, $R^2$ is substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, or substituted or unsubstituted amino.

Further preferably, $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

Particularly preferably, $R^2$ is substituted or unsubstituted aryl.

Most preferably, $R^2$ is $R^{2a}$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, $R^{2a}$ is hydrogen or halogen.

$R^{2b}$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

$R^{2d}$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

$R^{2e}$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

$R^{2c}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, $R^{2c}$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

Ring A is substituted aryl, substituted heteroaryl, substituted cycloalkyl, substituted cycloalkenyl, or substituted heterocyclyl.

Preferably, ring A is substituted aryl, or substituted heteroaryl.

Further preferably, ring A is substituted aryl.

Ring B is substituted aryl, substituted heteroaryl, substituted cycloalkyl, substituted cycloalkenyl, or substituted heterocyclyl.

Preferably, ring B is substituted aryl, substituted heteroaryl, substituted cycloalkenyl, or substituted heterocyclyl.

Y is $R^S R^{S\prime}(O=)S=N-$, $R^S R^{S\prime}(O=)S=N-R^{2f}-$, $R^S R^{S\prime}(O=)S=N-C(=O)-$, $(R^N)N=S(=O)(R^S)-$, $(R^N)N=S(=O)(R^S)-R^{2f}-$, $R^S R^{S\prime}(R^{N\prime}-N=)S=N-$, $((R^N)N=)_2 S(R^S)-$, $(R^N R^{N\prime})N-C(=O)-O-$, $R^O O-C(=O)-N(R^N)-$, or $R^O O-C(=O)-O-$.

Preferably, Y is $R^S R^{S\prime}(O=)S=N-$, $R^S R^{S\prime}(O=)S=N-C(=O)-$, $(R^N)N=S(=O)(R^S)-$, or $R^O O-C(=O)-N(R^N)-$.

Further preferably, Y is $R^S R^{S\prime}(O=)S=N-$, $(R^N)N=S(=O)(R^S)-$, or $R^O O-C(=O)-N(R^N)-$.

$R^S$ and $R^{S\prime}$ are each independently substituted or unsubstituted alkyl, substituted or unsubstituted cycloalkyl, substituted or unsubstituted heterocyclyl, substituted or unsubstituted aryl, or substituted or unsubstituted heteroaryl. $R^S$ and $R^{S\prime}$ bound to the same sulfur atom may form a substituted or unsubstituted ring together with the sulfur atom.

Preferably, $R^S$ and $R^{S\prime}$ are each independently substituted or unsubstituted alkyl.

The ring, which is formed by $R^S$ and $R^{S\prime}$ which are bound to the same sulfur atom, together with the sulfur atom, means a 3 to 15-membered saturated or unsaturated hetero ring that may contain one to four oxygen, nitrogen and/or sulfur atom(s) in the ring, other than the sulfur atom. Preferred is a non aromatic ring, and such non aromatic ring may be further cross-linked by a C1 to C4 alkyl chain, and may be fused with cycloalkane (preferably 5 to 6-membered) and a benzene ring. Examples of such a ring include

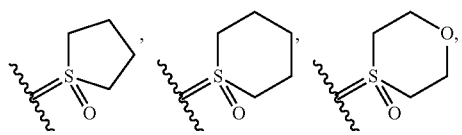

$R^{2f}$ is substituted or unsubstituted alkylene.

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl.

$R^N$ together with the adjacent nitrogen atom may form a substituted or unsubstituted ring when Y is $((R^N)N=)_2 S(R^S)-$.

Preferably, $R^N$ is hydrogen, substituted or unsubstituted alkyl, or substituted or unsubstituted carbamoyl.

Examples of a ring which $R^N$ together with the adjacent nitrogen atom forms when Y is $((R^N)N=)_2 S(R^S)-$ include

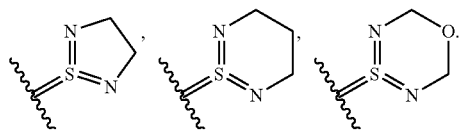

$R^{N\prime}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl.

Preferably, $R^{N\prime}$ is hydrogen, cyano, substituted or unsubstituted alkyl, substituted or unsubstituted cycloalkyl, substituted or unsubstituted aryl, or substituted or unsubstituted heteroaryl.

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

$R^3$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

Preferably, $R^3$ is halogen, cyano, carboxy, substituted or unsubstituted alkyl, substituted or unsubstituted alkylsulfonyl, or substituted or unsubstituted carbamoyl.

Further preferably, $R^3$ is halogen, cyano, or substituted alkyl, wherein the substituent of the substituted alkyl is halogen.

$R^4$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

Preferably, $R^4$ is hydrogen, halogen, hydroxy, cyano, nitro, carboxy, or substituted or unsubstituted alkyl.

Further preferably, $R^4$ is hydrogen or halogen.

Preferred embodiments of a compound represented by formula (I) include the following 1) to 3):

1) a compound wherein X is substituted or unsubstituted heterocyclyl, $R^1$ is cyano, $R^2$ is substituted or unsubstituted aryl, $R^3$ is halogen, and $R^4$ is hydrogen;

2) a compound wherein X is substituted or unsubstituted heterocyclyl, $R^1$ is halogen, $R^2$ is substituted or unsubstituted aryl, $R^3$ is halogen, and $R^4$ is hydrogen; and 3) a compound wherein X is substituted or unsubstituted heterocyclyl, $R^1$ is hydrogen, $R^2$ is substituted or unsubstituted aryl, $R^3$ is halogen, cyano, or substituted alkyl, wherein the substituent of the substituted alkyl is halogen, and $R^4$ is hydrogen.

One or more hydrogen, carbon, or other atoms of a compound of formula (I) of the present invention can be replaced by an isotope of the hydrogen, carbon, or other atoms.

For example, compounds of formula (I) include all radiolabeled forms of compounds of formula (I). Such "radioactive labeling," "radiolabeled forms", and the like of compounds of formula (I) are encompassed by the present invention and useful as a research and/or diagnostic tool in metabolism pharmacokinetic studies and in binding assays. Examples of isotopes that can be incorporated into a compound of formula (I) of the present invention include isotopes of hydrogen, carbon, nitrogen, oxygen, phosphorus, sulfur, fluorine, and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the present invention can be prepared by methods well-known in the art. For example, tritium-labeled compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

As a pharmaceutically acceptable salt of the present compound, the following salts can be included.

As a basic salt, examples include alkali metal salts such as sodium salts or potassium salts; alkaline earth metal salts such as calcium salts or strontium salts; metal salts such as beryllium salts, or magnesium salts; transition metal salts such as zinc salts; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts or ethylenediamine salts; aralkylamine salts such as N,N-dibenzylethylenediamine salts or benethamine salts; heterocyclic aromatic amine salts such as pyridine salts, picoline salts, quinoline salts, or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts, or tetrabutylammonium salts; basic amino acids salt such as arginine salts or lysine salts, or the like.

As an acidic salt, examples include inorganic acid salts such as hydrochloride, sulfate, nitrate, phosphate, carbonate, hydrogencarbonate, or perchlorate; organic acid salts such as acetate, propionate, lactate, maleate, fumarate, tartrate, malate, citrate or ascorbate; sulfonate salts such as methanesulfonate, isethionate, benzenesulfonate or p-toluenesulfonate; acidic amino acid salts such as aspartate or glutamate, or the like.

Compounds represented by formula (I) of the present invention or their pharmaceutically acceptable salts may form a solvate (e.g., hydrate, etc.), a cocrystal, and/or a crystal polymorph, and the present invention also contains such various types of solvate, cocrystal, and crystal polymorph. In a "solvate", any number of solvent molecules (e.g., water molecule, etc.) may be coordinated with a compound represented by formula (I). When left in the atmosphere, a compound represented by formula (I) or its pharmaceutically acceptable salt may absorb water, and a case where adsorbed water is attached thereto or a case where hydrate is formed may arise. In addition, by recrystallization of a compound represented by formula (I) or its pharmaceutically acceptable salt, a crystal polymorph thereof can be formed. A "cocrystal" means that a compound represented by formula (I) or a salt thereof and a counter molecule are present in the same crystal lattice, and can be formed with any number of counter molecules.

Compounds represented by formula (I) of the present invention or their pharmaceutically acceptable salts can form prodrugs, and the present invention also contains such various types of prodrug. The prodrugs are a derivative of the compound of the present invention, which has a chemically or metabolically decomposable group, and a compound which is changed into the compound of the present invention, which is pharmaceutically active, by solvolysis or in vivo under physiological conditions. The prodrugs contain a compound which is converted into a compound represented by formula (I) by enzymatic oxidation, reduction, hydrolysis and the like in living organisms under physiological conditions; a compound which is converted into a compound represented by formula (I) by hydrolysis by e.g., gastric acid; and the like. A method for selecting and a method for producing a proper prodrug derivative are described in e.g., Design of Prodrugs, Elsevier, Amsterdam 1985. Prodrugs can have activity in themselves.

When a compound represented by formula (I) or its pharmaceutically acceptable salt has a hydroxyl group, prodrugs such as an acyloxy derivative and a sulfonyloxy derivative are exemplified, which derivatives are produced, for example, by a reaction of a compound having a hydroxyl group and a proper acyl halide, a proper acid anhydride, a proper sulfonyl chloride, a proper sulfonyl anhydride and a mixed anhydride, or a reaction using a condensing agent. Examples thereof include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, CF$_3$SO$_3$—, CH$_2$FSO$_3$—, CF$_3$CH$_2$SO$_2$—, p-CH$_3$O-PhSO$_3$—, PhSO$_3$— and p-CH$_3$PhSO$_2$—.

The term "activating" means that the compound of the present invention activates the function of AMPK.

The term "pharmaceutically acceptable" means preventively or therapeutically harmless.

A general method for producing the compound of the present invention will be illustrated below. For extraction, purification and the like, treatments which are carried out in common experiments in organic chemistry may be carried out.

A compound represented by formula (I) can be synthesized as follows.

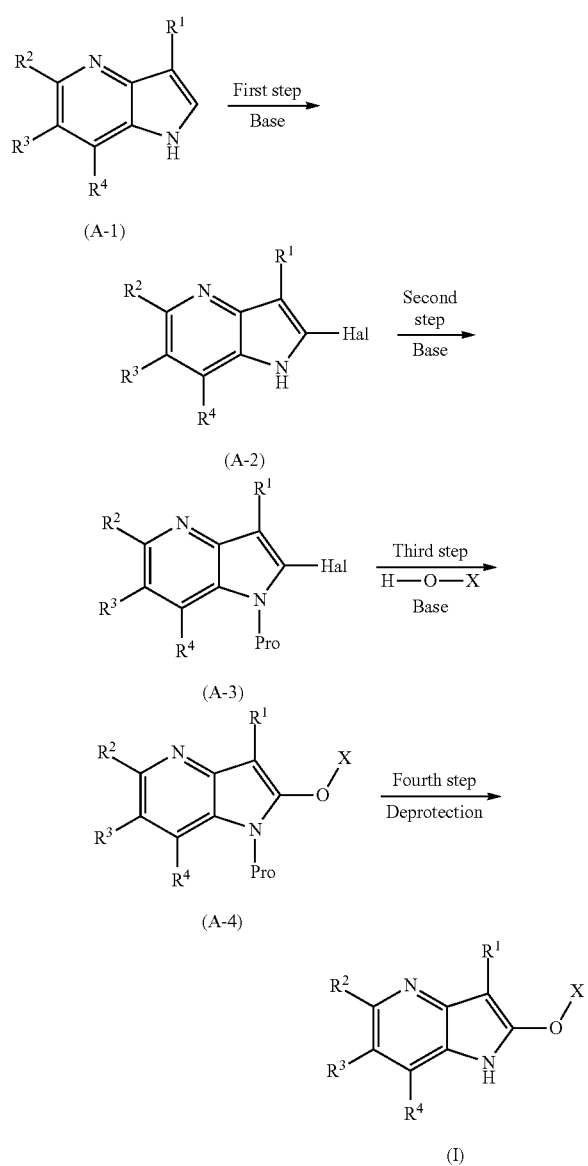

wherein, each symbol has the same meaning as above, and as a compound represented by formula (A-1), a known compound can be used, or a compound which is derived from a known compound by a conventional method can be used. "Hal" means a halogen, and Pro means a protecting group. Pro includes a benzyl group, a benzyol group, SEM (trimethylsilylethoxymethyl), and the like.

First Step

The first step is a step in which compound represented by formula (A-1) is halogenated to produce a compound represented by formula (A-2).

As a reaction solvent, examples include N,N-dimethylformamide, dimethyl sulfoxide, aromatic hydrocarbons (e.g., toluene, benzene, xylene, etc.), saturated hydrocarbons (e.g., cyclohexane, hexane, etc.), halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), ketones (e.g., acetone, methyl ethyl ketone, etc.), nitriles (e.g., acetonitrile, etc.), alcohols (e.g., methanol, ethanol, t-butanol, etc.), water, a mixed solvent thereof, or the like.

Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.) or nitriles (e.g., acetonitrile, etc.) can be used. Further preferably, alcohols (e.g., methanol, ethanol, t-butanol, etc.) can be used.

As a base, examples include metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogencarbonate, metal sodium, metal amides, organic amines (e.g., triethylamine, diisopropylethylamine, DBU, 2,6-lutidine, etc.), pyridine, alkyllithiums (n-BuLi, sec-BuLi, tert-BuLi), or the like.

A base may be used, or may not be used. Preferably, metal hydrides (e.g., sodium hydride, etc.), metal amides (e.g., lithium hexamethyldisilazide, etc.), alkyllithiums (n-BuLi, sec-BuLi, tert-BuLi) or the like can be used.

The reaction can be carried out at −78 to 100° C. for 0.5 to 24 hours.

As a halogenating agent, I$_2$, Br$_2$, NIS (N-iodosuccinimide), NBS (N-bromosuccinimide), or NCS (N-chlorosuccinimide) can be used.

Second Step

The second step is a step in which a compound represented by formula (A-3) is produced from the compound represented by formula (A-2).

As a reaction solvent, solvents described for the first step can be used. Preferably, N,N-dimethylformamide, ethers (e.g., tetrahydrofuran, diethyl ether, dioxane, 1,2-dimethoxyethane, etc.), halogenated hydrocarbons (e.g., dichloromethane, chloroform, 1,2-dichloroethane, etc.), nitriles (e.g., acetonitrile, etc.), or the like can be used.

As a base, bases described for the first step can be used. Preferably, metal hydrides (e.g., sodium hydride, etc.), metal sodium, organic amines (e.g., triethylamine, diisopropylethylamine, DBU, 2,6-lutidine, etc.), pyridine or the like can be used.

The reaction can be carried out at 0 to 100° C. for 0.5 to 12 hours.

Third Step

The third step is a step in which the compound represented by formula (A-3) and a compound represented by formula: H—O—X are reacted to produce a compound represented by formula (A-4).

As the compound represented by formula: H—O—X, examples include phenol, methanol, ethanol, or the like.

As a reaction solvent, solvents described for the first step can be used. Preferably, N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.), or the like can be used.

As a base, bases described for the first step can be used. Preferably, metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi), or the like can be used.

Further preferably, metal hydrides (e.g., sodium hydride, etc.) or metal carbonates (e.g., sodium carbonate, calcium carbonate, cesium carbonate, etc.) can be used.

The reaction can be carried out at 0 to 100° C. for 0.5 to 12 hours.

(When Hal is Bromine or Iodine)

The reaction can be carried out using conditions for a reaction which is known as the Ullmann reaction.

As a reaction solvent, solvents described for the first step can be used. Preferably, N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.), or the like can be used.

As a base, bases described for the first step can be used. Preferably, metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi), or the like can be used.

Further preferably, metal carbonates (e.g., sodium carbonate, calcium carbonate, cesium carbonate, etc.) can be used.

As a catalyst, copper iodide can be used.

The reaction can be carried out at from room temperature to 100° C. for 0.5 to 12 hours.

Fourth Step

The fourth step is a step in which the compound represented by formula (A-4) is deprotected to produce a compound represented by formula (I).

As a reaction solvent, solvents described for the first step can be used. Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), nitriles (e.g., acetonitrile, etc.), alcohols (e.g., methanol, ethanol, t-butanol, etc.), or the like can be used.

The reaction can be carried out in the presence of hydrochloric acid, TFA (trifluoroacetic acid), TBAF (tetrabutylammonium fluoride) or the like at 0 to 100° C. for 0.5 to 168 hours.

The substituents $R^1$, $R^2$, $R^3$, and $R^4$ can be introduced in any step of the above-described first to fourth steps.

For example, the substituent $R^2$ can be introduced as follows.

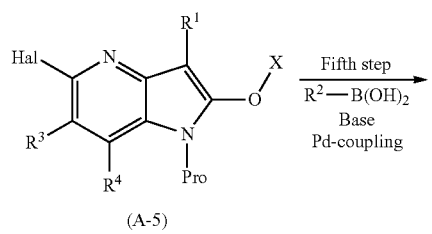

(A-5)

Fifth step
$R^2$—B(OH)$_2$
Base
Pd-coupling

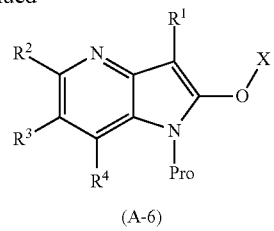

(A-6)

wherein, each symbol has the same meaning as above, and as a compound represented by formula (A-5), a known compound can be used, or a compound which is derived from a known compound by a conventional method can be used. "Hal" means a halogen, and Pro means a protecting group. Pro includes a benzyl group, a benzoyl group, SEM (trimethylsilylethoxymethyl), and the like.

Fifth Step

The fifth step is a step in which a compound represented by formula (A-5) and a compound represented by formula: $R^2$—B(OH)$_2$ are reacted in the presence of a palladium catalyst to produce a compound represented by formula (A-6). As the compound represented by formula $R^2$—B(OH)$_2$, a boronic acid ester can be used.

As a solvent, solvents described for the first step can be used. Preferably, N,N-dimethylformamide, aromatic hydrocarbons (e.g., toluene, benzene, xylene, etc.) or ethers (e.g., tetrahydrofuran, diethyl ether, dioxane, 1,2-dimethoxyethane, etc.) can be used.

As a base, bases described for the first step can be used. Preferably, metal carbonates (e.g., sodium carbonate, calcium carbonate, cesium carbonate, etc.) or organic amines (e.g., triethylamine, diisopropylethylamine, DBU, 2,6-lutidine, etc.) can be used.

The reaction may be carried out in the presence of a palladium catalyst (e.g., Pd(PPh$_3$)$_4$, PdCl$_2$, Pd(OAc)$_2$, Pd(dba)$_2$, etc.) and a phosphine ligand (e.g., PPh$_3$, BINAP, etc.) at a temperature at which the solvent used is refluxed, for 0.5 to 12 hours.

When using microwave, the reaction can be carried out at 80 to 200° C. for 5 minutes to 1 hour.

Examples of a compound represented by formula: $R^2$—B(OH)$_2$ include phenylboronic acid or the like.

Among compounds represented by formula (A-6), a compound wherein $R^2$ is substituted or unsubstituted alkyloxy, substituted or unsubstituted cycloalkyloxy, substituted or unsubstituted cycloalkenyloxy, or substituted or unsubstituted heterocyclyloxy can be synthesized by converting the halogen group of the compound represented by formula (A-5) into a hydroxyl group via a boronic acid ester, and then performing Mitsunobu reaction or an alkylation reaction using various halide.

As a boronic acid ester, examples include pinacol boronic acid ester or the like.

A compound represented by formula (A-2) can also be synthesized by the following method.

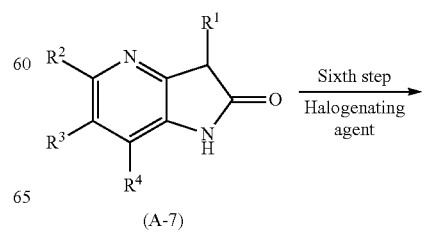

(A-7)

Sixth step
Halogenating agent

-continued

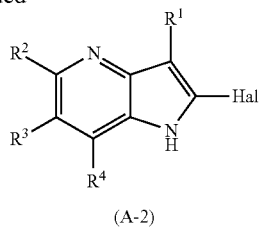

(A-2)

wherein, each symbol has the same meaning as above, and as a compound represented by formula (A-7), a known compound can be used, or a compound which is derived from a known compound by a conventional method can be used. "Hal" means a halogen.

Sixth Step

The sixth step is a step in which a compound represented by formula (A-7) and a halogenating agent are reacted to produce a compound represented by formula (A-2).

As a reaction solvent, solvents described for the first step can be used, but need not be used.

As a halogenating agent, examples include phosphorus oxychloride, phosphorus pentachloride, oxalyl chloride, thionyl chloride, sulfuryl chloride, dichlorotriphenylphosphorane, or the like. Particularly preferably, phosphorus oxychloride, phosphorus pentachloride, oxalyl chloride, or thionyl chloride can be used.

The reaction can be carried out at 0 to 120° C. for 0.5 to 24 hours.

Various types of substituent on compounds of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS, and the like.

A compound of the present invention has an excellent AMPK activating effect. Therefore, the compound can be used for the treatment or prevention of diseases associated with AMPK, particularly diseases such as type II diabetes, hyperglycemia, metabolic syndrome, obesity, hypercholesterolemia, and/or hypertension. Particularly, the compound is useful in the treatment or prevention of type II diabetes, hyperglycemia, metabolic syndrome, or obesity.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration, and the like.

In the case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may be prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, disintegrants, lubricants and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

A compound of the present invention can be used in combination with an insulin secretagogue (e.g., a sulfonylurea (SU) drug), a fast-acting insulin secretagogue (e.g., a phenylalanine derivative), a glucose uptake inhibitor (e.g., an α-glucosidase inhibitor (α-GI drug)), an insulin resistance improving drug (e.g., a biguanide drug (BG drug), a thiazolidine derivative (TZD drug)), an insulin formulation, a peptidyl peptidase TV (DPP-TV) inhibitor, a GLP-1 receptor agonist, a sodium-dependent glucose transporter 1 (SGLT1) inhibitor, a sodium-dependent glucose transporter 2 (SGLT 2) inhibitor and the like (hereinafter, abbreviated as concomitant drugs) for the purpose of an increase in the effect of the compound, a decrease in a dose of the compound or the like. In this case, the time when a compound of the present invention and a concomitant drug are administered is not restricted, and they can be administered to a subject of administration simultaneously or at intervals. Further, a compound of the present invention and a concomitant drug can be administered as two kinds of formulation comprising each active ingredient and as a single formulation comprising both active ingredients.

The dose of a concomitant drug can be suitably selected on the basis of a dosage which is clinically used. In addition, the mixing ratio of a compound of the present invention and a concomitant drug can be suitably selected depending on a subject of administration, an administration route, a target disease, symptoms, combination and the like. When a subject of administration is a human, for example, 0.01 to 100 parts by weight of a concomitant drug can be used per part by weight of a compound of the present invention.

The present invention is described in more detail below with reference to Examples, which are not intended to limit the scope of the present invention.

NMR spectrum data of the compounds and intermediates thereof of the present invention are shown. NMR analysis in each example was performed at 400 MHz using CDCl$_3$, deuterated methanol (MeOD) or dimethyl sulfoxide (d6-DMSO).

LC/MS was measured under the following conditions.
(Method A)
  Column: ACQUITY UPLC BEH C18 (1.7 μm, i.d. 2.1×50 mm) (Waters)
  Flow rate: 0.8 mL/min
  UV detection wavelength: 254 nm
  Mobile phase: [A] 0.1% formic acid-containing aqueous solution, [B] 0.1% formic acid-containing acetonitrile solution
  Gradient: a linear gradient of the solvent [B] from 5 to 100% was carried out for 3.5 minutes and the solvent [B] at 100% was maintained for 0.5 minutes.
(Method B)
  Column: Shim-pack XR-ODS (2.2 μm, i.d. 3.0×50 mm) (Shimadzu)
  Flow rate: 1.6 mL/min
  UV detection wavelength: 254 nm
  Mobile phase: [A] 0.1% formic acid-containing aqueous solution, [B] 0.1% formic acid-containing acetonitrile solution
  Gradient: a linear gradient of the solvent [B] from 10 to 100% was carried out for 3 minutes and the solvent [B] at 100% was maintained for 0.5 minutes.
(Method C)
  Column: ACQUITY UPLC (Registered trademark) BEH C18 (1.7 μm, i.d. 2.1×50 mm) (Waters)
  Flow rate: 0.55 mL/min
  UV detection wavelength: 254 nm
  Mobile phase: [A] 0.1% formic acid-containing aqueous solution, [B] 0.1% formic acid-containing acetonitrile solution
  Gradient: a linear gradient of the solvent [B] from 5 to 100% was carried out for 3 minutes and the solvent [B] at 100% was maintained for 0.5 minutes.

The meaning of each term in Examples is as follows.
CDI: 1,1'-carbonyldiimidazole
DMF: N,N-dimethylformamide
THF: tetrahydrofuran
Pd(PPh$_3$)$_4$: tetrakis(triphenylphosphine)palladium(0)
POCl$_3$: phosphorus oxychloride
PdCl$_2$(dtbpf): [1,1'-Bis(di-tert-butylphosphino)ferrocene]dichloropalladium(II)
NCS: N-chlorosuccinimide
NBS: N-bromosuccinimide
NIS: N-iodosuccinimide
TFA: trifluoroacetic acid
TBAF: tetrabutylammonium fluoride
DIAD: diisopropyl azodicarboxylate
UHP: urea hydrogen peroxide
mCPBA: m-chloroperoxybenzoic acid
HMPA: hexamethylphosphoric triamide
DMAP: N,N-dimethyl-4-aminopyridine
MTBE: methyl tert-butyl ether
TEMPO: 2,2,6,6-tetramethylpiperidine 1-oxyl free radical
  MS4A: molecular sieve 4A
TMEDA: N,N,N',N'-tetramethylethylenediamine
NFSI: N-fluorobenzenesulfonimide
RuPhos: 2-dicyclohexylphosphino-2',6'-diisopropoxybiphenyl
PdCl$_2$(dppf)CH$_2$Cl$_2$: [1,1'-bis(diphenylphosphino)ferrocene]palladium(II) dichloride dichloromethane adduct
NMO: 4-methylmorpholine-N-oxide
DMSO: dimethyl sulfoxide
TBSCl: tert-butyldimethylsilyl chloride
X-Phos: 2-dicyclohexylphosphino-2',4',6'-triisopropylbiphenyl
Pd$_2$(dba)$_3$: tris(dibenzylideneacetone)dipalladium(0)
DME: 1,2-dimethoxyethane
HOBt: 1-hydroxybenzotriazole
EDC-HCl: 1-(3-dimethylaminopropyl)-3-ethylcarbodiimide hydrochloride
HATU: O-(7-azabenzotriazol-1-yl)-N,N,N',N'-tetramethyluronium hexafluorophosphate Example 1

Compound 1 (1.70 g, 8.81 mmol) was dissolved in DMF (17 mL), to which was then added t-butyl ethylmalonate (3.34 ml, 17.62 mmol), and the resulting mixture was cooled in an ice bath. 60% NaH (705 mg, 17.62 mmol) was added to the reaction mixture, which was then stirred at room temperature. After completion of the reaction, the reaction mixture was cooled in an ice bath, followed by addition of a 2 mol/L aqueous solution of hydrochloric acid (10 ml), and the resulting mixture was extracted with ethyl acetate. After that, the organic layer was washed with water. The obtained organic layer was dried over magnesium sulfate, and then the solvent was removed by concentration under reduced pressure. The obtained residue was purified by silica gel column chromatography to obtain Compound 2 (2.69 g, 88.8%). Compound 2; $^1$H-NMR (CDCl$_3$) δ: 1.30 (3H, t, J=7.2 Hz), 1.49 (9H, s), 4.25-4.36 (2H, m), 5.38 (1H, s), 8.46 (1H, s), 8.77 (1H, s).

Compound 2 (1.00 g, 2.90 mmol) was dissolved in chloroform (5 mL) and trifluoroacetic acid (5 ml), and the reaction mixture was stirred at room temperature. After completion of the reaction, the solvent was removed by concentration under reduced pressure. The obtained residue was diluted with chloroform, and the resulting mixture was neutralized with 2 mol/L aqueous solution of potassium carbonate. The obtained organic layer was dried over magnesium sulfate, and then the solvent, was removed by concentration under reduced pressure. A portion of the obtained residue (500 mg) was dissolved in dichloromethane (5 ml), to which were then added UHP (385 mg, 4.09 mmol) and trifluoroacetic acid anhydride (0.383 ml, 2.72 mmol), and the resulting mixture was stirred at room temperature.

After completion of the reaction, a saturated aqueous solution of sodium hydrogencarbonate was added to the reaction mixture, which was then extracted with chloroform. The obtained residue was purified by silica gel column chromatography to obtain Compound 3 (0.417 g, 76.4%).

Compound 3; $^1$H-NMR (CDCl$_3$) δ: 1.28 (3H, t, J=7.2 Hz), 4.21 (2H, q, J=6.9 Hz), 4.36 (2H, s), 7.89 (1H, s), 8.50 (1H, s).

To Compound 3 (400 mg, 1.53 mmol) were added phosphorus oxychloride (4 ml) and tetrabutylammonium chloride (427 mg, 1.53 mmol), and the reaction mixture was stirred at 70° C. After completion of the reaction, ice was added to the reaction mixture, which was then extracted with diethyl ether. The obtained organic layer was dried over magnesium sulfate, and then the solvent was removed by concentration under reduced pressure. The obtained residue was purified by silica gel column chromatography to obtain Compound 4 (210 mg, 49.2%).

Compound 4; $^1$H-NMR (CDCl$_3$) δ: 1.27 (3H, t, J=6.9 Hz), 4.19 (2H, q, J=6.9 Hz), 4.28 (2H, s), 8.54 (1H, s).

Example 2

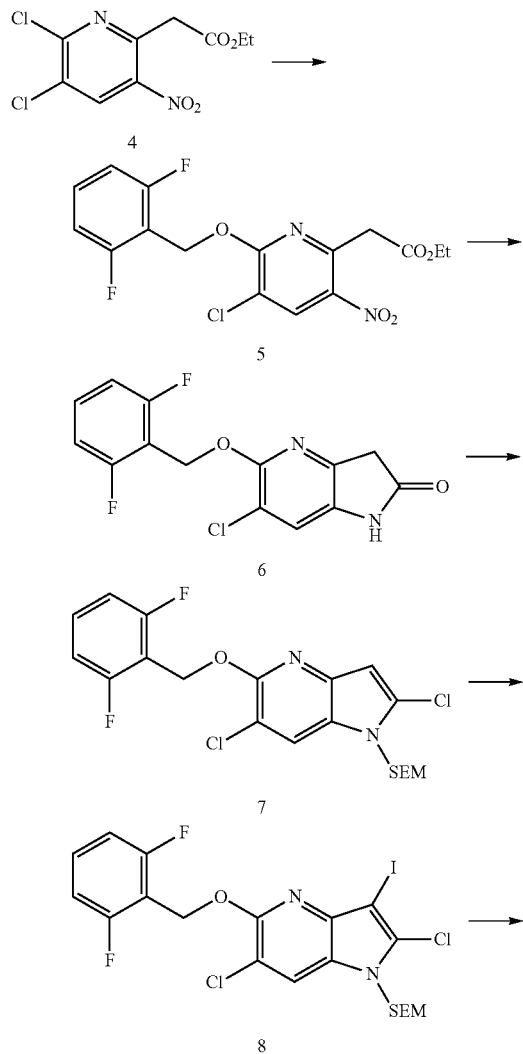

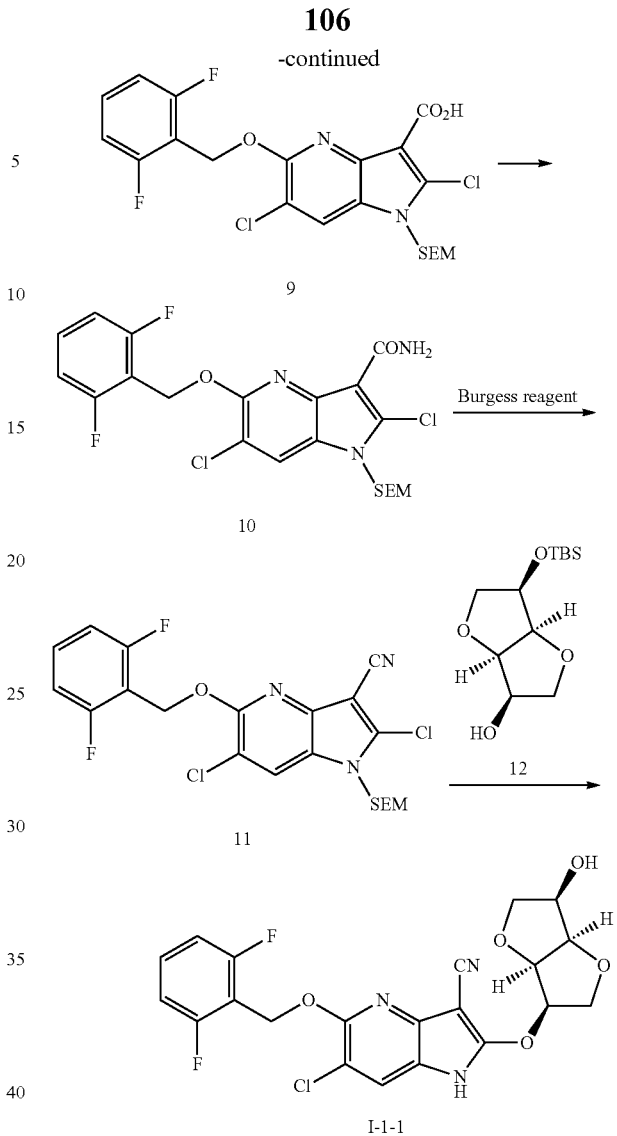

2,6-Difluorophenylmethanol (14.202 g, 99 mmol) was diluted in DMF (50 ml), followed by addition of 60 wt % NaH (3.58 g, 90 mmol) under ice cooling, and the resulting mixture was stirred at 0° C. for 3 minutes, and then at room temperature. A solution of Compound 4 (5000 mg, 17.92 mmol) dissolved in DMF (10 ml) was added to the reaction mixture, which was further stirred at room temperature. The reaction mixture was cooled, followed by addition of 2 mol/L aqueous solution of hydrochloric acid and extraction with ethyl acetate. The organic layer was washed with water, and concentrated under reduced pressure. The obtained residue was purified by silica gel column chromatography to obtain Compound 5 (4.9053 g, 70.8%).

Compound 5; Method B
LC/MS retention time=2.49 min.
MS (ESI) m/z=386.95 (M+H)+.

Compound 5 (4800 mg, 12.41 mmol) was dissolved in THF (25 ml) and methanol (25 ml), followed by addition of a solution of ammonium chloride (3319 mg, 62.1 mmol) dissolved in water (12.5 ml). The reaction mixture was heated to 60° C., followed by addition of iron powder (3466 mg, 62.1 mmol), and the resulting mixture was stirred at 60° C. After completion of the reaction, ethyl acetate and saturated aqueous NaCl were added to the reaction mixture.

Insoluble materials were filtered off through Celite, and then the filtrate was extracted with ethyl acetate. The obtained organic layer was dried over magnesium sulfate, and then the solvent was removed by concentration under reduced pressure. To the obtained residue were added toluene (45 ml) and acetic acid (3.55 ml, 62.1 mmol), and the resulting mixture was stirred at 80 to 90° C. After completion of the reaction, the solvent was removed by concentration under reduced pressure, followed by addition of ethyl acetate. The resulting suspension was filtered to obtain Compound 6 (3.0626 g, 79.4%).

Compound 6; Method B
LC/MS retention time=1.81 min.
MS (ESI) m/z=311.95 (M+H)+.

To Compound 6 (2500 mg, 8.05 mmol) were added 1,2-dichloroethane (25 ml), phosphorus oxychloride (1.495 ml, 16.09 mmol), and pyridine (976 ml, 12.07 μmol), and the reaction mixture was stirred at 70° C. After completion of the reaction, the solvent was removed by concentration under reduced pressure. To the residue was added ice to quench the unreacted phosphorus oxychloride, followed by extraction with ethyl acetate. The obtained organic layer was dried over magnesium sulfate, and then the solvent was removed by concentration under reduced pressure. To the obtained residue was added DMF (30 ml), followed by addition of 60 wt % NaH (483 mg, 12.08 mmol) and 2-(trimethylsilyl)ethoxymethyl chloride (1.713 ml, 9.66 mmol) under ice cooling, and the resulting mixture was stirred at room temperature. During the reaction, two further additions of 60 wt % NaH (241 mg, 6.04 mmol) and three further additions of 2-(trimethylsilyl)ethoxymethyl chloride (514 μl, 2.89 mmol) were performed under ice cooling. After completion of the reaction, water was added to the reaction mixture, which was then extracted with ethyl acetate. The organic layer was washed with water, and concentrated under reduced pressure. The obtained residue was purified by silica gel column chromatography to obtain Compound 7 (2.153 g, 58.2%).

Compound 7; Method B
LC/MS retention time=3.19 min.
MS (ESI) m/z=459.15 (M+H)+.

To Compound 7 (250 mg, 0.544 mmol) were added DMF (2.5 ml) and NIS (147 mg, 0.653 mmol), and the reaction mixture was heated from room temperature to 70° C. and stirred. After completion of the reaction, ethyl acetate was added to the reaction mixture, which was then washed with water. The obtained organic layer was concentrated under reduced pressure to remove the solvent. The obtained residue was purified by silica gel column chromatography to obtain Compound 8 (226 mg).

Compound 8; Method B
LC/MS retention time=3.30 min.
MS (ESI) m/z=585.15 (M+H)+.

To Compound 8 (119 mg, 0.203 mmol) were added DMF (1.5 ml), triethylamine (141 μl, 1.017 mmol), PdCl$_2$(PPh$_3$)$_2$ (28.5 mg, 0.041 mmol), and water (1.0 ml). The reaction mixture was stirred at 80° C. under a carbon monoxide atmosphere. After completion of the reaction, ethyl acetate was added to the reaction mixture, which was then washed with 2 mol/L aqueous solution of hydrochloric acid and with water. The obtained organic layer was concentrated under reduced pressure to remove the solvent. The obtained residue was purified by silica gel column chromatography to obtain Compound 9 (105 mg).

Compound 9; Method B
LC/MS retention time=2.81 min.
MS (ESI) m/z=503.10 (M+H)+.

To Compound 9 (100 mg, 0.199 mmol) was added THF (1 ml), and then added CDI (64.4 mg, 0.397 mmol) under ice cooling. The reaction mixture was stirred at room temperature, and then added to a 28% aqueous solution of ammonia (2 ml) under ice cooling, and the resulting mixture was stirred at 0° C. After completion of the reaction, ethyl acetate was added to the reaction mixture, which was then washed with saturated aqueous NaCl. The obtained organic layer was dried over magnesium sulfate, and the solvent was removed by concentration under reduced pressure to obtain Compound 10 (116 mg).

Compound 10; Method B
LC/MS retention time=2.70 min.
MS (ESI) m/z=502.10 (M+H)+.

To Compound 10 (91 mg, 0.181 mmol) were added 1,4-dioxane (1 ml) and Burgess reagent (216 mg, 0.905 mmol), and the reaction mixture was stirred at 80 to 100° C. After completion of the reaction, the reaction mixture was cooled to room temperature, and ethyl acetate was added to the reaction mixture, which was then neutralized with a saturate aqueous solution of sodium hydrogencarbonate and additionally washed with saturated aqueous NaCl. The obtained organic layer was dried over magnesium sulfate, and then the solvent was removed by concentration under reduced pressure. The obtained residue was purified by silica gel column chromatography to obtain Compound 11 (32.2 mg, 36.7%).

Compound 11; Method B
LC/MS retention time=3.02 min.
MS (ESI) m/z=485.95 (M+H)+.

Compound 12 (83 mg, 0.318 mmol) was dissolved in DMF (0.5 ml), to which was then added 60 wt % NaH (11.56 mg, 0.289 mmol) under ice-cooling, and the resulting mixture was stirred at 0° C. for 5 minutes. After that, a solution of Compound 11 (28 mg, 0.058 mmol) dissolved in DMF (1 ml) was added to the reaction mixture under ice cooling, and the resulting mixture was further stirred at 0° C. After completion of the reaction, ethyl acetate was added to the reaction mixture, which was then washed with water. The obtained organic layer was dried over magnesium sulfate, and then the solvent was removed by concentration under reduced pressure. To the obtained residue was added TFA (2 ml), and the reaction mixture was stirred at room temperature. After completion of the reaction, the TFA was removed by concentration under reduced pressure, followed by dilution in MeOH, and addition of and neutralization with an aqueous solution of sodium hydrogencarbonate. The desired product was extracted with chloroform, and the obtained organic layer was dried over magnesium sulfate, and then the solvent was removed by concentration under reduced pressure. The obtained residue was purified by silica gel column chromatography to obtain Compound (I-1-1) (16 mg, 59.7%).

Compound (I-1-1); Method B
LC/MS retention time=1.85 min.
MS (ESI) m/z=464.0 (M+H)+.

Example 3

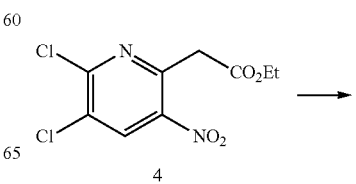

4

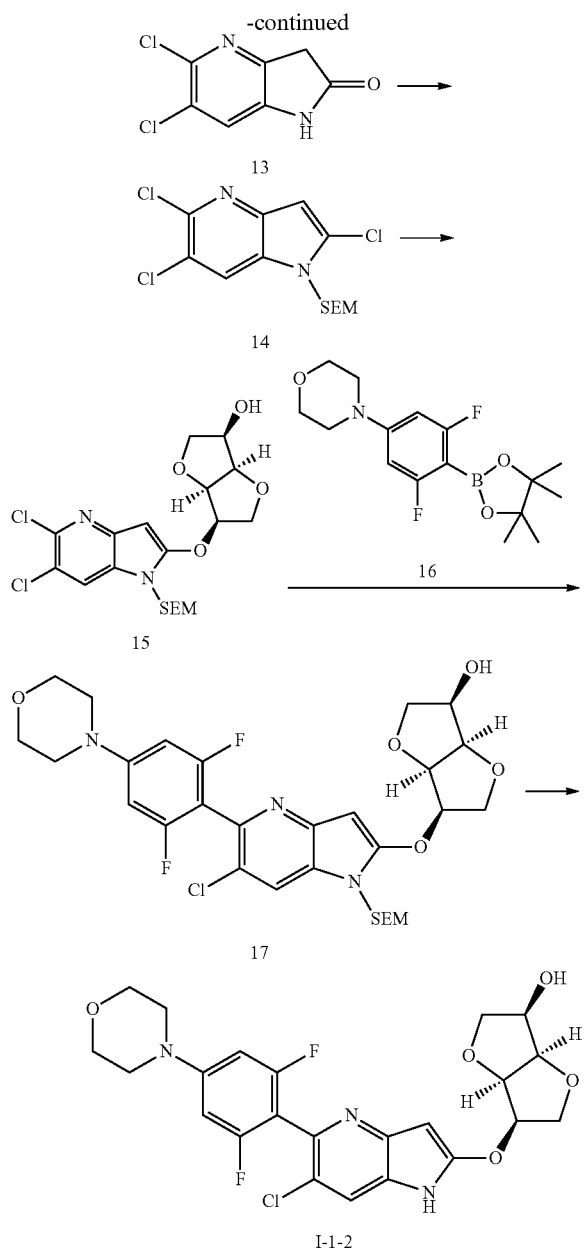

water. The obtained organic layer was dried over magnesium sulfate, and then the solvent was removed by concentration under reduced pressure. The obtained residue was purified by silica gel column chromatography to obtain Compound 15 (285 mg, 66.8%).

Compound 15; Method B
LC/MS retention time=2.40 min.
MS (ESI) m/z=461.05 (M+H)+.

To Compound 15 (100 mg, 0.217 mmol) were added toluene (1.0 ml), 2 mol/L aqueous solution of potassium carbonate (0.163 ml, 0.325 mmol), $PdCl_2(dtbpf)$ (28.3 mg, 0.043 mmol), and Compound 16 (106 mg, 0.325 mmol), and the reaction mixture was stirred at 150° C. under microwave irradiation. To the reaction mixture was added a mixed solvent of chloroform and methanol, and the resulting mixture was washed with saturated aqueous NaCl. The obtained organic layer was dried over magnesium sulfate, and then the solvent was removed by concentration under reduced pressure. The obtained residue was purified by silica gel column chromatography to obtain Compound 17 (51.8 mg, 38.3%).

Compound 17; Method B
LC/MS retention time=2.35 min.
MS (ESI) m/z=624.20 (M+H)+.

To Compound 17 (51 mg, 0.082 mmol) was added TFA (1 ml), and the reaction mixture was stirred at room temperature. After completion of the reaction, the TFA was removed by concentration under reduced pressure, followed by dilution in MeOH, and neutralization with au aqueous solution of sodium hydrogencarbonate. Extraction was performed with a mixed solvent of chloroform and methanol, the obtained organic layer was dried over magnesium sulfate, and then the solvent was removed by concentration under reduced pressure. The obtained residue was purified by silica gel column chromatography to obtain Compound (I-1-2) (21 mg, 52.0%).

Compound (I-1-2); Method B
LC/MS retention time=1.29 min.
MS (ESI) m/z=494.15 (M+H)+.

Example 4

Compound 13 was synthesized from Compound 4 in a similar way as in the case of Compound 6.
Compound 13; Method B
LC/MS retention time=1.21 min.
MS (ESI) m/z=202.85 (M+H)+.
Compound 14 was synthesized from Compound 13 in a similar way as in the case of Compound 7.
Compound 14; Method B
LC/MS retention time=2.98 min.
MS (ESI) m/z=352.65 (M+H)+.

To Compound 14 (325 mg, 0.924 mmol) and isomannide (1350 mg, 9.24 mmol) were added DMF (3.0 ml), and then 60 wt % NaH (111 mg, 2.77 mmol), and the resulting mixture was stirred at room temperature for 5 minutes. After that, the reaction mixture was stirred at 120° C. The reaction mixture was cooled to room temperature, followed by addition of ethyl acetate, and the resulting mixture was washed with 1 mol/L aqueous solution of hydrochloric acid and with

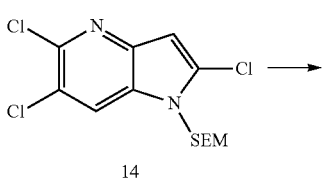

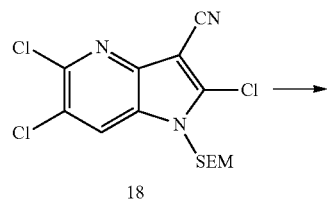

-continued

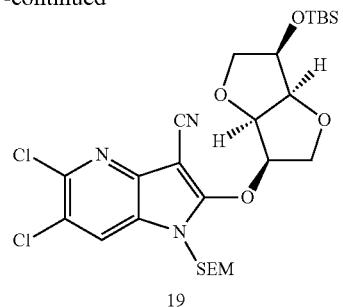

19

Compound 18 was synthesized from Compound 14 in a similar way as in the case of Compound 11.

Compound 18; Method B
LC/MS retention time=2.84 min.
MS (ESI) m/z=376.10 (M+H)+.

Compound 18 (975 mg, 2.59 mmol) was dissolved in DMF (9.75 ml), to which was then added Compound 12 (876 mg, 3.36 mmol), followed by addition of 60 wt % NaH (135 mg, 3.36 mmol) under ice cooling, and the resulting mixture was stirred at 0° C. After completion of the reaction, water was added to the reaction mixture, which was then extracted with ethyl acetate. The obtained organic layer was washed with saturated aqueous NMI and dried over sodium sulfate, and then the solvent was removed by concentration under reduced pressure. The obtained residue was purified by silica gel column chromatography to obtain Compound 19 (1.282 g, 82.5%).

Compound 19; Method C
LC/MS retention time=3.24 min.
MS (ESI) m/z=600.10 (M+H)+.

Example 5

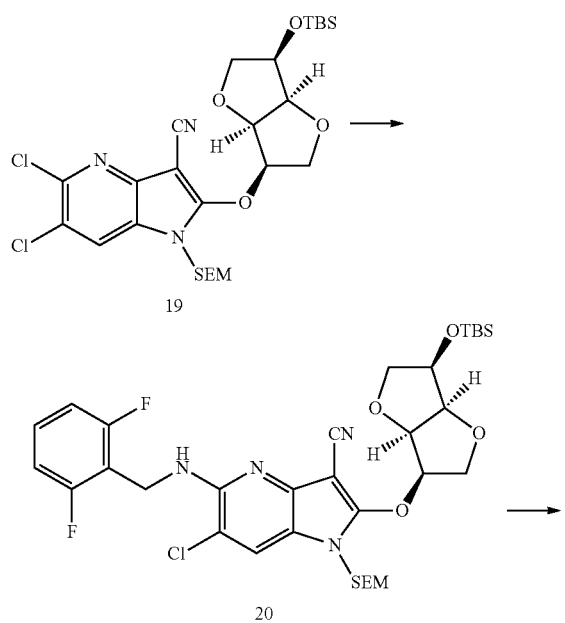

-continued

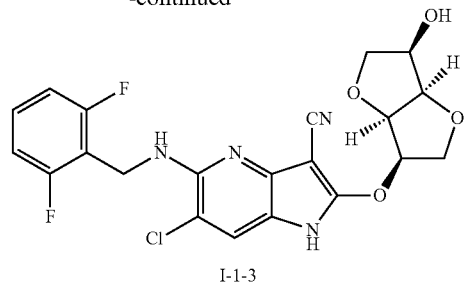

I-1-3

To X-Phos (15.87 mg, 0.033 mmol) and Pd$_2$(dba)$_3$ (15.24 mg, 0.017 mmol) were added toluene (1 ml), and then Compound 19 (100 mg, 0.166 mmol), 6-difluorophenyl-methanamine (23.89 μl, 0.200 mmol), and sodium tert-butoxide (32.0 mg, 0.333 mmol), and the reaction mixture was stirred at 80° C. After completion of reaction, saturated aqueous NaCl was added to the reaction mixture, which was then extracted with a mixed solvent of chloroform and methanol. The obtained organic layer was dried over magnesium sulfate, and then the solvent was removed by concentration under reduced pressure. The obtained residue was purified by silica gel column chromatography to obtain Compound 20 (16 mg, 13.6%).

Compound 20; Method B
LC/MS retention time=3.33 min.
MS (ESI) m/z=707.25 (M+H)+.

To Compound 20 (15 mg, 0.021 mmol) was added TFA (1 ml), and the reaction mixture was stirred at room temperature. After completion of the reaction, the TFA was removed by concentration under reduced pressure, followed by dilution in MeOH, and neutralization with an aqueous solution of sodium hydrogencarbonate. Extraction was performed with chloroform, the obtained organic layer was dried over magnesium sulfate, and then the solvent was removed by concentration under reduced pressure. The obtained residue was purified by silica gel column chromatography to obtain Compound (I-1-3) (6 mg, 61.1%).

Compound (I-1-3); Method B
LC/MS retention time=1.79 min.
MS (ESI) m/z=463.30 (M+H)+.

Example 6

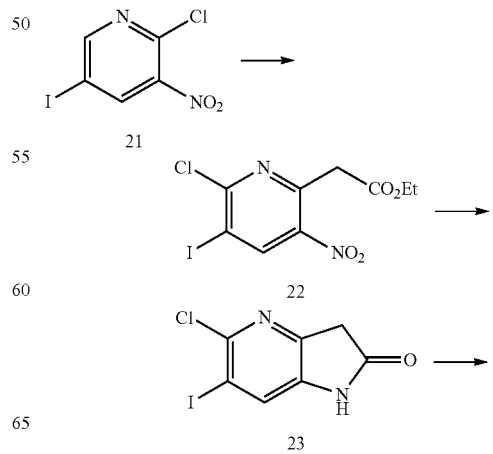

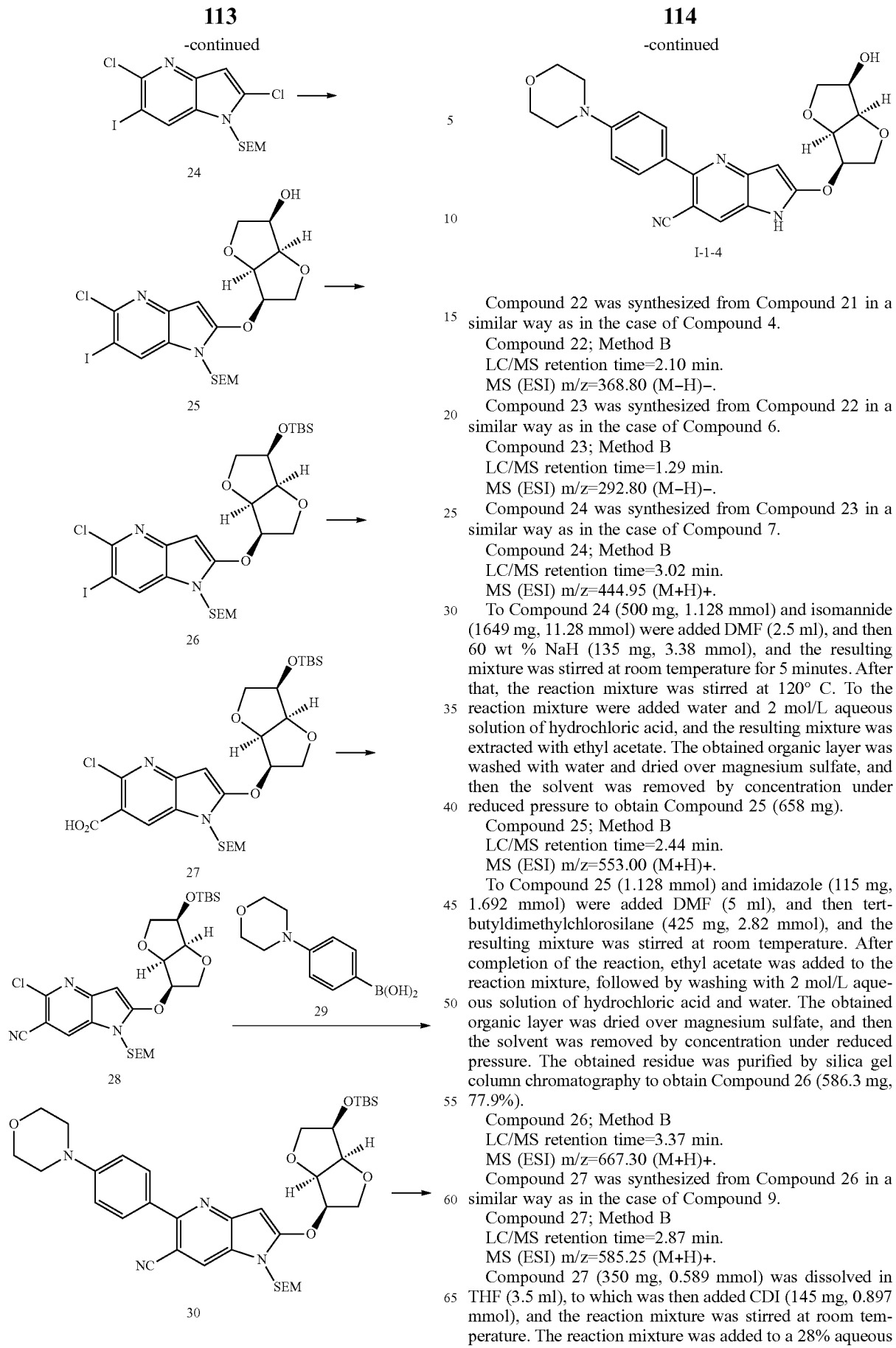

I-1-4

Compound 22 was synthesized from Compound 21 in a similar way as in the case of Compound 4.
Compound 22; Method B
LC/MS retention time=2.10 min.
MS (ESI) m/z=368.80 (M−H)−.
Compound 23 was synthesized from Compound 22 in a similar way as in the case of Compound 6.
Compound 23; Method B
LC/MS retention time=1.29 min.
MS (ESI) m/z=292.80 (M−H)−.
Compound 24 was synthesized from Compound 23 in a similar way as in the case of Compound 7.
Compound 24; Method B
LC/MS retention time=3.02 min.
MS (ESI) m/z=444.95 (M+H)+.
To Compound 24 (500 mg, 1.128 mmol) and isomannide (1649 mg, 11.28 mmol) were added DMF (2.5 ml), and then 60 wt % NaH (135 mg, 3.38 mmol), and the resulting mixture was stirred at room temperature for 5 minutes. After that, the reaction mixture was stirred at 120° C. To the reaction mixture were added water and 2 mol/L aqueous solution of hydrochloric acid, and the resulting mixture was extracted with ethyl acetate. The obtained organic layer was washed with water and dried over magnesium sulfate, and then the solvent was removed by concentration under reduced pressure to obtain Compound 25 (658 mg).
Compound 25; Method B
LC/MS retention time=2.44 min.
MS (ESI) m/z=553.00 (M+H)+.
To Compound 25 (1.128 mmol) and imidazole (115 mg, 1.692 mmol) were added DMF (5 ml), and then tert-butyldimethylchlorosilane (425 mg, 2.82 mmol), and the resulting mixture was stirred at room temperature. After completion of the reaction, ethyl acetate was added to the reaction mixture, followed by washing with 2 mol/L aqueous solution of hydrochloric acid and water. The obtained organic layer was dried over magnesium sulfate, and then the solvent was removed by concentration under reduced pressure. The obtained residue was purified by silica gel column chromatography to obtain Compound 26 (586.3 mg, 77.9%).
Compound 26; Method B
LC/MS retention time=3.37 min.
MS (ESI) m/z=667.30 (M+H)+.
Compound 27 was synthesized from Compound 26 in a similar way as in the case of Compound 9.
Compound 27; Method B
LC/MS retention time=2.87 min.
MS (ESI) m/z=585.25 (M+H)+.
Compound 27 (350 mg, 0.589 mmol) was dissolved in THF (3.5 ml), to which was then added CDI (145 mg, 0.897 mmol), and the reaction mixture was stirred at room temperature. The reaction mixture was added to a 28% aqueous solution of ammonia (4 ml) under ice cooling, and the resulting mixture was stirred at room temperature. After completion of the reaction, ethyl acetate was added to the reaction mixture, which was then washed with aqueous NaCl. The obtained organic layer was dried over magnesium sulfate, and then the solvent was removed by concentration under reduced pressure. The obtained residue was dissolved in pyridine (3.5 ml), to which was then added trifluoroacetic anhydride (169 μl, 1.196 mmol) under ice cooling, and the reaction mixture was stirred at room temperature. During the reaction, additional trifluoroacetic anhydride (42 μl, 0.299 mmol) was added under ice cooling, and the reaction mixture was further stirred at room temperature. After completion of the reaction, ethyl acetate was added to the reaction mixture, followed by washing with 2 mol/L aqueous solution of hydrochloric acid and water. The obtained organic layer was dried over magnesium sulfate, and then the solvent was removed by concentration under reduced pressure. The obtained residue was purified by silica gel column chromatography to obtain Compound 28 (223 mg, 65.9%).

Compound 28; Method B
LC/MS retention time=3.16 min.
MS (ESI) m/z=566.20 (M+H)+.

To Compound 28 (60 mg, 0.106 mmol) were added 1,4-dioxane (0.6 ml), PdCl$_2$(dtbpf) (13.81 mg, 0.021 mmol), and Compound 29 (43.9 mg, 0.212 mmol) and 2 mol/L aqueous solution of potassium carbonate (0.106 ml, 0.212 mmol), and the reaction mixture was stirred at 135° C. under microwave irradiation. To the reaction mixture was added a mixed solvent of chloroform and methanol, and the resulting mixture was dried over magnesium sulfate, and then the solvent was removed by concentration under reduced pressure. The obtained residue was purified by silica gel column chromatography to obtain Compound 30 (41.1 mg, 56.0%).

Compound 30; Method C
LC/MS retention time=3.05 min.
MS (ESI) m/z=693.20 (M+H)+.

To Compound 30 (41 mg, 0.059 mmol) was added TFA (1 ml), and the reaction mixture was stirred at room temperature. After completion of the reaction, the TFA was removed by concentration under reduced pressure, followed by dilution in MeOH, and neutralization with an aqueous solution of sodium hydrogencarbonate. Extraction was performed with a mixed solvent of chloroform and methanol, the obtained organic layer was dried over magnesium sulfate, and then the solvent was removed by concentration under reduced pressure. The obtained residue was purified by silica gel column chromatography to obtain Compound (I-1-4) (19.2 mg, 72.4%).

Compound (I-1-4); Method B
LC/MS retention time=1.05 min.
MS (ESI) m/z=449.40 (M+H)+.

Example 7

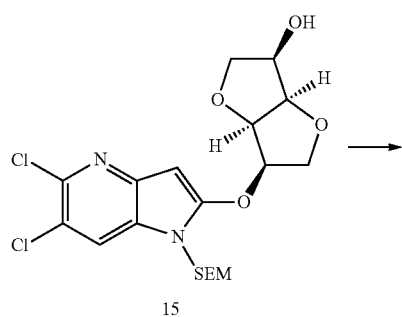

15

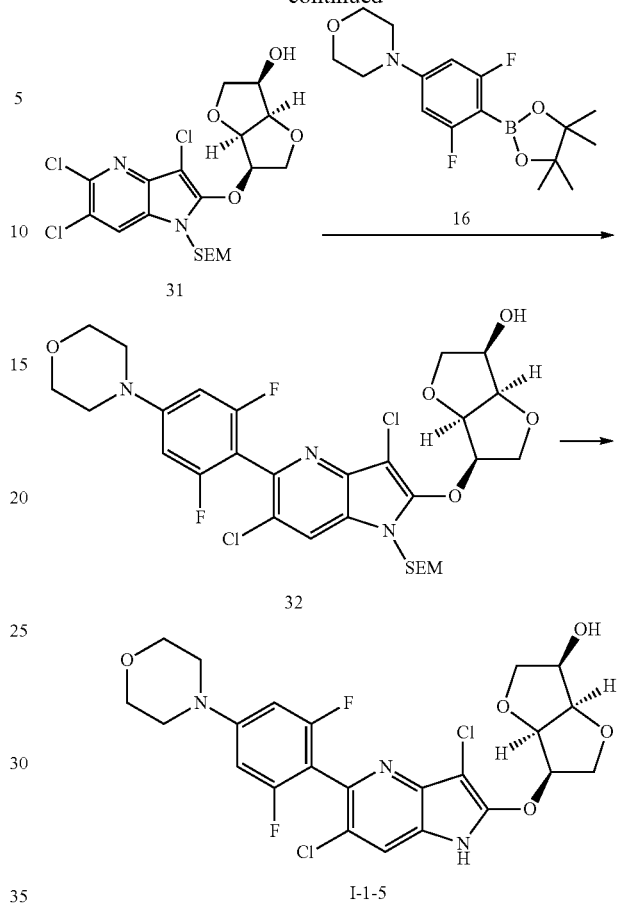

Compound 15 (500 mg, 1.084 mmol) was dissolved in DMF (5 ml), to which was then added NCS (159 mg, 1.192 mmol) under ice cooling, and the reaction mixture was stirred at room temperature. To the reaction mixture was added ethyl acetate, and the organic layer was washed with water and concentrated under reduced pressure. The obtained residue was purified by silica gel column chromatography to obtain Compound 31 (429.5 mg, 79.9%).

Compound 31; Method B
LC/MS retention time=2.58 min.
MS (ESI) m/z=496.95 (M+H)+.

To Compound 31 (150 mg, 0.217 mmol) were added toluene (1.5 ml), 2 mol/L aqueous solution of potassium carbonate (0.190 ml, 0.380 mmol), PdCl$_2$(dtbpf) (33.0 mg, 0.051 mmol), and Compound 16 (124 mg, 0.380 mmol), and the reaction mixture was stirred at 150° C. under microwave irradiation. To the reaction mixture was added a mixed solvent of chloroform and methanol, and the resulting mixture was washed with saturated aqueous NaCl. The obtained organic layer was dried over magnesium sulfate, and then the solvent was removed by concentration under reduced pressure. The obtained residue was purified by silica gel column chromatography to obtain Compound 32 (46 mg, 24.1%).

Compound 32; Method B
LC/MS retention time=2.20 min.
MS (ESI) m/z=658.15 (M+H)+.

Compound (I-1-5) was synthesized from Compound 32 in a similar way as in the case of Compound (I-1-4).

Compound (I-1-5); Method B
LC/MS retention time=1.70 min.
MS (ESI) m/z=528.05 (M+H)+.

Example 8

Example 9

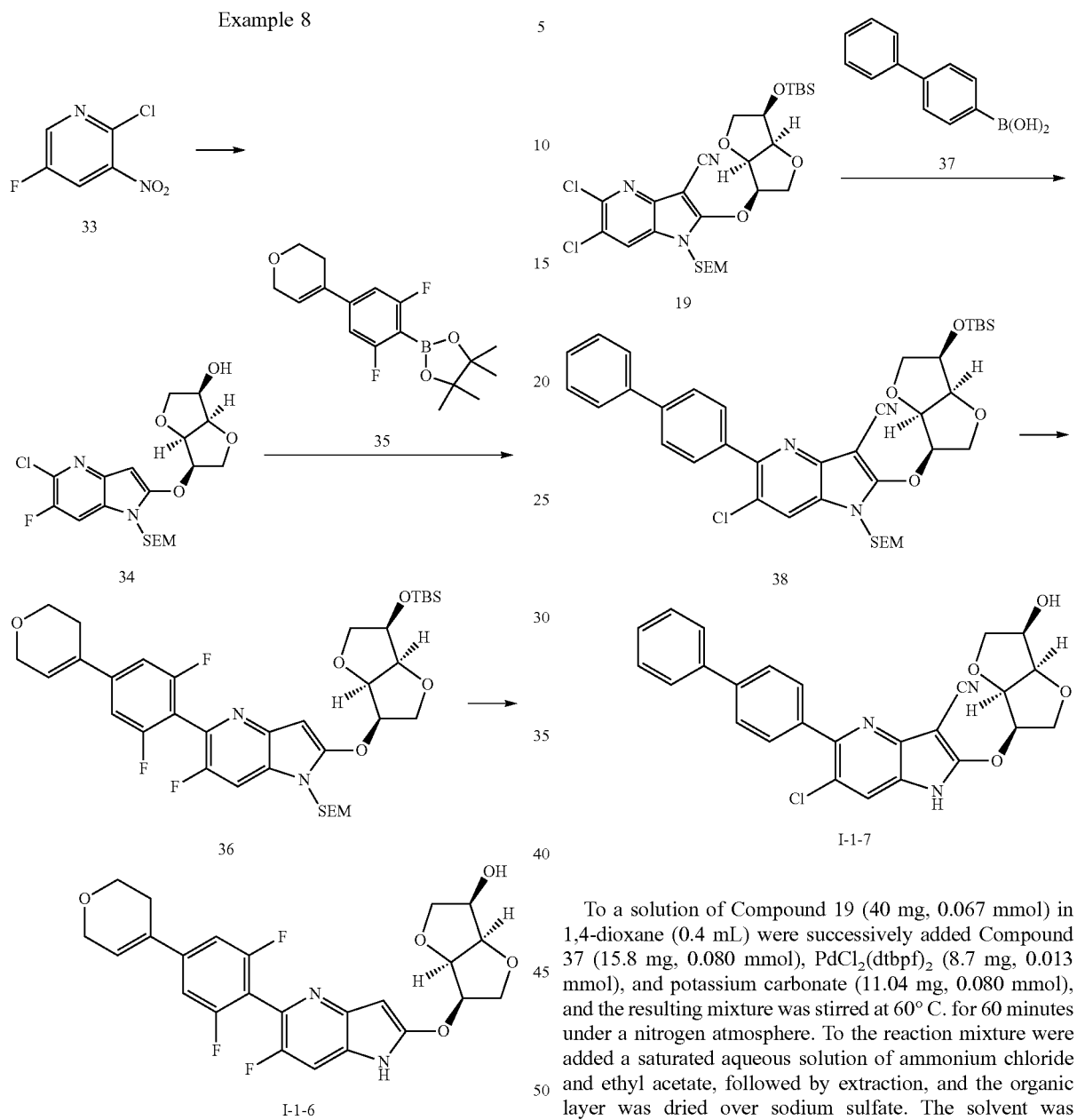

Compound 34 was synthesized from Compound 33 in a similar way as in the case of Compound 25.
Compound 34; Method B
LC/MS retention time=2.26 min.
MS (ESI) m/z=445.00 (M+H)+.
Compound 36 was synthesized from Compound 34 in a similar way as in the case of Compound 32.
Compound 36; Method B
LC/MS retention time=2.42 min.
MS (ESI) m/z=605.15 (M+H)+.
Compound (I-1-6) was synthesized from Compound 36 in a similar way as in the case of Compound (I-1-4).
Compound (I-1-6); Method B
LC/MS retention time=1.43 min.
MS (ESI) m/z=475.15 (M+H)+.

To a solution of Compound 19 (40 mg, 0.067 mmol) in 1,4-dioxane (0.4 mL) were successively added Compound 37 (15.8 mg, 0.080 mmol), PdCl$_2$(dtbpf)$_2$ (8.7 mg, 0.013 mmol), and potassium carbonate (11.04 mg, 0.080 mmol), and the resulting mixture was stirred at 60° C. for 60 minutes under a nitrogen atmosphere. To the reaction mixture were added a saturated aqueous solution of ammonium chloride and ethyl acetate, followed by extraction, and the organic layer was dried over sodium sulfate. The solvent was removed under reduced pressure, and the obtained residue was purified by silica gel column chromatography to obtain Compound 38 (37.6 mg, 0.052 mmol, 78.6%) as a brown solid.

Compound 38; Method A
LC/MS retention time=3.81 min.
MS (ESI) m/z=718.3 (M+H)+.

To a solution of Compound 38 (37.6 mg, 0.052 mmol) in dichloromethane (0.38 mL) was added trifluoroacetic acid (0.36 mL, 4.71 mmol), and the reaction mixture was stirred at room temperature for 4 hours. To the reaction mixture were added a saturated aqueous solution of sodium bicarbonate and ethyl acetate, followed by extraction, and the organic layer was dried over sodium sulfate. The solvent was removed under reduced pressure, and the obtained residue was purified by silica gel column chromatography to obtain Compound (I-1-7) (12.7 mg, 0.052 mmol, 51.2%) as a slightly yellowish white solid.

Compound (I-1-7); $^1$H-NMR (DMSO-D$_6$) δ: 3.78 (t, J=8.0 Hz, 1H), 4.01 (dd, J=12.0, 4.0 Hz, 1H), 4.11 (brd, J=4.0 Hz, 2H), 4.34 (t, J=4.0 Hz, 1H), 4.91 (t, J=4.0 Hz, 1H), 5.09 (d, J=8.0 Hz, 1H), 5.41 (brs, 1H), 7.39-7.43 (m, 1H), 7.49-7.53 (m, 2H), 7.75-7.84 (m, 7H).

Method A

LC/MS retention time=2.23 min.

MS (ESI) m/z=474.1 (M+H)+.

Example 10

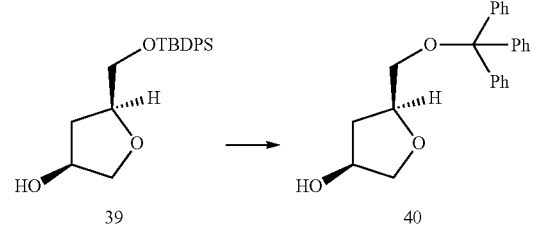

To a solution of Compound 39 (4.52 g, 12.7 mmol) in methylene chloride (45 ml) were successively added benzoyl chloride (4.42 ml, 38.0 mmol), triethylamine (5.62 ml, 40.6 mmol), and DMAP (0.310 g, 2.54 mmol) under ice cooling, and the reaction mixture was stirred at room temperature for 2 hours. The reaction mixture was quenched with a saturated aqueous solution of ammonium chloride, and then extracted with methylene chloride, which was then dried over sodium sulfate. The solvent was removed under reduced pressure, the obtained residue was dissolved in THF (45 ml), to which was then added a solution of TBAF in THF (a 1 mol/L solution, 25.4 mL, 25.4 mmol) under ice cooling, and the resulting mixture was stirred overnight at room temperature. The reaction mixture was concentrated, and the obtained crude product (86 g) was used directly in the next reaction. To a solution of the product (2.86 g) in methylene chloride (30 ml) were successively added trityl chloride (5.38 g, 19.3 mmol), triethylamine (3.57 ml, 25.7 mmol), and DMAP (0.157 g, 1.29 mmol) at room temperature, and the reaction mixture was stirred at room temperature for 2 hours. To the residue after the reaction mixture was concentrated were added MeOH (30 ml), followed by addition of a 2 mol/L aqueous solution of sodium hydroxide (19.3 ml, 38.6 mmol) under ice cooling, and the resulting mixture was stirred at room temperature for 2 hour. The reaction mixture was extracted with ethyl acetate, which was then washed with saturated aqueous ammonium chloride. The solvent was removed under reduced pressure, and the obtained residue was purified by silica gel column chromatography to obtain Compound 40 (2.76 g, 7.67 mmol, 60% in 4 steps) as a white solid.

Compound 40; $^1$H-NMR (CDCl$_3$) δ: 1.77-1.80 (m, 1H), 2.21-2.24 (m, 1H), 3.06 (dd, J=10.3, 3.3 Hz, 1H), 3.40 (d, J=10.0 Hz, 1H), 3.57 (dd, J=10.2, 2.9 Hz, 1H), 3.71 (dd, J=9.4, 3.4 Hz, 1H), 4.00 (d, J=9.3 Hz, 1H), 4.12-4.17 (m, 1H), 4.32 (t, J=4.5 Hz, 1H), 7.24-7.25 (m, 3H), 7.30-7.33 (m, 6H), 7.45-7.46 (m, 6H).

Example 11

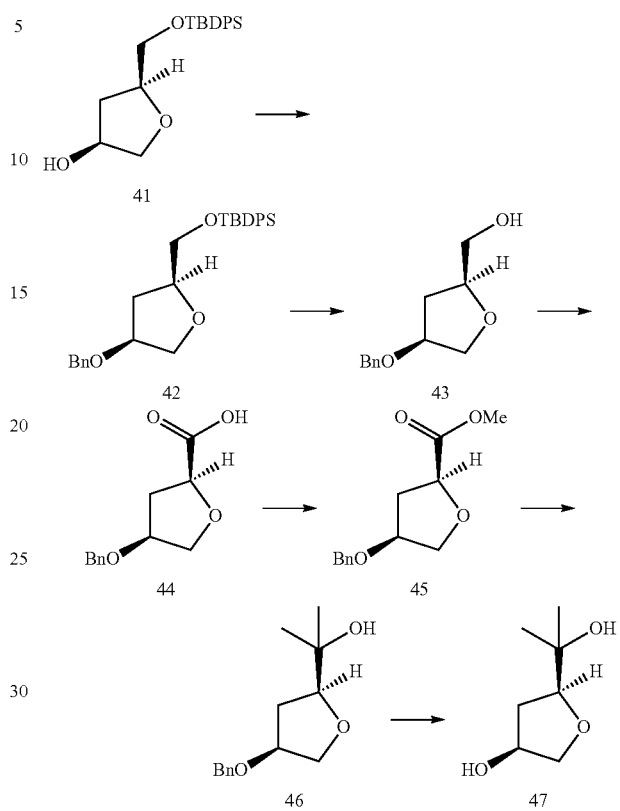

To a solution of Compound 41 (3.50 g, 9.81 mmol) and benzyl bromide (2.69 g, 15.7 mmol) in THF (35 ml) was added KOt-Bu (1.43 g, 12.8 mmol) under ice cooling, and the reaction mixture was stirred under ice cooling for 2 hours. The reaction mixture was quenched with a saturated aqueous solution of ammonium chloride, and then extracted with MTBE, which was then washed with saturated aqueous NaCl. The organic layer was dried over sodium sulfate, and after that, the solvent was removed under reduced pressure, and the obtained residue was purified by silica gel column chromatography to obtain Compound 42 (3.28 g, 7.34 mmol, 75%) as a yellow oil.

Compound 42; LC-MS: m/z=357 [M+H]+

To a solution of Compound 42 (3.28 g, 7.34 mmol) in THF (33 ml) was added a solution of TBAF in THF (1 mol/L solution, 8.82 ml, 8.82 mmol) at room temperature, and the reaction mixture was stirred at room temperature for 3 hours. The reaction mixture was quenched with a saturated aqueous solution of ammonium chloride, and then extracted with ethyl acetate, which was then washed with saturated aqueous NaCl. The organic layer was dried over sodium sulfate, and then the solvent was removed under reduced pressure, and the obtained residue was purified by silica gel column chromatography to obtain Compound 43 (1.28 g, 6.16 mmol, 84%) as a colorless oil.

Compound 43; LC-MS: m/z=209 [M+H]+

To a solution of Compound 43 (1.28 g, 6.16 mmol) in methylene chloride (25 ml) were successively added water (12.5 ml), PhI(OAc)$_2$ (4.36 g, 13.5 mmol), and TEMPO (0.192 g, 1.23 mmol) at room temperature, and the reaction mixture was stirred at room temperature for 3 hours. The reaction mixture was quenched with a 10% aqueous solution of sodium thiosulfate, and then the solvent was removed under reduced pressure. The residue was extracted with ethyl acetate, which was then washed with saturated aqueous NaCl, followed by drying over sodium sulfate. The solvent was removed under reduced pressure, and the obtained residue was purified by silica gel column chromatography to obtain Compound 44 (1.06 g, 4.77 mmol, 78%) as a yellow oil.

Compound 44; LC-MS: m/z=223 [M+H]+

To a solution of Compound 44 (1.20 g, 5.40 mmol) in methanol (24 ml) was added thionyl chloride (1.60 g, 13.5 mmol) under ice cooling, and the reaction mixture was stirred overnight at room temperature. The reaction mixture was concentrated, followed by addition of ethyl acetate, and the resulting mixture was washed successively with a saturated aqueous solution of sodium hydrogencarbonate and with saturated aqueous NaCl. The organic layer was dried over sodium sulfate, the solvent was removed under reduced pressure, and the obtained residue was purified by silica gel column chromatography to obtain Compound 45 (1.20 g, 5.08 mmol, 94%) as a yellow oil.

Compound 45; LC-MS: m/z=237 [M+H]+

To a solution of Compound 45 (1.00 g, 4.24 mmol) in THF (20 ml) was added methylmagnesium bromide (3 mol/L solution, 7.06 ml, 21.2 mmol) under ice cooling, and the reaction mixture was stirred at room temperature for 4 hours. The reaction mixture was quenched with saturated ammonium chloride, followed by extraction with ethyl acetate. The organic layer was washed with saturated aqueous NaCl and dried over sodium sulfate, and the solvent was removed under reduced pressure. The obtained residue was purified by silica gel column chromatography to obtain Compound 46 (802 mg, 3.39 mmol, 80%) as a yellow oil.

Compound 46; LC-MS: m/z=146 [M−90]+

To a solution of Compound 46 (802 mg, 3.39 mmol) in MeOH (16 ml) and ethyl acetate (16 ml) was added Pd/C (10%, 802 mg), and the resulting mixture was stirred overnight at room temperature under hydrogen gas atmosphere. The reaction mixture was filtered, and after that, the solvent was removed under reduced pressure to obtain Compound 47 (442 mg, 3.02 mmol, 89%) as a yellow oil.

Compound 47; $^1$H-NMR (CDCl$_3$) δ: 1.19 (s, 3H), 1.36 (s, 3H), 1.99-1.94 (m, 1H), 2.23-2.16 (m, 1H), 3.70 (dd, J=3.6, 10.0 Hz, 1H), 3.81 (dd, J=4.0, 9.2 Hz, 1H), 3.94 (d, J=9.2 Hz, 1H), 4.33 (t, J=4.4 Hz, 1H).

Example 12

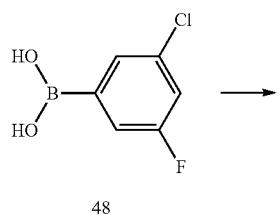

48

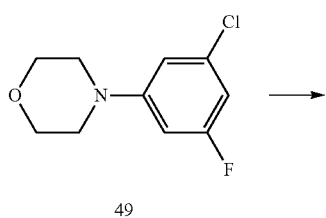

49

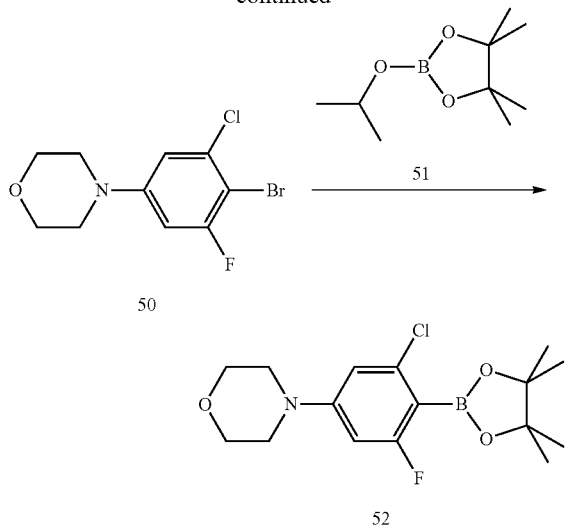

To a solution of Compound 48 (4.62 g, 26.5 mmol) in methylene chloride (69 ml) were successively added morpholine (4.62 ml, 53.0 mmol), triethylamine (7.35 ml, 53.0 mmol), MS4A (6.00 g), and Cu(OAc)$_2$ (7.22 g, 39.7 mmol) at room temperature, and the reaction mixture was stirred at room temperature for 2 days. The reaction mixture was filtered, and the solvent was removed under reduced pressure. The obtained residue was purified by silica gel column chromatography to obtain Compound 49 (971 mg, 4.50 mmol, 17%) as a yellow oil.

Compound 49; $^1$H-NMR (CDCl$_3$) δ: 3.15-3.16 (m, 4H), 3.83-3.84 (m, 4H), 6.44-6.47 (m, 1H), 6.56-6.58 (m, 1H), 6.65 (s, 1H).

To a solution of Compound 49 (750 mg, 3.48 mmol) in acetonitrile (7.5 ml) was added NBS (681 mg, 3.83 mmol) under ice cooling, and the reaction mixture was stirred at room temperature for 40 minutes. The reaction mixture was quenched with a saturated aqueous solution of sodium hydrogencarbonate, and then extracted with ethyl acetate, and the solvent was removed under reduced pressure. The obtained residue was purified by silica gel column chromatography to obtain Compound 50 (960 mg, 3.26 mmol, 94%) as a colorless oil.

Compound 50; $^1$H-NMR (CDCl$_3$) δ: 3.13-3.15 (m, 4H), 3.83-3.84 (m, 4H), 6.54-6.57 (m, 1H), 6.78-6.78 (m, 1H).

To a solution of Compound 50 (960 mg, 3.26 mmol) in THF (19 ml) was added n-BuLi (a 1.65 M solution in hexane, 2.17 ml, 3.59 mmol) at −78° C., and the reaction mixture was stirred at −78° C. for 1 hour. To the reaction mixture was added Compound 51 (0.988 ml, 4.89 mmol) at −78° C., and the resulting mixture was gradually warmed to room temperature over 1.5 hours and stirred overnight at room temperature. The reaction mixture was quenched with a saturated aqueous solution of ammonium chloride, and then extracted with ethyl acetate, which was then dried over sodium sulfate. The solvent was removed under reduced pressure, and the obtained residue was purified by silica gel column chromatography to obtain Compound 52 (512 mg, 1.50 mmol, 44%) as a white solid.

Compound 52; $^1$H-NMR (CDCl$_3$) δ: 1.38 (s, 13H), 3.16-3.17 (m, 4H), 3.81-3.82 (m, 4H), 6.38-6.41 (m, 1H), 6.63-6.63 (m, 1H).

Example 13

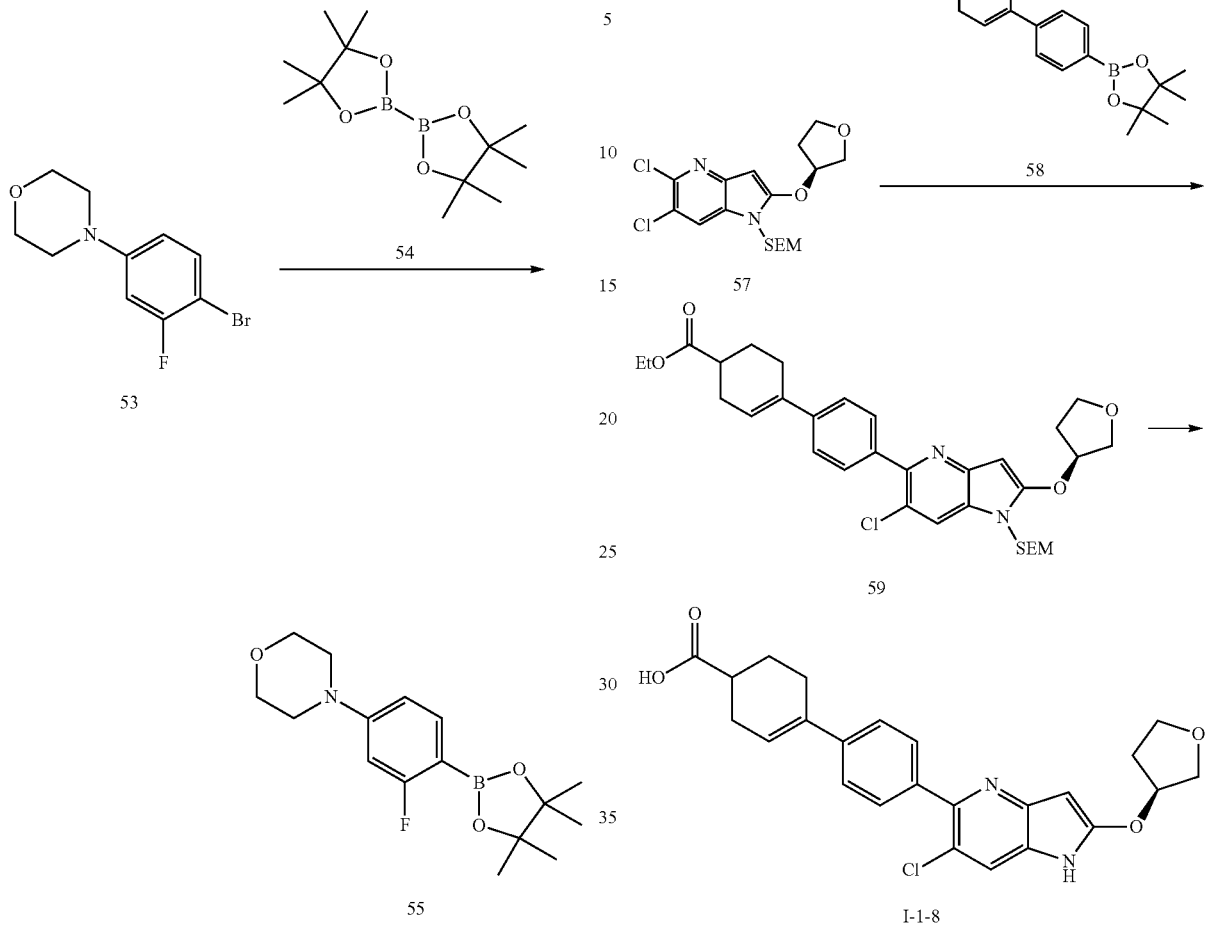

To Compound 53 (800 mg, 3.08 mmol) were added 1,4-dioxane (10 ml), Compound 54 (937 mg, 3.69 mmol), PdCl$_2$(dppf)CH$_2$Cl$_2$ (251 mg, 0.308 mmol), and potassium acetate (906 mg, 9.23 mmol), and the resulting mixture was stirred at 130° C. under microwave irradiation. The reaction mixture was filtered through Celite, and the filtrate was concentrated under reduced pressure. The obtained residue was purified by silica gel column chromatography to obtain Compound 55 (771 mg, 81.6%).

Example 14

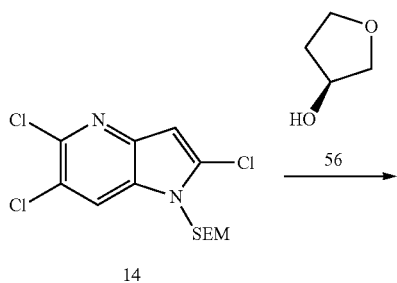

Compound 14 (1000 mg, 2.84 mmol) and Compound 56 (827 mg, 9.38 mmol) were dissolved in DMF (5 ml), to which was then added 60 wt % NaH (341 mg, 8.53 mmol) under ice cooling, and the resulting mixture was stirred at 0° C. for 5 minutes. After that, a solution of Compound 11 (28 mg, 0.058 mmol) dissolved in DMF (1 ml) was added to the reaction mixture under ice cooling, and the mixture was stirred at room temperature. After completion of the reaction, the reaction mixture was neutralized with 2 mol/L aqueous solution of hydrochloric acid, followed by extraction of the desired product with ethyl acetate. The organic layer was washed with water, dried over magnesium sulfate, and then the solvent was removed by concentration under reduced pressure. Diisopropyl ether was added to the obtained residue, whereby the product was crystallized to obtain Compound 57 (594 mg, 51.8%).

Compound 57; Method B
LC/MS retention time=2.90 min.
MS (ESI) m/z=403.10 (M+H)+.

Compound 59 was obtained from Compound 57 in a similar way as in the case of Compound 32.

Compound 59; Method B
LC/MS retention time=3.12 min.
MS (ESI) m/z=597.20 (M+H)+.

Compound 59 (110 mg, 0.184 mmol) was dissolved in THF (1 ml) and methanol (1 ml), followed by addition of 2 mol/L aqueous solution of sodium hydroxide (0.5 ml), and the resulting mixture was stirred at room temperature. After completion of the reaction, the reaction mixture was neutralized with 2 mol/L aqueous solution of hydrochloric acid, and extracted with a mixed solvent of chloroform and methanol. The obtained organic layer was dried over magnesium sulfate, and then the solvent was removed by concentration under reduced pressure. To the obtained residue was added TFA (1 ml), and the reaction mixture was stirred at room temperature. After completion of the reaction, the TFA was removed by concentration under reduced pressure, and the residue was diluted in MeOH, followed by addition of an aqueous solution of sodium hydrogencarbonate. The reaction mixture was neutralized with 2 mol/L aqueous solution of hydrochloric acid, and extracted with a mixed solvent of chloroform and methanol. The obtained organic layer was dried over magnesium sulfate, and then the solvent was removed by concentration under reduced pressure. The obtained residue was purified by reverse-phase column chromatography to obtain Compound (I-1-8) (20.8 mg, 25.7%).

Compound (I-1-8); Method B

LC/MS retention time=1.56 min.

MS (ESI) m/z=439.15 (M+H)+.

Example 15

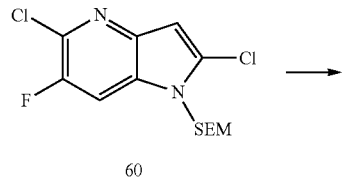

60

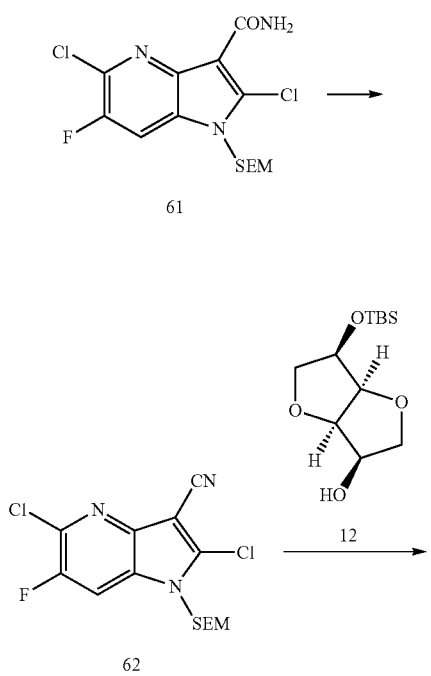

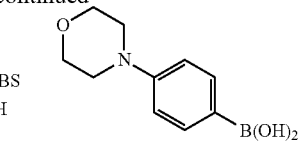

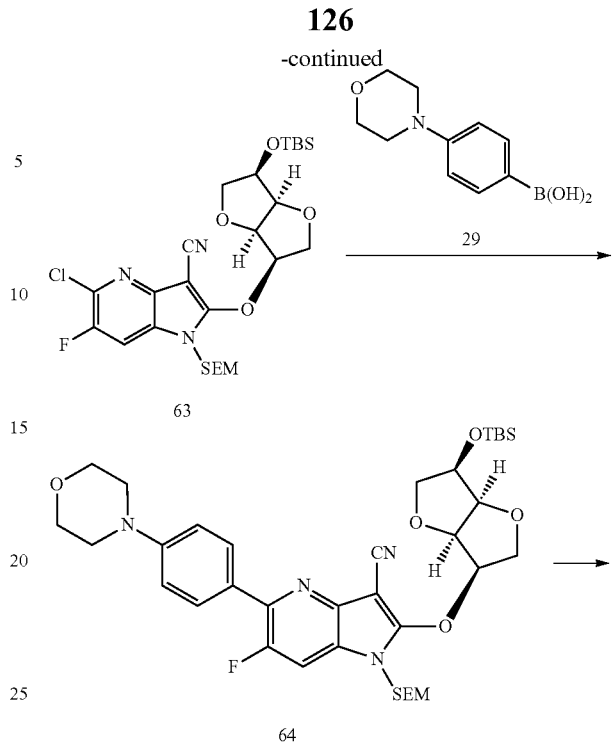

Compound 61 was synthesized from Compound 60 in a similar way that Compound 10 was synthesized from Compound 7.

Compound 61; Method B

LC/MS retention time=2.40 min.

MS (ESI) m/z=378.20 (M+H)+.

Compound 61 (149 mg, 0.395 mmol) was dissolved in pyridine (0.5 ml), to which was then added trifluoroacetic anhydride (84 µl, 0.593 mmol) under ice cooling, and the reaction mixture was stirred at room temperature. During the reaction, additional trifluoroacetic anhydride (84 µl, 0.593 mmol) was added under ice cooling, and the reaction mixture was further stirred at room temperature. After completion of the reaction, ethyl acetate was added to the reaction mixture, followed by washing with 2 mol/L aqueous solution of hydrochloric acid and water. The obtained organic layer was dried over magnesium sulfate, and then the solvent was removed by concentration under reduced pressure. The obtained residue was purified by silica gel column chromatography to obtain Compound 62 (121.2 mg, 85.2%).

Compound 62; Method B

LC/MS retention time=2.74 min.

MS (ESI) m/z=360.00 (M+H)+.

Compound 62 (115 mg, 0.319 mmol) and Compound 12 (125 mg, 0.479 mmol) were dissolved in DMF (1.0 ml), followed by addition of 60 wt % sodium hydride (15.3 mg, 0.383 mmol) under ice cooling, and the resulting mixture was stirred under ice cooling. After completion of the reaction, ethyl acetate was added to the reaction mixture, followed by washing with aqueous NaCl. The obtained organic layer was dried over magnesium sulfate, and then the solvent was removed by concentration under reduced pressure. The obtained residue was purified by silica gel column chromatography to obtain Compound 63 (246.9 mg).

Compound 63; Method B

LC/MS retention time=3.24 min.

MS (ESI) m/z=584.15 (M+H)+.

To Compound 63 (0.045 mmol) were added 1,4-dioxane (0.5 ml), $PdCl_2(dtbpf)$ (5.8 mg, 0.0089 mmol), Compound 29 (18.6 mg, 0.090 mmol), and 2 mol/L aqueous solution of potassium carbonate (44.9 µl, 0.090 mmol), and the reaction mixture was stirred at 110° C. After completion of the reaction, the solvent was removed by concentration under reduced pressure. The obtained residue was purified by silica gel column chromatography to obtain Compound 64 (8.7 mg, 27.2%).

Compound 64; Method B

LC/MS retention time=3.32 min.

MS (ESI) m/z=711.30 (M+H)+.

To Compound 64 (8.7 mg, 0.012 mmol) was added TFA (1 ml), and the reaction mixture was stirred at room temperature. After completion of the reaction, the TFA was removed by concentration under reduced pressure, and residue was diluted in methanol, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound (I-2-1) (4.6 mg, 80.6%).

Compound (I-2-1); Method B

LC/MS retention time=1.52 min.

MS (ESI) m/z=467.15 (M+H)+.

Example 16

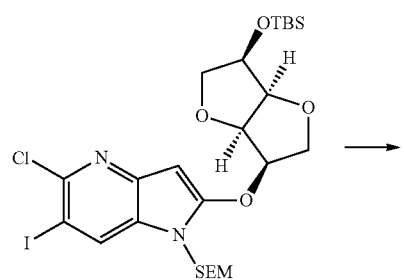

26

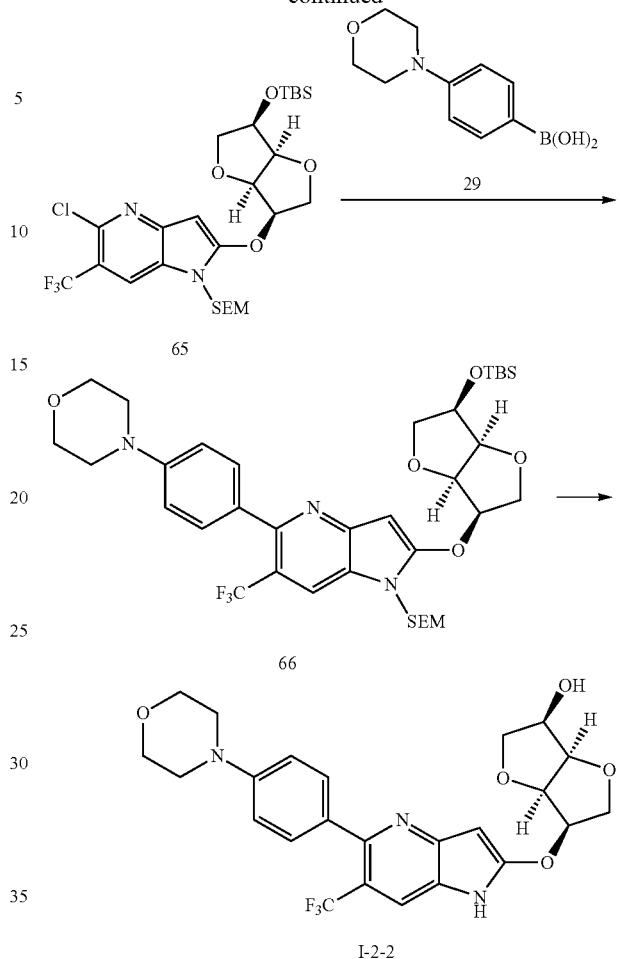

To Compound 26 (250 mg, 0.375 mmol) and copper iodide (214 mg, 1.124 mmol) were added DMF (2.5 ml), and then potassium fluoride (65.3 mg, 1.124 mmol) and (trimethylsilyl)trifluoromethane (179 µl, 1.124 mmol), and the reaction mixture was stirred at 100° C. in a closed vessel. After completion of the reaction, the reaction mixture was cooled to room temperature, followed by addition of ethyl acetate and filtration through Celite. To the obtained filtrate was added water, and the mixture was filtered again through Celite. The obtained organic layer was washed with water and dried over magnesium sulfate, and then the solvent was removed by concentration under reduced pressure. The obtained residue was purified by silica gel column chromatography to obtain Compound 65 (87 mg, 38.1%).

Compound 65; Method B

LC/MS retention time=3.33 min.

MS (ESI) m/z=609.15 (M+H)+.

To Compound 65 (50 mg, 0.082 mmol) were added 1,4-dioxane (0.5 ml), $PdCl_2(dtbpf)$ (10.7 mg, 0.016 mmol), Compound 29 (34.0 mg, 0.164 mmol), and 2 mol/L aqueous solution of potassium carbonate (82 µl, 0.164 mmol), and the resulting mixture was stirred at 135° C. under microwave irradiation. Additional same amounts of $PdCl_2(dtbpf)$, Compound 29, and 2 mol/L aqueous solution of potassium carbonate as those at which they were initially added were added, and the resulting mixture was stirred at 150° C. under microwave irradiation. After completion of the reaction, the reaction mixture was dried over magnesium sulfate, which was then filtered off and washed with a mixed solvent of chloroform and methanol, and then the solvent was removed by concentration under reduced pressure. The obtained residue was purified by silica gel column chromatography to obtain Compound 66 (47.6 mg, 78.8%).

Compound 66; Method B

LC/MS retention time=3.19 min.

MS (ESI) m/z=736.25 (M+H)+.

To Compound 66 (47 mg, 0.064 mmol) was added TFA (2 ml), and the reaction mixture was stirred at room temperature. After completion of the reaction, the TFA was removed by concentration under reduced pressure, and residue was diluted in methanol, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound (I-2-2) (26.7 mg, 85.1%).

Compound (I-2-2); Method B

LC/MS retention time=1.11 min.

MS (ESI) m/z=492.15 (M+H)+.

Example 17

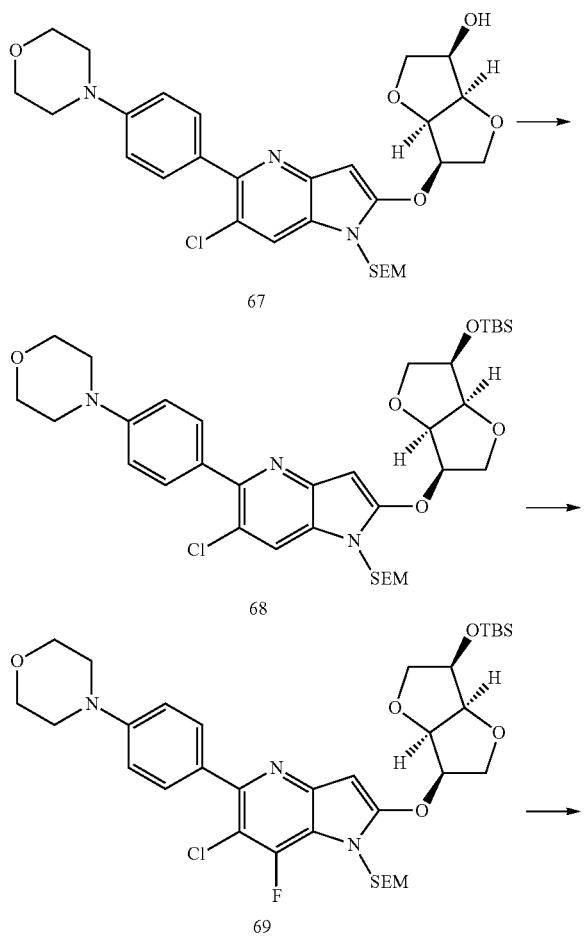

-continued

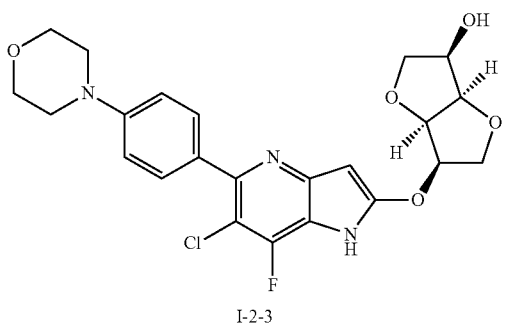

I-2-3

Compound 67 (380 mg, 0.646 mmol) and imidazole (66 mg, 0.969 mmol) were dissolved in DMF (4 ml), to which was then added tert-butyldimethylsilyl chloride (195 mg, 1.292 mmol), and the resulting mixture was stirred at room temperature. After completion of the reaction, ethyl acetate was added to the reaction mixture, the resulting mixture was washed with water, and the solvent was removed by concentration under reduced pressure. The obtained residue was purified by silica gel column chromatography to obtain Compound 68 (381.5 mg, 84.1%).

Compound 68; Method B

LC/MS retention time=3.12 min.

MS (ESI) m/z=702.25 (M+H)+.

Compound 68 (100 mg, 0.142 mmol) was dissolved in THF (1 mL), and the mixture was cooled to −78° C., followed by addition of TMEDA (23.6 µl, 0.157 mmol) and a solution of n-butyllithium in hexane (98 µl, 0.157 mmol), and the resulting mixture was stirred at −78° C. Five minutes later, a solution of NFSI (67.3 mg, 0.214 mmol) dissolved in THF (0.5 ml) was added to the reaction mixture, which was further stirred. A saturated aqueous solution of ammonium chloride was added to the reaction mixture, which was then extracted with ethyl acetate. The organic layer was dried over magnesium sulfate, and then the solvent was removed by concentration under reduced pressure. The obtained residue was purified by silica gel column chromatography to obtain Compound 69 (50.5 mg, 49.2%).

Compound 69; Method B

LC/MS retention time=3.39 min.

MS (ESI) m/z=720.55 (M+H)+.

To Compound 69 (50 mg, 0.069 mmol) was added TFA (1 ml), and the reaction mixture was stirred at room temperature. After completion of the reaction, the TFA was removed by concentration under reduced pressure, and residue was diluted in methanol, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by reverse-phase chromatography to obtain Compound (I-2-3) (13.5 mg, 40.9%).

Compound (I-2-3); Method B

LC/MS retention time=1.26 min.

MS (ESP) m/z=476.15 (M+H)+.

Example 18

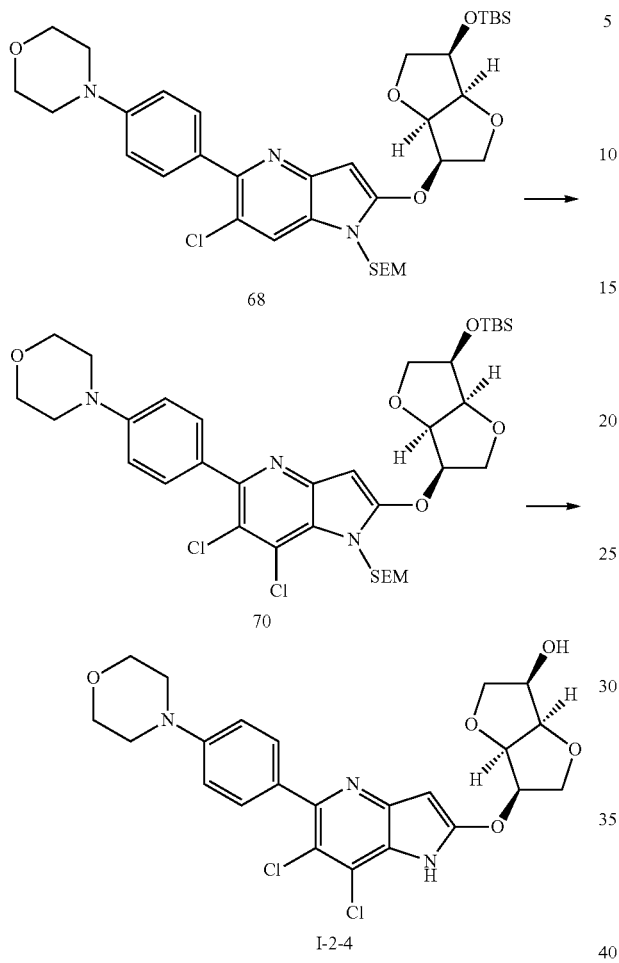

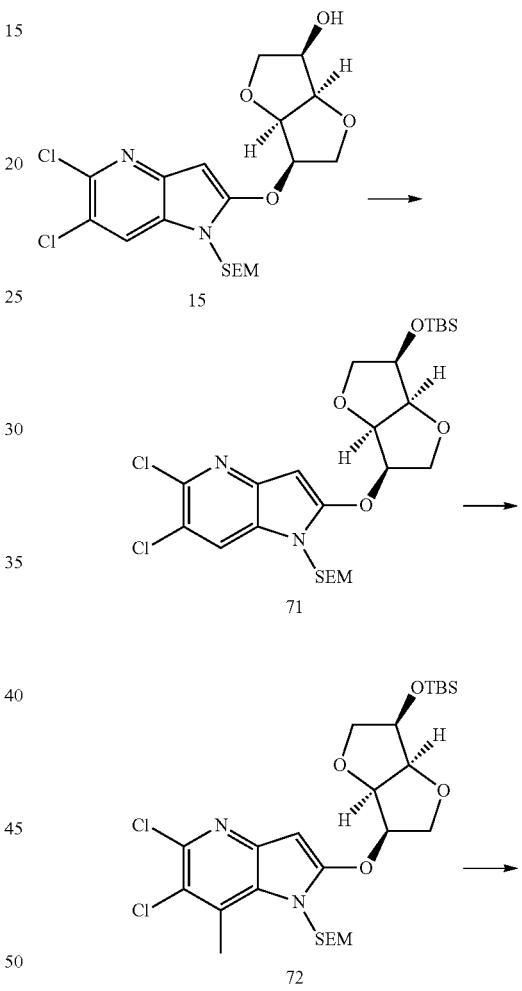

Compound 68 (100 mg, 0.142 mmol) was dissolved in THF (1 ml), and the mixture was cooled to −78° C., followed by addition of TMEDA (70.8 µl, 0.471 mmol), a solution of n-butyllithium in hexane (784 µl, 1.256 mmol), and a solution of hexachloroethane (404.8 mg, 1.712 mmol) in THF, and the resulting mixture was stirred. After completion of the reaction, a saturated aqueous solution of ammonium chloride was added to the reaction mixture, which was then extracted with ethyl acetate. The organic layer was dried over magnesium sulfate, and then the solvent was removed by concentration under reduced pressure. The obtained residue was purified by silica gel column chromatography to obtain Compound 70 (79.8 mg, 76.1%).

Compound 70; Method B
LC/MS retention time=3.47 min.
MS (ESI) m/z=736.20 (M+H)+.

To Compound 70 (79 mg, 0.107 mmol) was added TFA (1 ml), and the reaction mixture was stirred at room temperature. After completion of the reaction, the TFA was removed by concentration under reduced pressure, and residue was diluted in methanol, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by reverse-phase chromatography to obtain Compound (I-2-4) (3.4 mg, 6.4%).

Compound (I-2-4); Method B
LC/MS retention time=1.36 min.
MS (ESI) m/z=492.05 (M+H)+.

Example 19

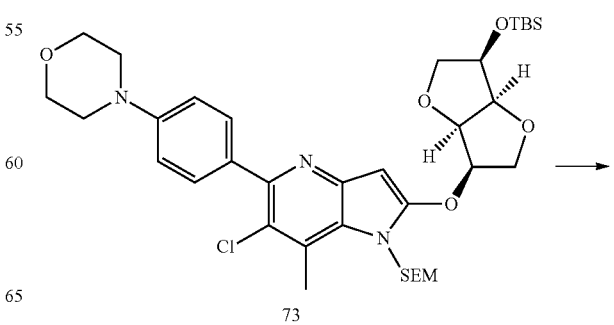

-continued

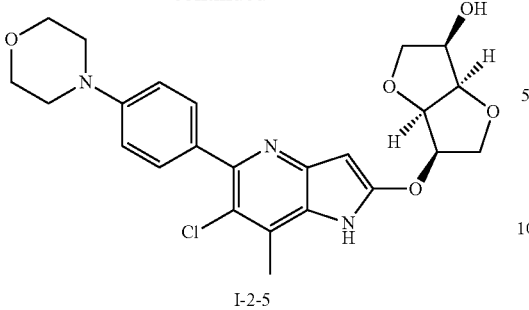

I-2-5

Compound 71 was synthesized from Compound 15 in a similar that Compound 68 was synthesized from Compound 67.

Compound 71; Method B
LC/MS retention time=3.34 min.
MS (ESI) m/z=576.80 (M+H)+.

Compound 71 (100 mg, 0.174 mmol) was dissolved in THF (1 ml), and the mixture was cooled to −78° C., followed by addition of TMEDA (39.3 μl, 0.261 mmol) and a solution of n-butyllithium in hexane (163 μl, 0.261 mmol), and the resulting mixture was stirred at −78° C. Fifteen minutes later, a solution of methyl iodide (21.7 μl, 0.347 mmol) dissolved in THF (0.1 ml) was added to the reaction mixture, which was further stirred. After completion of the reaction, a saturated aqueous solution of ammonium chloride was added to the reaction mixture, which was then extracted with ethyl acetate. The organic layer was dried over magnesium sulfate, and then the solvent was removed by concentration under reduced pressure. The obtained residue was purified by silica gel column chromatography to obtain Compound 72 (88.8 mg, 86.7%).

Compound 72; Method B
LC/MS retention time=3.46 min.
MS (ESI) m/z=589.25 (M+H)+.

To Compound 72 (85 mg, 0.144 mmol) were added 1,4-dioxane (0.5 ml), PdCl$_2$(dtbpf) (18.8 mg, 0.029 mmol), Compound 29 (38.8 mg, 0.187 mmol), and 2 mol/L aqueous solution of potassium carbonate (94 μl, 0.187 mmol), and the resulting mixture was stirred at 145° C. under microwave irradiation. After completion of the reaction, the reaction mixture was dried over magnesium sulfate, which was then filtered off and washed with a mixed solvent of chloroform and methanol, and then the solvent was removed by concentration under reduced pressure. The obtained residue was purified by silica gel column chromatography to obtain Compound 73 (43.7 mg, 42.3%).

Compound 73; Method B
LC/MS retention time=2.93 min.
MS (ESI) m/z=716.20 (M+H)+.

To Compound 73 (43 mg, 0.060 mmol) was added TFA (2 ml), and the reaction mixture was stirred at room temperature. After completion of the reaction, the TFA was removed by concentration under reduced pressure, and residue was diluted in methanol, followed by neutralization with au aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound (I-2-5) (21.0 mg, 74.1%).

Compound (I-2-5); Method B
LC/MS retention time=1.18 min.
MS (ESI) m/z=472.15 (M+H)+.

Example 20

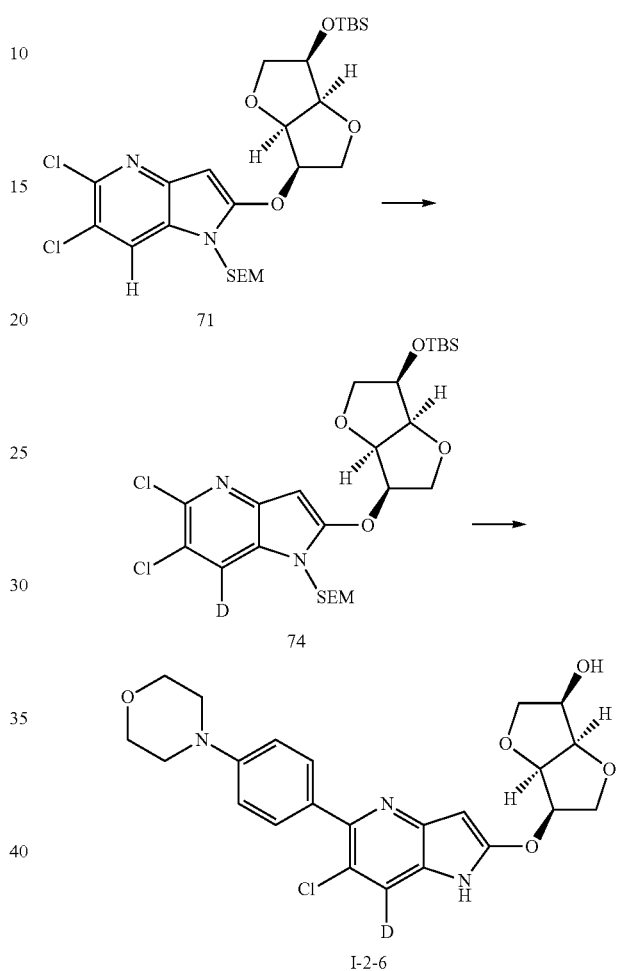

Compound 71 (100 mg, 0.174 mmol) was dissolved in THF (1 ml), and the mixture was cooled to −78° C., followed by addition of TMEDA (28.8 μl, 0.191 mmol) and a solution of n-butyllithium in hexane (119 μl, 0.191 mmol), and the resulting mixture was stirred at −78° C. Fifteen minutes later, methanol-d4 (750 μl) was added to reaction mixture, which was further stirred. After completion of the reaction, water was added to the reaction mixture, which was then extracted with ethyl acetate. The organic layer was dried over magnesium sulfate, and then the solvent was removed by concentration under reduced pressure to obtain Compound 74 (97.6 mg, 97.4%) as a crude product.

Compound 74; Method B
LC/MS retention time=3.35 min.
MS (ESI) m/z=576.90 (M+H)+.

Compound (I-2-6) was synthesized from Compound 74 in a similar way that Compound (I-2-5) was synthesized from Compound 72.

Compound (I-2-6); Method B
LC/MS retention time=1.09 min.
MS (ESI) m/z=459.05 (M+H)+.

Example 21

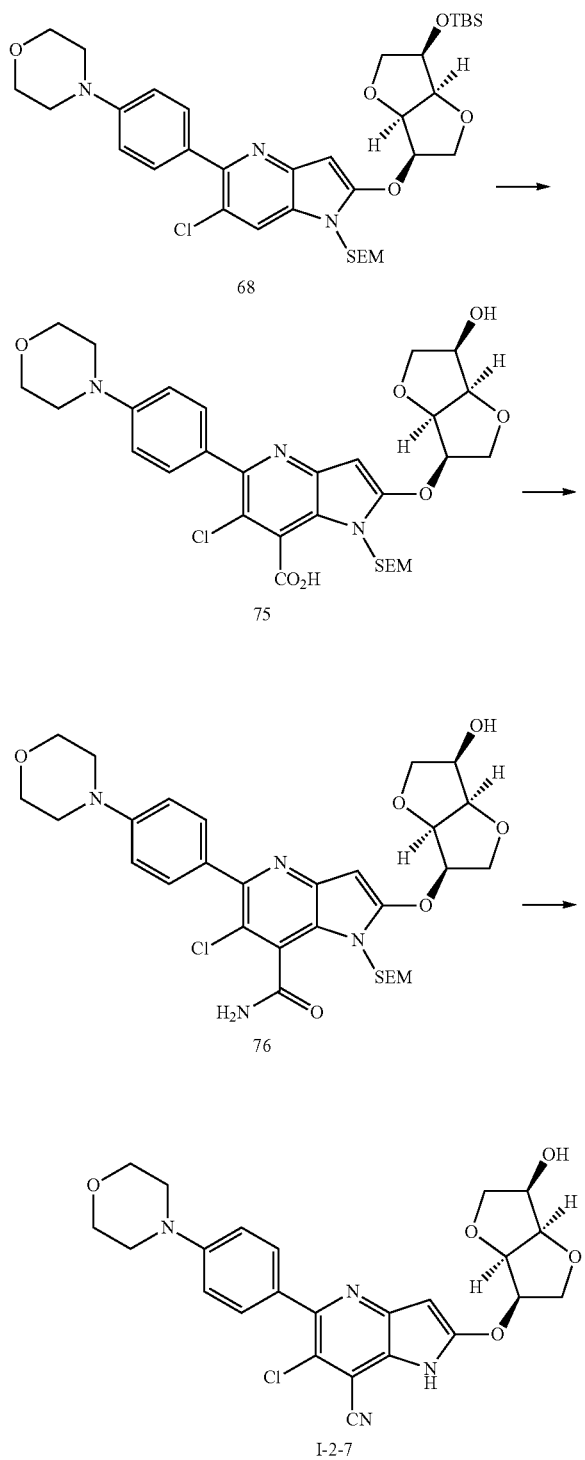

Compound 68 (400 mg, 0.569 mmol) was dissolved in THF (4 ml), and the mixture was cooled to −78° C., followed by addition of TMEDA (284 μl, 1.879 mmol) and a solution of n-butyllithium in hexane (1174 μl, 1.879 mmol), and the resulting mixture was stirred at −78° C. Fifteen minutes later, carbon dioxide was bubbled into the reaction mixture, which was further stirred. After completion of the reaction, a saturated aqueous solution of ammonium chloride was added to the reaction mixture, which was then extracted with ethyl acetate. The organic layer was dried over magnesium sulfate, and then the solvent was removed by concentration under reduced pressure. The obtained residue was purified by silica gel column chromatography to obtain Compound 75 (272 mg, 64.0%).

Compound 75; Method B

LC/MS retention time=2.52 min.

MS (ESI) m/z=746.30 (M+H)+.

Compound 75 (270 mg, 0.362 mmol) was dissolved in THF (3 ml), to which was then added CDI (292.5 mg, 1.8075 mmol), and the reaction mixture was stirred at 50° C. The reaction mixture was concentrated under reduced pressure to remove the solvent. The obtained residue was dissolved in DMF (2 ml), to which was then added CDT (409.5 mg, 2.5305 mmol), and the resulting mixture was stirred at 110° C. After completion of the reaction, water was added to the reaction mixture, which was then extracted with a mixed solvent of ethyl acetate and hexane. The obtained organic layer was washed with water and dried over magnesium sulfate, and then the solvent was removed by concentration under reduced pressure. The obtained residue was dissolved in THF (2 ml), to which was then added 28% aqueous ammonia (2 ml). The reaction mixture was gradually heated from room temperature in a closed vessel, and finally 110° C. under microwave irradiation. After completion of the reaction, the reaction mixture was cooled to room temperature, followed by addition of ethyl acetate and washing with saturated aqueous NaCl. The obtained organic layer was dried over magnesium sulfate, and then the solvent was removed by concentration under reduced pressure. The obtained residue was purified by silica gel column chromatography to obtain Compound 76 (84.7 mg, 41.1%).

Compound 76; Method B

LC/MS retention time=2.74 min.

MS (ESI) m/z=745.25 (M+H)+.

Compound 76 (35 mg, 0.047 mmol) was dissolved in pyridine (3.5 ml), to which was then added trifluoroacetic anhydride (13 μl, 0.094 mmol) at room temperature, and the reaction mixture was stirred at room temperature. During the reaction, additional trifluoroacetic anhydride (13 μl, 0.094 mmol) was added, and the reaction mixture was further stirred at room temperature. After completion of the reaction, ethyl acetate was added to the reaction mixture, followed by washing with 2 mol/L aqueous solution of hydrochloric acid and water. To the obtained residue was added TFA (1 ml), and the reaction mixture was stirred at room temperature. After completion of the reaction, the TFA was removed by concentration under reduced pressure, and residue was diluted in methanol, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound (I-2-7) (17.3 mg, 76.2%).

Compound (I-2-7); Method B

LC/MS retention time=1.58 min.

MS (ESI) m/z=483.15 (M+H)+.

Example 22

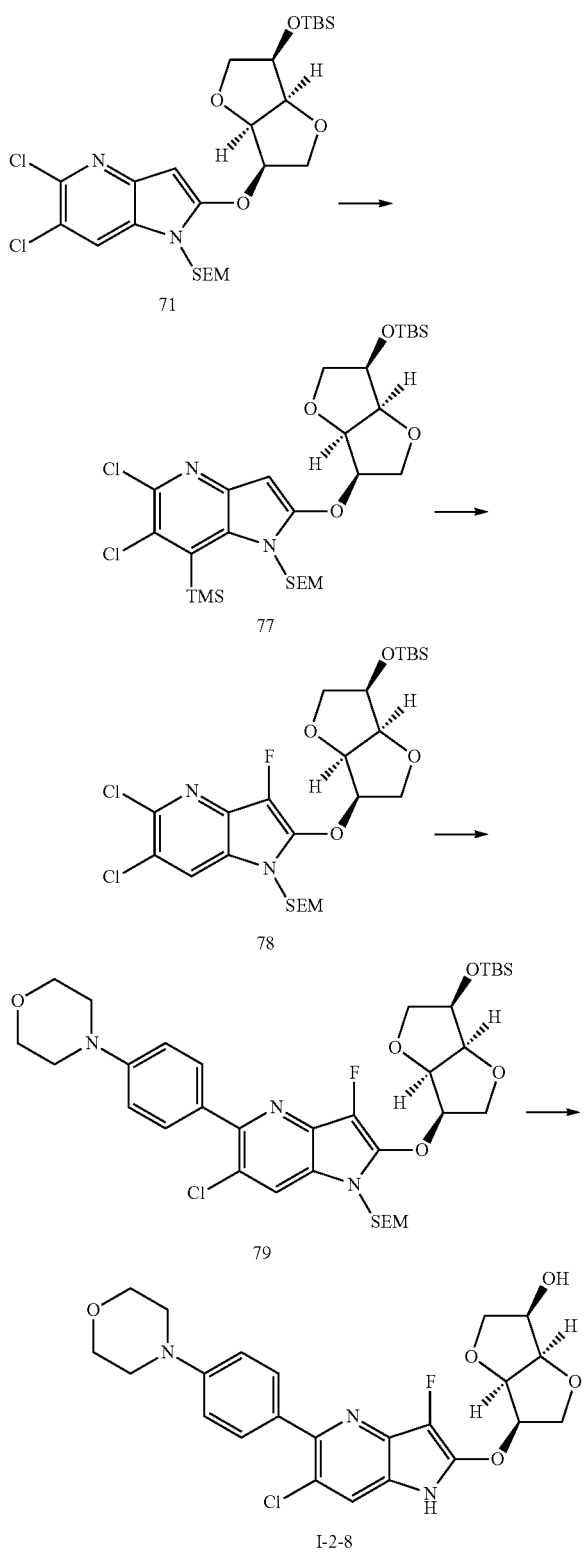

Compound 71 (1000 mg, 1.737 mmol) was dissolved in THF (5 ml), and the mixture was cooled to −78° C., followed by addition of TMEDA (393 μl, 2.61 mmol) and a solution of n-butyllithium in hexane (1629 μl, 2.61 mmol), and the resulting mixture was stirred at −78° C. Thirty minutes later, trimethylsilyl chloride (444 μl, 3.47 mmol) was added to the reaction mixture, which was further stirred. After completion of the reaction, a 1 mol/L aqueous solution of hydrochloric acid was added to the reaction mixture, which was then extracted with ethyl acetate. The obtained organic layer was washed with water and saturated aqueous NaCl and dried over magnesium sulfate, and then the solvent was removed by concentration under reduced pressure. The obtained residue was purified by silica gel column chromatography to obtain Compound 77 (850 mg, 75.5%).

Compound 77; Method B

LC/MS retention time=3.57 min.

MS (ESI) m/z=647.10 (M+H)+.

Compound 77 (678 mg, 1.047 mmol) was dissolved in THF (5 ml), and the mixture was cooled to −78° C., followed by addition of TMEDA (237 μl, 1.57 mmol) and a solution of n-butyllithium in hexane (981 μl, 1.57 mmol), and the resulting mixture was stirred at −78° C. Twenty-five minutes later, a solution of NFSI (660 mg, 2.093 mmol) dissolved in THF (1.5 ml) was added to the reaction mixture, which was further stirred. After completion of the reaction, a 1 mol/L aqueous solution of hydrochloric acid was added to the reaction mixture, which was then extracted with ethyl acetate. After that, to the reaction mixture were added a 2 mol/L aqueous solution of potassium carbonate (2 ml) and methanol (2 ml), and the resulting mixture was stirred at room temperature. After completion of the reaction, ethyl acetate was added to the reaction mixture, and insoluble materials were filtered off. The obtained filtrate was washed with saturated aqueous NaCl and dried over magnesium sulfate, and then the solvent was removed by concentration under reduced pressure. The obtained residue was purified by silica gel column chromatography to obtain Compound 78 (613 mg, 98.7%).

Compound 78; Method B

LC/MS retention time=3.38 min.

MS (ESI) m/z=593.10 (M+H)+.

Compound 79 was synthesized from Compound 78 in a similar way that Compound 73 was synthesized from Compound 72.

Compound 79; Method B

LC/MS retention time=3.38 min.

MS (ESI) m/z=720.55 (M+H)+.

To Compound 79 (96 mg, 0.133 mmol) was added TFA (1 ml), and the reaction mixture was stirred at room temperature. After completion of the reaction, the TFA was removed by concentration under reduced pressure, and residue was diluted in methanol, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by reverse-phase chromatography to obtain Compound (I-2-8) (24.5 mg, 38.6%).

Compound (I-2-8); Method B

LC/MS retention time=1.38 min.

MS (ESI) m/z=476.10 (M+H)+.

Example 23

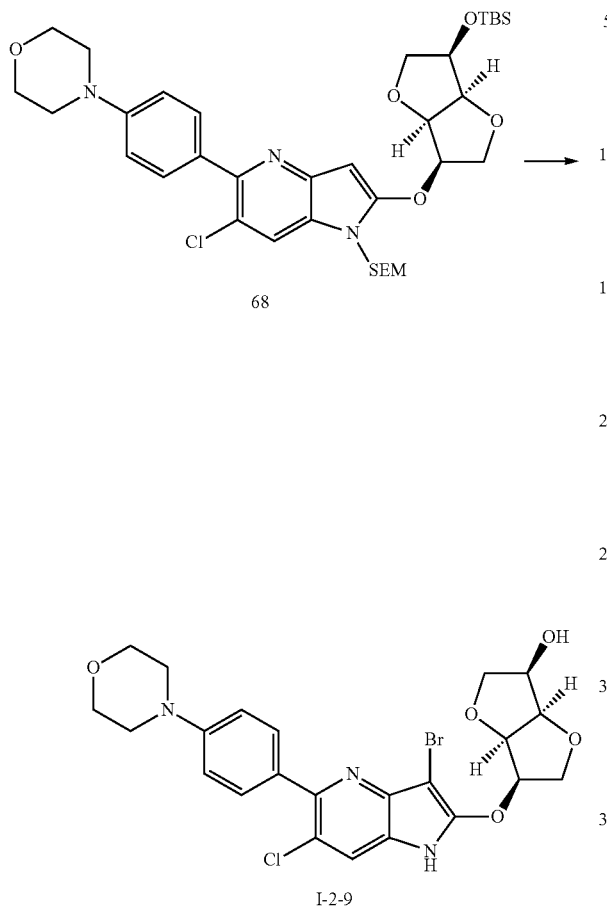

Compound 68 (75 mg, 0.107 mmol) was dissolved in DMF (1 ml), the mixture was cooled to −78° C., followed by addition of NBS (20.9 mg, 0.117 mmol), and the resulting mixture was stirred at −78° C. After completion of the reaction, a 1 mol/L aqueous solution of sodium thiosulfate was added to the reaction mixture, which was then extracted with ethyl acetate. The obtained organic layer was washed with water and dried over magnesium sulfate, and then the solvent was removed by concentration under reduced pressure. To the obtained residue was added TFA (1 ml), and the reaction mixture was stirred at room temperature. After completion of the reaction, the TFA was removed by concentration under reduced pressure, and residue was diluted in methanol, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel chromatography and then by reverse-phase chromatography to obtain Compound (I-2-9) (21.5 mg, 37.4%).

Compound (I-2-9); Method B
LC/MS retention time=1.54 min.
MS (ESI) m/z=537.85 (M+H)+.

Example 24

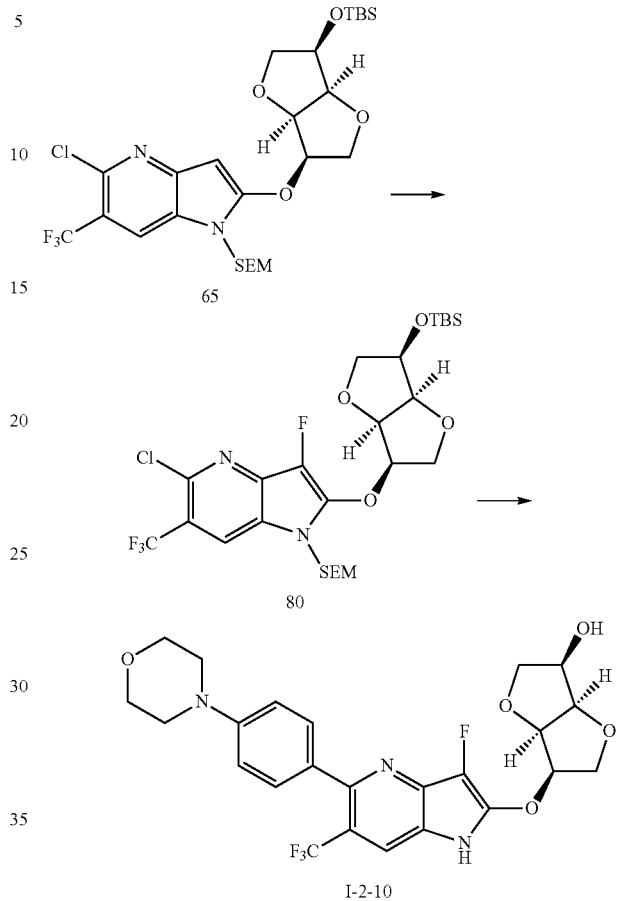

Compound 80 was synthesized from Compound 65 in a similar way that Compound 78 was synthesized from Compound 77.

Compound 80; Method B
LC/MS retention time=3.36 min.
MS (ESI) m/z=628.20 (M+H)+.

Compound (I-2-10) was synthesized from Compound 80 in a similar way that Compound (I-2-8) was synthesized from Compound 80.

Compound (I-2-10); Method B
LC/MS retention time=1.54 min.
MS (ESI) m/z=510.35 (M+H)+.

Example 25

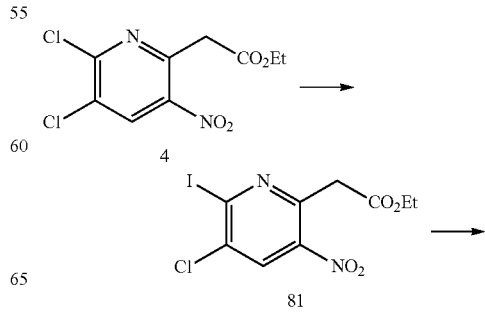

-continued

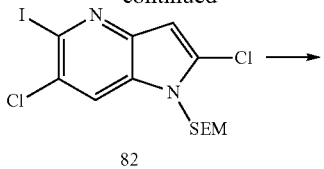

82

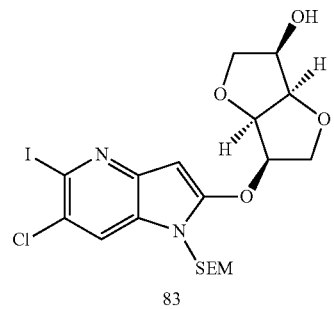

83

To Compound 4 (50 mg, 0.179 mmol) were added 1,4-dioxane (0.5 ml), trimethylsilyl chloride (45.8 µl, 0.358 mmol), and sodium iodide (134 mg, 0.896 mmol), and the reaction mixture was heated from room temperature and stirred at 70° C. Subsequently, Compound 4 (169 mg, 0.606 mmol) was reacted in a similar way as described above. The reaction mixtures were combined, followed by addition of ethyl acetate, and the resulting mixture was filtered and washed with a saturated aqueous solution of sodium hydrogencarbonate. Purification by silica gel column chromatography was carried out to obtain Compound 81 (191 mg, 65.6%).

Compound 81; Method B
LC/MS retention time=2.17 min.
MS (ESI) m/z=370.65 (M+H)+.

Compound 82 was synthesized from Compound 81 in a similar way that Compound 7 was synthesized from Compound 5.

Compound 82; Method B
LC/MS retention time=3.04 min.
MS (ESI) m/z=444.90 (M+H)+.

To Compound 82 (1000 mg, 2.256 mmol) and isomannide (3298 mg, 22.56 mmol) were added DMF (5 ml), and then 60 wt % NaH (271 mg, 6.77 mmol), and the resulting mixture was stirred at room temperature for 5 minutes. After that, the reaction mixture was stirred at 130° C. The reaction mixture was cooled to room temperature, followed by addition of ethyl acetate, and the resulting mixture was washed with 1 mol/L aqueous solution of hydrochloric acid and with water. The obtained organic layer was dried over magnesium sulfate, and then the solvent was removed by concentration under reduced pressure. The obtained residue was purified by silica gel column chromatography to obtain Compound 83 (967.3 mg, 77.5%).

Compound 83; Method B
LC/MS retention time=2.44 min.
MS (ESI) m/z=553.05 (M+H)+.

Example 26

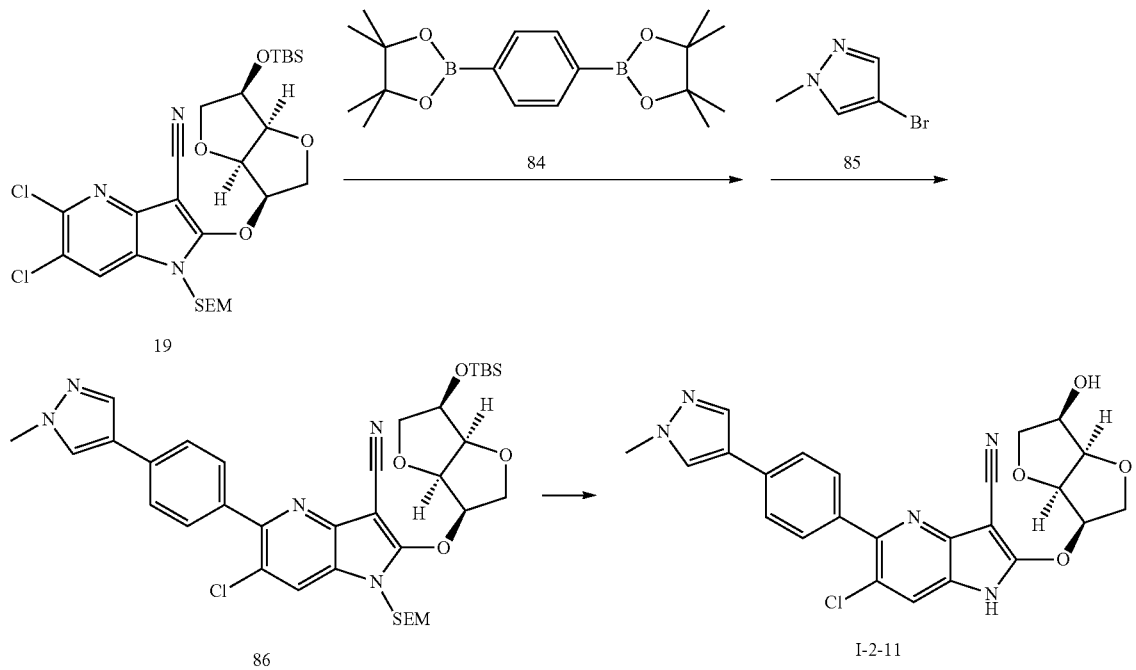

To a solution of Compound 19 (30.0 mg, 0.050 mmol) in dioxane (0.3 ml) were successively added Compound 84 (33.0 mg, 0.100 mmol), tetrakis(triphenylphosphine)palladium (5.8 mg, 5.0 µmol), and 2 mol/L aqueous solution of potassium carbonate (0.070 ml, 0.140 mmol) at room temperature, and the reaction mixture was stirred at 80° C. for 2 hours. Subsequently, Compound 85 (0.052 ml, 0.500 mmol) was added to the reaction mixture at room temperature, and the resulting mixture was stirred at 100° C. for 1.5 hours. The reaction mixture was purified by silica gel column chromatography to obtain Compound 86 (12.7 mg, 0.018 mmol, 35%) as a brown solid.

Compound 86; Method C
LC/MS retention time=3.20 min.
MS (EI) m/z=722.15 (M+H)+.

To a solution of Compound 86 (12.7 mg, 0.018 mmol) in dichloromethane (0.4 ml) was added TFA (0.4 ml, 5.2 mmol), and the reaction mixture was stirred overnight at room temperature. After completion of the reaction, the TFA was removed by concentration under reduced pressure, and the residue was diluted in MeOH, followed by neutralization with an aqueous solution of sodium hydrogencarbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound (I-2-11) (3.7 mg, 7.7 μmol, 44%).

Compound (I-2-11); Method C
LC/MS retention time=1.60 min.
MS (EI) m/z=478.00 (M+H)+

Example 27

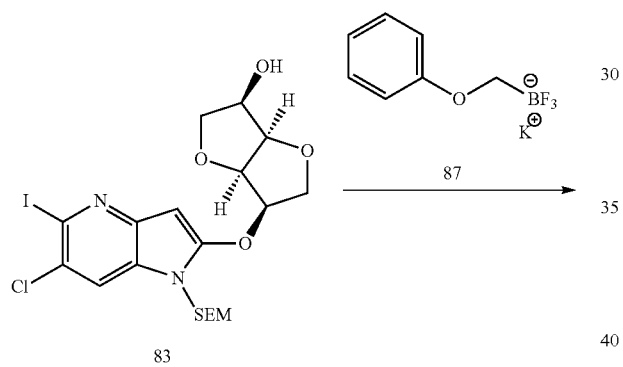

To a solution of Compound 83 (200 mg, 0.362 mmol) and Compound 87 (155 mg, 0.724 mmol) in dioxane and water (10:1, 2.2 ml) were successively added cesium carbonate (354 mg, 1.09 mmol), RuPhos (67.5 mg, 0.145 mmol), and palladium acetate (16.2 mg, 0.072 mmol) at room temperature, and the reaction mixture was stirred at 145° C. for 1 hour under microwave irradiation. Purification of the reaction mixture by silica gel column chromatography was conducted but it was difficult to remove impurities. A crude product (33.1 mg), containing Compound 88, was used directly in the next reaction.

To a solution of the crude product (33.1 mg) in dichloromethane (0.4 ml) was added TFA (0.4 ml, 5.2 mmol), and the reaction mixture was stirred at room temperature for 5 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound (I-2-12) (4.4 mg, 10.9 μmol, 3% in 2 steps).

Compound (I-2-12); Method C
LC/MS retention time=1.45 min.
MS (ET) m/z=402.95 (M+H)+

Example 28

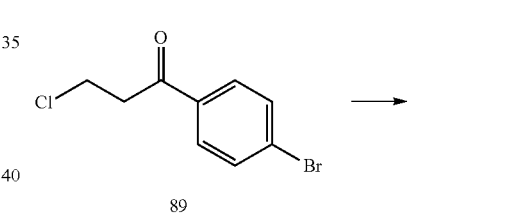

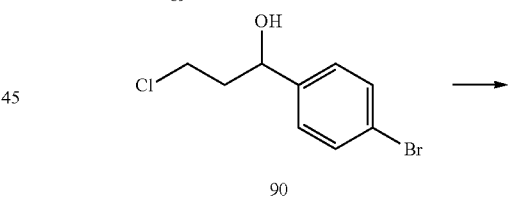

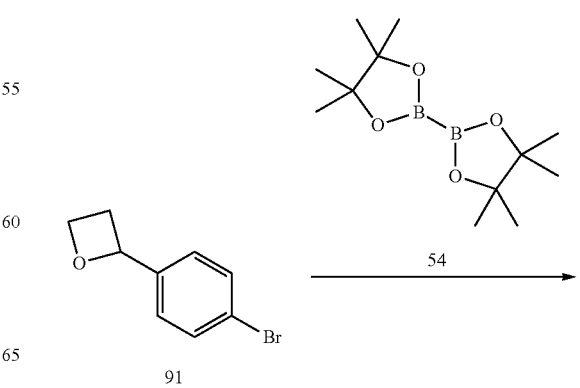

-continued

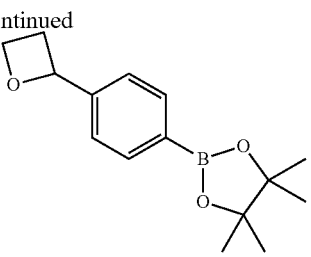

92

To a solution of Compound 89 (1.00 g, 4.04 mmol) in methanol (20 ml) was added sodium borohydride (306 mg, 8.08 mmol) under ice cooling, and the reaction mixture was stirred under ice cooling for 1 hour. The reaction mixture was quenched with a saturated aqueous solution of ammonium chloride, and then extracted with ethyl acetate, which was then dried over sodium sulfate. The solvent was removed under reduced pressure, the obtained residue was dissolved in THF (20 ml), to which was then added KOt-Bu (1.43 g, 12.8 mmol) under ice cooling, and the resulting mixture was stirred at room temperature for 2 hours. The reaction mixture was quenched with a saturated aqueous solution of ammonium chloride, and then extracted with ethyl acetate, which was then washed with saturated aqueous NaCl. The organic layer was dried over sodium sulfate, and the solvent was removed under reduced pressure. The obtained residue was purified by silica gel column chromatography to obtain Compound 91 (376 mg, 1.77 mmol, 44% in 2 steps) as a yellow oil. To Compound 91 (100 mg, 0.469 mmol) were added dioxane (1 ml), Compound 54 (179 mg, 0.704 mmol), PdCl₂(dppf)CH₂Cl₂ (38.3 mg, 0.047 mmol), and potassium acetate (184 mg, 1.88 mmol), and the reaction mixture was stirred at 100° C. for 2 hours. The reaction mixture was purified by silica gel column chromatography to obtain Compound 92 (104 mg, 0.400 mmol, 85%).

Compound 92; ¹H-NMR (CDCl₃) δ: 1.35 (s, 12H), 2.61-2.65 (m, 1H), 3.00-3.08 (m, 1H), 4.65-4.68 (m, 1H), 4.82-4.84 (m, 1H), 5.83 (t, J=7.5 Hz, 1H), 7.43 (d, J=7.8 Hz, 2H), 7.84 (d, J=7.9 Hz, 2H).

Example 29

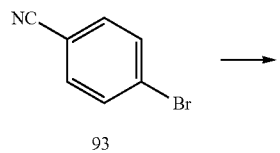

93

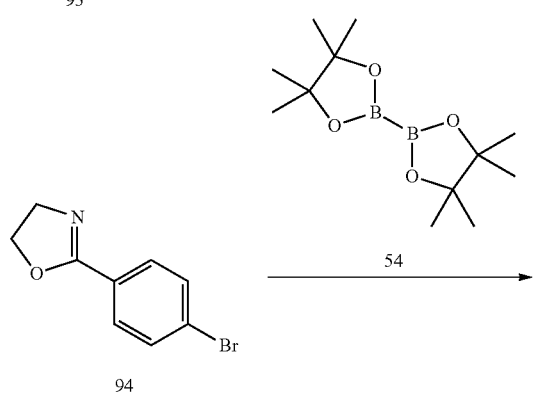

94

-continued

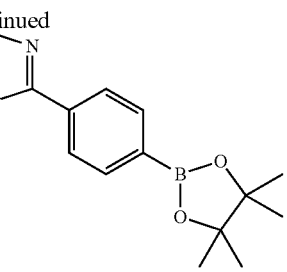

95

To a solution of Compound 93 (500 mg, 2.75 mmol) in methanol (2.75 ml) were added 2-aminoethanol (0.831 ml, 13.7 mmol) and sodium carbonate (582 mg, 5.49 mmol), and the reaction mixture was stirred at 80° C. for 13 hours. Purification of the reaction mixture by silica gel column chromatography was conducted but it was difficult to remove impurities. A crude product (91.7 mg), containing Compound 94, was used directly in the next reaction. To a solution of the crude product (91.7 mg) in dioxane (1 ml) were added Compound 54 (154 mg, 0.606 mmol), PdCl₂(dppf)CH₂Cl₂ (33 mg, 0.040 mmol), and potassium acetate (159 mg, 1.62 mmol), and the resulting mixture was stirred at 100° C. for 5 hours. The reaction mixture was filtered through Celite, and the filtrate was concentrated under reduced pressure. Purification of the reaction mixture by silica gel column chromatography was conducted but it was difficult to remove impurities. A crude product (104.6 mg), containing Compound 95, was used directly in the next reaction.

Compound 95; Method C
LC/MS retention time=1.83 min.
MS (EI) m/z=274.05 (M+H)+

Example 30

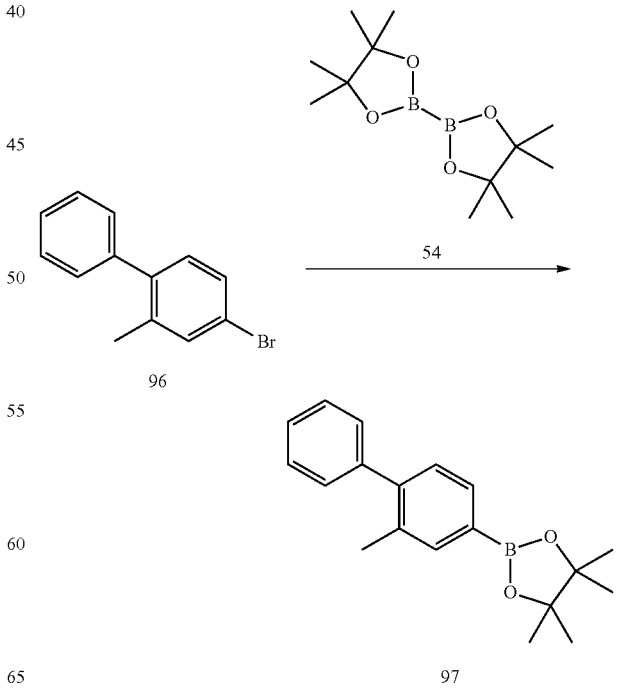

To Compound 96 (150 mg, 0.607 mmol) were added dioxane (1.5 ml), Compound 54 (231 mg, 0.910 mmol), PdCl$_2$(dppf)CH$_2$Cl$_2$ (49.6 mg, 0.061 mmol), and potassium acetate (238 mg, 2.43 mmol), and the reaction mixture was stirred at 100° C. for 2 hours. The reaction mixture was filtered through Celite, and the filtrate was concentrated under reduced pressure. The obtained residue was purified by silica gel column chromatography to obtain Compound 97 (105 mg, 0.356 mmol, 59%).

Compound 97; $^1$H-NMR (CDCl$_3$) δ: 1.35 (s, 2H), 2.28 (s, 3H), 7.24-7.26 (m, 1H), 7.35-7.39 (m, 5H), 7.69 (d, J=7.5 Hz, 1H), 7.73 (s, 1H).

Example 31

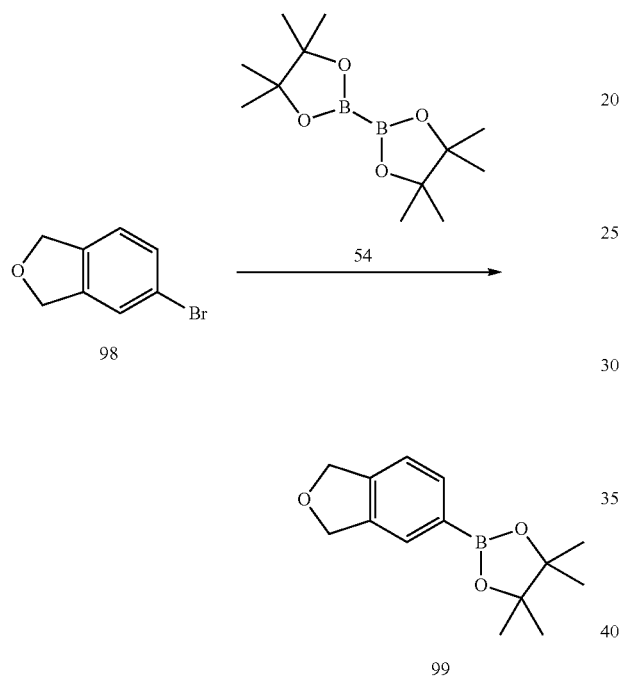

To Compound 98 (300 mg, 1.51 mmol) were added dioxane (3 ml), Compound 54 (574 mg, 2.26 mmol), PdCl$_2$(dppf)CH$_2$Cl$_2$ (123 mg, 0.151 mmol), and potassium acetate (592 mg, 6.03 mmol), and the reaction mixture was stirred at 100° C. for 1.5 hours. The reaction mixture was filtered through Celite, and the filtrate was concentrated under reduced pressure. The obtained residue was purified by silica gel column chromatography to obtain Compound 99 (268 mg, 1.09 mmol, 72%).

Compound 99; $^1$H-NMR (CDCl$_3$) δ: 1.35 (s, 12H), 5.11-5.12 (m, 4H), 7.23-7.28 (m, 1H), 7.67-7.75 (m, 2H).

Example 32

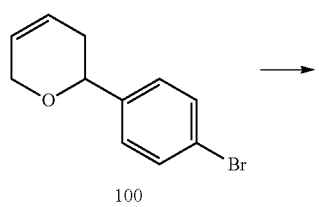

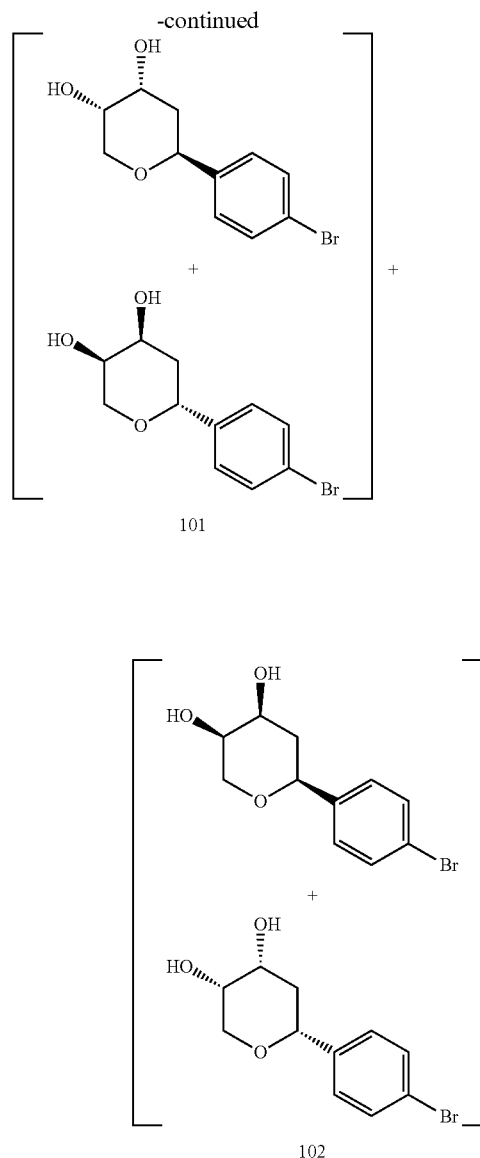

To a solution of Compound 100 (630 mg, 2.63 mmol) in THF and water (2:1, 11.7 ml) were successively added NMO (812 mg, 6.03 mmol) and K$_2$OsO$_4$ (255 mg, 0.693 mmol) at room temperature, and the reaction mixture was stirred at room temperature for 4 hours. The reaction mixture was quenched with a saturated aqueous solution of sodium thiosulfate, and then extracted with ethyl acetate, which was then dried over sodium sulfate. The solvent was removed under reduced pressure. The obtained residue was purified by silica gel column chromatography to obtain Compound 101 (180 mg, 0.659 mmol, 25%) and Compound 102 (190 mg, 0.696 mmol, 26%), each as a yellow oil.

Compound 101; $^1$H-NMR (DMSO-D$_6$) δ: 1.62-1.68 (m, 1H), 1.87-1.90 (m, 1H), 3.58-3.62 (m, 3H), 3.94 (s, 1H), 4.59-4.62 (m, 1H), 4.69-4.72 (m, 1H), 7.27 (d, J=8.4 Hz, 2H), 7.50 (d, J=8.4 Hz, 2H).

Compound 102; $^1$H-NMR (DMSO-D$_6$) δ: 1.67-1.72 (m, 2H), 3.54-3.58 (m, 2H), 3.70-3.72 (m, 1H), 3.88-3.91 (m, 1H), 4.29-4.32 (m, 1H), 4.46 (d, J=4.3 Hz, 1H), 4.65 (d, J=6.0 Hz, 1H), 7.29 (d, J=8.6 Hz, 2H), 7.50 (d, J=7.8 Hz, 2H).

Example 33

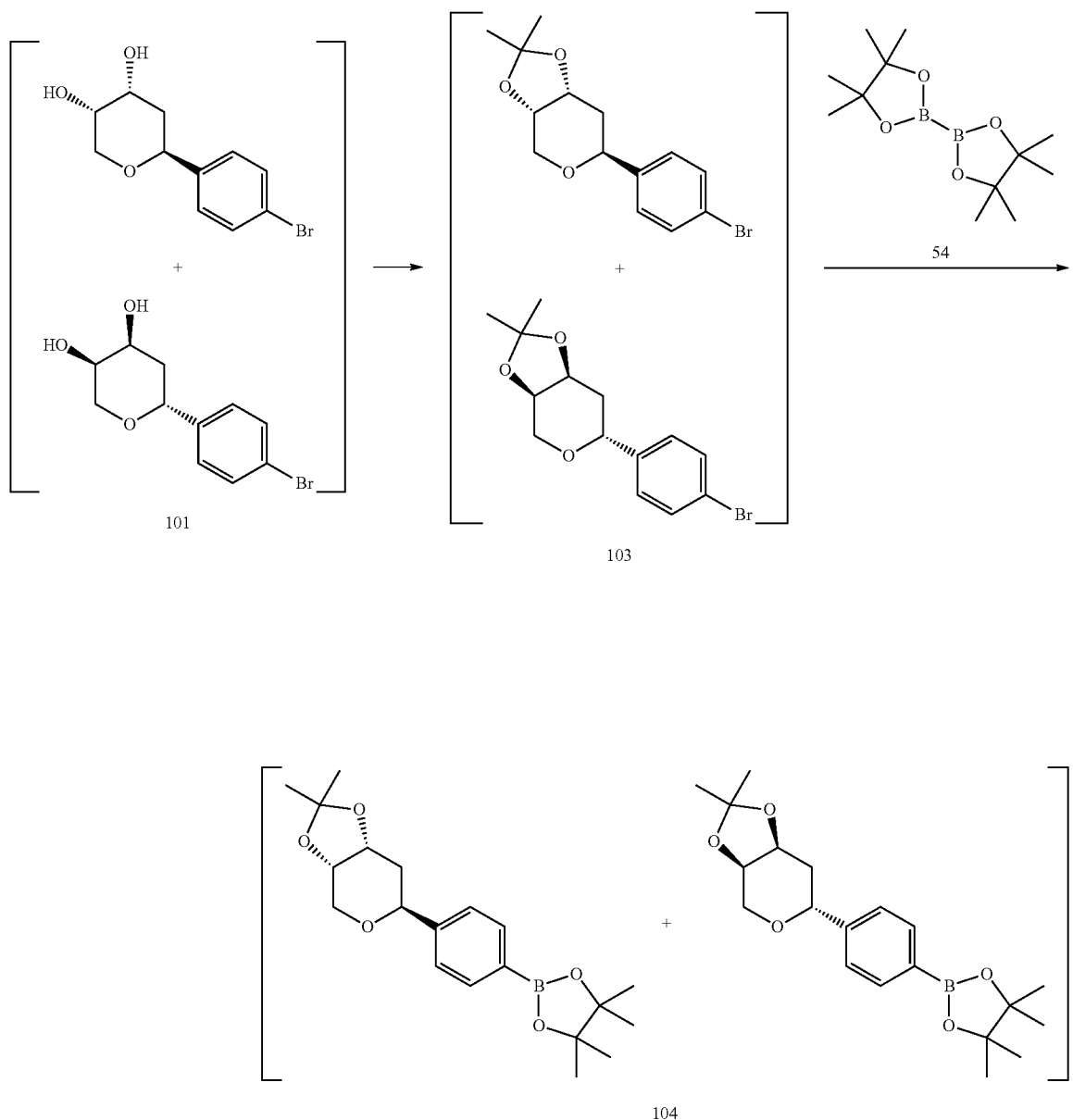

To a solution of Compound 101 (180 mg, 0.659 mmol) in acetone (2 ml) were added 2,2-dimethoxypropane (0.440 ml, 3.59 mmol) and p-toluene sulfonic acid monohydrate (13.7 mg, 0.072 mmol) at room temperature, and the reaction mixture was stirred at room temperature overnight. The reaction mixture was concentrated under reduced pressure, and the obtained residue was purified by silica gel column chromatography to obtain Compound 103 (83.1 mg, 0.265 mmol, 40%) as a colorless oil.

Compound 103; $^1$H-NMR (CDCl$_3$) δ: 1.40 (s, 3H), 1.57 (s, 3H), 1.93 (ddd, J=15.3, 11.8, 3.8 Hz, 1H), 2.30 (ddd, J=15.1, 2.5, 2.5 Hz, 1H), 3.54 (dd, J=11.5, 9.3 Hz, 1H), 4.05 (dd, J=11.5, 6.5 Hz, 1H), 4.22 (ddd, J=9.3, 6.5, 6.5 Hz, 1H), 4.44-4.45 (m, 1H), 4.59 (dd, J=11.8, 2.5 Hz, 1H), 7.22 (d, J=8.5 Hz, 2H), 7.47 (d, J=8.9 Hz, 2H).

To Compound 103 (79.8 mg, 0.255 mmol) were added dioxane (1.5 ml), Compound 54 (97 mg, 0.382 mmol), PdCl$_2$(dppf)CH$_2$Cl$_2$ (20.8 mg, 0.025 mmol), and potassium acetate (100 mg, 1.02 mmol), and the reaction mixture was stirred at 100° C. for 3.5 hours. The reaction mixture was purified by silica gel column chromatography to obtain Compound 104 (59.1 mg, 0.164 mmol, 64%).

Compound 104; $^1$H-NMR (CDCl$_3$) δ: 1.34 (s, 12H), 1.55-1.57 (m, 6H), 1.93-2.00 (m, 1H), 2.32 (dt, J=15.1, 2.4 Hz, 1H), 3.55 (dd, J=11.7, 9.4 Hz, 1H), 4.07 (dd, J=11.5, 6.5 Hz, 1H), 4.23 (dt, J=10.7, 4.6 Hz, 1H), 4.44-4.45 (m, 1H), 4.65 (dd, J=11.8, 2.8 Hz, 1H), 7.35 (d, J=8.0 Hz, 2H), 7.79 (d, J=8.0 Hz, 2H).

Example 34

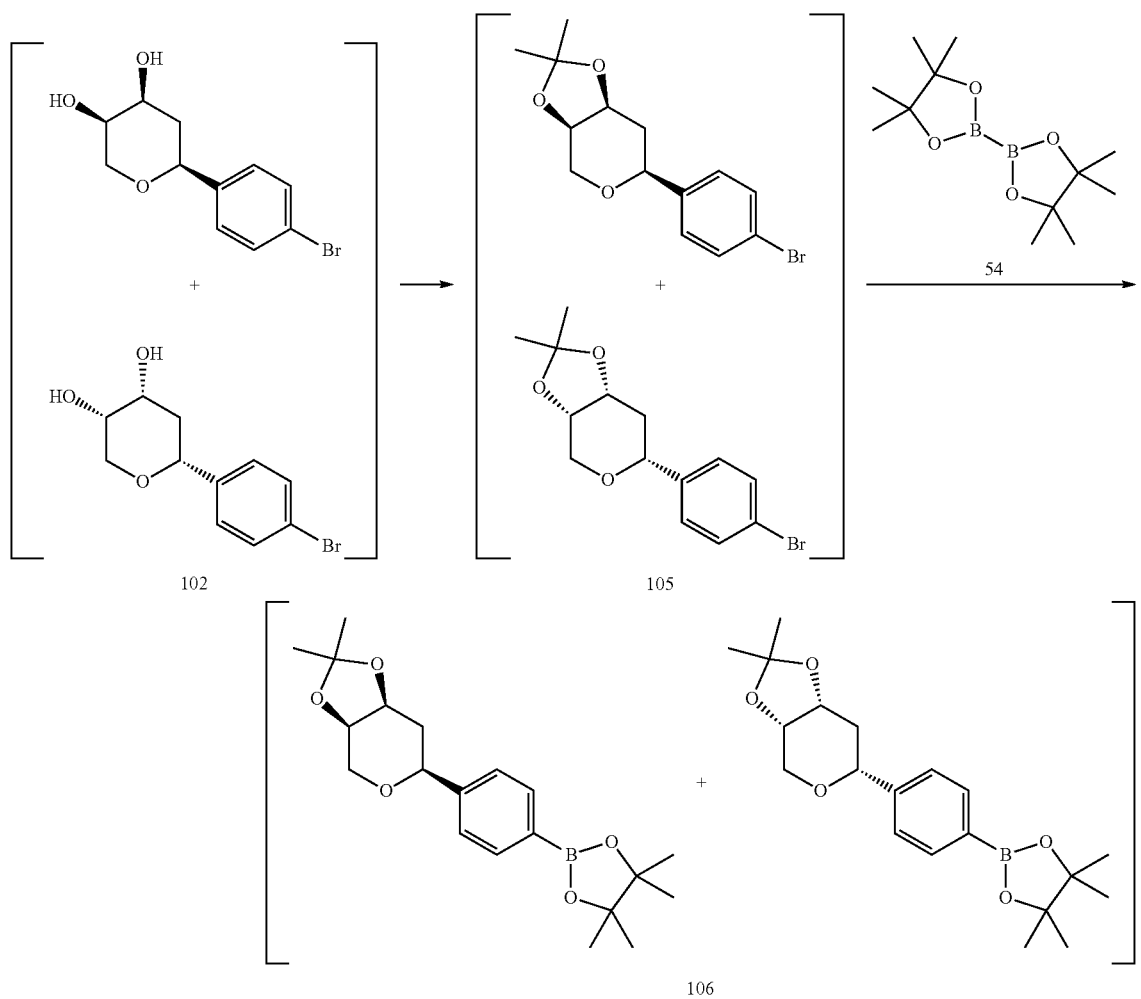

To a solution of Compound 102 (190 mg, 0.696 mmol) in acetone (2 ml) were added 2,2-dimethoxypropane (0.440 ml, 3.59 mmol) and p-toluene sulfonic acid monohydrate (13.7 mg, 0.072 mmol) at room temperature, and the reaction mixture was stirred at room temperature overnight. The reaction mixture was concentrated under reduced pressure, and the obtained residue was purified by silica gel column chromatography to obtain Compound 105 (68.3 mg, 0.218 mmol, 31%) as a colorless oil.

Compound 105; $^1$H-NMR (CDCl$_3$) δ: 1.38 (s, 3H), 1.55 (s, 3H), 1.75 (ddd, J=13.3, 11.8, 10.0 Hz, 1H), 2.11 (ddd, J=13.4, 7.0, 1.9 Hz, 1H), 3.91 (dd, J=13.6, 2.5 Hz, 1H), 4.09-4.10 (m, 1H), 4.20 (dd, J=11.8, 1.5 Hz, 1H), 4.36 (ddd, J=10.0, 6.5, 5.3 Hz, 1H), 4.47 (d, J=13.8 Hz, 1H), 7.23 (d, J=8.3 Hz, 2H), 7.45-7.48 (m, 2H).

To Compound 105 (62.5 mg, 0.200 mmol) were added dioxane (1.5 ml), Compound 54 (76 mg, 0.299 mmol), PdCl$_2$(dppf)CH$_2$Cl$_2$ (16.3 mg, 0.020 mmol), and potassium acetate (78 mg, 0.798 mmol), and the reaction mixture was stirred at 100° C. for 5 hours. The reaction mixture was purified by silica gel column chromatography to obtain Compound 106 (62.6 mg, 0.174 mmol, 87%).

Compound 106; $^1$H-NMR (CDCl$_3$) δ: 1.34-1.35 (m, 12H), 1.54-1.56 (m, 6H), 1.73-1.82 (m, 1H), 2.13 (ddd, J=13.3, 6.9, 1.8 Hz, 1H), 3.92 (dd, J=13.7, 2.5 Hz, 1H), 4.10-4.11 (m, 1H), 4.25-4.26 (m, 1H), 4.37 (dt, J=10.9, 5.0 Hz, 1H), 4.48 (d, J=13.7 Hz, 1H), 7.36 (d, J=7.9 Hz, 2H), 7.79 (d, J=8.0 Hz, 2H).

Example 35

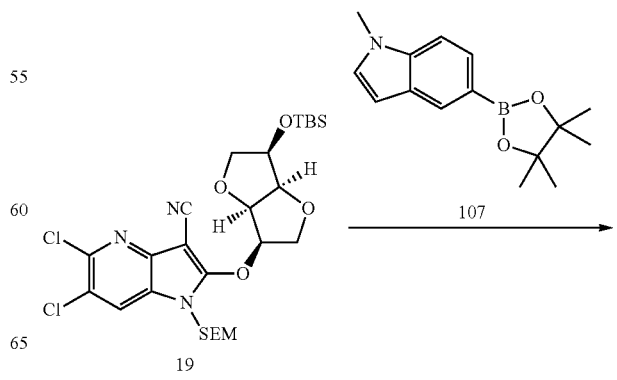

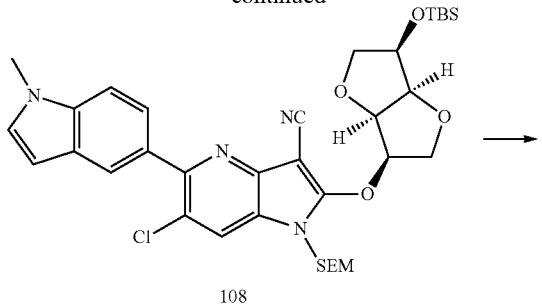

108

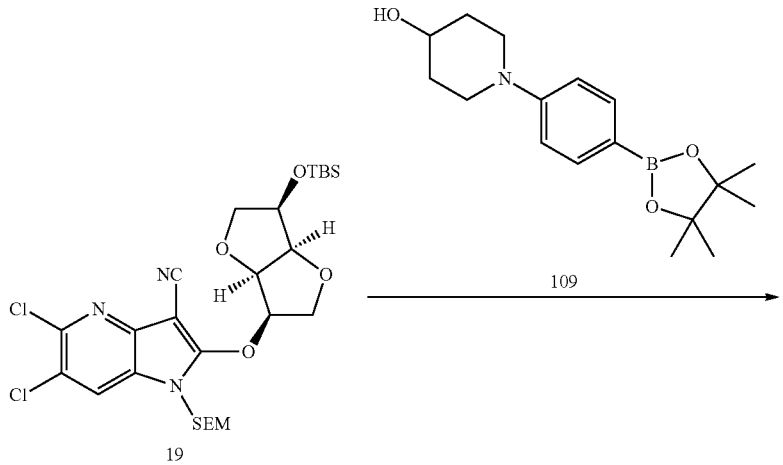

I-2-13

Compound 19 (50 mg, 0.083 mmol) was dissolved in dioxane (500 uL), to which were then successively added Compound 107 (25.7 mg, 0.100 mmol), Pd(PPh₃)₄ (19.24 mg, 0.017 mmol), and potassium carbonate (49.9 μl, 0.100 mmol), and the resulting mixture was stirred at 110° C. for 7 hours under a nitrogen atmosphere. The reaction mixture was cooled to room temperature, washed with water, and extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound 108 (34 mg, 58.0%).

Compound 108: Method C
LC/MS retention time=3.29 min.
MS (ESI) m/z=695.15 (M+H)+.

Compound 108 (30 mg, 0.043 mmol) was dissolved in methylene chloride (300 uL), to which was then added TFA (300 uL), and the resulting mixture was stirred overnight at room temperature. The reaction mixture, which was diluted in MeOH (1 mL), was added dropwise to a saturated aqueous solution of sodium hydrogen carbonate (5 mL), and the resulting mixture was stirred at room temperature for 30 minutes. After that, the reaction mixture was extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound (I-2-13) (15 mg, 63.6%).

Compound (I-2-13): Method C
LC/MS retention time=1.92 min.
MS (ESI) m/z=546.95 (M+H)+.

Example 36

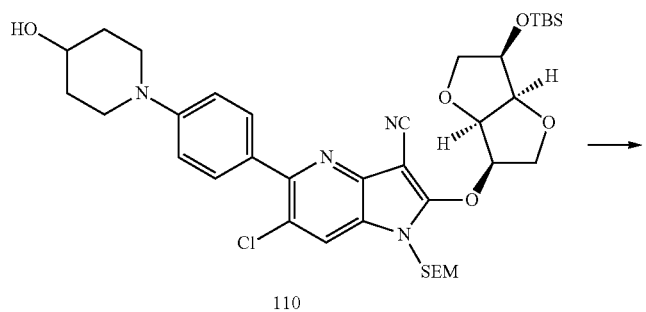

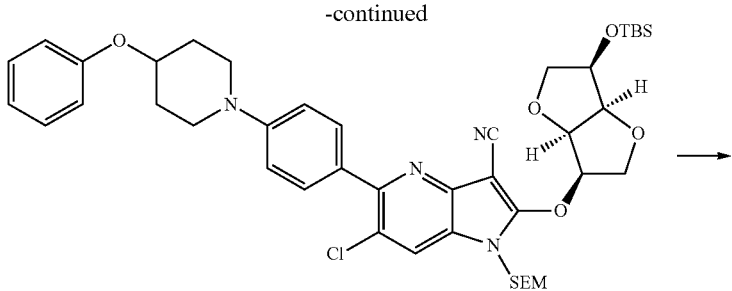

111

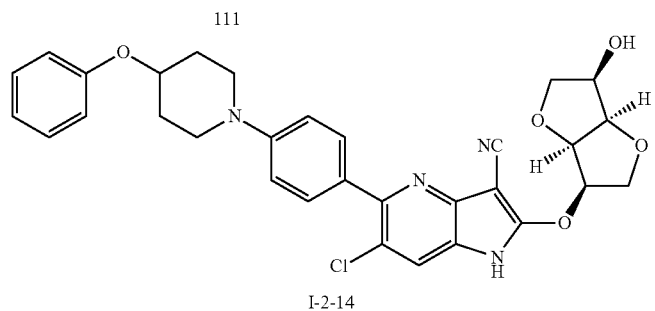

I-2-14

Compound 19 (40 mg, 0.067 mmol) was dissolved in dioxane (400 uL), to which were then successively added Compound 109 (24.23 mg, 0.080 mmol), Pd(PPh$_3$)$_4$ (15.39 mg, 0.013 mmol), and potassium carbonate (40.0 μl, 0.080 mmol) in this order, and the resulting mixture was stirred at 110° C. for 3 hours under a nitrogen atmosphere. The reaction mixture was cooled to room temperature, and purified by silica gel column chromatography to obtain Compound 110 (32.4 mg, 65.6%).

Compound 110: Method C
LC/MS retention time=3.07 min.
MS (ESI) m/z=741.20 (M+H)+.

Compound 110 (30 mg, 0.040 mmol) was dissolved in THF (600 uL), to which were then added phenol (4.27 μl, 0.049 mmol), PPh$_3$ (21.22 mg, 0.081 mmol), and DIAD (15.73 μl, 0.081 mmol) (2.85 μl, 0.032 mmol), and the resulting mixture was stirred overnight at room temperature. The solvent was removed by concentration under reduced pressure. The obtained residue was purified by silica gel column chromatography, whereby Compound 111 was quantitatively obtained (43 mg).

Compound 111: Method C
LC/MS retention time=3.45 min.
MS (ESI) m/z=817.15 (M+H)+.

Compound 111 (40 mg, 0.049 mmol) was dissolved in methylene chloride (400 uL), to which was then added TFA (400 uL), and the resulting mixture was stirred overnight at room temperature. The reaction mixture, which was diluted in MeOH (1 mL), was added dropwise to a saturated aqueous solution of sodium hydrogen carbonate (5 mL), and the resulting mixture was stirred at room temperature for 30 minutes. After that, the reaction mixture was extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound (I-2-14) (8.1 mg, 28.9%).

Compound (I-2-14): Method C
LC/MS retention time=2.20 min.
MS (ESI) m/z=573.05 (M+H)+.

Example 37

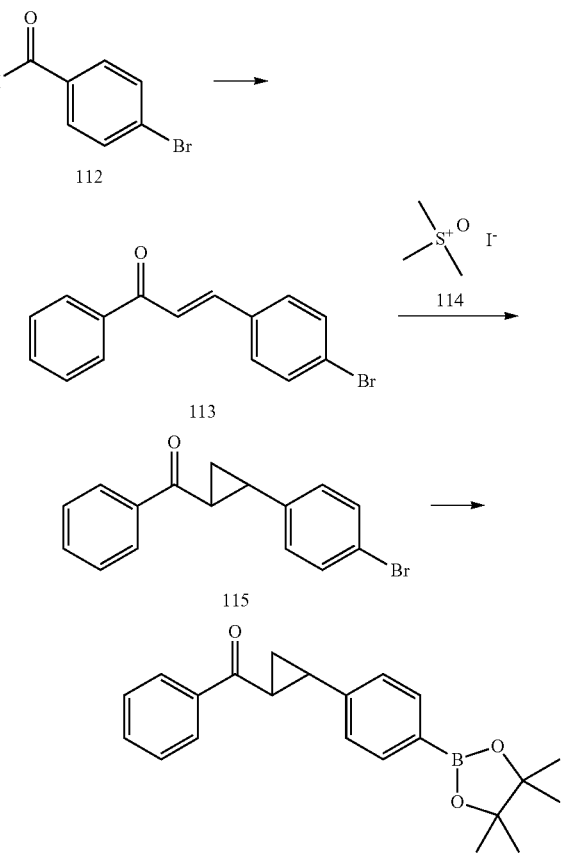

Compound 112 (770 mg, 4.16 mmol) and acetophenone (485 uL, 4.16 mmol) were dissolved in ethanol (7.5 mL), to which was then added dropwise a solution of KOH (514 mg, 9.16 mmol) in water (5 mL) under ice cooling, and the resulting mixture was stirred at room temperature for 1.5 hours. Precipitates formed were collected by filtration, washed with water, and dried under reduced pressure to obtain Compound 113 (1137 mg, 95.1%).

Compound 113: Method C
LC/MS retention time=2.49 min.
MS (ESI) m/z=286.85 (M+H)+.

Compound 113 (730 mg, 2.54 mmol) was dissolved in DMSO (7.3 mL), to which were then added Compound 114 (671 mg, 3.05 mmol) and NaH (122 mg, 3.05 mmol) under ice cooling, and the resulting mixture was stirred at room temperature for 1 hour. The reaction mixture was washed with water, and then extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound 115 (570.8 mg, 74.6%).

Compound 115: Method C
LC/MS retention time=2.55 min.
MS (ESI) m/z=300.85 (M+H)+.

Compound 115 (94 mg, 0.312 mmol) was dissolved in dioxane (940 uL), to which were then added PdCl$_2$(dppf) CH$_2$Cl$_2$ adduct (25.5 mg, 0.031 mmol), Bis(pinacolato) diboron (119 mg, 0.468 mmol), and KOAc (61.3 mg, 0.624 mmol), and the resulting mixture was stirred at 100° C. for 2 hours. The solvent was removed by concentration under reduced pressure, and the obtained residue was purified by silica gel column chromatography to obtain Compound 116 (88.3 mg, 81.2%).

Compound 116: Method C
LC/MS retention time=2.70 min.
MS (ESI) m/z=349.00 (M+H)+.

Example 38

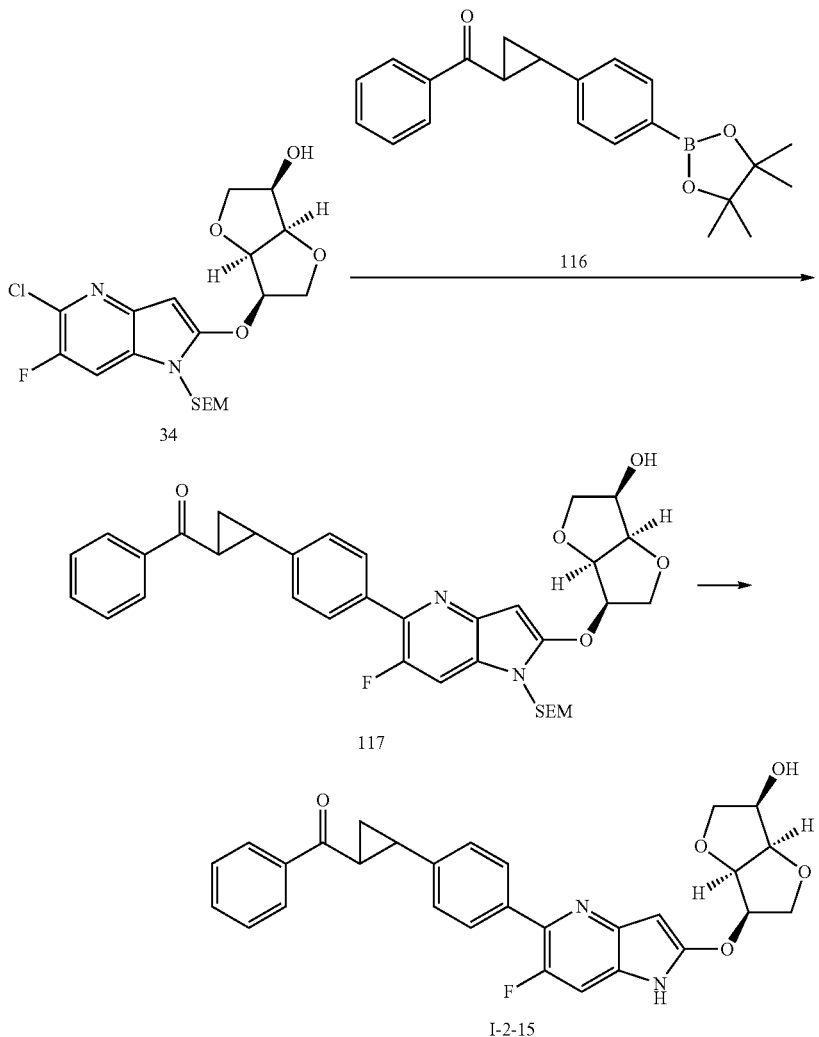

Compound 34 (20 mg, 0.045 mmol) was dissolved in DMF (200 μL), to which were then successively added Compound 116 (23.48 mg, 0.067 mmol), PdCl$_2$(dtbpf) (5.86 mg, 8.99 μmol), and Cs$_2$CO$_3$ (58.6 mg, 0.180 mmol), and the resulting mixture was stirred at 100° C. for 1.5 hours under a nitrogen atmosphere. The reaction mixture was purified by silica gel column chromatography to obtain Compound 117 (16.5 mg, 58.2%).

Compound 117: Method C
LC/MS retention time=2.61 min.
MS (ESI) m/z=631.10 (M+H)+.

Compound 117 (15 mg, 0.024 mmol) was dissolved in methylene chloride (150 uL), to which was then added TFA (150 uL), and the resulting mixture was stirred at room temperature for 4 hours. The reaction mixture, which was diluted in MeOH (1 mL), was added dropwise to a saturated aqueous solution of sodium hydrogen carbonate (5 mL), and the resulting mixture was stirred at room temperature for 30 minutes. After that, the reaction mixture was extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound (I-2-15) (6.8 mg, 57.1%).

Compound (I-2-15): Method C
LC/MS retention time=1.70 min.
MS (ESI) m/z=501.00 (M+H)+.

Example 39

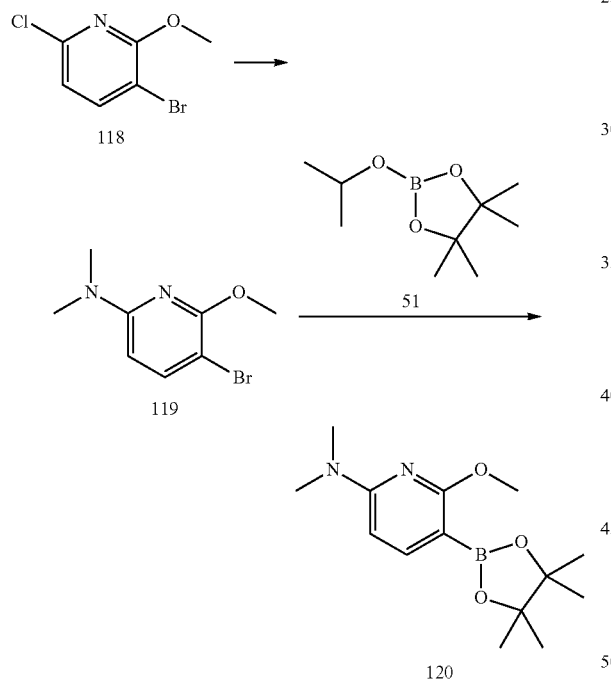

Compound 118 (155 mg, 0.697 mmol) was dissolved in DMSO (1.55 mL), to which were then added Et$_3$N (193 uL, 1.393 mmol) and dimethylamine (523 uL, 1.045 mmol), and the resulting mixture was stirred at 150° C. for 2 hours in a closed tube. The reaction mixture was cooled to room temperature, washed with water, and extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound 119 (124.8 mg, 77.5%).

Compound 119: Method C
LC/MS retention time=2.35 min.
MS (ESI) m/z=230.80 (M+H)+.

Compound 119 (105 mg, 0.454 mmol) was dissolved in THF (2.1 mL), to which was then added n-BuLi (1.63 M, 335 uL, 0.545 mmol) at −78° C., and the resulting mixture was stirred for 15 minutes. Subsequently, Compound 51 (184 uL, 0.909 mmol) was added to the reaction mixture at −78° C., and the resulting mixture was stirred for 1.5 hours. After the disappearance of the starting material, the reaction mixture was quenched with a saturated aqueous solution of ammonium chloride and extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound 120 (58.6 mg, 46.4%).

Compound 120: Method C
LC/MS retention time=2.37 min.
MS (ESI) m/z=279.00 (M+H)+.

Example 40

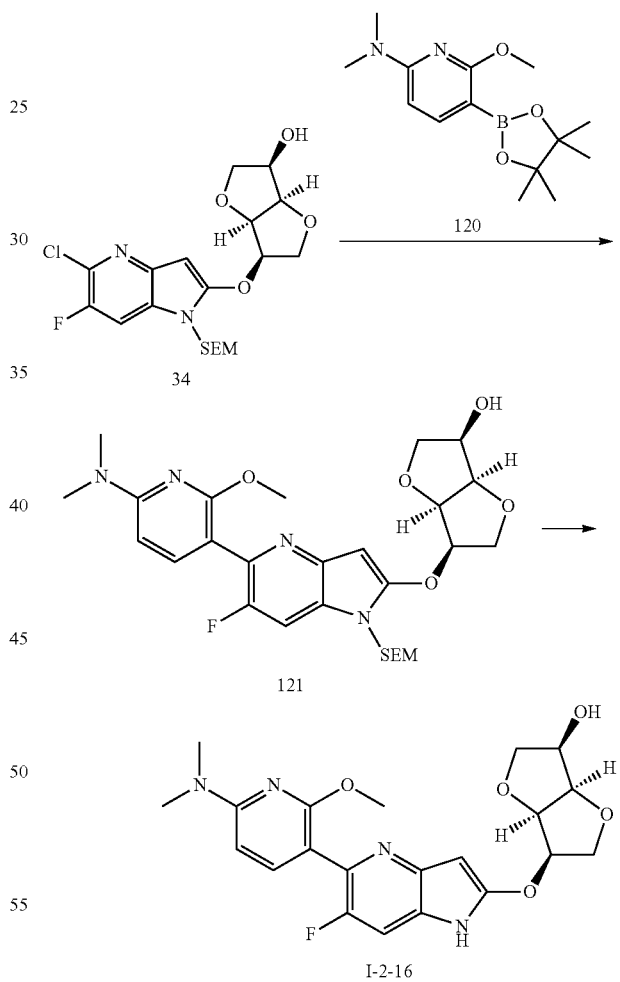

Compound 34 (20 mg, 0.045 mmol) was dissolved in dioxane (200 uL), to which were then added PdCl$_2$(dtbpf) (5.86 mg, 8.99 μmol), Compound 120 (18.75 mg, 0.067 mmol), and Cs$_2$CO$_3$ (58.6 mg, 0.180 mmol), and the resulting mixture was stirred at 120° C. for 3 hours under microwave irradiation. The obtained residue was purified by silica gel column chromatography to obtain Compound 121 (9.4 mg, 37.3%).

Compound 121: Method C
LC/MS retention time=2.70 min.
MS (ESI) m/z=561.10 (M+H)+.

Compound 121 (9 mg, 0.016 mmol) was dissolved in methylene chloride (90 uL), to which was then added TFA (90 uL), and the resulting mixture was stirred overnight at room temperature. The reaction mixture, which was diluted in MeOH (1 mL), was added dropwise to a saturated aqueous solution of sodium hydrogen carbonate (5 mL), and the resulting mixture was stirred at room temperature for 30 minutes. After that, the reaction mixture was extracted with ethyl acetate, which was then washed with saturated aqueous NaCl. The obtained organic layer was dried over sodium sulfate, and then the solvent was removed by concentration under reduced pressure. The obtained residue was purified by silica gel column chromatography to obtain Compound (I-2-16) (3.2 mg, 46.3%).

Compound (I-2-16): Method C
LC/MS retention time=1.42 min.
MS (ESI) m/z=431.00 (M+H)+.

Example 41

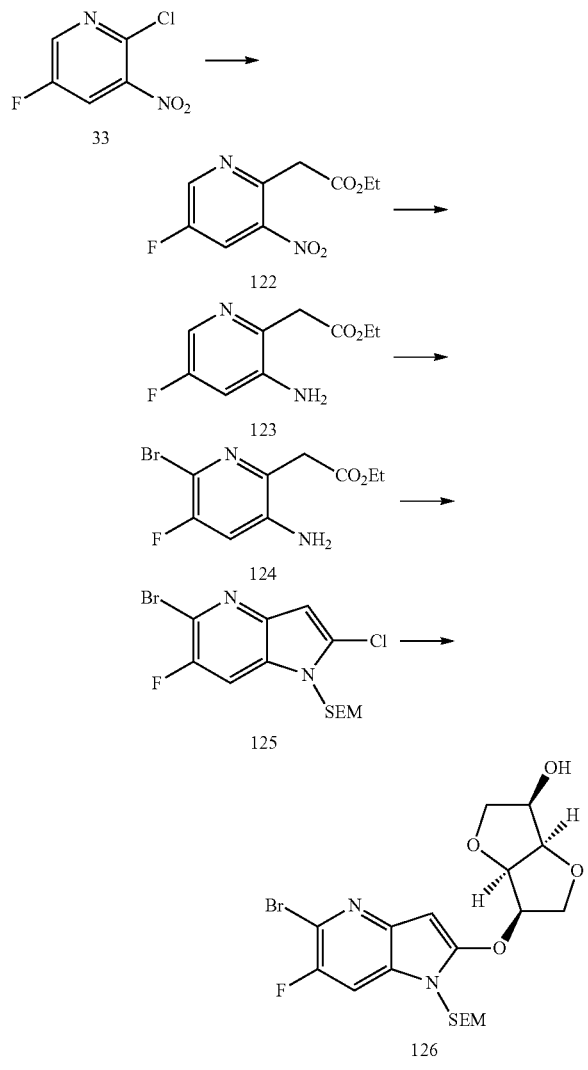

Diethyl malonate (9.98 g, 62.3 mmol) was diluted in DMF (50 ml), to which was then added 60 wt % sodium hydride (2.266 g, 56.6 mmol) under ice cooling, and the resulting mixture was stirred under ice cooling and at room temperature. After that, a solution of Compound 33 (5.00 g, 28.3 mmol) dissolved in DMF (5 ml) was added to the reaction mixture under ice cooling, and the resulting mixture was stirred at room temperature. After completion of the reaction, ethyl acetate was added to the reaction mixture under ice cooling, and the resulting mixture was washed with 2 mol/L aqueous solution of hydrochloric acid and with water. The obtained organic layer was dried over magnesium sulfate, and then the solvent was removed by concentration under reduced pressure. The obtained residue was purified by silica gel column chromatography. About 80% portion of the purified product was diluted in DMSO (50 ml), to which were then added water (0.5 ml) and lithium chloride (4.86 g, 115 mmol), and the resulting mixture was stirred at 110° C. After completion of the reaction, a mixed solvent of ethyl acetate and hexane was added to the reaction mixture, from which insoluble materials were removed, and which was then washed with water. The obtained organic layer was dried over magnesium sulfate, and then the solvent was removed by concentration under reduced pressure. The obtained residue was purified by silica gel column chromatography to obtain Compound 122 (2.98 g).

Compound 122; Method B
LC/MS retention time=1.65 min.
MS (ESI) m/z=229.15 (M+H)+.

Compound 122 (1.00 g, 4.38 mmol) was diluted in ethanol (10 ml), to which was then added 10% Pd/C (200 mg), and the resulting mixture was stirred under a hydrogen atmosphere. After completion of the reaction, the reaction mixture was filtered through Celite, and the solvent was removed by concentration under reduced pressure. The obtained residue was purified by silica gel column chromatography to obtain Compound 123 (0.6966 g, 80.2%).

Compound 123; Method B
LC/MS retention time=0.92 min.
MS (ESI) m/z=199.25 (M+H)+.

Compound 123 (0.50 g, 2.52 mmol) was dissolved in DMF (5 ml), to which was then added NBS (0.494 g, 2.52 mmol) under ice cooling, and the resulting mixture was stirred. After completion of the reaction, a 1 mol/L aqueous solution of sodium thiosulfate was added to the reaction mixture, which was then extracted with ethyl acetate. The obtained organic layer was dried over magnesium sulfate, and then the solvent was removed by concentration under reduced pressure. The obtained residue was purified by silica gel column chromatography to obtain Compound 124 (0.4418 g).

Compound 124; Method B
LC/MS retention time=1.66 min.
MS (ESI) m/z=229.00 (M+H)+.

Compound 125 was synthesized from Compound 124 in a similar way as in the case of Compound 7.

Compound 125; Method B
LC/MS retention time=2.88 min.
MS (ESI) m/z=379.00 (M+H)+.

To Compound 125 (1.00 g, 2.63 mmol) and isomannide (3.849 g, 26.3 mmol) were added DMF (6 ml), and then potassium fluoride (0.459 g, 7.90 mmol), 18-crown 6-ether (4.176 g, 15.8 mmol), and 60 wt % sodium hydride (0.316 g, 7.90 mmol), and the resulting mixture was stirred at room temperature for 5 minutes. After that, the reaction mixture was stirred at 90° C. After completion of the reaction, a 1 mol/L aqueous solution of hydrochloric acid was added to the reaction mixture at room temperature, followed by extraction with ethyl acetate. The obtained organic layer was washed with water, dried over magnesium sulfate, and the solvent was removed by concentration under reduced pressure. The obtained residue was purified by silica gel column chromatography to obtain Compound 126 (0.724 mg, 56.2%).

Compound 126; Method B
LC/MS retention time=2.29 min.
MS (ESI) m/z=489.10 (M+H)+.

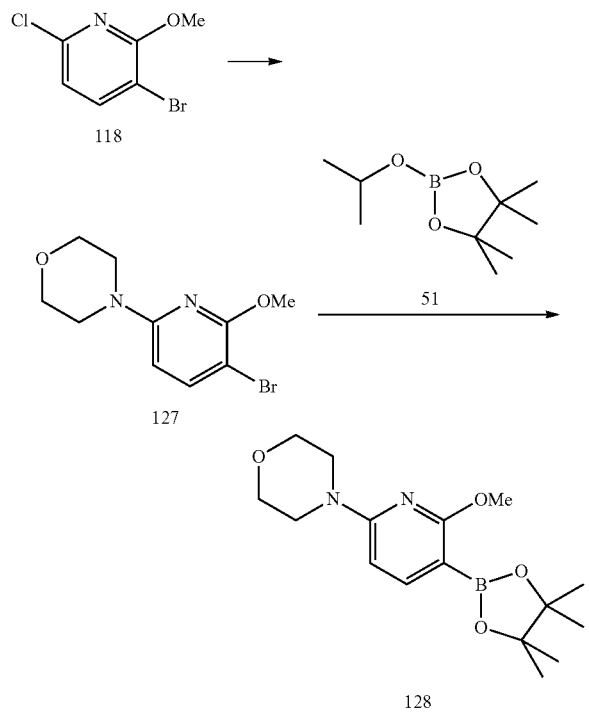

Compound 118 (1.00 g, 4.50 mmol) was dissolved in DMSO (5 ml), to which was then added morpholine (1.37 ml, 15.73 mmol), and the resulting mixture was stirred at 150° C. After completion of the reaction, a mixed solvent of ethyl acetate and hexane was added to the reaction mixture, which was then washed with water. The obtained organic layer was dried over magnesium sulfate, and then the solvent was removed by concentration under reduced pressure. The obtained residue was purified by silica gel column chromatography to obtain Compound 127 (2.98 g).

Compound 127; Method B
LC/MS retention time=2.09 min.
MS (ESI) m/z=275.05 (M+H)+.

To Compound 127 (0.325 g, 1.19 mmol) was added THF (3 ml) under a nitrogen atmosphere, and the mixture was cooled to −78° C., followed by addition of a solution of n-butyllithium in hexane (1.095 ml, 1.785 mmol). Subsequently, Compound 51 (0.491 ml, 2.38 mmol) was added to the reaction mixture, and the resulting mixture was further stirred at −78° C. After completion of the reaction, ethyl acetate was added to the reaction mixture, which was then washed with aqueous NaCl. The obtained organic layer was dried over magnesium sulfate, and then the solvent was removed by concentration under reduced pressure. The obtained residue was purified by silica gel column chromatography to obtain Compound 128 (0.254 g, 66.7%).

Compound 128; Method B
LC/MS retention time=2.16 min.
MS (ESI) m/z=321.15 (M+H)+.

Compound 130 was synthesized from Compound 129 in a similar way as in the case of Compound 128.

Compound 130; Method B
LC/MS retention time=1.32 min.
MS (ESI) m/z=305.20 (M+H)+.

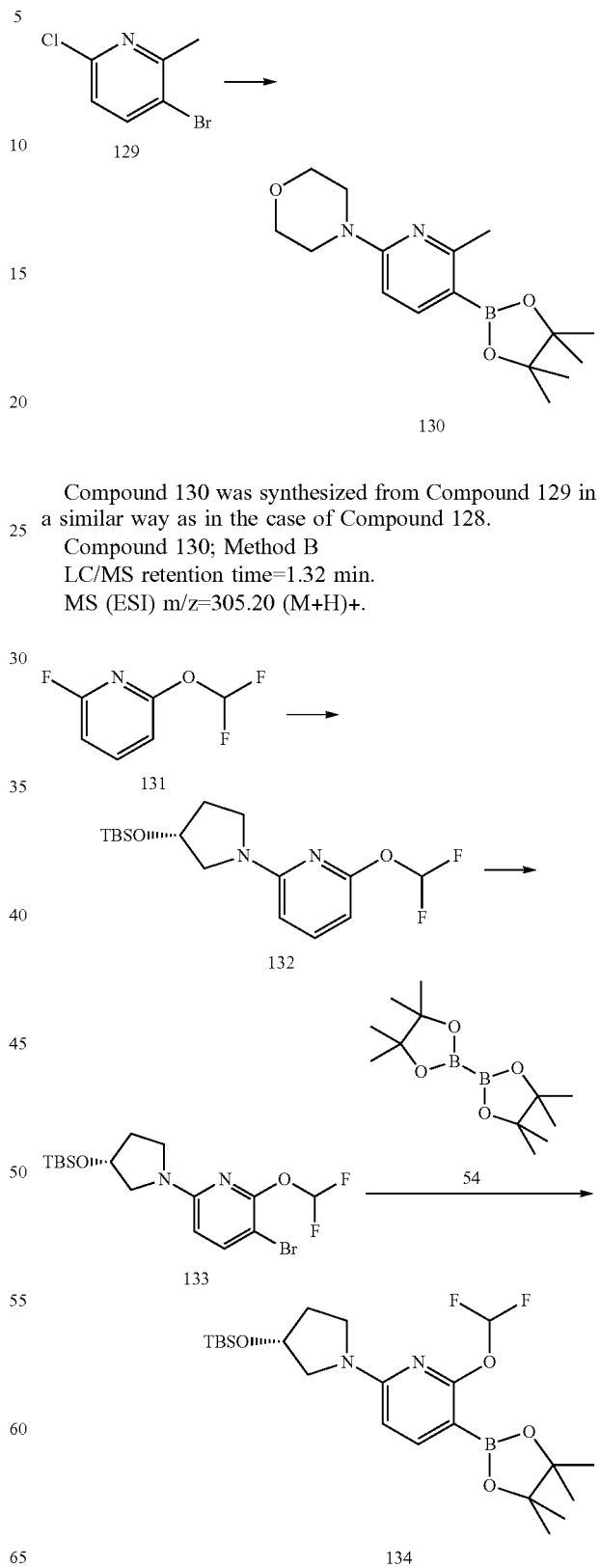

Compound 131 (1.00 g, 6.13 mmol) and (R)-3-pyrrolidinol (1.175 g, 13.49 mmol) were stirred at 80° C. After completion of the reaction, ethyl acetate was added to the reaction mixture, which was then washed with water. The obtained organic layer was dried over magnesium sulfate, and then the solvent was removed by concentration under reduced pressure. The obtained residue and imidazole (0.835 g, 12.26 mmol) were dissolved in DMF (5 ml), to which was then added tert-butyldimethylsilyl chloride (1.848 g, 12.26 mmol), and the resulting mixture was stirred at room temperature. After completion of the reaction, ethyl acetate was added to the reaction mixture, the resulting mixture was washed with water, and the solvent was removed by concentration under reduced pressure. The obtained residue was purified by silica gel column chromatography to obtain Compound 132 (1.5012 g, 71.1%).

Compound 132; Method B
LC/MS retention time=3.14 min.
MS (ESI) m/z=345.20 (M+H)+.

Compound 132 (0.515 g, 1.494 mmol) was dissolved in DMF (5 ml), to which was then added NBS (0.270 g, 1.52 mmol) under ice cooling, and the resulting mixture was stirred. After completion of the reaction, ethyl acetate was added to the reaction mixture, which was then washed with water. The obtained organic layer was dried over magnesium sulfate, and then the solvent was removed by concentration under reduced pressure. The obtained residue was purified by silica gel column chromatography to obtain Compound 133 (0.623 g).

Compound 133; Method B
LC/MS retention time=3.18 min.
MS (ESI) m/z=423.05 (M+H)+.

To Compound 133 (100 mg, 0.236 mmol) were added 1,4-dioxane (1 ml), Compound 54 (78 mg, 0.307 mmol), PdCl$_2$(dppf)CH$_2$Cl$_2$ (9.64 mg, 0.012 mmol), and potassium acetate (69.5 mg, 0.709 mmol), and the reaction mixture was stirred at 110° C. The reaction mixture was filtered through Celite, and the filtrate was concentrated under reduced pressure. The obtained residue was purified by silica gel column chromatography to obtain Compound 134 (26.9 mg, 24.2%).

Compound 134; Method B
LC/MS retention time=3.31 min.
MS (ESI) m/z=471.10 (M+H)+.

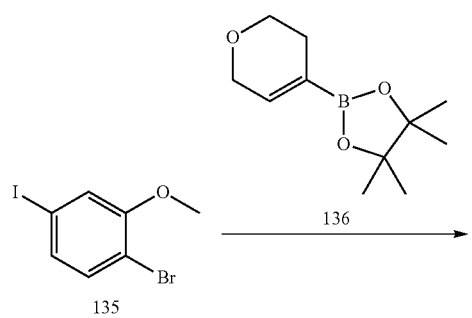

135

136 →

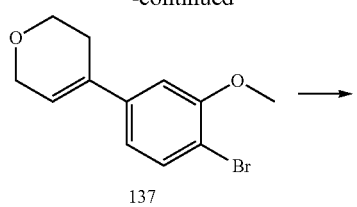

137

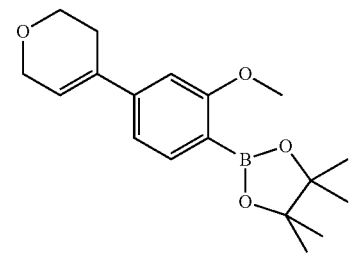

138

To a solution of Compound 135 (1.00 g, 3.20 mmol) in 1,4-dioxane (10 ml) were added 2 mol/T, aqueous solution of potassium carbonate (0.070 ml, 0.140 mmol), and then tetrakis(triphenylphosphine)palladium (0.369 g, 0.320 mmol) and Compound 136 (0.806 g, 3.83 mmol), and the reaction mixture was stirred at 100° C. After completion of the reaction, ethyl acetate and water were added to the reaction mixture, which was then concentrated under reduced pressure and extracted with chloroform. The obtained organic layer was dried over magnesium sulfate, and then the solvent was removed by concentration under reduced pressure. The obtained residue was purified by silica gel column chromatography to obtain Compound 137 (0.259 g, 30.1%).

Compound 138 was synthesized from Compound 137 in a similar way as in the case of Compound 134.

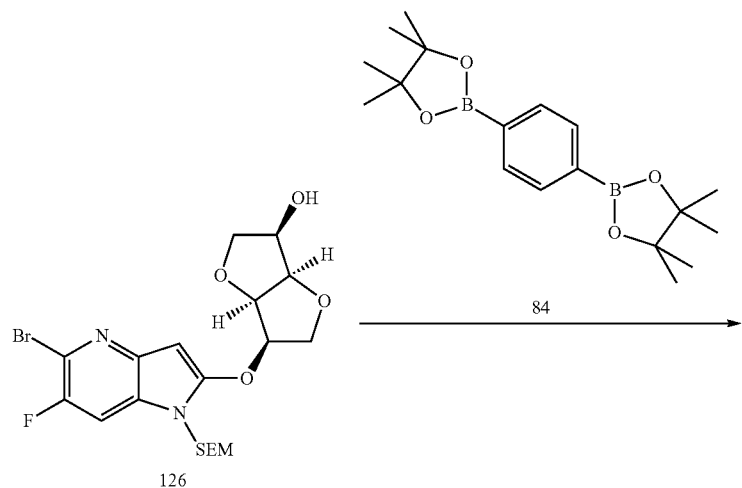
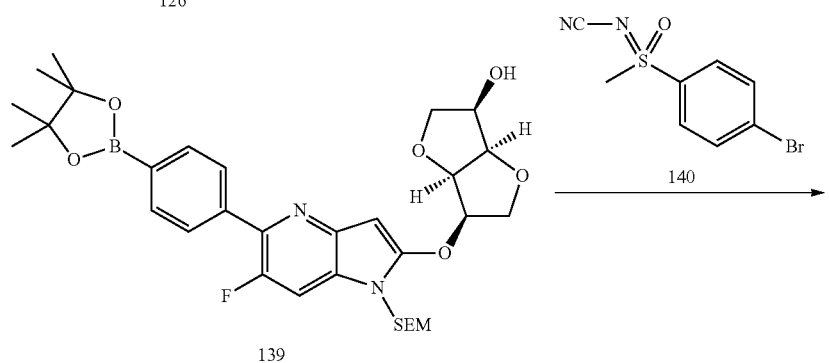
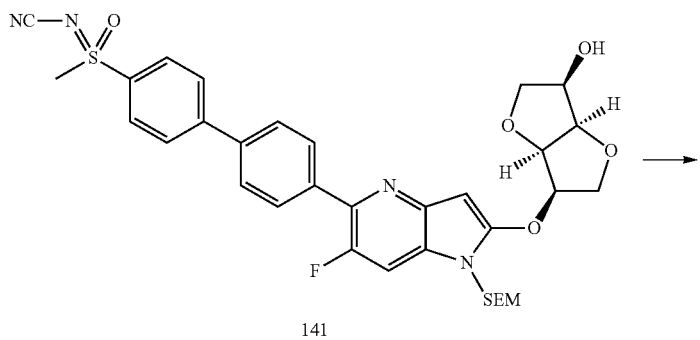
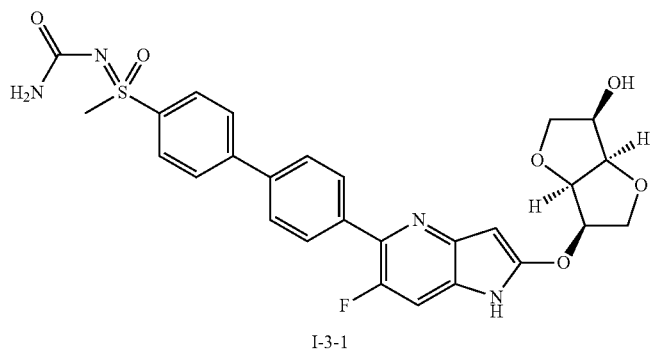

To Compound 126 (500 mg, 1.022 mmol) were added 1,4-dioxane (0.5 ml), PdCl₂(dtbpf) (133 mg, 0.204 mmol), Compound 84 (674 mg, 2.043 mmol), and 2 mol/L aqueous solution of potassium carbonate (0.766 ml, 1.532 mmol), and the resulting mixture was stirred at 145° C. under microwave irradiation. After completion of the reaction, the reaction mixture was dried over magnesium sulfate, and concentrated under reduced pressure. The obtained residue was purified by silica gel column chromatography to obtain Compound 139 (202 mg, 32.3%).

Compound 139; Method B

LC/MS retention time=2.75 min.

MS (ESI) m/z=613.00 (M+H)+.

To Compound 139 (60 mg, 0.098 mmol) were added 1,4-dioxane (0.6 ml), PdCl₂(dtbpf) (13.81 mg, 0.021 mmol), Compound 140 (50.8 mg, 0.196 mmol), and 2 mol/L aqueous solution of potassium carbonate (0.098 ml, 0.196 mmol), and the reaction mixture was stirred at 60° C. After completion of the reaction, the reaction mixture was purified by silica gel column chromatography to obtain Compound 141.

Compound 141; Method B

LC/MS retention time=2.20 min.

MS (ESI) m/z=665.10 (M+H)+.

To Compound 141 (5 mg, 0.00594 mmol) were added chloroform (0.5 ml), and then TFA (0.5 ml), and the resulting mixture was stirred at room temperature. After completion of the reaction, the TFA was removed by concentration under reduced pressure, followed by dilution in MeOH, and neutralization with an aqueous solution of sodium hydrogen carbonate. Extraction was performed with chloroform, the obtained organic layer was dried over magnesium sulfate, and then the solvent was removed by concentration under reduced pressure. The obtained residue was purified by reverse-phase column chromatography to obtain Compound I-3-1.

Compound I-3-1; Method B

LC/MS retention time=0.99 min.

MS (ESI) m/z=553.45 (M+H)+.

Example 42

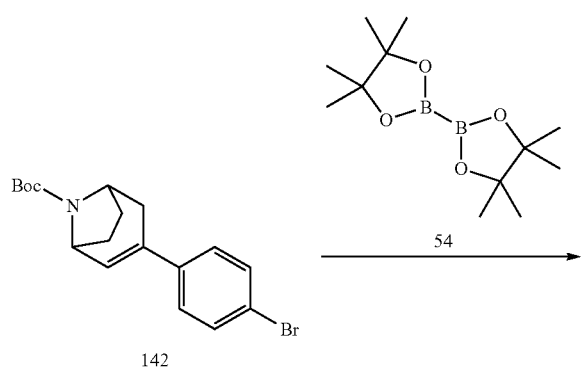

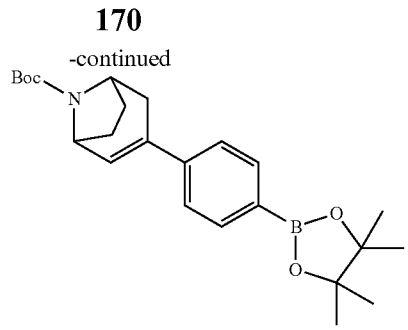

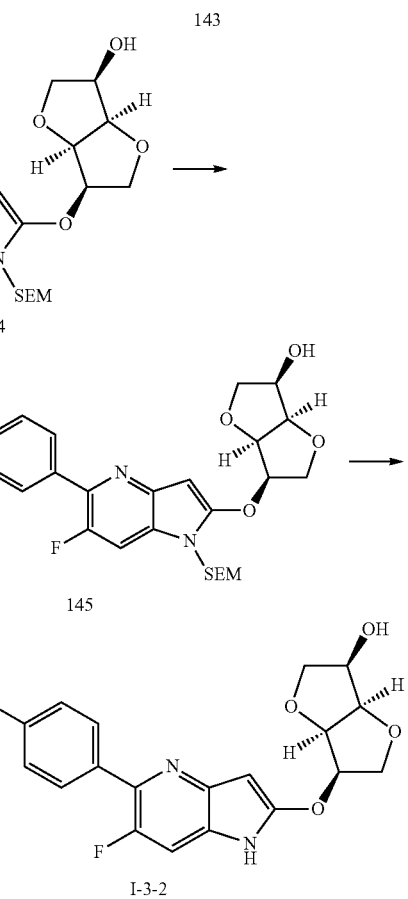

To a solution of Compound 142 (430 mg, 1.18 mmol) in 1,4-dioxane (4.3 ml) were added Compound 54 (449 mg, 1.77 mmol), PdCl₂(dppf)CH₂Cl₂ (96.8 mg, 0.118 mmol), and potassium acetate (463 mg, 4.72 mmol), and the reaction mixture was stirred at 100° C. for 1 hour. The reaction mixture was filtered, the solvent was removed under reduced pressure, and the obtained residue was purified by silica gel column chromatography to obtain Compound 143 (411 mg, 0.999 mmol, 85%) as a white solid.

Compound 143; Method C

LC/MS retention time=2.90 min.

MS (EI) m/z=412.20 (M+H)+

To a solution of Compound 144 (30.0 mg, 0.067 mmol) in 1,4-dioxane (0.6 ml) were added Compound 143 (41.6 mg, 0.101 mmol), 2 mol/L aqueous solution of potassium carbonate (0.067 ml, 0.135 mmol), and PdCl₂(dtbpf) (8.8 mg, 0.013 mmol), and the resulting mixture was stirred at 130° C. for 30 minutes under microwave irradiation. The reaction mixture was purified by silica gel column chromatography to obtain Compound 145 (26.1 mg, 0.038 mmol, 56%).

Compound 145; Method C

LC/MS retention time=2.78 min.

MS (EI) m/z=694.20 (M+H)+

To a solution of Compound 145 (13.0 mg, 0.049 mmol) in methylene chloride (0.26 ml) was added TFA (0.26 ml, 3.37 mmol), and the reaction mixture was stirred at room temperature for 3 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-2 (4.4 mg, 9.5 μmol, 51%) as a white solid.

Compound I-3-2; Method C

LC/MS retention time=0.99 min.

MS (EI) m/z=464.50 (M+H)+

Example 43

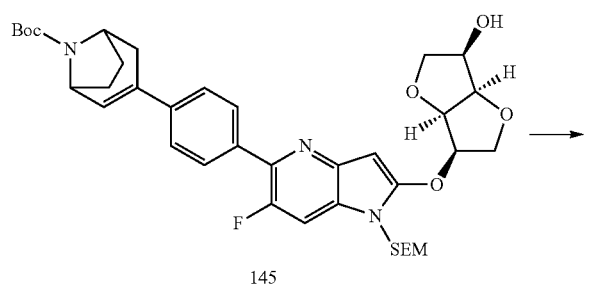

145

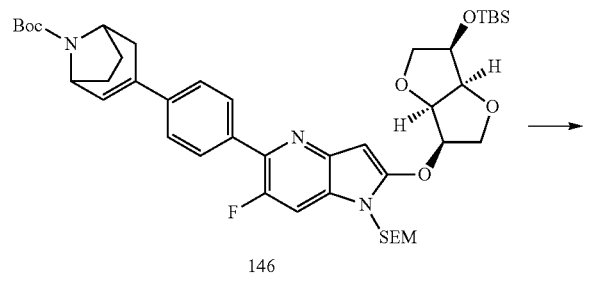

146

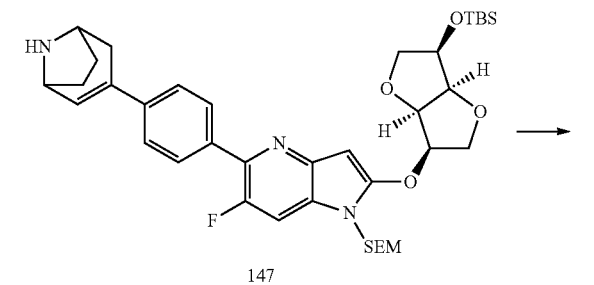

147

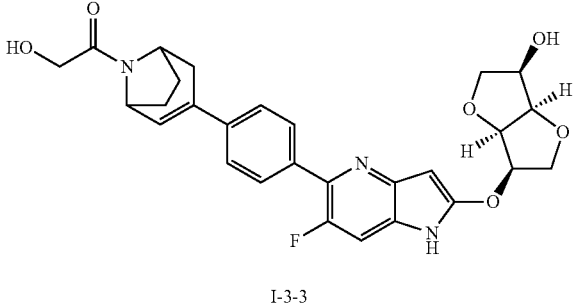

I-3-3

To a solution of Compound 145 (181 mg, 0.260 mmol) in DMF (1.8 ml) were added imidazole (26.6 mg, 0.391 mmol) and TBSCl (58.9 mg, 0.391 mmol) under ice cooling, and the reaction mixture was stirred at, room temperature for 3 hours. The reaction mixture was quenched with water, and then extracted with ethyl acetate. The organic layer was washed with saturated aqueous NaCl and dried over magnesium sulfate, and the solvent was removed under reduced pressure. The obtained residue was purified by silica gel column chromatography to obtain Compound 146 (190 mg, 0.235 mmol, 90%) as a white solid.

Compound 146; Method C

LC/MS retention time=3.52 min.

MS (EI) m/z=808.60 (M+H)+

To a solution of Compound 146 (190 mg, 0.235 mmol) in methylene chloride (3.8 ml) was added TFA (1.9 ml, 24.7 mmol) under ice cooling, and the reaction mixture was stirred under ice cooling for 20 minutes. After completion of the reaction, the reaction mixture was quenched with a saturated aqueous solution of sodium hydrogen carbonate, and then extracted with ethyl acetate. The organic layer was dried over magnesium sulfate. The solvent was removed under reduced pressure to obtain Compound 147 (166 mg, 0.235 mmol, 100%).

Compound 147; Method C

LC/MS retention time=2.50 min.

MS (EI) m/z=708.30 (M+H)+

To a solution of Compound 147 (41.0 mg, 0.058 mmol) in methylene chloride (1 mL) were successively added glycolic acid (5.3 mg, 0.070 mmol), HATU (28.7 mg, 0.070 mmol), and triethylamine (0.032 ml, 0.232 mmol) under ice cooling, and the reaction mixture was warmed to room temperature and then stirred for 2.5 hours. Purification of the reaction mixture by silica gel column chromatography was conducted but it was difficult to remove impurities. The obtained crude product (50.7 mg) was used directly in the next reaction.

To a solution of the crude product (50.7 mg) in methylene chloride (0.5 ml) was added TFA (0.5 ml, 6.49 mmol), and the reaction mixture was stirred overnight at room temperature. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-3 (14.4 mg, 0.028 mmol, 47%) as a white solid.

Compound I-3-3; Method C
LC/MS retention time=1.25 min.
MS (EI) m/z=522.05 (M+H)+

Example 44

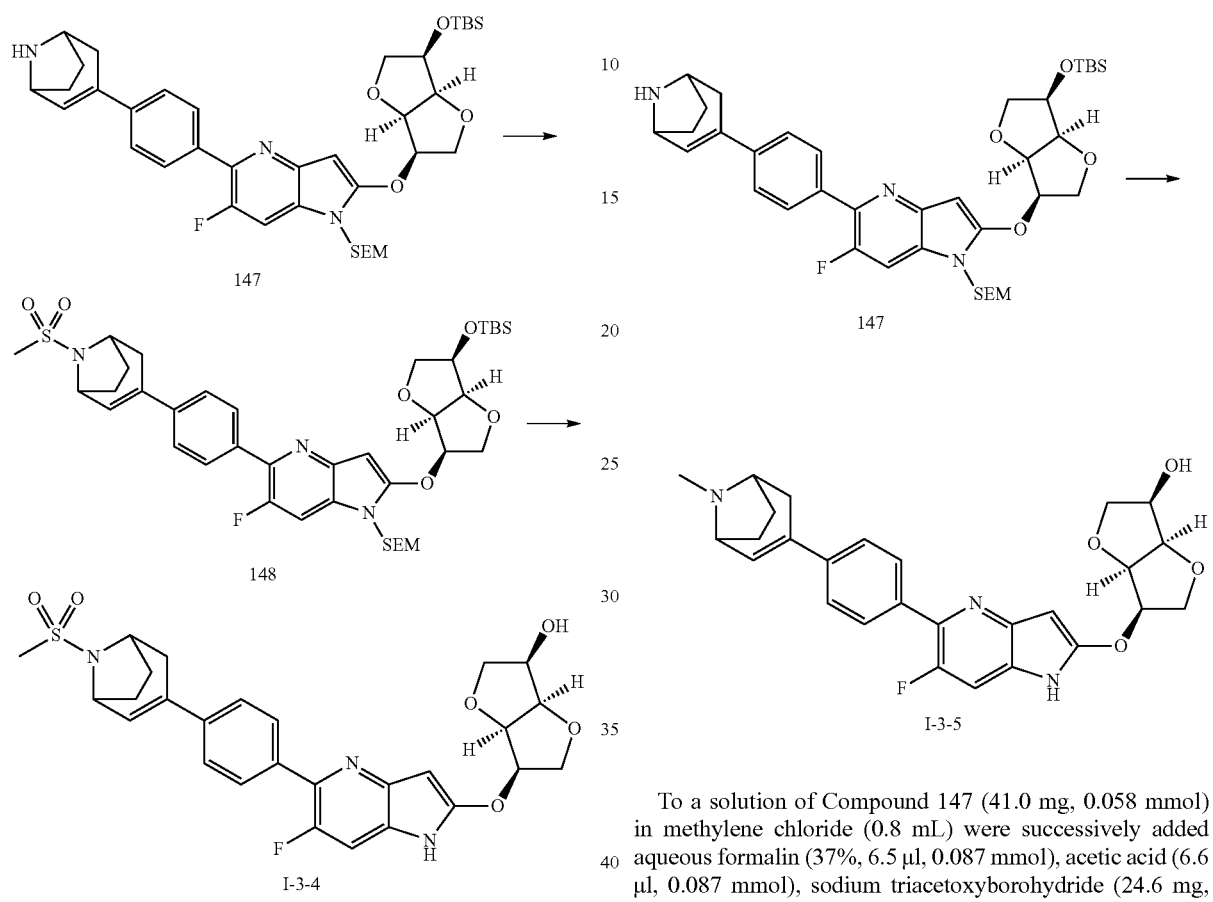

To a solution of Compound 147 (41.0 mg, 0.058 mmol) in methylene chloride (1 mL) were successively added methanesulfonyl chloride (5.9 µl, 0.075 mmol) and triethylamine (0.040 ml, 0.290 mmol) under ice cooling, and the reaction mixture was warmed to room temperature and then stirred for 1 hour. The reaction mixture was purified by silica gel column chromatography to obtain Compound 148 (40.9 mg, 0.052 mmol, 90%) as a white solid.

Compound 148; Method C
LC/MS retention time=3.13 min.
MS (EI) m/z=786.25 (M+H)+

To a solution of Compound 148 (40.9 mg, 0.052 mmol) in methylene chloride (0.5 ml) was added TFA (0.5 ml, 6.49 mmol), and the reaction mixture was stirred overnight at room temperature. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-4 (16.4 mg, 0.030 mmol, 58%) as a white solid.

Compound I-3-4; Method C
LC/MS retention time=1.40 min.
MS (EI) m/z=542.05 (M+H)+

Example 45

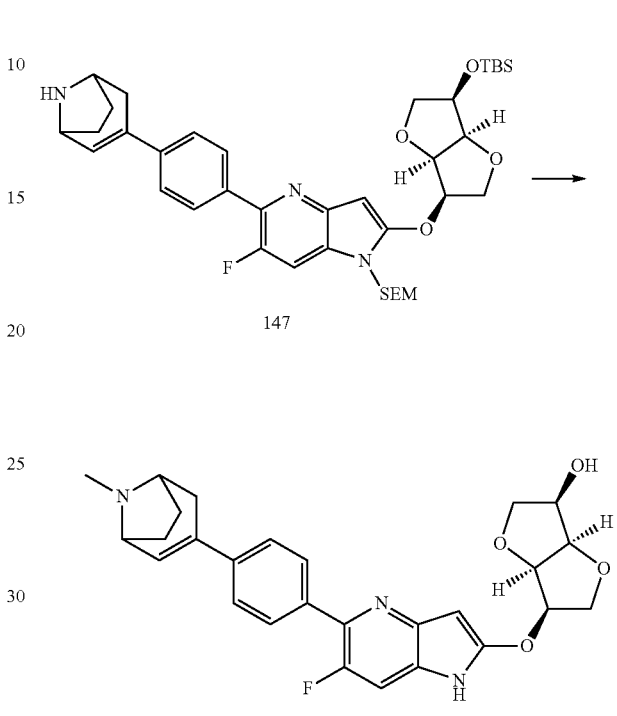

To a solution of Compound 147 (41.0 mg, 0.058 mmol) in methylene chloride (0.8 mL) were successively added aqueous formalin (37%, 6.5 µl, 0.087 mmol), acetic acid (6.6 µl, 0.087 mmol), sodium triacetoxyborohydride (24.6 mg, 0.116 mmol) under ice cooling, and the reaction mixture was stirred overnight at room temperature. After completion of the reaction, the reaction mixture was quenched with a saturated aqueous solution of sodium hydrogen carbonate, and then extracted with ethyl acetate. The organic layer was dried over magnesium sulfate. The solvent was removed under reduced pressure, and the obtained residue (40.6 mg) was used directly in the next reaction.

To a solution of the residue (40.6 mg) in methylene chloride (0.5 ml) was added TFA (0.5 ml, 6.49 mmol), and the reaction mixture was stirred overnight at room temperature. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-5 (0.5 mg, 1.1 µmol, 2%).

Compound I-3-5; Method C
LC/MS retention time=1.00 min.
MS (EI) m/z=478.00 (M+H)+

Example 46

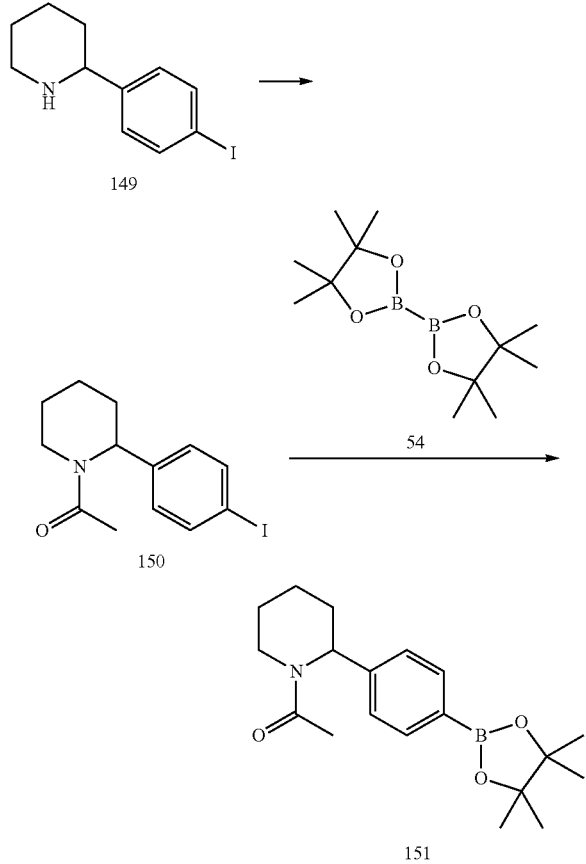

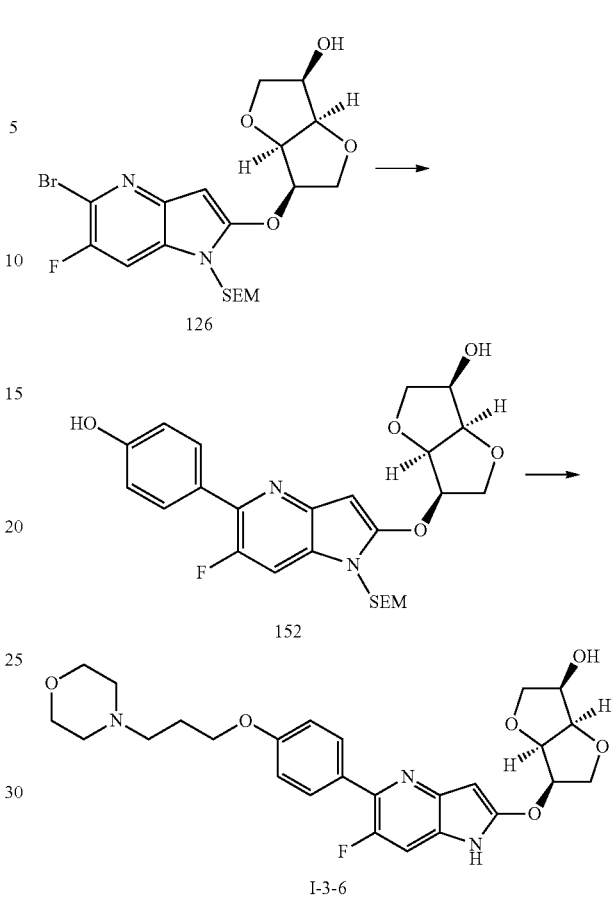

To a solution of Compound 149 (200 mg, 0.695 mmol) in dichloromethane (2 ml) were added acetic anhydride (0.099 ml, 1.05 mmol) and triethylamine (0.193 mmol, 1.39 mmol) at room temperature, and the reaction mixture was stirred at room temperature for 1.5 hours. The reaction mixture was concentrated under reduced pressure, and the obtained residue was purified by silica gel column chromatography to obtain Compound 150 (229 mg, 0.695 mmol, 100%) as a yellow oil.

Compound 150; Method C
LC/MS retention time=2.09 min.
MS (EI) m/z=329.85 (M+H)+

To a solution of Compound 150 (100 mg, 0.304 mmol) in 1,4-dioxane (1 ml) were added Compound 54 (154 mg, 0.608 mmol), X-phos (14.5 mg, 0.030 mmol), $Pd_2(dba)_3$ (13.9 mg, 0.015 mmol), and potassium acetate (119 mg, 1.22 mmol), and the reaction mixture was stirred at 100° C. for 4 hours. Purification of the reaction mixture by silica gel column chromatography was conducted but it was difficult to remove impurities. The obtained crude product (111.5 mg), containing Compound 151, was used directly in the next reaction.

Compound 151; Method C
LC/MS retention time=2.26 min.
MS (EI) m/z=330.10 (M+H)+

To a solution of Compound 126 (350 mg, 0.715 mmol) in 1,4-dioxane (3.5 ml) were added 4-hydroxyphenylboronic acid (197 mg, 1.43 mmol), 2 mol/L aqueous solution of potassium carbonate (0.537 ml, 1.07 mmol), and $PdCl_2$ (dtbpf) (93.3 mg, 0.144 mmol), and the resulting mixture was stirred at 145° C. for 45 minutes under microwave irradiation. The reaction mixture was quenched with saturated ammonium chloride, followed by extraction with ethyl acetate. The organic layer was washed with saturated aqueous NaCl and dried over magnesium sulfate, and the solvent was removed under reduced pressure. The obtained residue was purified by silica gel column chromatography to obtain Compound 152 (184.7 mg, 0.367 mmol, 51%) as a brown solid.

Compound 152; Method C
LC/MS retention time=1.83 min.
MS (EI) m/z=503.10 (M+H)+

To a solution of Compound 152 (30 mg, 0.060 mmol) in DMF (0.3 ml) were added 4-(3-chloropropyl)morpholine (19.5 mg, 0.119 mmol) and cesium carbonate (38.9 mg, 0.119 mmol), and the reaction mixture was stirred at 80° C. for 4 hours. Purification of the reaction mixture by silica gel column chromatography was conducted but it was difficult to remove impurities. The obtained crude product (39.7 mg) was used directly in the next reaction.

To a solution of the crude product (39.7 mg) in methylene chloride (0.5 ml) was added TFA (0.5 ml, 6.49 mmol), and the reaction mixture was stirred at room temperature for 4 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-6 (12.1 mg, 0.024 mmol, 38%).

Compound I-3-6; Method C
LC/MS retention time=0.90 min.
MS (EI) m/z=500.00 (M+H)+

Example 47 sium sulfate. The solvent was removed under reduced pressure, and the obtained residue was used directly in the next reaction. To a solution of the product in methylene chloride (1 mL) were successively added glycolic acid (5.01 mg, 0.066 mmol), HATU (27.1 mg, 0.071 mmol), and triethylamine (0.030 ml, 0.219 mmol) under ice cooling, and the reaction mixture was warmed to room temperature and then stirred for 1.5 hours. The reaction mixture was purified by silica gel column chromatography to obtain Compound 154 (25.6 mg, 0.041 mmol, 69% in 3 steps) as a yellow oil.

Compound 154; Method C
LC/MS retention time=1.87 min.
MS (EI) m/z=618.15 (M+H)+

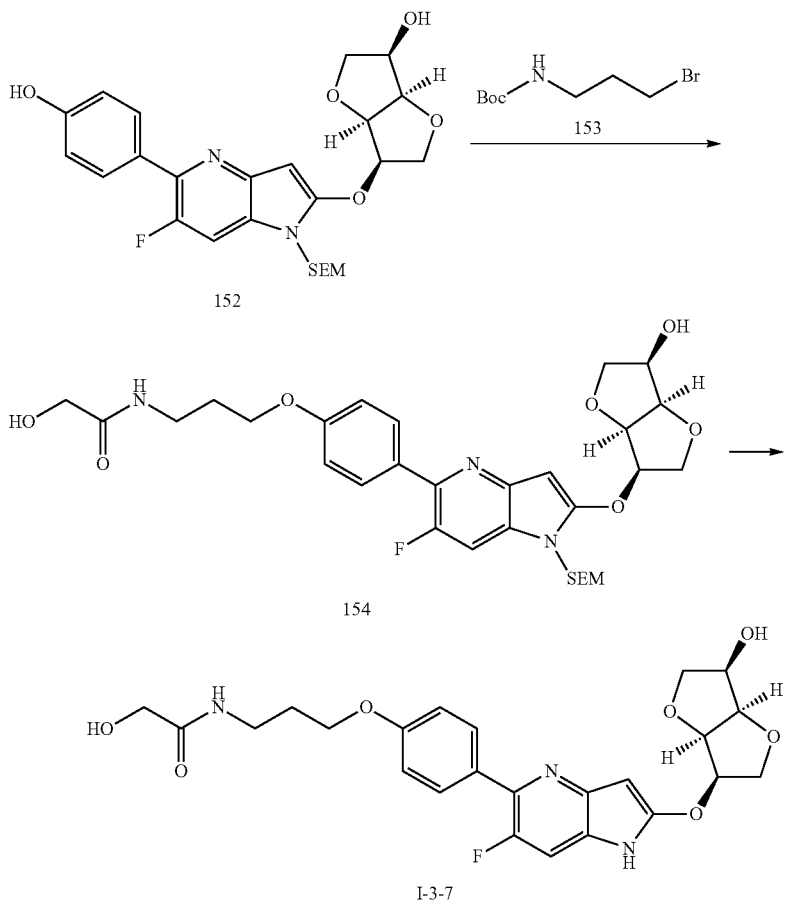

To a solution of Compound 152 (30 mg, 0.060 mmol) in DMF (0.3 ml) were added Compound 153 (28.4 mg, 0.119 mmol) and cesium carbonate (38.9 mg, 0.119 mmol), and the reaction mixture was stirred at 80° C. for 5 hours. Purification of the reaction mixture by silica gel column chromatography was conducted but it was difficult to remove impurities. The obtained crude product (50.4 mg) was used directly in the next reaction.

To a solution of the crude product (50.4 mg) in methylene chloride (1.0 ml) was added TFA (0.5 ml, 6.49 mmol) under ice cooling, and the reaction mixture was stirred under ice cooling for 30 minutes. After completion of the reaction, the reaction mixture was quenched with a saturated aqueous solution of sodium hydrogen carbonate, and then extracted with chloroform. The organic layer was dried over magne- To a solution of Compound 154 (25.6 mg, 0.041 mmol) in methylene chloride (0.5 ml) was added TFA (0.5 ml, 6.49 mmol), and the reaction mixture was stirred at room temperature for 5 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-7 (9.6 mg, 0.020 mmol, 48%).

Compound I-3-7; Method C
LC/MS retention time=1.09 min.
MS (EI) m/z=488.05 (M+H)+

Example 48

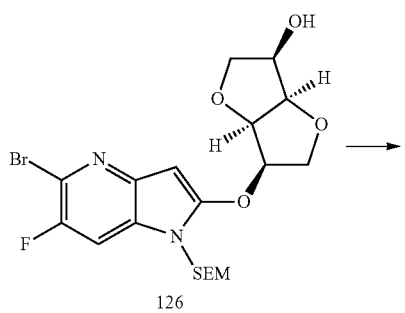
126

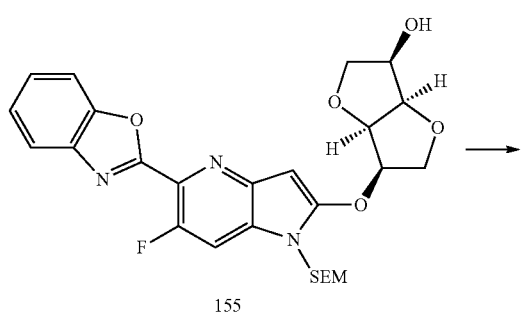
155

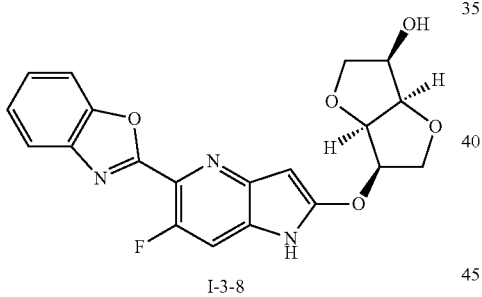
I-3-8

To a solution of Compound 126 (70.0 mg, 0.143 mmol) in DMF (0.7 ml) were added benzoxazole (34.1 mg, 0.286 mmol), copper iodide (5.5 mg, 0.029 mmol), 1,10-phenanthroline (5.2 mg, 0.029 mmol), cesium carbonate (186 mg, 0.572 mmol), and PdCl$_2$(dtbpf) (28.3 mg, 0.043 mmol), and the reaction mixture was stirred at 100° C. for 1.5 hours. The reaction mixture was purified by silica gel column chromatography to obtain Compound 155 (74.0 mg, 0.140 mmol, 98%).

Compound 155; Method C
LC/MS retention time=2.32 min.
MS (EI) m/z=528.10 (M+H)+

To a solution of Compound 155 (74.0 mg, 0.140 mmol) in dichloromethane (0.6 ml) was added TFA (0.6 ml, 7.79 mmol), and the reaction mixture was stirred at room temperature for 4 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-8 (19.7 mg, 0.050 mmol, 35%).

Compound I-3-8; Method C
LC/MS retention time=1.48 min.
MS (ET) m/z=397.95 (M+H)+

Example 49

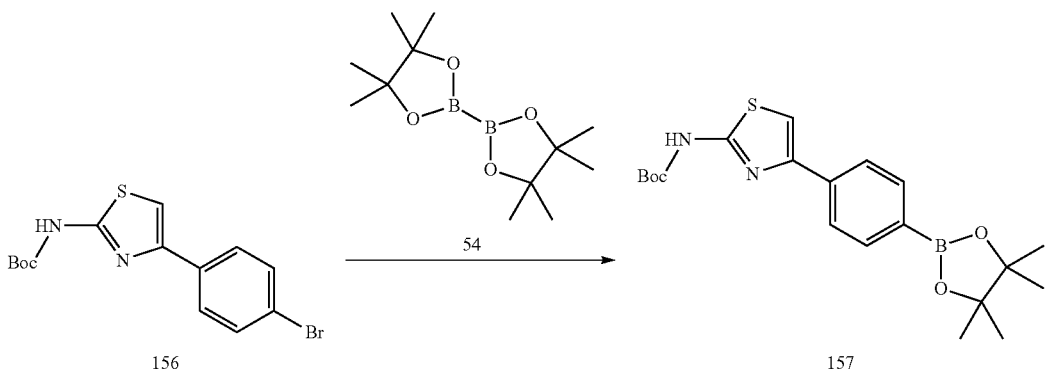
156    157

-continued

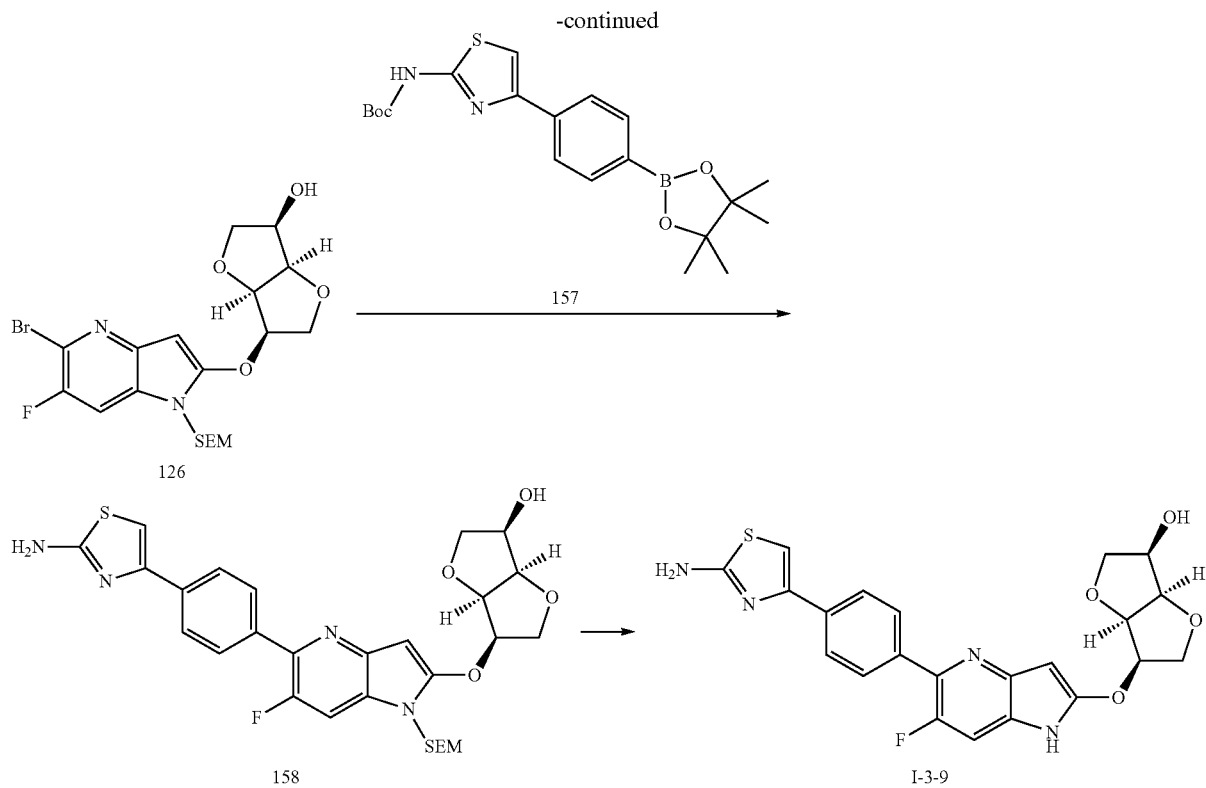

126

158

I-3-9

To Compound 156 (236 mg, 0.663 mmol) were added 1,4-dioxane (2.4 ml), Compound 54 (253 mg, 0.995 mmol), $PdCl_2(dppf)CH_2Cl_2$ (54.2 mg, 0.066 mmol), and potassium acetate (260 mg, 2.65 mmol), and the reaction mixture was stirred at 100° C. for 1.5 hours. The reaction mixture was filtered, the solvent was removed under reduced pressure, and the obtained residue was purified by silica gel column chromatography to obtain Compound 157 (241 mg, 0.599 mmol, 90%) as a white solid.

Compound 157; Method C
LC/MS retention time=2.73 min.
MS (EI) m/z=403.05 (M+H)+

To a solution of Compound 126 (50 mg, 0.102 mmol) in 1,4-dioxane (0.5 ml) were added Compound 157 (61.7 mg, 0.153 mmol), 2 mol/L aqueous solution of potassium carbonate (0.102 ml, 0.204 mmol), and $PdCl_2(dtbpf)$ (13.3 mg, 0.020 mmol), and the resulting mixture was stirred at 145° C. for 30 minutes under microwave irradiation. The reaction mixture was purified by silica gel column chromatography to obtain Compound 158 (28.5 mg, 0.049 mmol, 48%) as a red oil.

Compound 158; Method C
LC/MS retention time=1.96 min.
MS (EI) m/z=585.05 (M+H)+

To a solution of Compound 158 (28.5 mg, 0.049 mmol) in methylene chloride (0.5 ml) was added TFA (0.5 ml, 6.49 mmol), and the reaction mixture was stirred at room temperature for 5 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-9 (9.9 mg, 0.022 mmol, 45%).

Compound I-3-9; Method C
LC/MS retention time=1.10 min.
MS (EI) m/z=455.00 (M+H)+

Example 50

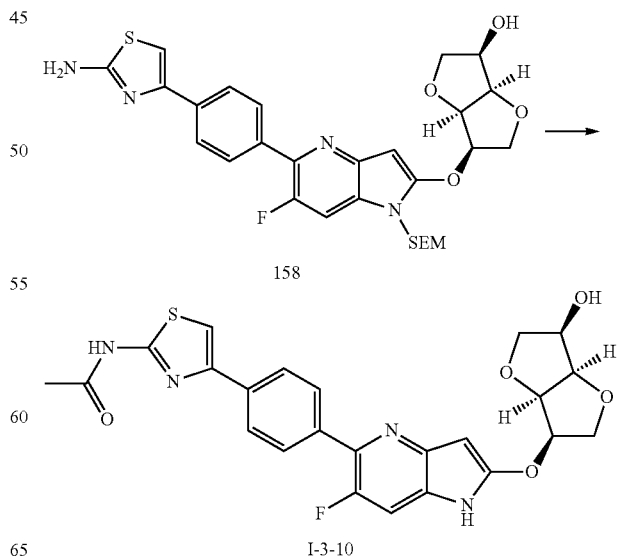

158

I-3-10

To a solution of Compound 158 (32.3 mg, 0.055 mmol) in methylene chloride (1 mL) were successively added acetic acid (3.8 µg, 0.066 mmol), HATU (27.2 mg, 0.072 mmol), and triethylamine (0.031 ml, 0.220 mmol) under ice cooling, and the reaction mixture was warmed to room temperature and then stirred overnight. To the reaction mixture were added methanol and potassium carbonate, and the resulting mixture was filtered and the solvent was removed under reduced pressure. Purification of the obtained residue by silica gel column chromatography was conducted but it was difficult to remove impurities. The obtained crude product (14.9 mg) was used directly in the next reaction.

To a solution of the crude product (14.9 mg) in methylene chloride (0.5 ml) was added TFA (0.5 ml, 6.49 mmol), and the reaction mixture was stirred overnight at room temperature. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-10 (3.9 mg, 7.9 µmol, 14%) as a yellow solid.

Compound I-3-10; Method C

LC/MS retention time=1.30 min.

MS (EI) m/z=497.05 (M+H)+

Example 51

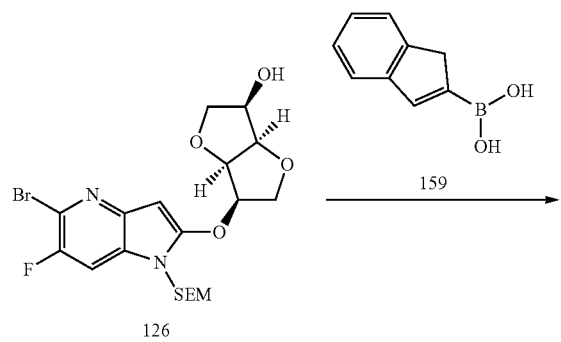

126

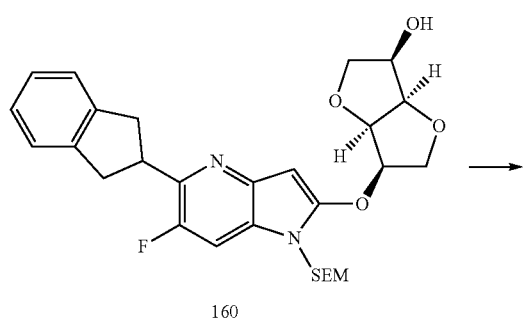

160

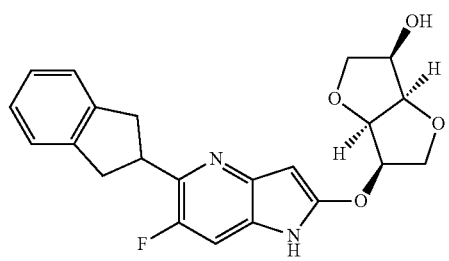

I-3-11

To a solution of Compound 126 (100 mg, 0.204 mmol) in DMF (1.0 ml) were added Compound 159 (65.4 mg, 0.409 mmol), cesium carbonate (266 mg, 0.817 mmol), and PdCl$_2$(dtbpf) (26.6 mg, 0.041 mmol), and the reaction mixture was stirred at 100° C. for 2 hours. Purification of the reaction mixture by silica gel column chromatography was conducted but it was difficult to remove impurities. A 60-mg portion of the obtained crude product (120 mg) was used directly in the next reaction. To a solution of the crude product (60.0 mg) in methanol (2.0 ml) was added Pd/C (5%, 24.3 mg), and the resulting mixture was stirred at room temperature for 5 hours under hydrogen gas atmosphere (15 psi). The reaction mixture was filtered, and the solvent was removed under reduced pressure to obtain Compound 160 (39.5 mg, 0.075 mmol, 74%) as a brown solid.

Compound 160; Method C

LC/MS retention time=2.50 min.

MS (EI) m/z=527.15 (M+H)+

To a solution of Compound 160 (39.5 mg, 0.075 mmol) in methylene chloride (0.5 ml) was added TFA (0.5 ml, 6.49 mmol), and the reaction mixture was stirred at room temperature for 5.5 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-11 (17.7 mg, 0.045 mmol, 60%).

Compound I-3-11; Method C

LC/MS retention time=1.41 min.

MS (EI) m/z=397.00 (M+H)+

Example 52
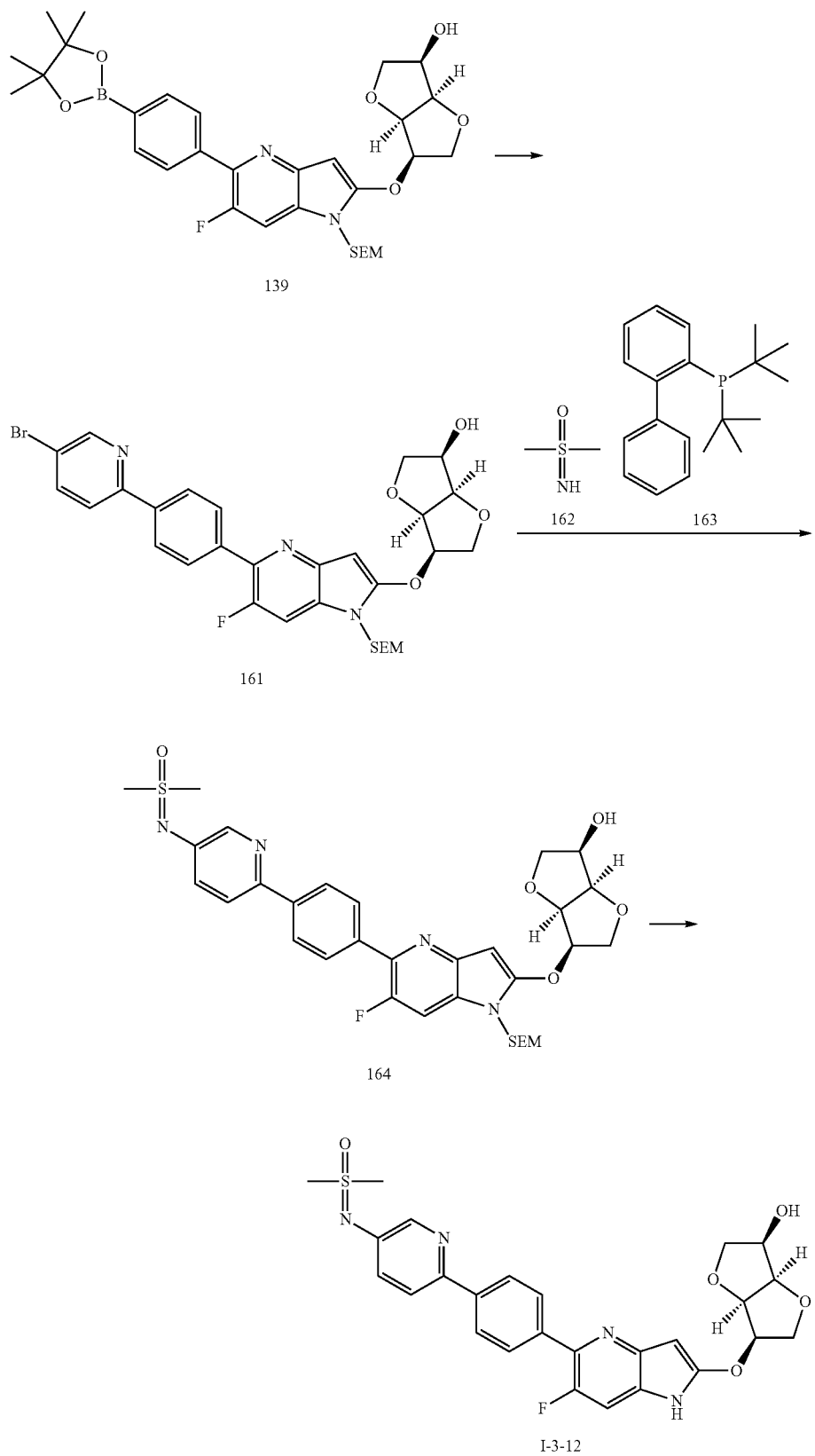

To a solution of Compound 139 (90.0 mg, 0.147 mmol) in 1,4-dioxane (1.8 ml) were successively added 2,5-dibromopyridine (139 mg, 0.588 mmol), tetrakis(triphenylphosphine)palladium (17.0 mg, 0.014 mmol), and 2 mol/L aqueous solution of potassium carbonate (0.294 ml, 0.588 mmol) at room temperature, and the reaction mixture was stirred at 80° C. for 9 hours. The reaction mixture was purified by silica gel column chromatography to obtain Compound 161 (76.6 mg, 0.119 mmol, 81%) as a brown solid.

Compound 161; Method C
LC/MS retention time=2.74 min.
MS (EI) m/z=644.10 (M+H)+

To a solution of Compound 161 (76.6 mg, 0.119 mmol) in 1,4-dioxane (1.5 ml) were added Compound 162 (13.9 mg, 0.148 mmol), NaOt-Bu (16.6 mg, 0.173 mmol), Compound 163 (7.2 mg, 0.024 mmol), and Pd$_2$(dba)$_3$ (8.3 mg, 0.009 mmol) at room temperature, and the reaction mixture was stirred at 80° C. for 2.5 hours. The reaction mixture was purified by silica gel column chromatography to obtain Compound 164 (38.9 mg, 0.059 mmol, 50%) as a brown solid.

Compound 164; Method C
LC/MS retention time=1.91 min.
MS (EI) m/z=655.15 (M+H)+

To a solution of Compound 164 (38.9 mg, 0.059 mmol) in methylene chloride (0.5 ml) was added TFA (0.5 ml, 6.49 mmol), and the reaction mixture was stirred at room temperature for 2.5 hours. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-3-12 (16.6 mg, 0.032 mmol, 53%).

Compound I-3-12; Method C
LC/MS retention time=1.11 min.
MS (EI) m/z=524.95 (M+H)+

Example 53

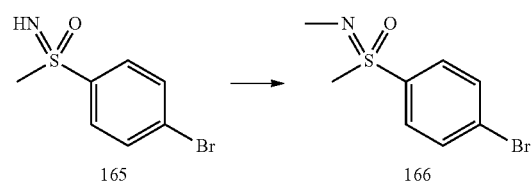

165 → 166

-continued

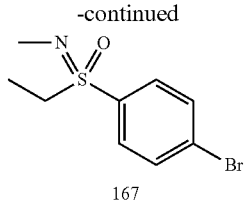

167

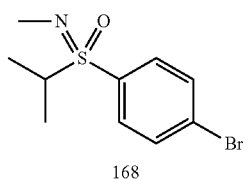

168

Compound 165 (2.98 g, 12.73 mmol) was diluted in DME (89 ml), to which was then added 60 wt % sodium hydride (1.527 g, 38.2 mmol) under ice cooling, and the resulting mixture was stirred under ice cooling and at room temperature. After that, the reaction mixture was cooled in an ice bath, followed by addition of methyl iodide (3.98 ml, 63.6 mmol), and the resulting mixture was stirred at room temperature. After completion of the reaction, water was added to the reaction mixture, which was then extracted with ethyl acetate. The obtained organic layer was dried over magnesium sulfate, and then the solvent was removed by concentration under reduced pressure. The obtained residue was purified by silica gel column chromatography to obtain Compound 166 (1.325 g, 41.9%), Compound 167 (1.014 g, 30.4%), and Compound 168 (0.1317 g, 3.7%).

Compound 166; Method B
LC/MS retention time=1.15 min.
MS (ESI) m/z=248.00 (M+H)+.

Compound 167; Method B
LC/MS retention time=1.28 min.
MS (ESI) m/z=262.00 (M+H)+.

Compound 168; Method B
LC/MS retention time=1.43 min.
MS (ESI) m/z=276.00 (M+H)+.

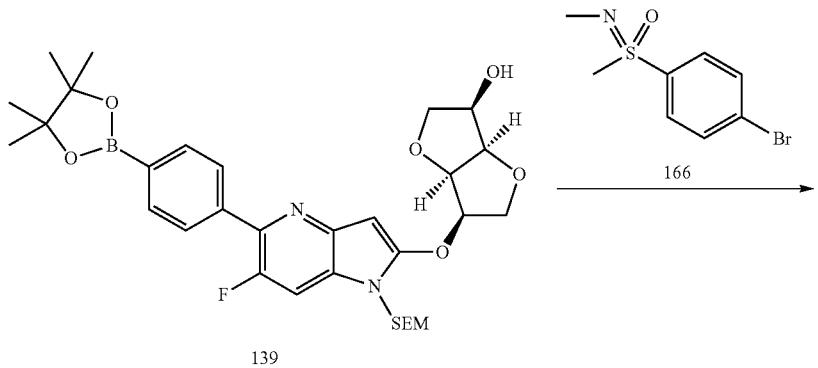

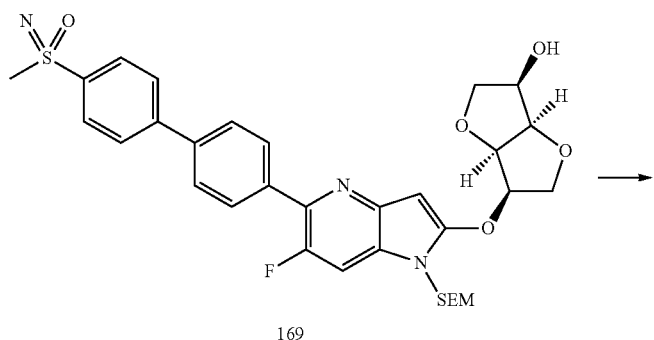

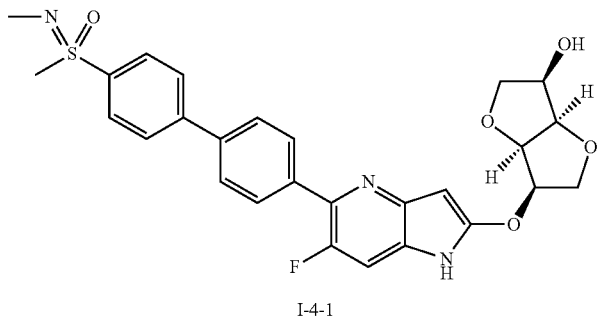

I-4-1

To Compound 139 (40 mg, 0.065 mmol) were added 1,4-dioxane (0.5 ml) and PdCl$_2$(dtbpf) (12.77 mg, 0.020 mmol), Compound 166 (32.4 mg, 0.131 mmol), and 2 mol/L aqueous solution of potassium carbonate (0.0653 ml, 0.131 mmol), and the reaction mixture was stirred at 60° C. After completion of the reaction, the reaction mixture was purified by silica gel column chromatography to obtain Compound 169.

Compound 169; Method B
LC/MS retention time=2.01 min.
MS (ESI) m/z=654.10 (M+H)+.

To Compound 169 (42.5 mg, 0.065 mmol) was added TFA (1 ml), and the reaction mixture was stirred at room temperature. After completion of the reaction, the TFA was removed by concentration under reduced pressure. The obtained residue was diluted in MeOH, followed by neutralization with an aqueous solution of sodium hydrogen carbonate. Extraction was performed with chloroform, the obtained organic layer was dried over magnesium sulfate, and then the solvent was removed by concentration under reduced pressure. The obtained residue was purified by reverse-phase column chromatography to obtain Compound I-4-1.

Compound I-4-1; Method B
LC/MS retention time=1.01 min.
MS (ESI) m/z=524.25 (M+H)+

Compound I-4-1 was subjected to optical resolution to obtain Compounds I-4-36 and I-4-37.

Compound I-4-36; Method B
LC/MS retention time=1.02 min.
MS (ESI) m/z=524.25 (M+H)+

Compound I-4-37; Method B
LC/MS retention time=1.02 min.
MS (ESI) m/z=524.25 (M+H)+

191 192
Example 54
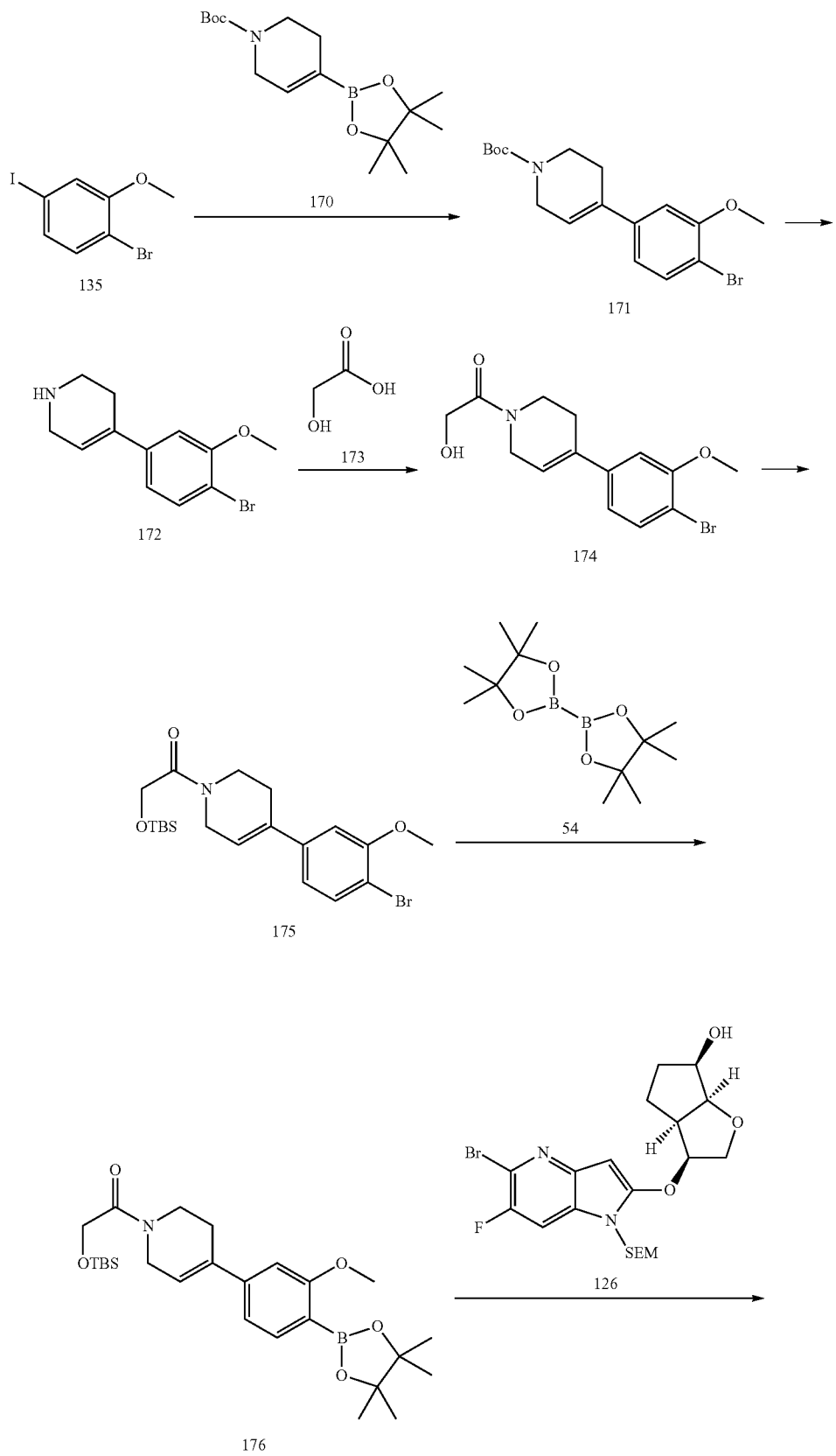

-continued

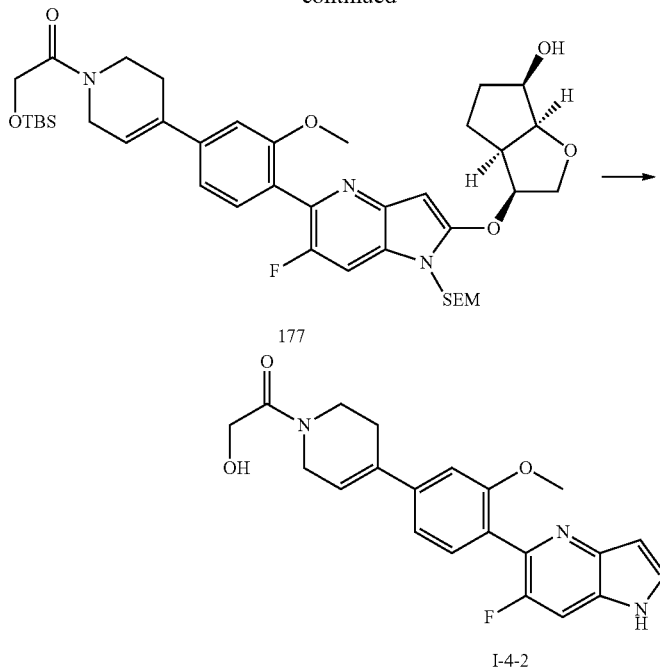

177

I-4-2

Compound 135 (2.00 g, 6.39 mmol) and Compound 170 (2.174 g, 7.03 mmol) were dissolved in 1,4-dioxane (20 ml), to which were then added tetrakis(triphenylphosphine)palladium (0.739 g, 0.639 mmol) and 2 mol/L aqueous solution of potassium carbonate (4.79 ml, 9.59 mmol), and the reaction mixture was stirred at 100° C. After completion of the reaction, chloroform and water were added to the reaction mixture, and the resulting mixture was filtered. The obtained filtrate was extracted with chloroform. The obtained organic layer was dried over magnesium sulfate, and then the solvent was removed by concentration under reduced pressure. The obtained residue was purified by silica gel column chromatography to obtain Compound 171.

To Compound 171 (2.353 g, 6.39 mmol) were added chloroform (20 ml) and TFA (5 ml), and the reaction mixture was stirred at room temperature. After completion of the reaction, the TFA was removed by concentration under reduced pressure. The obtained residue was diluted with chloroform, and the resulting mixture was neutralized with 2 mol/L aqueous solution of potassium carbonate. The obtained organic layer was dried over magnesium sulfate, and concentrated under reduced pressure to obtain Compound 172.

Compound 172; Method B
LC/MS retention time=1.00 min.
MS (ESI) m/z=268.05 (M+H)+.

Compound 172 (1.714 g, 6.39 mmol), Compound 173 (0.535 g, 7.03 mmol), and HOBt (0.950 g, 7.03 mmol) were dissolved in DMF, the mixture was cooled in an ice bath, followed by addition of EDC.HCl (1.347 g, 7.03 mmol), and the resulting mixture was stirred at room temperature. After completion of the reaction, ethyl acetate and 1 mol/L aqueous solution of hydrochloric acid were added to the reaction mixture, and the resulting mixture was filtered. The obtained filtrate was extracted with ethyl acetate. The obtained organic layer was dried over magnesium sulfate, and concentrated under reduced pressure. The obtained residue was purified by silica gel column chromatography to obtain Compound 174.

Compound 174; Method B
LC/MS retention time=1.74 min.
MS (ESI) m/z=327.95 (M+H)+.

To a solution of Compound 174 (1.605 g, 4.92 mmol) in DMF were added tert-butyldimethylsilyl chloride (0.964 g, 6.40 mmol) and imidazole (0.435 g, 6.40 mmol), and the mixture was stirred at room temperature. After completion of the reaction, ethyl acetate was added to the reaction mixture, the resulting mixture was washed with water, and the solvent was removed by concentration under reduced pressure. The obtained residue was purified by silica gel column chromatography to obtain Compound 175 (0.856 g, 39.5%).

Compound 175; Method B
LC/MS retention time=2.86 min.
MS (ESI) m/z=441.90 (M+H)+.

To Compound 175 (250 mg, 0.568 mmol) were added 1,4-dioxane (5 ml), Compound 54 (173 mg, 0.681 mmol), PdCl$_2$(dppf)CH$_2$Cl$_2$ (69.5 mg, 0.085 mmol), and potassium acetate (111 mg, 1.135 mmol), and the reaction mixture was stirred at 110° C. The reaction mixture was filtered through Celite, and the filtrate was concentrated under reduced pressure. The obtained residue was purified by silica gel column chromatography to obtain Compound 176 (176 mg, 63.6%).

Compound 176; Method B
LC/MS retention time=2.92 min.
MS (ESI) m/z=488.10 (M+H)+.

Compound 126 (115 mg, 0.235 mmol) and Compound 176 (172 mg, 0.352 mmol) were dissolved in 1,4-dioxane (1 ml), to which were then added PdCl$_2$(dtbpf) (45.9 mg, 0.070 mmol) and 2 mol/L aqueous solution of potassium carbonate (0.176 ml, 0.352 mmol), and the resulting mixture was stirred at 150° C. under microwave irradiation. After completion of the reaction, the reaction mixture was dried over magnesium sulfate, and diluted in chloroform, and the resulting mixture was filtered. The filtrate was concentrated under reduced pressure, and the obtained residue was purified by silica gel column chromatography to obtain Compound 177 (0.0278 g, 14.4%).

Compound 177; Method C
LC/MS retention time=2.62 min.
MS (ESI) m/z=770.25 (M+H)+.

To Compound 177 (27 mg, 0.035 mmol) was added TFA (1 ml), and the reaction mixture was stirred at room temperature. After completion of the reaction, the TFA was removed by concentration under reduced pressure. The obtained residue was diluted in MeOH, followed by neutralization with an aqueous solution of sodium hydrogen carbonate. Extraction was performed with chloroform, the obtained organic layer was dried over magnesium sulfate, and then the solvent was removed by concentration under reduced pressure. The obtained residue was purified by silica gel column chromatography to obtain Compound I-4-2.

Compound I-4-2; Method B
LC/MS retention time=0.94 min.
MS (ESI) m/z=526.2 (M+H)+.

Example 55

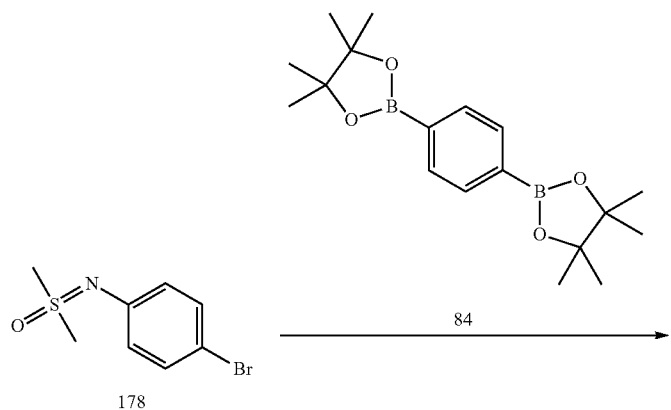

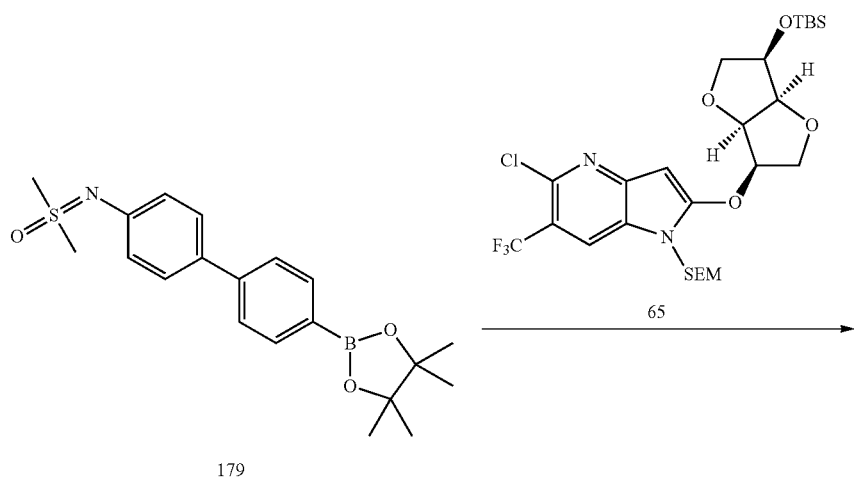

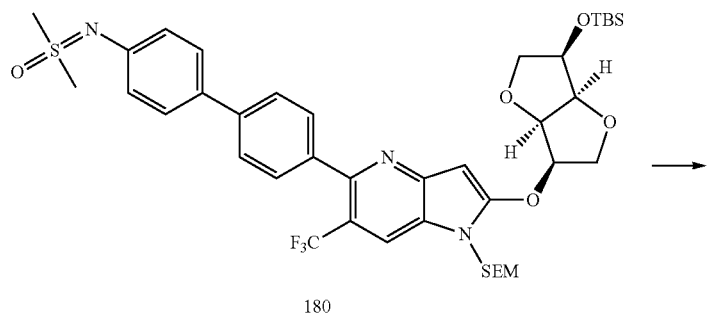

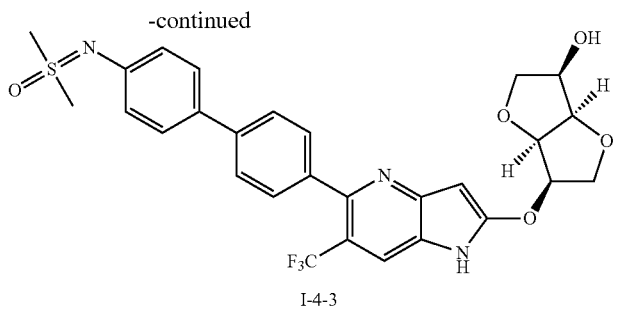

I-4-3

To Compound 178 (500 mg, 2.015 mmol) and Compound 84 (1995 mg, 6.05 mmol) was added 1,4-dioxane (10 ml), and the reaction mixture was heated to 80° C. After that, PdCl₂(dtbpf) (197 mg, 0.302 mmol) and 2 mol/L aqueous solution of potassium carbonate (1.511 ml, 3.02 mmol) were added to the reaction mixture, which was then stirred at 80° C. After completion of the reaction, chloroform and saturated aqueous NaCl were added to the reaction mixture, and the organic layer was dried over magnesium sulfate, and concentrated under reduced pressure. The obtained residue was purified by silica gel column chromatography to obtain Compound 179 (636 mg, 85.0%).

Compound 179; Method B

LC/MS retention time=2.18 min.

MS (ESI) m/z=372.25 (M+H)+.

To Compound 65 (50 mg, 0.082 mmol) were added 1,4-dioxane (0.6 ml), PdCl₂(dtbpf) (16.05 mg, 0.025 mmol), Compound 179 (60.9 mg, 0.164 mmol), and 2 mol/L aqueous solution of potassium carbonate (0.082 ml, 0.164 mmol), and the resulting mixture was stirred at 150° C. under microwave irradiation. After completion of the reaction, the reaction mixture was purified by silica gel column chromatography to obtain Compound 180 (0.0193 g, 28.7%).

Compound 180; Method C

LC/MS retention time=3.13 min.

MS (ESI) m/z=819.20 (M+H)+.

Compound I-4-3 was synthesized from Compound 180 in a similar way as in the case of Compound I-4-2.

Compound I-4-3; Method B

LC/MS retention time=1.24 min.

MS (ESI) m/z=574.5 (M+H)+

Example 56

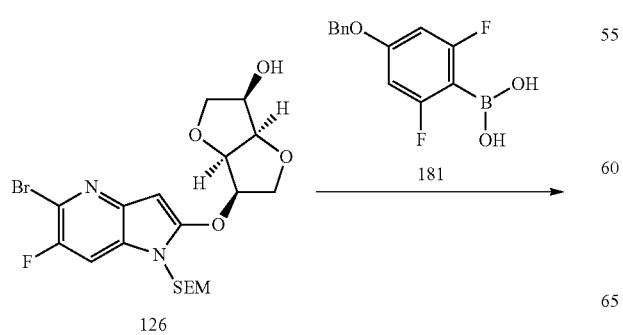

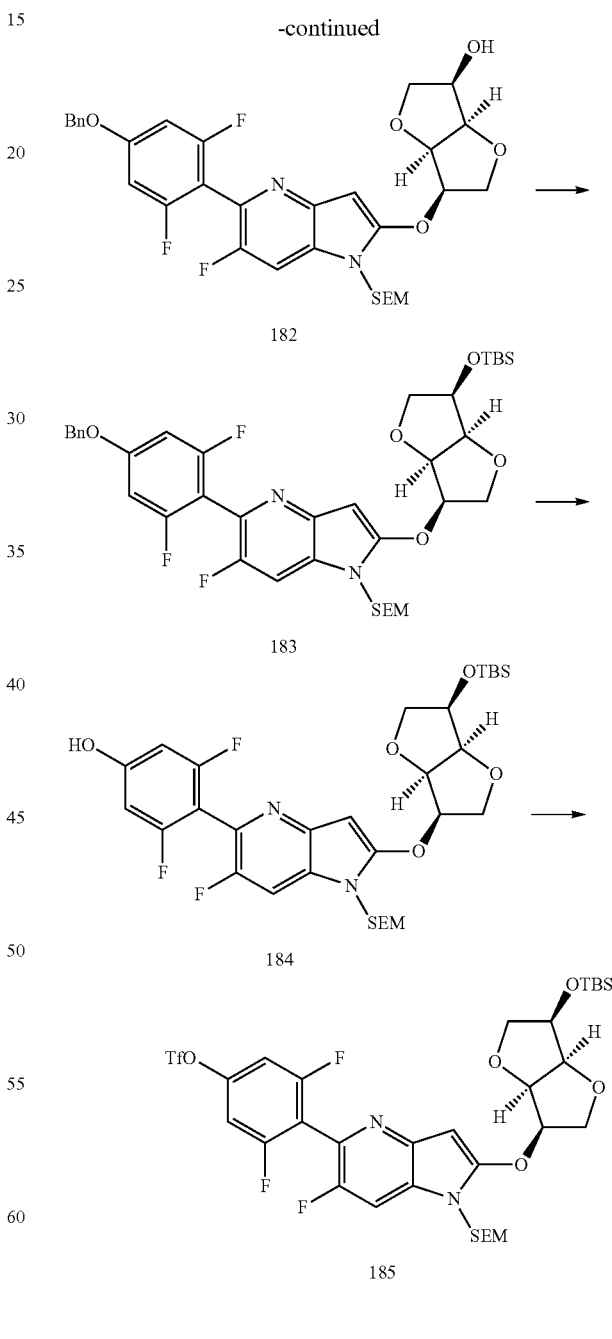

To a solution of Compound 126 (1.81 g, 3.70 mmol) in toluene (18 ml) were added Compound 181 (1.95 g, 7.40 mmol), 2 mol/L aqueous solution of potassium carbonate (3.70 ml, 7.40 mmol), and PdCl₂(dtbpf) (0.482 g, 0.740 mmol), and the resulting mixture was stirred at 150° C. for 45 minutes under microwave irradiation. The reaction mixture was purified by silica gel column chromatography to obtain Compound 182 (1.32 g, 2.09 mmol, 57%) as a brown solid.

Compound 182; Method C
LC/MS retention time=2.71 min.
MS (ESI) m/z=629.15 (M+H)+.

To a solution of Compound 182 (1.32 g, 2.09 mmol) in DMF (9.9 ml) were added imidazole (0.214 g, 3.15 mmol) and TBSCl (0.475 mg, 3.15 mmol) under ice cooling, and the reaction mixture was stirred at room temperature for 3 hours. The obtained residue was purified by silica gel column chromatography to obtain Compound 183 (1.46 g, 1.96 mmol, 94%) as a red solid.

Compound 183; Method B
LC/MS retention time=3.39 min.
MS (ESI) m/z=743.50 (M+H)+.

To a solution of Compound 183 (1.46 g, 1.96 mmol) in ethyl acetate (27 ml) was added Pd/C (5%, 0.418 g), and the resulting mixture was stirred at room temperature for 4 hours under hydrogen gas atmosphere (15 psi). The reaction mixture was filtered, and the solvent was removed under reduced pressure, whereby Compound 184 was quantitatively obtained as an orange solid (1.30 g, 1.99 mmol).

Compound 184; Method C
LC/MS retention time=3.04 min.
MS (ESI) m/z=653.15 (M+H)+.

To a solution of Compound 184 (300 mg, 0.460 mmol) in THF (3 ml) were added N-phenyl bis(trifluoromethanesulfonimide) (213 mg, 0.597 mmol), triethylamine (0.191 ml, 1.38 mmol), and DMAP (5.6 mg, 0.046 mmol) under ice cooling, and the reaction mixture was stirred at room temperature for 1.5 hours. The obtained residue was purified by silica gel column chromatography to obtain Compound 185 (334 g, 0.425 mmol, 93%) as a white solid.

Compound 185; Method C
LC/MS retention time=3.35 min.
MS (ESI) m/z=785.10 (M+H)+.

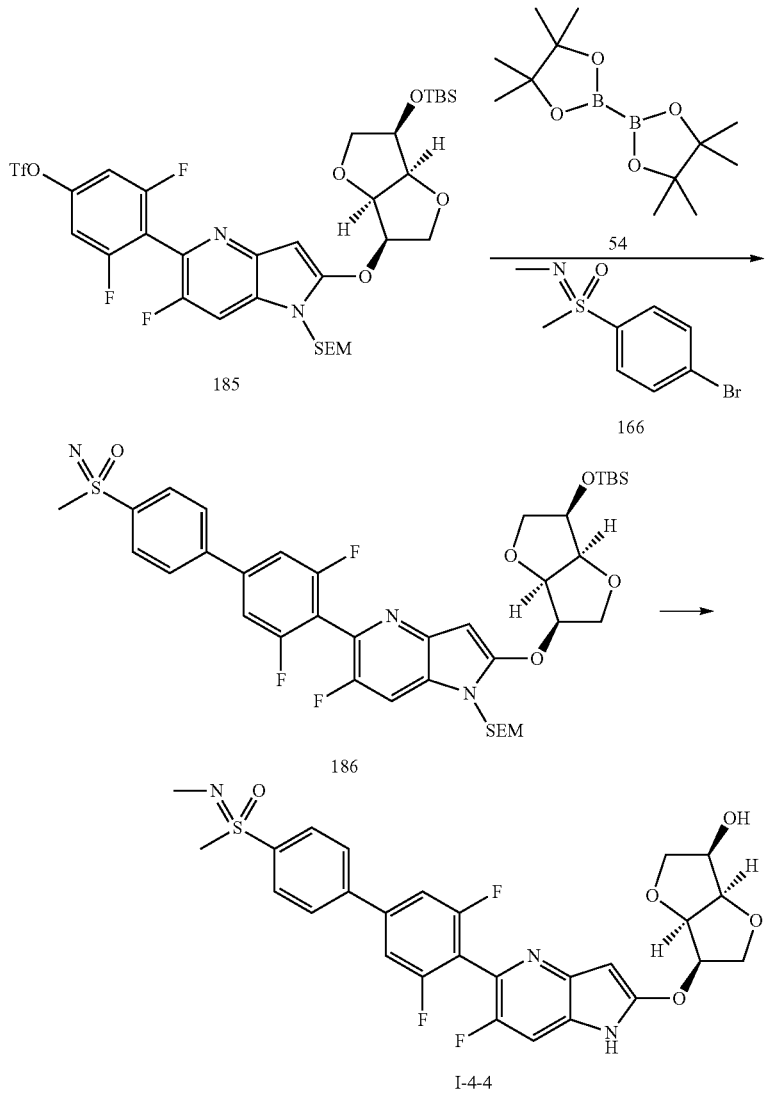

To Compound 185 (130 mg, 0.166 mmol) were added 1,4-dioxane (1.3 ml), Compound 54 (50.5 mg, 0.199 mmol), PdCl₂(dtbpf) (21.59 mg, 0.033 mmol), and potassium acetate (19.51 mg, 0.199 mmol), and the reaction mixture was stirred at 80° C. After that, Compound 166 (82 mg, 0.331 mmol) was added to the reaction mixture, followed by addition of 1,4-dioxane (0.5 ml). Subsequently, PdCl₂(dtbpf) (21.59 mg, 0.033 mmol) and 2 mol/L aqueous solution of potassium carbonate (0.166 ml, 0.331 mmol) were added to the reaction mixture, which was then stirred at 80° C. After completion of the reaction, the reaction mixture was purified by silica gel column chromatography to obtain Compound 186 (108 mg, 81.1%).

Compound 186; Method B
LC/MS retention time=3.11 min.
MS (ESI) m/z=804.40 (M+H)+.

Compound I-4-4 was synthesized from Compound 186 in a similar way as in the case of Compound I-4-2.

Compound I-4-4; Method B
LC/MS retention time=1.21 min.
MS (ESI) m/z=560.25 (M+H)+.

Example 57

To a solution of Compound 187 (0.700 g, 3.41 mmol) in 1,4-dioxane (5 ml) were added Compound 188 (0.861 g, 4.10 mmol) and PdCl₂(dtbpf) (0.223 g, 0.341 mmol), and then 2 mol/L aqueous solution of potassium carbonate (2.561 ml, 5.12 mmol), and the reaction mixture was stirred at 70° C. After completion of the reaction, water was added to the reaction mixture, and the resulting mixture was extracted with chloroform, which was then concentrated under reduced pressure. The obtained residue was purified by silica gel column chromatography to obtain Compound 189 (0.667 g, 93.8%).

Compound 189; Method B
LC/MS retention time=1.99 min.
MS (ESI) m/z=209.35 (M+H)+.

To Compound 189 (0.200 g, 0.960 mmol) was added THF (2 ml) under a nitrogen atmosphere, and the resulting mixture was cooled to −78° C., followed by addition of TMEDA (0.217 ml, 1.441 mmol) and a solution of n-butyllithium in hexane (0.929 ml, 1.441 mmol). Subsequently, Compound 190 (0.392 ml, 1.921 mmol) was added to the reaction mixture, which was further stirred at −78° C. After completion of the reaction, a 1 mol/L aqueous solution of hydrochloric acid was added to the reaction mixture, which was then extracted with ethyl acetate. The organic layer was dried over magnesium sulfate, and the solvent was removed by concentration under reduced pressure. The obtained residue was purified by silica gel column chromatography to obtain Compound 191.

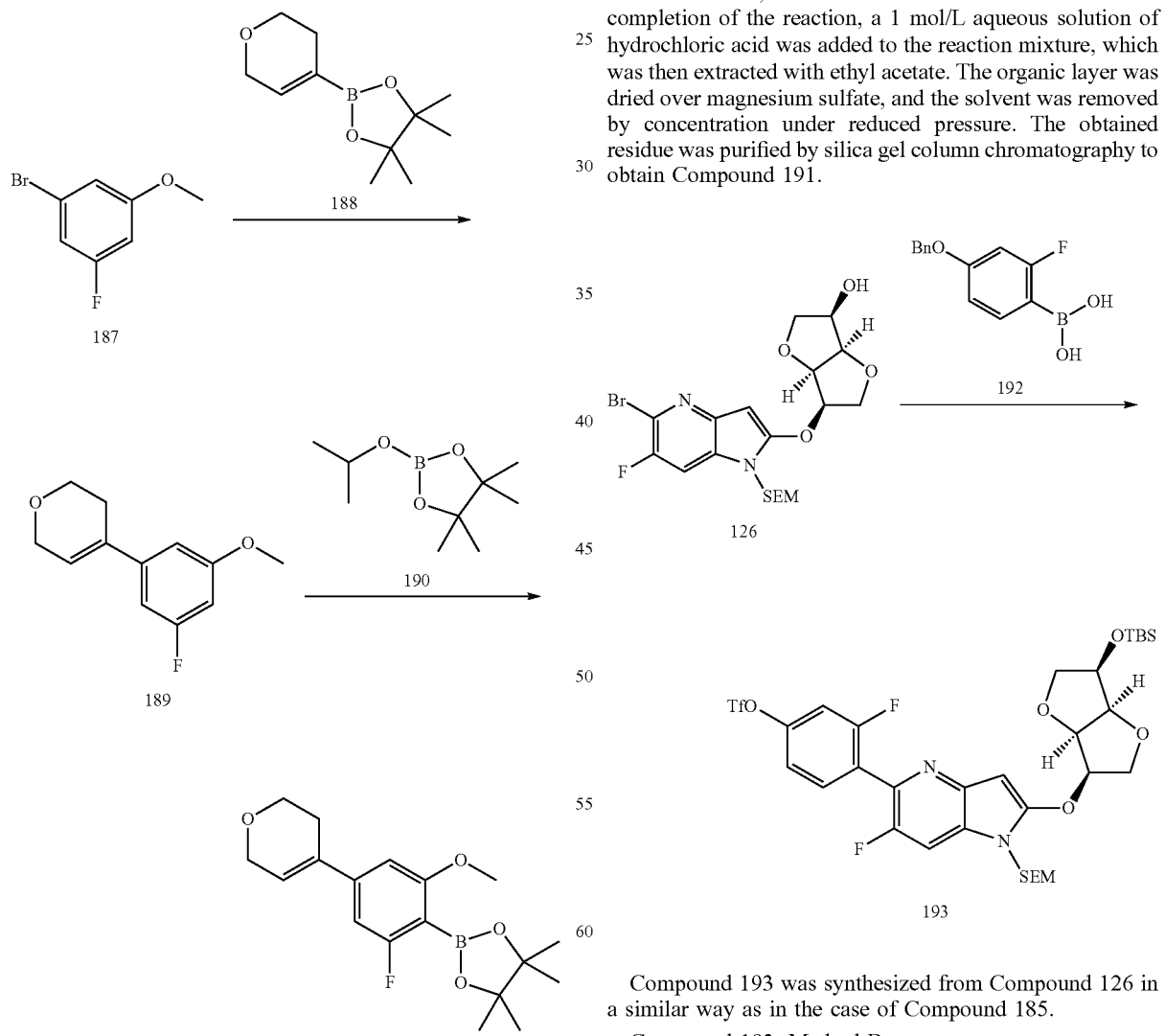

Compound 193 was synthesized from Compound 126 in a similar way as in the case of Compound 185.

Compound 193; Method B
LC/MS retention time=3.36 min.
MS (ESI) m/z=767.30 (M+H)+.

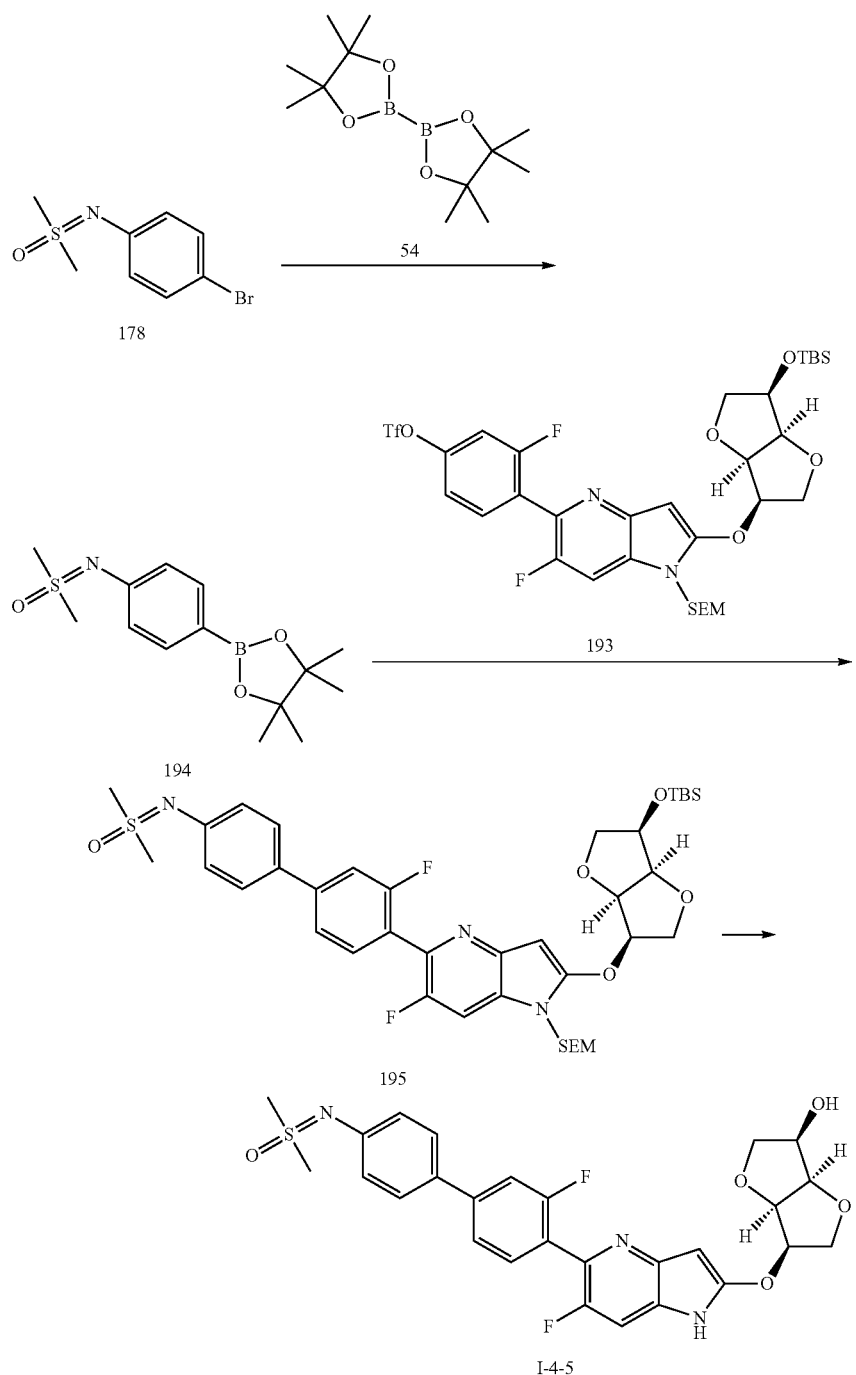

Compound 194 was synthesized from Compound 178 in a similar way as in the case of Compound 176.

Compound 194; Method B

LC/MS retention time=1.69 min.

MS (ESI) m/z=296.35 (M+H)+.

To Compound 193 (100 mg, 0.130 mmol) were added 1,4-dioxane (1 ml), PdCl$_2$(dtbpf) (17.00 mg, 0.026 mmol), Compound 194 (57.7 mg, 0.196 mmol), and 2 mol/L aqueous solution of potassium carbonate (0.098 ml, 0.196 mmol), and the resulting mixture was stirred at 150° C. under microwave irradiation. After completion of the reaction, the reaction mixture was purified by silica gel column chromatography to obtain Compound 195 (49.8 mg, 48.6%).

Compound 195; Method B

LC/MS retention time=3.13 min.

MS (ESI) m/z=786.50 (M+H)+.

Compound I-4-5 was synthesized from Compound 195 in a similar way as in the case of Compound I-4-2.

Compound I-4-5; Method B

LC/MS retention time=1.14 min.

MS (ESI) m/z=542.2 (M+H)+.

Example 58

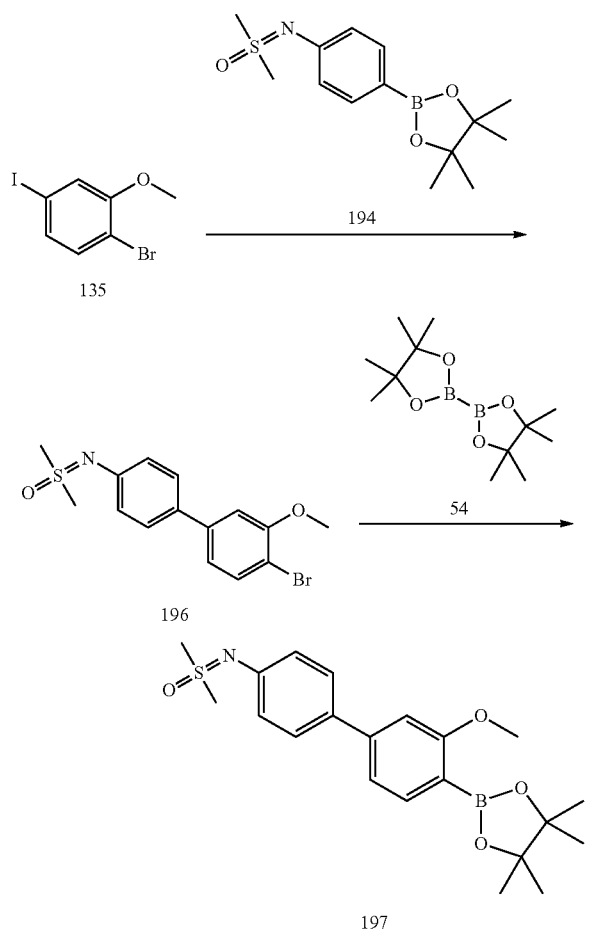

To Compound 135 (509 mg, 1.626 mmol) and Compound 194 (400 mg, 1.355 mmol) were added 1,4-dioxane (10 ml), PdCl$_2$(dtbpf) (88 mg, 0.135 mmol), and 2 mol/L aqueous solution of potassium carbonate (1.016 ml, 2.032 mmol), and the reaction mixture was stirred at 80° C. The reaction mixture was dried over magnesium sulfate and filtered, and the filtrate was concentrated under reduced pressure. The obtained residue was purified by silica gel column chromatography to obtain Compound 196 (193 mg, 40.2%).

Compound 197 was synthesized from Compound 196 in a similar way as in the case of Compound 176.

Example 59

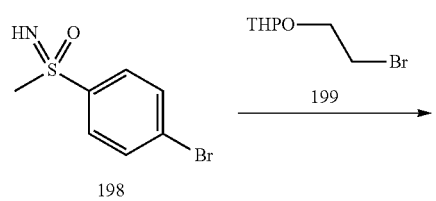

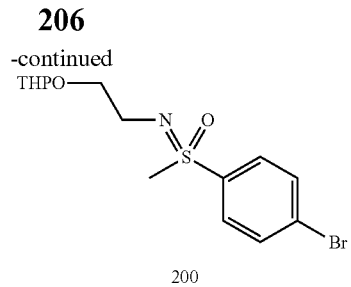

Compound 198 (50.0 mg, 0.214 mmol) was dissolved in DMSO (0.5 ml) under a nitrogen atmosphere, followed by addition of potassium hydroxide powder (85 wt %, 28.2 mg, 0.427 mmol), and the resulting mixture was stirred at room temperature. After that, Compound 199 (67.0 mg, 0.320 mmol) was added to the reaction mixture, which was then stirred at room temperature. Water was added to the reaction mixture, which was then extracted with ethyl acetate. The obtained organic layer was dried over magnesium sulfate and filtered, and the filtrate was concentrated under reduced pressure. The obtained residue was purified by silica gel column chromatography to obtain Compound 200.

Compound 200; Method B

LC/MS retention time=1.71 min.

MS (ESI) m/z=362.10 (M+H)+.

Example 60

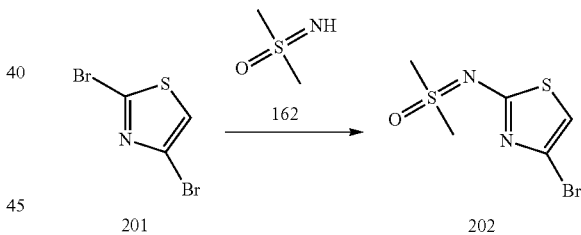

1,4-Dioxane (3 ml) was added to Compound 201 (782 mg, 3.22 mmol), cesium carbonate (490 mg, 1.503 mmol), Compound 162 (100 mg, 1.074 mmol), and Xantphos (46.6 mg, 0.081 mmol). Subsequently, to this mixture was added Pd$_2$(dba)$_3$ (24.58 mg, 0.027 mmol), and the resulting mixture was stirred at 105° C. The reaction mixture was filtered through Celite, and the filtrate was concentrated under reduced pressure. The obtained residue was purified by silica gel column chromatography to obtain Compound 202 (115 mg, 43.1%).

Compound 202; Method B

LC/MS retention time=1.17 min.

MS (ESI) m/z=254.95 (M+H)+.

Example 61

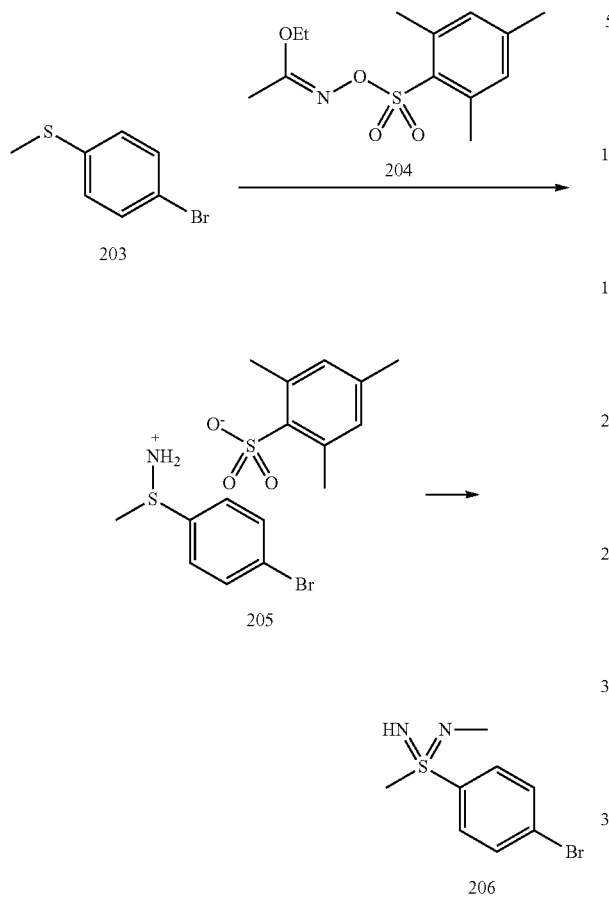

Example 62

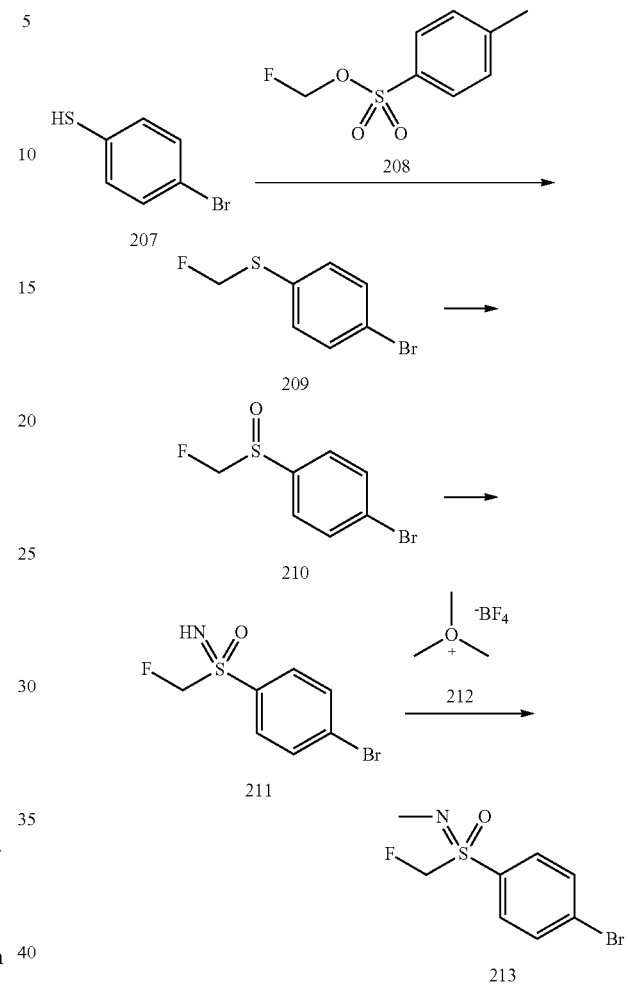

Compound 204 (7.14 g, 25.01 mmol) was dissolved in DMSO (25 ml), to which was then added dropwise perchloric acid (70 wt %, 27 ml, 291 mmol) under ice cooling, and the resulting mixture was stirred at 0° C. The reaction mixture was extracted with dichloromethane, which was then dried over magnesium sulfate and filtered.

Into another reaction vessel were placed Compound 203 (5.08 g, 25.01 mmol) and dichloromethane (25 ml), and the filtrate was added dropwise under ice cooling. The reaction mixture was stirred at 0° C., and then concentrated under reduced pressure. To the residue was added diethyl ether to precipitate Compound 205, and Compound 205 (8.87 g, 84.8%) was obtained as solid.

Compound 205 (8.87 g, 21.20 mmol) was dissolved in DMF (63 ml), to which were then added sodium carbonate (2.70 g, 25.4 mmol) and NCS (3.40 g, 25.4 mmol) under ice cooling, and the resulting mixture was stirred at 0° C. After that, a solution of methylamine in ethanol (7.92 ml, 63.6 mmol) was added to the reaction mixture, which was then stirred overnight at room temperature. Water was added to the reaction mixture, which was then extracted with dichloromethane. The obtained organic layer was washed with saturated aqueous NaCl, dried over sodium sulfate, and filtered. The obtained filtrate was concentrated under reduced pressure, and the obtained residue was purified by silica gel column chromatography to obtain Compound 206 (1.90 g, 36.3%).

Compound 207 (3.00 g, 15.87 mmol) was dissolved in DMF (15 ml), to which was then added cesium carbonate (3.56 g, 17.45 mmol), and the resulting mixture was stirred at room temperature. After that, a solution of Compound 208 (2.21 g, 6.78 mmol) diluted in DMF (3 ml) was added to the reaction mixture, and the resulting mixture was further stirred at room temperature. Water was added to the reaction mixture, which was then extracted with dichloromethane. The obtained organic layer was washed with water, dried over magnesium sulfate, and filtered. The obtained filtrate was concentrated under reduced pressure to obtain Compound 209 (7.44 g, 91.4%).

Compound 209 (7.42 g, 43.1% (wt), 14.46 mmol) was diluted in chloroform (22.26 ml), and the mixture was cooled in an ice bath, followed by addition of a solution of mCPBA (3.33 g, 14.46 mmol) in chloroform (22.26 ml). The reaction mixture was stirred at 0° C. and at room temperature, followed by addition of another mCPBA (0.250 g, 1.446 mmol), and the resulting mixture was stirred overnight at room temperature. Water was added to the reaction mixture, which was then extracted with chloroform. The obtained organic layer was dried over sodium sulfate, and filtered. The obtained filtrate was concentrated under reduced pressure, and the obtained residue was purified by silica gel column chromatography to obtain Compound 210 (2.04 g, 59.5%).

To Compound 210 (4.00 g, 16.87 mmol) and sodium azide (1.207 g, 18.56 mmol) was added chloroform (30 ml), followed by dropwise addition of sulfuric acid (7.42 ml, 135 mmol) at room temperature. After completion of the dropwise addition, the reaction mixture was stirred at room temperature and at 45° C. The chloroform layer and the sulfuric acid layer were separated. To the sulfuric acid layer was added water, and the mixture was extracted with chloroform. The combined organic layers were washed with a saturated aqueous solution of sodium hydrogen carbonate, dried over magnesium sulfate, and filtered. The obtained filtrate was concentrated under reduced pressure, and the obtained residue was purified by silica gel column chromatography to obtain Compound 211 (3.50 g, 77.4%).

Compound 211 (1.00 g, 3.89 mmol) was dissolved in dichloromethane (5 ml), to which was then added a solution of Compound 212 (0.739 mg) diluted in dichloromethane (5 ml), and the resulting mixture was refluxed. The reaction mixture was cooled to room temperature, followed by addition of a 2 mol/L aqueous solution of sodium hydroxide, and the resulting mixture was extracted with diethyl ether. The obtained organic layer was dried over sodium sulfate, and filtered. The obtained filtrate was concentrated under reduced pressure, and the obtained residue was purified by silica gel column chromatography to obtain Compound 213 (0.534 g, 50.6%).

Example 63

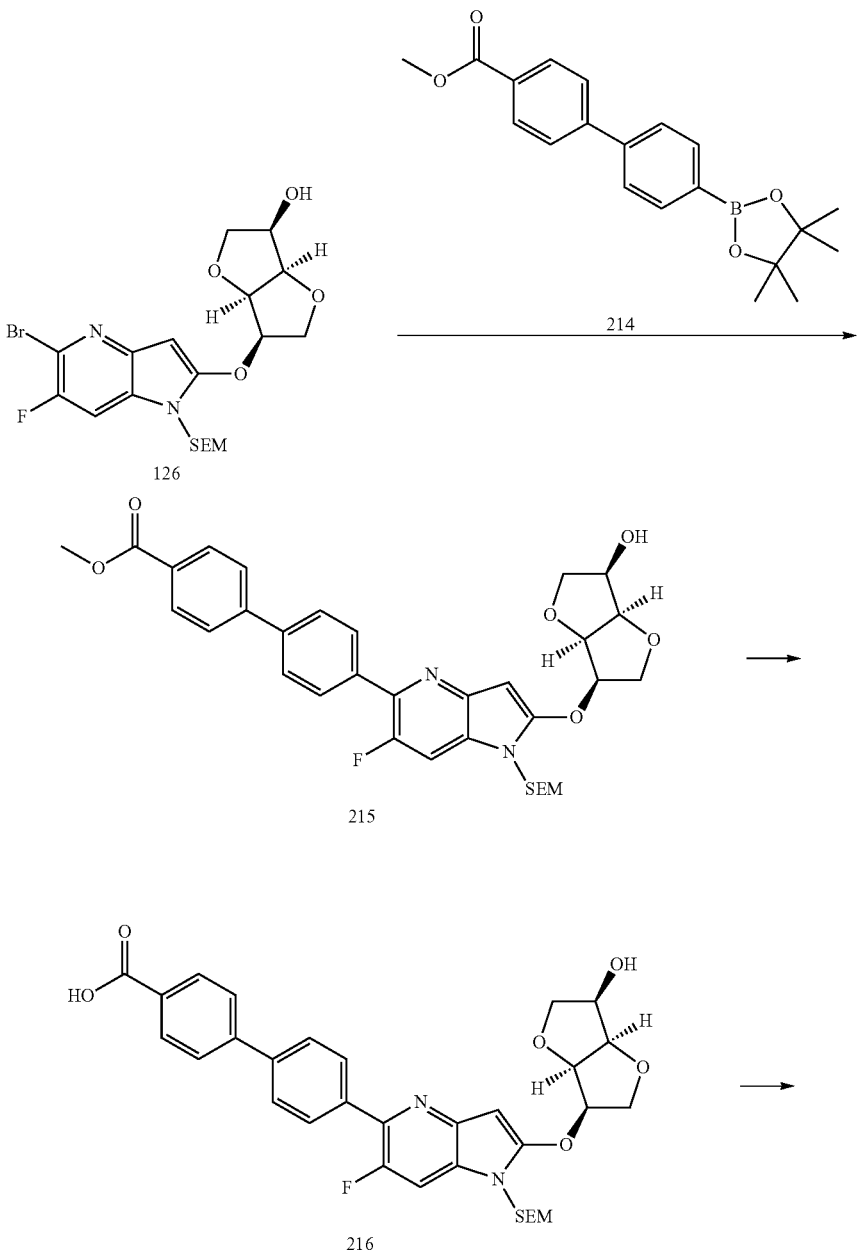

-continued

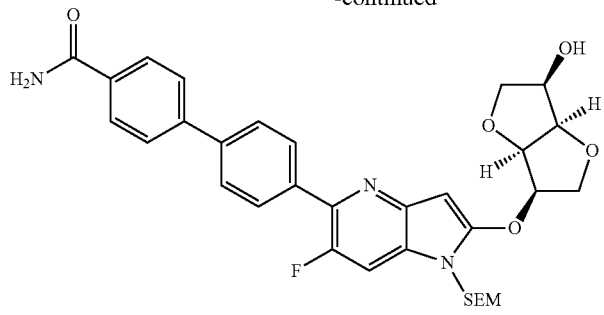
217

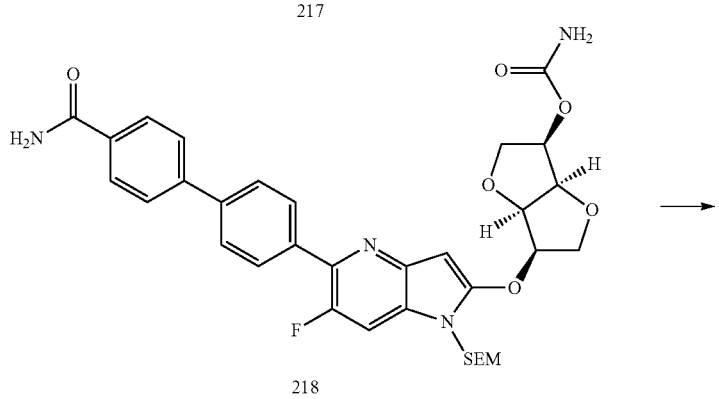
218

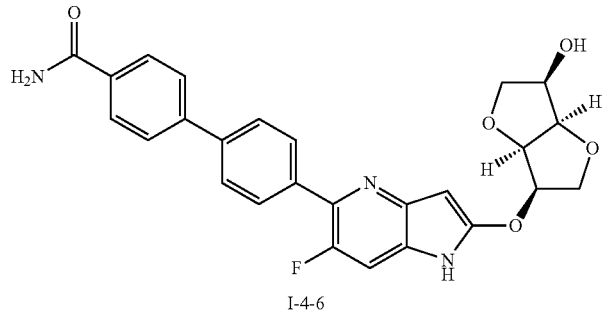
I-4-6

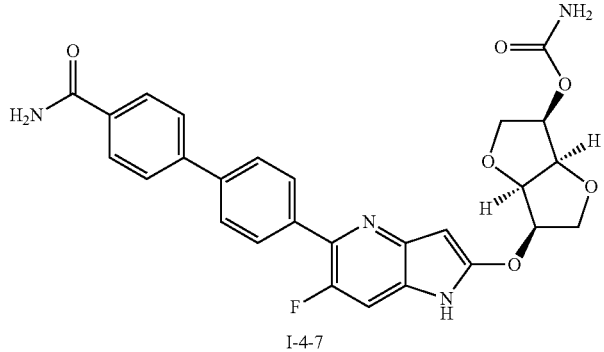
I-4-7

To Compound 126 (200 mg, 0.409 mmol) and Compound 214 (166 mg, 0.490 mmol) was added DMF (2 ml), and the reaction mixture was heated to 100° C. After that, PdCl₂ (dtbpf) (26.6 mg, 0.041 mmol) and 2 mol/L aqueous solution of potassium carbonate (0.306 ml, 0.613 mmol) were added to the reaction mixture, which was then stirred at 100° C. After completion of the reaction, ethyl acetate was added to the reaction mixture, which was then washed with water. The obtained organic layer was concentrated under reduced pressure, and the obtained residue was purified by silica gel column chromatography to obtain Compound 215 (181 mg, 71.4%).

Compound 215; Method B
LC/MS retention time=2.67 min.
MS (ESI) m/z=621.35 (M+H)+.

Compound 215 (180 mg, 0.290 mmol) was dissolved in a mixed solvent of THF (1.5 ml) and methanol (1.5 ml), followed by addition of 2 M aqueous solution of sodium hydroxide (0.290 ml, 0.580 mmol), and the resulting mixture was stirred at room temperature. After completion of the reaction, the reaction mixture was neutralized with 2 mol/L aqueous solution of hydrochloric acid (0.290 ml, 0.580 mmol). After concentration under reduced pressure, the residue was extracted with a mixed solvent of chloroform and methanol. The obtained organic layer was washed with saturated aqueous NaCl, dried over magnesium sulfate, and filtered. The obtained filtrate was concentrated under reduced pressure to obtain Compound 216.

Compound 216; Method B

LC/MS retention time=2.20 min.

MS (ESI) m/z=607.35 (M+H)+.

Compound 216 (90.2 wt %, 77.0 mg, 0.114 mmol) was dissolved in DMF (0.7 ml), to which was then added CDI (37.1 mg, 0.229 mmol), and the reaction mixture was stirred at room temperature. The reaction mixture was cooled to 0° C., followed by addition of a 28% aqueous solution of ammonia (1.5 ml), and the resulting mixture was stirred at 0° C. To the reaction mixture was added ethyl acetate, which was then washed with water. The obtained organic layer was dried over magnesium sulfate, and filtered. The obtained filtrate was concentrated under reduced pressure to obtain a mixture of Compounds 217 and 218.

Compounds I-4-6 and I-4-7 were synthesized from the mixture of Compounds 217 and 218 in a similar way as in the case of Compound I-4-2.

Compound I-4-6; Method B

LC/MS retention time=1.03 min.

MS (ESI) m/z=476.25 (M+H)+.

Compound I-4-7; Method B

LC/MS retention time=1.06 min.

MS (ESI) m/z=519.25 (M+H)+.

Example 64

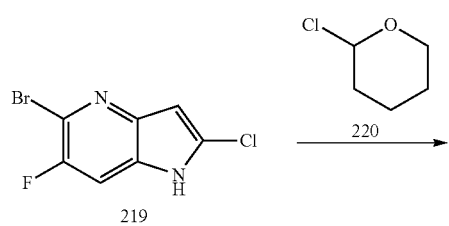

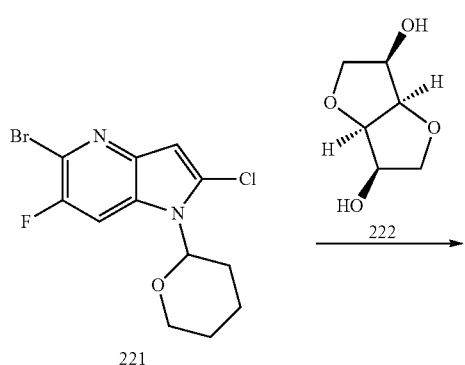

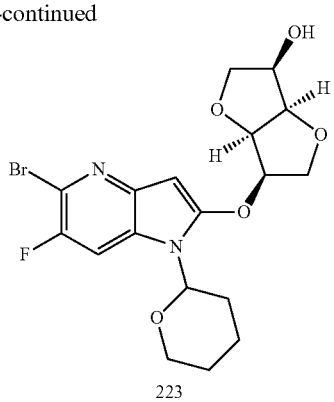

Compound 219 (100 mg, 0.409 mmol) was dissolved in DMF (1 ml), to which was then added 60 wt % sodium hydride (19.24 mg, 0.481 mmol) under ice cooling, followed by addition of Compound 220 (58.0 mg, 0.481 mmol). The reaction mixture was stirred under ice cooling, followed by addition of ethyl acetate and washing with water. The obtained organic layer was concentrated under reduced pressure, and the obtained residue was purified by silica gel column chromatography to obtain Compound 221 (103 mg, 77.0%).

Compound 221; Method B

LC/MS retention time=2.45 min.

MS (ESI) m/z=335.10 (M+H)+.

To Compound 221 (100 mg, 0.300 mmol) and Compound 222 (438 mg, 3.00 mmol) was added DMF (1 ml), followed by addition of potassium fluoride (52.2 mg, 0.899 mmol), 18-crown 6-ether (475 mg, 1.799 mmol), and 60 wt % sodium hydride (36.0 mg, 0.899 mmol) under a nitrogen atmosphere, and the resulting mixture was stirred at room temperature. After that, the reaction mixture was stirred at 100° C. The reaction mixture was cooled to room temperature, followed by addition of ethyl acetate and washing with water. The obtained organic layer was concentrated under reduced pressure, and the obtained residue was purified by silica gel column chromatography to obtain Compound 223 (99.0 mg, 74.5%).

Compound 223; Method B

LC/MS retention time=1.77 min.

MS (ESI) m/z=444.90 (M+H)+.

Example 65

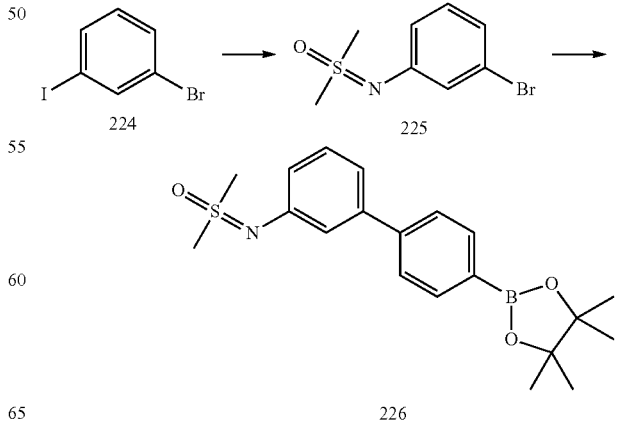

Compound 225 was synthesized from Compound 224 in a similar way as in the case of Compound 200.

Compound 224; Method A

LC/MS retention time=1.41 min.

MS (ESI) m/z=247.9 (M+H)+.

Compound 226 was synthesized from Compound 225 in a similar way as in the case of Compound 179.

Compound 225; Method A

LC/MS retention time=2.24 min.

MS (ESI) m/z=372.2 (M+H)+.

Example 66 acetate, which was then washed with water. The obtained organic layer was dried over magnesium sulfate, and filtered. The obtained filtrate was concentrated under reduced pressure to obtain Compound 227 (122 mg, 0.179 mmol).

Compound 227; Method A

LC/MS retention time=2.25 min.

MS (ESI) m/z=682.3 (M+H)+.

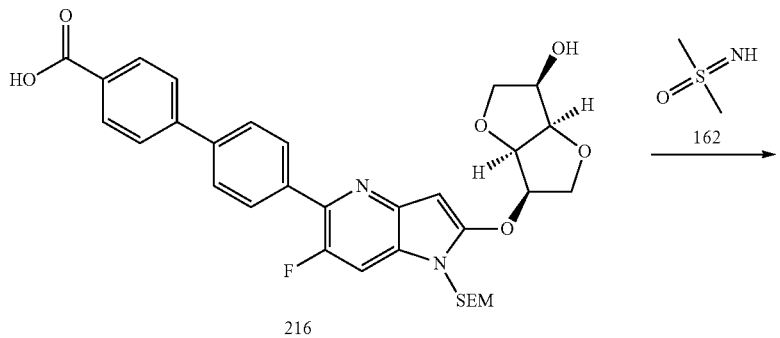

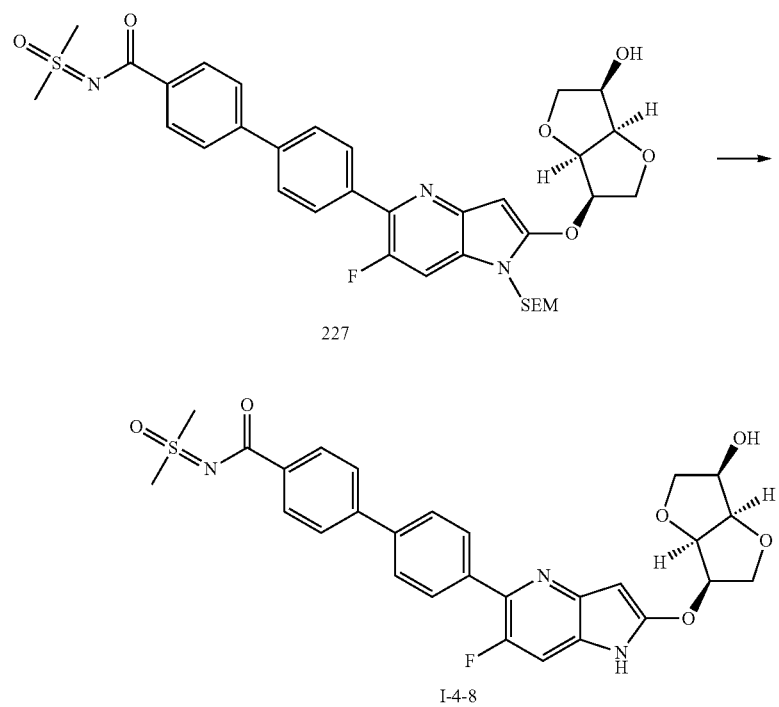

Compound 216 (117 mg, 0.193 mmol) was dissolved in DMF (3 ml), to which were then added HATU (88 mg, 0.231 mmol) and N,N-diisopropylethylamine (0.084 ml, 0.482 mmol), and the mixture was stirred at room temperature for 5 minutes. After that, Compound 162 (21.6 mg, 0.231 mmol) was added to the reaction mixture, which was then stirred at room temperature. To the reaction mixture was added ethyl Compound I-4-8 was synthesized from Compound 227 in a similar way as in the case of Compound I-4-2.

Compound I-4-8; Method A

LC/MS retention time=1.26 min.

MS (ESI) m/z=552.2 (M+H)+.

Example 67

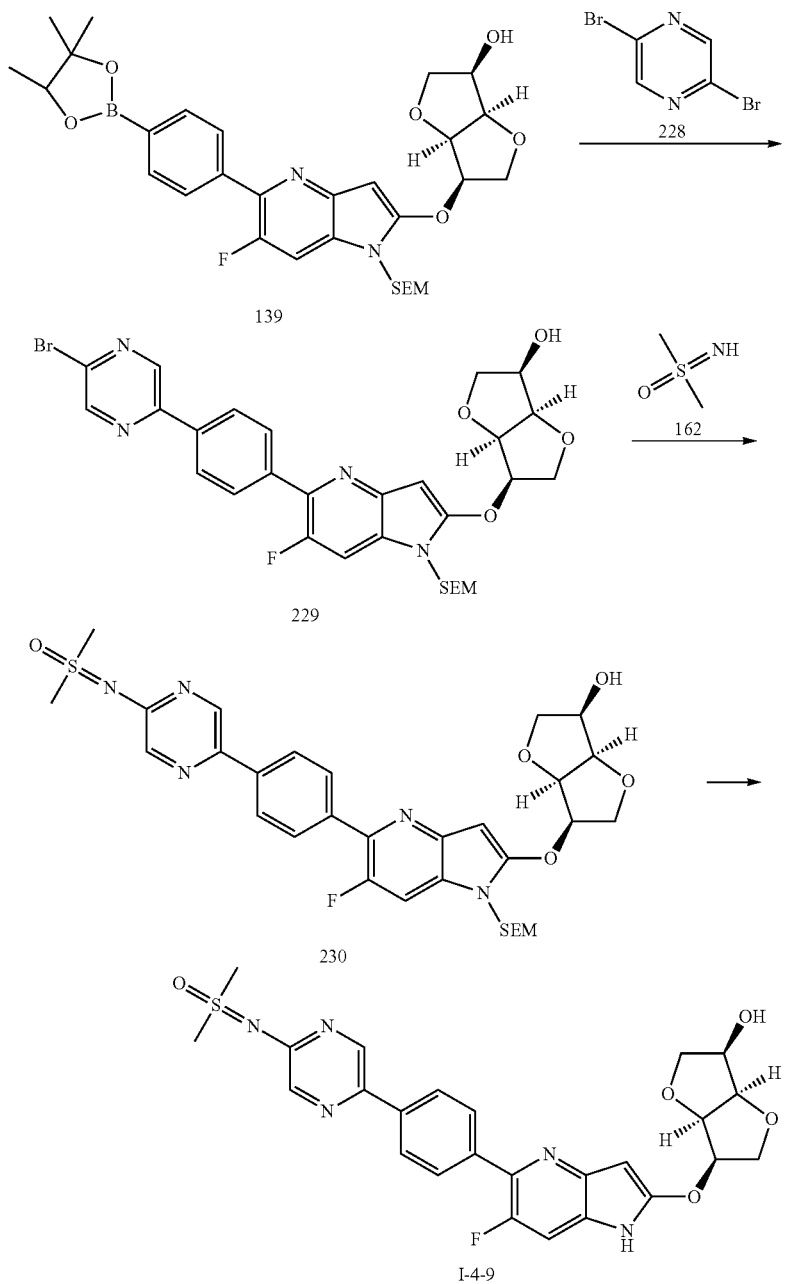

To Compound 139 (72 mg, 0.118 mmol) were added 1,4-dioxane (0.72 ml) and Pd(PPh$_3$)$_4$ (14 mg, 0.012 mmol), Compound 228 (112 mg, 0.470 mmol), and 2 mol/L aqueous solution of potassium carbonate (0.235 ml, 0.470 mmol), and the reaction mixture was stirred at 90° C. After completion of the reaction, the reaction mixture was purified by silica gel column chromatography to obtain Compound 229.

Compound 229; Method A

LC/MS retention time=2.79 min.

MS (ESI) m/z=643.4 (M+H)+.

Compound 230 was synthesized from Compound 229 in a similar way as in the case of Compound 200.

Compound 230; Method A

LC/MS retention time=2.05 min.

MS (ESI) m/z=656.5 (M+H)+.

Compound I-4-9 was synthesized from Compound 230 in a similar way as in the case of Compound I-4-2.

Compound I-4-9; Method A

LC/MS retention time=1.07 min.

MS (ESI) m/z=526.2 (M+H)+.

Example 68

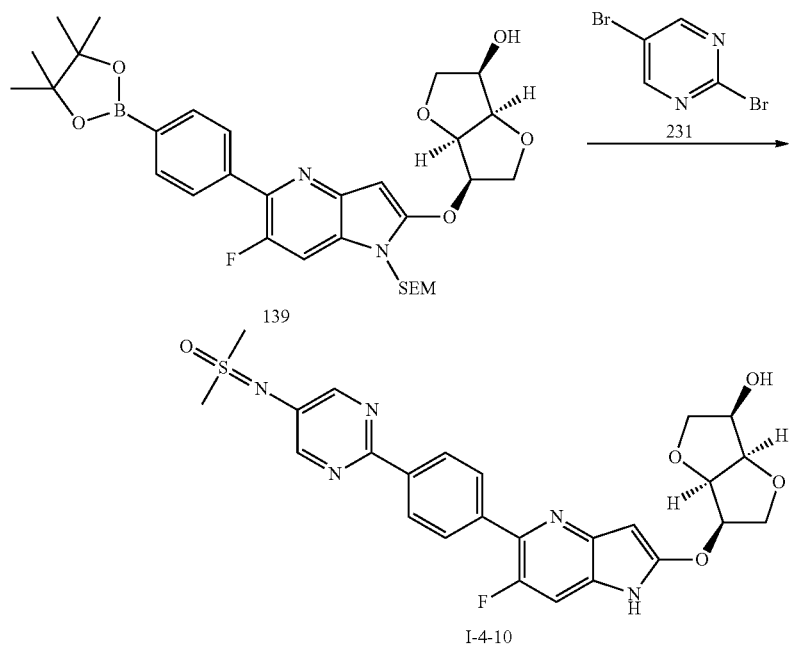

Compound I-4-10 was synthesized from Compound 139 in a similar way as in the case of Compound I-4-9.
Compound I-4-10; Method A
LC/MS retention time=1.21 min.
MS (ESI) m/z=526.1 (M+H)+.

Example 69

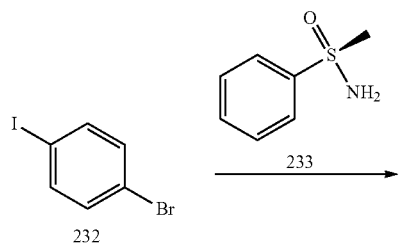

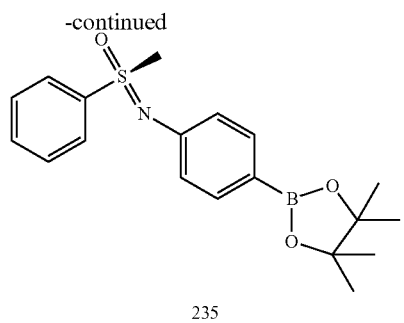

Compound 234 was synthesized from Compound 232 in a similar way as in the case of Compound 200.
Compound 234; Method A
LC/MS retention time=2.02 min.
MS (ESI) m/z=310.2 (M+H)+.
Compound 235 was synthesized from Compound 234 in a similar way as in the case of Compound 176.
Compound 235; Method A
LC/MS retention time=2.19 min.
MS (ESI) m/z=358.2 (M+H)+.

Example 70

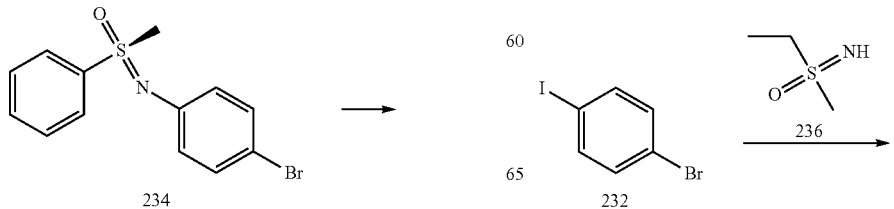

-continued

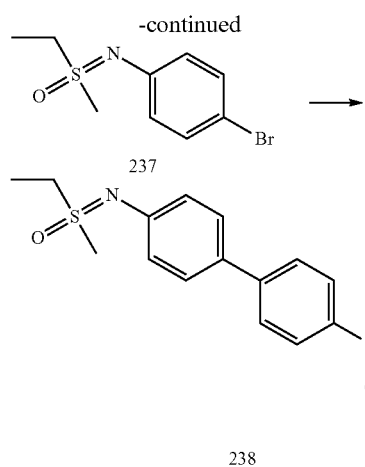

237

238

Compound 237 was synthesized from Compound 232 in a similar way as in the case of Compound 200.
Compound 237; Method A
LC/MS retention time=1.58 min.
MS (ESI) m/z=261.8 (M+H)+.
Compound 238 was synthesized from Compound 237 in a similar way as in the case of Compound 179.
Compound 238; Method A
LC/MS retention time=2.35 min.
MS (ESI) m/z=386.3 (M+H)+.

Example 71

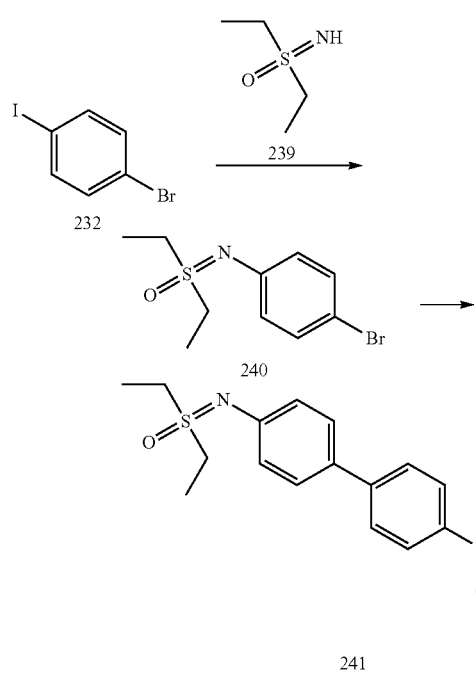

232

239

240

241

Compound 240 was synthesized from Compound 232 in a similar way as in the case of Compound 200.
Compound 240; Method A
LC/MS retention time=1.75 min.
MS (ESI) m/z=275.7 (M+H)+.
Compound 241 was synthesized from Compound 240 in a similar way as in the case of Compound 179.

Compound 241; Method A
LC/MS retention time=2.48 min.
MS (ESI) m/z=400.1 (M+H)+.

Example 72

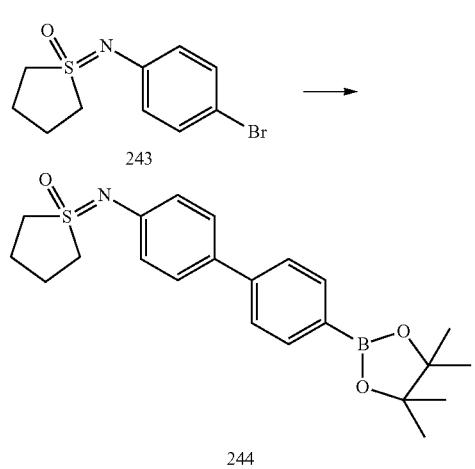

232

242

243

244

Compound 243 was synthesized from Compound 232 in a similar way as in the case of Compound 200.
Compound 243; Method A
LC/MS retention time=1.64 min.
MS (ESI) m/z=273.8 (M+H)+.
Compound 244 was synthesized from Compound 243 in a similar way as in the case of Compound 179.
Compound 244; Method A
LC/MS retention time=2.40 min.
MS (ESI) m/z=398.6 (M+H)+.

Example 73

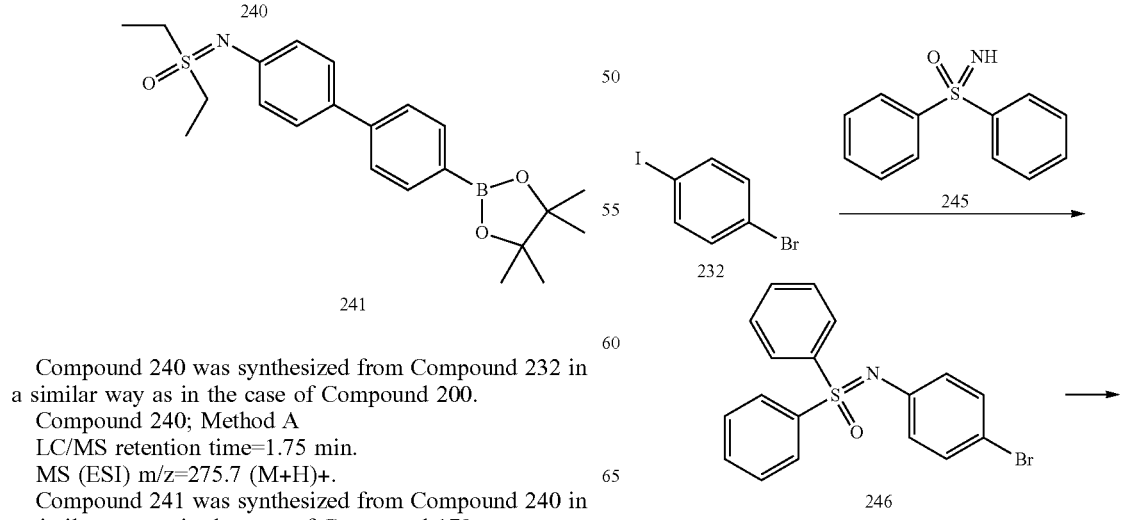

232

245

246

223

-continued

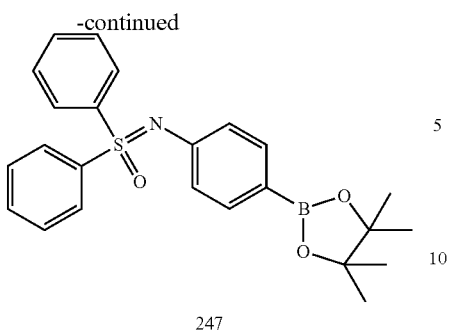

247

Compound 246 was synthesized from Compound 232 in a similar way as in the case of Compound 200.
Compound 246; Method A
LC/MS retention time=2.62 min.
MS (ESI) m/z=372.1 (M+H)+.
Compound 247 was synthesized from Compound 246 in a similar way as in the case of Compound 179.
Compound 247; Method A
LC/MS retention time=2.75 min.
MS (ESI) m/z=420.5 (M+H)+.

Example 74

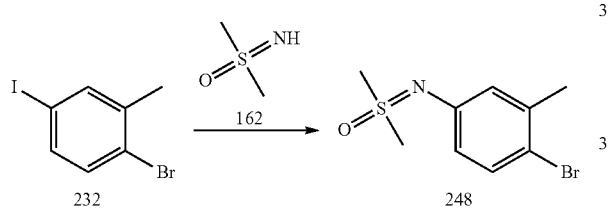

Compound 248 was synthesized from Compound 232 in a similar way as in the case of Compound 200.
Compound 248; Method A
LC/MS retention time=1.60 min.
MS (ESI) m/z=261.8 (M+H)+.

Example 75

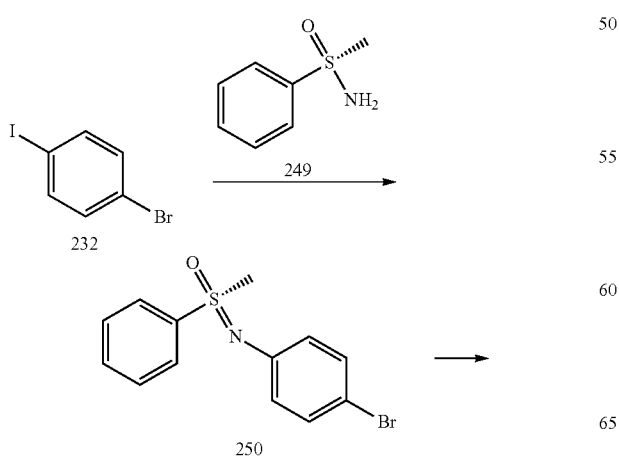

224

-continued

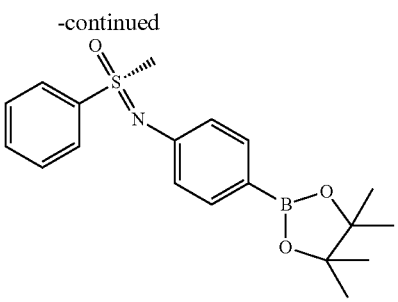

251

Compound 250 was synthesized from Compound 232 in a similar way as in the case of Compound 200.
Compound 250; Method A
LC/MS retention time=2.02 min.
MS (ESI) m/z=309.8 (M+H)+.
Compound 251 was synthesized from Compound 250 in a similar way as in the case of Compound 179.
Compound 251; Method A
LC/MS retention time=2.19 min.
MS (ESI) m/z=358.0 (M+H)+.

Example 76

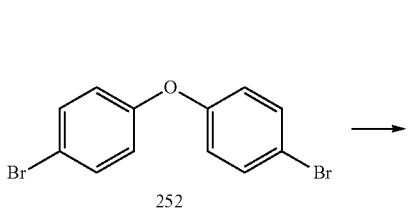

Compound 253 was synthesized from Compound 252 in a similar way as in the case of Compound 200.
Compound 253; Method A
LC/MS retention time=2.04 min.
MS (ESI) m/z=340.1 (M+H)+.
Compound 254 was synthesized from Compound 253 in a similar way as in the case of Compound 179.
Compound 254; Method A
LC/MS retention time=2.24 min.
MS (ESI) m/z=388.2 (M+H)+.

Example 77

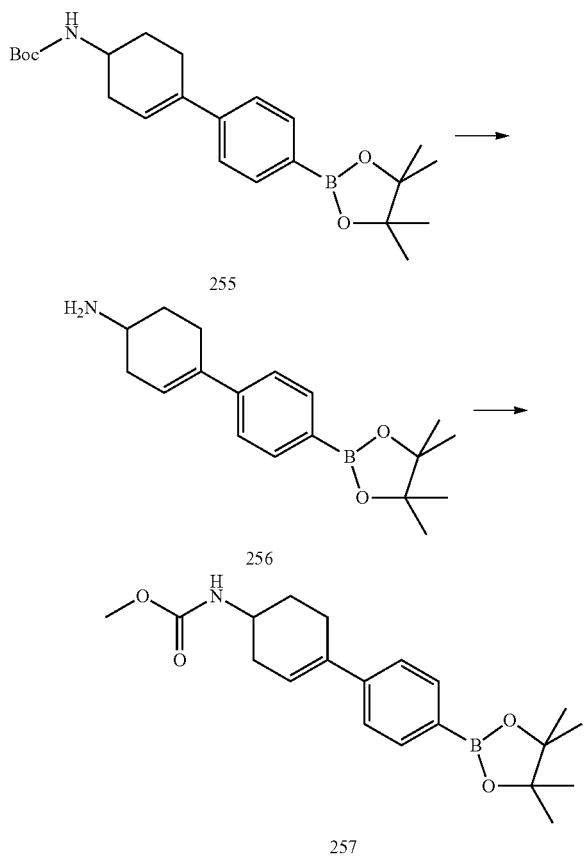

To Compound 255 (2.0 g, 5.0 mmol) were added dichloromethane (8 ml) and TFA (7.7 ml, 100 mmol), and the reaction mixture was stirred at room temperature. After completion of the reaction, the TFA was removed by concentration under reduced pressure. The obtained residue was dissolved in chloroform, and the mixture was neutralized with a saturated aqueous solution of sodium bicarbonate. The obtained organic layer was dried over magnesium sulfate, and concentrated under reduced pressure to obtain Compound 256.

Compound 256; Method A

LC/MS retention time=1.51 min.

MS (ESI) m/z=300.5 (M+H)+.

Compound 256 (250 mg, 0.84 mmol) was dissolved in THF (2.5 ml), to which were then added methyl chloroformate (0.096 ml, 1.25 mmol) and pyridine (0.10 ml, 1.25 mmol) under ice cooling, the reaction mixture was stirred at room temperature. Water was added to the reaction mixture, which was then extracted with chloroform. The obtained organic layer was washed with saturated aqueous NaCl, dried over magnesium sulfate, and filtered. The obtained filtrate was concentrated under reduced pressure, and the obtained residue was purified by silica gel column chromatography to obtain Compound 257.

Compound 257; Method A

LC/MS retention time=2.49 min.

MS (ESI) m/z=358.3 (M+H)+.

Example 78

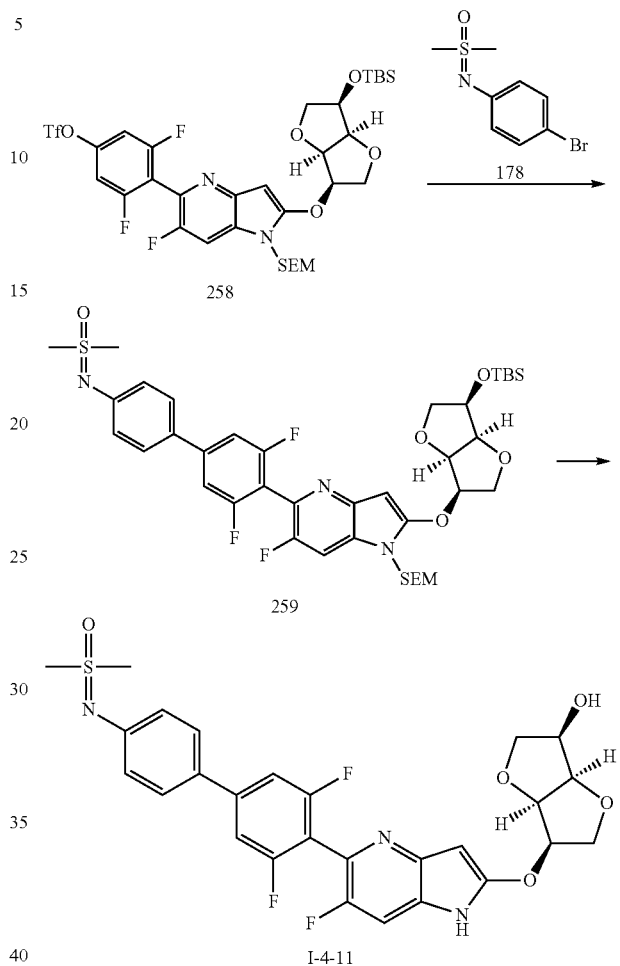

To a solution of Compound 258 (100 mg, 0.127 mmol) in dioxane (1 ml) were added Compound 178 (56.4 mg, 0.191 mmol), 2 mol/L aqueous solution of potassium carbonate (0.127 ml, 0.255 mmol), and PdCl$_2$(dtbpf) (16.6 mg, 0.025 mmol), and the resulting mixture was stirred at 145° C. for 60 minutes under microwave irradiation. The reaction mixture was purified by silica gel column chromatography to obtain Compound 259 (84.6 mg, 0.105 mmol, 83%) as a red solid.

Compound 259; Method C

LC/MS retention time=3.13 min.

MS (ESI) m/z=804.20 (M+H)+.

To a solution of Compound 259 (84.6 mg, 0.105 mmol) in methylene chloride (0.7 ml) was added TFA (0.7 ml, 9.09 mmol), and the reaction mixture was stirred overnight at room temperature. After completion of the reaction, the TFA was removed by concentration under reduced pressure, and the residue was diluted in MeOH, followed by neutralization with an aqueous solution of sodium hydrogen carbonate. Extraction was performed with a mixed solvent of chloroform and methanol to extract the desired product, and the obtained organic layer was dried over magnesium sulfate, and then the solvent was removed by concentration under reduced pressure. The obtained residue was purified by silica gel column chromatography to obtain Compound I-4-11 (22.1 mg, 0.039 mmol, 38%) as a white solid.

Compound I-4-11; Method C

LC/MS retention time=1.42 min.

MS (ESI) m/z=560.00 (M+H)+

Example 79

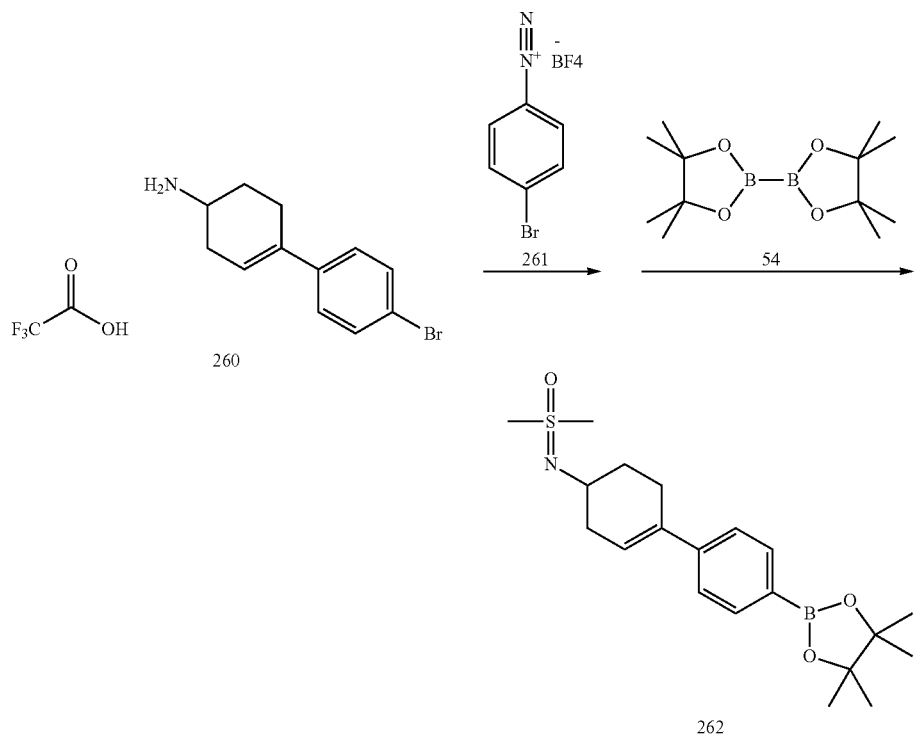

To dimethyl sulfone (1.88 g, 19.9 mmol) was added Compound 261 (1.80 g, 6.65 mmol) at 130° C., and at that temperature, the mixture was stirred with heating for 30 minutes. The reaction mixture was cooled to room temperature, followed by addition of acetonitrile (4 ml), followed by addition of a solution of Compound 260 (446 mg, 1.22 mmol) in acetonitrile (2 ml), and DIPEA (1 ml), and the resulting mixture was stirred overnight at room temperature. After completion of the reaction, a saturated aqueous solution of sodium bicarbonate was added to the reaction mixture, which was then extracted with ethyl acetate. The obtained organic layer was dried over magnesium sulfate, and then the solvent was removed by concentration under reduced pressure. Purification of the obtained residue by silica gel column chromatography was conducted but it was difficult to remove impurities. The obtained crude product (260 mg) was used directly in the next reaction. To a solution of the crude product (260 mg) in 1,4-dioxane (2 ml) were added Compound 54 (302 mg, 1.19 mmol), $PdCl_2(dppf)$ $CH_2Cl_2$ (64.7 mg, 0.079 mmol), and potassium acetate (311 mg, 3.17 mmol), and the mixture was stirred at 100° C. for 3 hours. The reaction mixture was filtered through Celite, and the filtrate was concentrated under reduced pressure. The obtained residue was purified by silica gel column chromatography to obtain Compound 262 (41.5 mg, 0.111 mmol, 9%) as a brown solid.

Compound 262; Method C
LC/MS retention time=1.81 min.
MS (ESI) m/z=376.10 (M+H)+.

Example 80

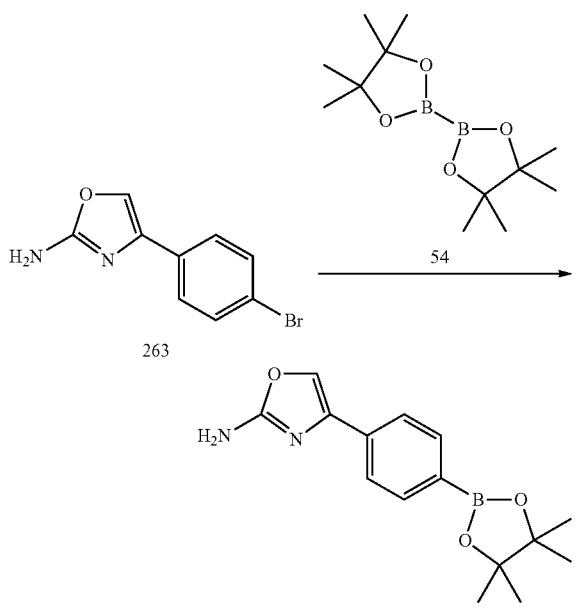

To Compound 263 (224 mg, 0.937 mmol) were added 1,4-dioxane (2.2 ml), Compound 54 (357 mg, 1.41 mmol), $PdCl_2(dppf)CH_2Cl_2$ (77 mg, 0.094 mmol), and potassium acetate (368 mg, 3.75 mmol), and the reaction mixture was stirred at 100° C. for 1 hour. The reaction mixture was filtered through Celite, and the filtrate was concentrated under reduced pressure. The obtained residue was purified by silica gel column chromatography, so that Compound 264 was quantitatively obtained (270 mg, 0.942 mmol).

Compound 264; Method B
LC/MS retention time=1.74 min.
MS (ESI) m/z=328.00 (M+H)+.

The compounds shown below were synthesized in a similar way. The measurement results of NMR or LC/MS of the respective compounds are shown.

TABLE 1

| No | Structure | NMR (δ) | retention time | Mass (M + H) | method |
|---|---|---|---|---|---|
| I-1-9 | 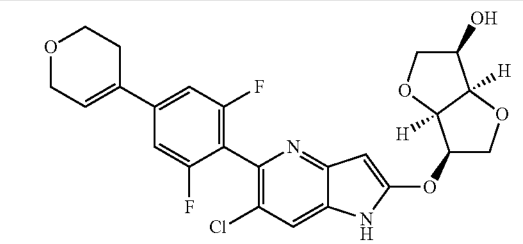 [SMILES: O[C@@H]1CO[C@H]2[C@@H]1OC[C@H]2Oc1cc2nc(-c3c(F)cc(C4=CCOCC4)cc3F)c(Cl)cc2[nH]1] | | 1.55 | 491.45 | B |
| I-1-10 | 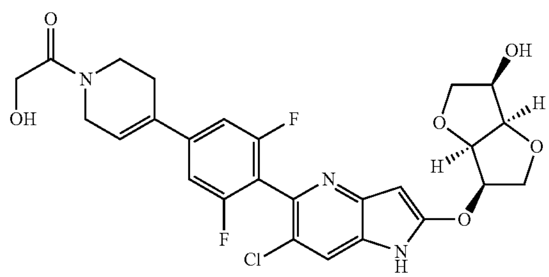 [SMILES: O=C(CO)N1CC=C(c2cc(F)c(-c3nc4cc(O[C@@H]5CO[C@H]6[C@@H]5OC[C@H]6O)[nH]c4cc3Cl)c(F)c2)CC1] | | 1.23 | 548.1 | B |
| I-1-11 | 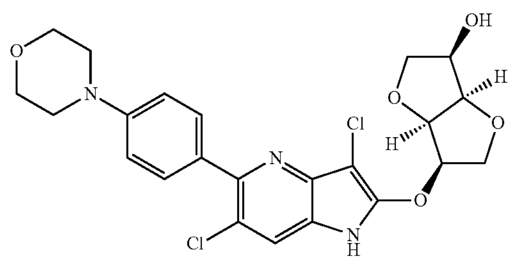 [SMILES: O[C@@H]1CO[C@H]2[C@@H]1OC[C@H]2Oc1[nH]c2cc(Cl)c(-c3ccc(N4CCOCC4)cc3)nc2c1Cl] | | 1.46 | 492.15 | B |
| I-1-12 | 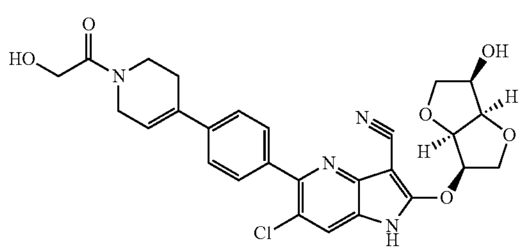 [SMILES: N#Cc1c(O[C@@H]2CO[C@H]3[C@@H]2OC[C@H]3O)[nH]c2cc(Cl)c(-c3ccc(C4=CCN(C(=O)CO)CC4)cc3)nc12] | (DMSO-d6) δ: 3.75-3.78 (m, 3H), 4.01-4.18 (m, 8H), 4.33 (t, J = 4.0 Hz, 1H), 4.61 (d, J = 25.2 Hz, 1H), 4.88 (m, 1H), 5.06 (d, J = 8.0 Hz, 1H), 5.40 (s, 1H), 6.27 (d, J = 17.0 Hz, 1H), 7.55-63 (m, 4H), 7.79 (s, 1H). | 1.39 | 537.2 | A |
| I-1-13 | 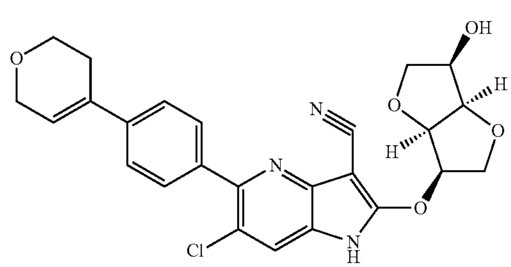 [SMILES: N#Cc1c(O[C@@H]2CO[C@H]3[C@@H]2OC[C@H]3O)[nH]c2cc(Cl)c(-c3ccc(C4=CCOCC4)cc3)nc12] | (DMSO-d6) δ: 3.77 (t, J = 7.0 Hz, 1H), 3.73-3.78 (m, 6H), 4.00 (dd, J = 12.0, 4.0 Hz, 1H), 4.10 (brd, J = 8.0 Hz, 3H), 4.26 (brs, 2H), 4.33 (t, J = 4.0 Hz, 1H), 4.90 (t, J = 4.0 Hz, 1H), 5.09 (d, J = 8.0 Hz, 1H), 5.40 (s, 1H), 6.37 (brs, 1H), 7.55-58 (d, J = 12.0 Hz, 2H), 7.62-64 (d, J = 12.0 Hz, 2H), 7.82 (s, 1H). | 1.79 | 480.2 | A |

TABLE 2

| ID | Structure | NMR | | | |
|---|---|---|---|---|---|
| I-1-14 | 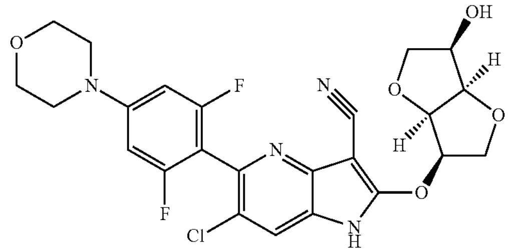 [SMILES: N#Cc1c(O[C@@H]2CO[C@H]3[C@@H]2OC[C@H]3O)[nH]c2cc(Cl)c(-c3c(F)cc(N4CCOCC4)cc3F)nc12] | (DMSO-d6) δ: 3.24 (brs, 4H), 3.86 (t, J = 4.0 Hz, 3H), 4.00 (dd, J = 12.0, 4.0 Hz, 1H), 4.09 (brd, J = 8.0 Hz, 2H), 4.32 (t, J = 4.0 Hz, 1H), 4.89 (t, J = 4.0 Hz, 1H), 5.07 (d, J = 8.0 Hz, 1H), 5.41 (brs, 1H), 6.77 (d, J = 12.0 Hz, 2H), 7.83 (s, 1H). | 1.66 | 519.2 | A |
| I-1-15 | 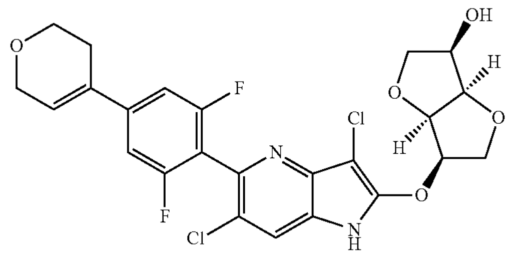 [SMILES: O[C@@H]1CO[C@H]2[C@@H]1OC[C@H]2Oc1[nH]c2cc(Cl)c(-c3c(F)cc(C4=CCOCC4)cc3F)nc2c1Cl] | | 1.84 | 523.2 | B |
| I-1-16 | 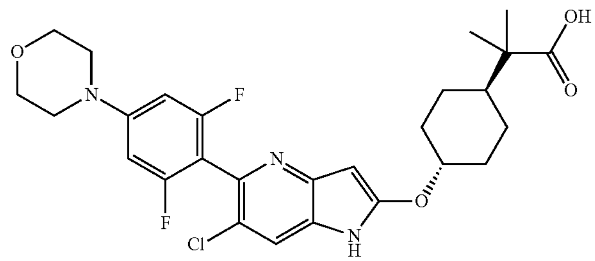 [SMILES: CC(C)(C(=O)O)[C@H]1CC[C@H](Oc2cc3nc(-c4c(F)cc(N5CCOCC5)cc4F)c(Cl)cc3[nH]2)CC1] | | 1.72 | 534.2 | B |
| I-1-17 | 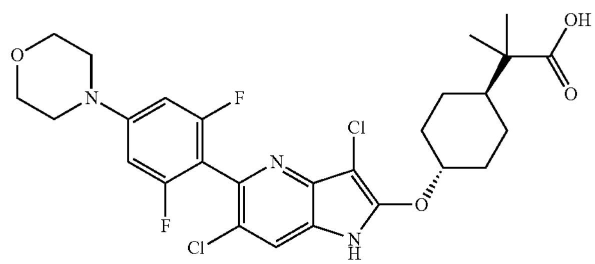 [SMILES: CC(C)(C(=O)O)[C@H]1CC[C@H](Oc2[nH]c3cc(Cl)c(-c4c(F)cc(N5CCOCC5)cc4F)nc3c2Cl)CC1] | | 2.23 | 569.9 | B |
| I-1-18 | 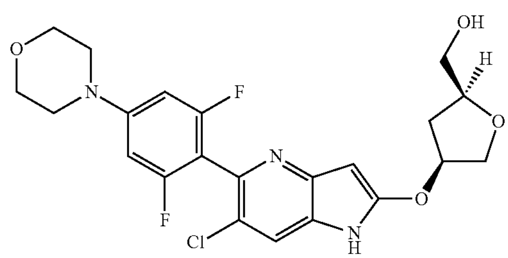 [SMILES: OC[C@@H]1C[C@H](Oc2cc3nc(-c4c(F)cc(N5CCOCC5)cc4F)c(Cl)cc3[nH]2)CO1] | 1H-NMR (MeOD) δ: 2.02-2.05 (m, 1H), 2.49-2.58 (m, 1H), 3.23-3.25 (m, 5H), 3.65-3.70 (m, 2H), 3.83-3.84 (m, 4H), 3.94-3.96 (m, 1H), 4.05-4.11 (m, 1H), 4.19-4.22 (m, 1H), 5.14 (s, 1H), 5.71 (s, 1H), 6.62-6.64 (m, 2H), 7.65 (s, 1H). | 1.47 | 466.05 | C |

TABLE 3

| ID | Structure | NMR | | | |
|---|---|---|---|---|---|
| I-1-19 | 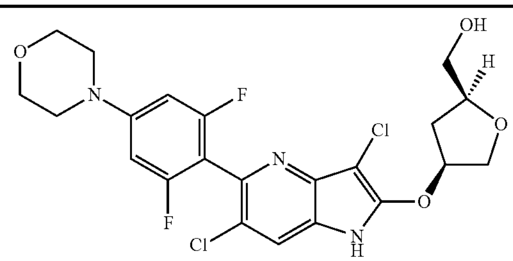 | 1H-NMR (MeOD) δ: 2.06 (dd, J = 14.5, 5.6 Hz, 1H), 2.45-2.52 (m, 1H), 3.24-3.26 (m, 4H), 3.66-3.72 (m, 2H), 3.83-3.84 (m, 4H), 3.91-3.94 (m, 1H), 4.08-4.11 (m, 1H), 4.19-4.22 (m, 1H), 4.60 (s, 1H), 5.49 (s, 1H), 6.62-6.65 (m, 2H), 7.76 (s, 1H). | 1.81 | 500.05 | C |

TABLE 3-continued

| ID | Structure | NMR | | | |
|---|---|---|---|---|---|
| I-1-20 | (structure) | | 1.65 | 533.2 | B |
| I-1-21 | (structure) | 1H-NMR (MeOD) δ: 2.01-2.07 (m, 1H), 2.44-2.52 (m, 1H), 3.22-3.24 (m, 4H), 3.66-3.72 (m, 2H), 3.86-3.87 (m, 4H), 3.91-3.93 (m, 1H), 4.07-4.13 (m, 1H), 4.20 (s, 1H), 4.59 (s, 1H), 5.47 (s, 1H), 7.05 (d, J = 8.8 Hz, 2H), 7.54 (d, J = 8.8 Hz, 2H), 7.71 (s, 1H). | 1.66 | 464 | C |
| I-1-22 | (structure) | 1H-NMR (DMSO-D6) δ: 3.43 (1H, t, J = 8.5 Hz), 3.77 (1H, t, J = 7.4 Hz), 3.84 (2H, t, J = 5.4 Hz), 3.97-4.09 (2H, m), 4.09-4.17 (1H, m), 4.26 (2H, d, J = 2.8 Hz), 4.34 (1H, t, J = 4.9 Hz), 4.86 (1H, t, J = 5.3 Hz), 5.02 (1H, d, J = 6.8 Hz), 5.41 (1H, q, J = 5.0 Hz), 6.54 (1H, s), 7.33 (2H, d, J = 8.8 Hz), 7.77 (1H, s). | 1.84 | 516.1 | C |
| I-1-23 | (structure) | | 1.66 | 475.15 | B |

TABLE 4

| ID | Structure | | | |
|---|---|---|---|---|
| I-1-24 | (structure) | 1.51 | 534.2 | B |

TABLE 4-continued

| ID | Structure | NMR | | | |
|---|---|---|---|---|---|
| I-1-25 | (structure) | | 1.13 | 476.15 | B |
| I-1-26 | (structure) | 1H-NMR (MeOD) δ: 1.81-1.91 (m, 1H), 2.02-2.05 (m, 1H), 2.21-2.22 (m, 1H), 2.48-2.58 (m, 6H), 3.65-3.67 (m, 2H), 3.94-3.97 (m, 1H), 4.05-4.11 (m, 1H), 4.19-4.22 (m, 1H), 4.58 (s, 1H), 5.15 (s, 1H), 5.73 (s, 1H), 6.34 (s, 1H), 7.12-7.14 (m, 2H), 7.68 (s, 1H) | 1.65 | 505.05 | C |
| I-1-27 | (structure) | | 1.91 | 489.2 | B |
| I-1-28 | (structure) | | 1.27 | 511.2 | B |

TABLE 5

| ID | Structure | NMR | | | |
|---|---|---|---|---|---|
| I-1-29 | (structure) | 1H-NMR (DMSO-D6) δ: 2.15-2.25 (1H, m), 2.29-2.42 (1H, m), 2.53-2.68 (2H, m), 3.59 (1H, t, J = 5.5 Hz), 3.74 (1H, t, J = 5.1 Hz), 3.79-3.87 (1H, m), 3.88-3.96 (2H, m), 4.02 (1H, d, J = 10.8 Hz), 4.06-4.24 (4H, m), 4.53-4.69 (1H, m), 5.59 (1H, t, J = 4.8 Hz), 6.22-6.35 (1H, m), 7.55 (2H, t, J = 6.0 Hz), 7.63 (2H, d, J = 8.5 Hz), 7.81 (1H, s), 12.71 (1H, br s). | 1.66 | 479.1 | C |

TABLE 5-continued

| | | | | | |
|---|---|---|---|---|---|
| I-1-30 | (structure) | | 1.65 | 516.1 | C |
| I-1-31 | (structure) | 1H-NMR (DMSO-D6) δ: 1.1 (6H, s), 1.2 (2H, t, J = 11.4 Hz), 1.5-1.7 (3H, m), 1.7 (2H, d, J = 12.3 Hz), 2.3 (2H, d, J = 10.8 Hz), 2.5-2.7 (2H, m), 3.6 (1H, t, J = 5.1 Hz), 3.7 (1H, t, J = 5.4 Hz), 4.1-4.2 (4H, m), 4.5-4.7 (1H, m), 4.7-4.9 (1H, m), 6.3 (1H, d, J = 16.1 Hz), 7.5 (2H, t, J = 6.7 Hz), 7.6 (2H, d, J = 8.5 Hz), 7.8 (1H, s), 12.1 (1H, br s), 12.6 (1H, br s). | 1.96 | 577.1 | C |
| I-1-32 | (structure) | 1H-NMR (DMSO-D6) δ: 2.2-2.3 (1H, m), 2.3-2.4 (1H, m), 3.8-3.9 (1H, m), 3.9-4.0 (2H, m), 4.0-4.1 (1H, m), 5.6 (1H, t, J = 4.6 Hz), 7.4 (1H, t, J = 7.3 Hz), 7.5 (2H, t, J = 7.7 Hz), 7.7-7.8 (6H, m), 7.9 (1H, s), 12.7 (1H, br s). | 2.38 | 416 | C |
| I-1-33 | (structure) | | 1.4 | 458.05 | C |

TABLE 6

| | | | | | |
|---|---|---|---|---|---|
| I-1-34 | (structure) | | 1.83 | 539 | C |

TABLE 6-continued
| | | | | |
|---|---|---|---|---|
| I-1-35 | 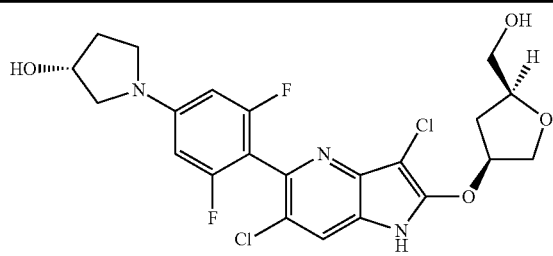 | 1.64 | 500 | C |
| I-1-36 | 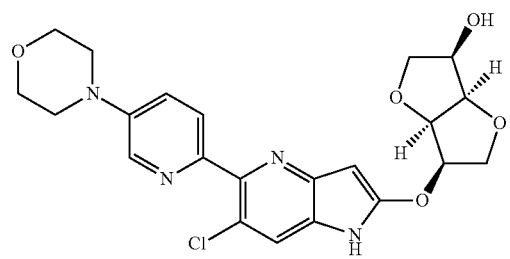 [SMILES: O[C@@H]1CO[C@H]2[C@@H]1OC[C@H]2Oc1cc2nc(-c3ccc(N4CCOCC4)cn3)c(Cl)cc2[nH]1] | 0.92 | 459.3 | B |
| I-1-37 | 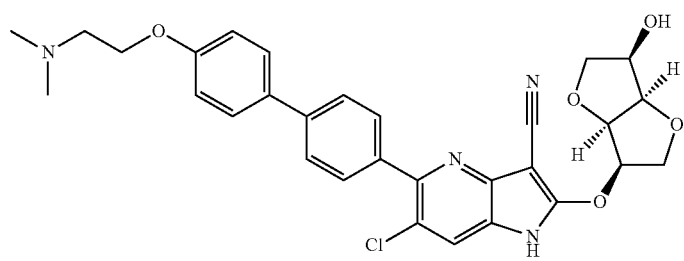 [SMILES: CN(C)CCOc1ccc(-c2ccc(-c3nc4c(C#N)c(O[C@@H]5CO[C@H]6[C@@H]5OC[C@H]6O)[nH]c4cc3Cl)cc2)cc1] | 1.37 | 561.05 | C |
| I-1-38 | 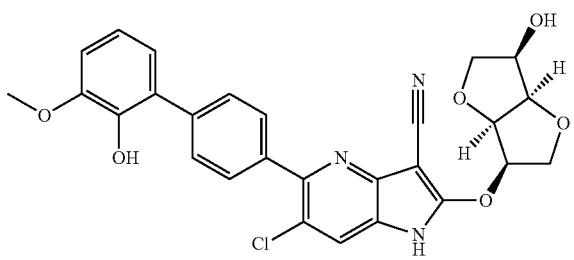 [SMILES: COc1cccc(-c2ccc(-c3nc4c(C#N)c(O[C@@H]5CO[C@H]6[C@@H]5OC[C@H]6O)[nH]c4cc3Cl)cc2)c1O] | 1.98 | 520 | B |
TABLE 7
| | | | | | |
|---|---|---|---|---|---|
| I-1-39 | 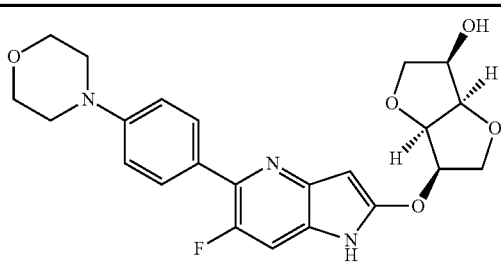 | 1H-NMR (DMSO-D6) δ: 3.16-3.19 (m, 4H), 3.44 (t, J = 8.3 Hz, 1H), 3.77-3.81 (m, 6H), 4.15-4.17 (m, 2H), 4.39 (s, 1H), 4.82 (s, 1H), 4.95-5.01 (m, 2H), 5.92 (s, 1H), 7.01-7.03 (m, 2H), 7.36-7.39 (m, 1H), 7.76-7.78 (m, 2H). | 1.25 | 442.05 | C |

TABLE 7-continued

| ID | Structure | NMR | RT | MS | Class |
|---|---|---|---|---|---|
| I-1-40 | 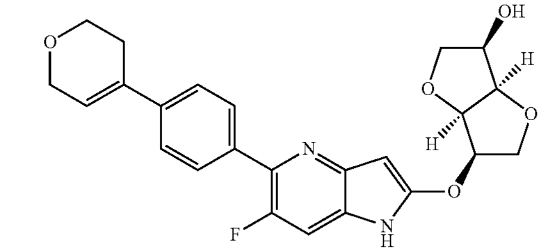 [SMILES: O[C@@H]1CO[C@H]2[C@@H]1OC[C@H]2Oc1cc2nc(-c3ccc(C4=CCOCC4)cc3)c(F)cc2[nH]1] | | 1.39 | 439.05 | C |
| I-1-41 | 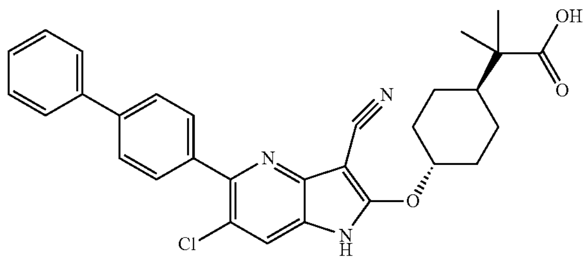 [SMILES: CC(C)(C(=O)O)[C@H]1CC[C@H](Oc2[nH]c3cc(Cl)c(-c4ccc(-c5ccccc5)cc4)nc3c2C#N)CC1] | 1H-NMR (DMSO-D6) δ: 1.07 (6H, s), 1.23 (2H, q, J = 12.0 Hz), 1.47-1.68 (3H, m), 1.70-1.81 (2H, m), 2.22-2.34 (2H, m), 4.73-4.85 (1H, m), 7.41 (1H, t, J = 7.4 Hz), 7.51 (2H, t, J = 7.5 Hz), 7.70-7.81 (6H, m), 7.83 (1H, s), 12.17 (1H, br s), 12.61 (1H, br s). | 2.59 | 514.1 | C |
| I-1-42 | 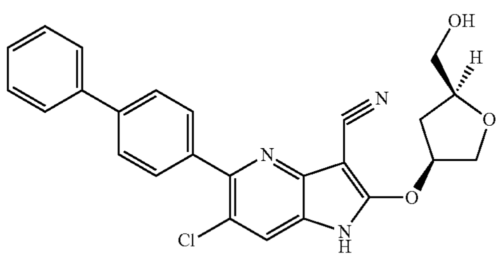 [SMILES: N#Cc1c(O[C@@H]2CO[C@H](CO)C2)[nH]c2cc(Cl)c(-c3ccc(-c4ccccc4)cc3)nc12] | 1H-NMR (DMSO-D6) δ: 2.00 (1H, dd, J = 14.4, 5.9 Hz), 3.42-3.58 (2H, m), 3.88 (1H, dd, J = 10.9, 3.9 Hz), 3.93-4.03 (1H, m), 4.15 (1H, d, J = 10.8 Hz), 4.76-4.86 (1H, m), 5.53-5.61 (1H, m), 7.41 (1H, t, J = 7.4 Hz), 7.51 (2H, t, J = 7.7 Hz), 7.71-7.82 (6H, m), 7.86 (1H, s), 12.70 (1H, br s). | 2.27 | 446 | C |
| I-1-43 | 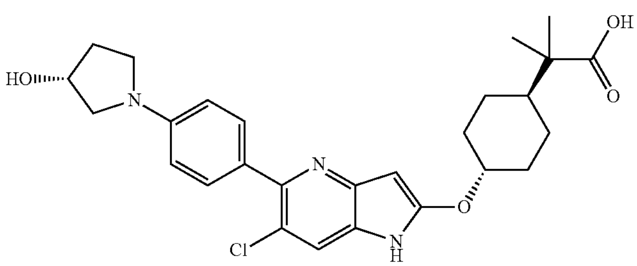 [SMILES: CC(C)(C(=O)O)[C@H]1CC[C@H](Oc2cc3nc(-c4ccc(N5CC[C@@H](O)C5)cc4)c(Cl)cc3[nH]2)CC1] | | 1.4 | 498.45 | B |

TABLE 8

| ID | Structure | RT | MS | Class |
|---|---|---|---|---|
| I-1-44 | | 1.76 | 512 | C |

TABLE 8-continued

| ID | Structure | NMR | a | b | c |
|---|---|---|---|---|---|
| I-1-45 | 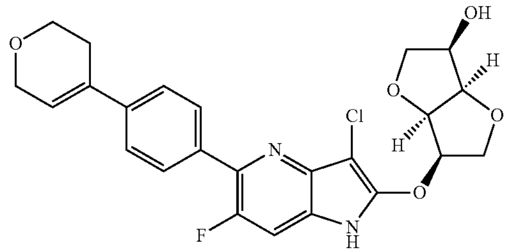 [SMILES: O[C@@H]1CO[C@H]2[C@@H]1OC[C@H]2Oc1[nH]c2cc(F)c(-c3ccc(C4=CCOCC4)cc3)nc2c1Cl] | | 1.93 | 473 | C |
| I-1-46 | 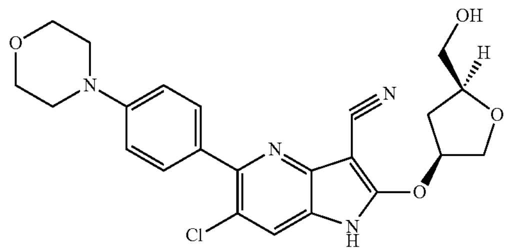 [SMILES: N#Cc1c(O[C@@H]2CO[C@H](CO)C2)[nH]c2cc(Cl)c(-c3ccc(N4CCOCC4)cc3)nc12] | 1H-NMR (DMSO-D6) δ: 1.92-2.05 (1H, m), 3.14-3.23 (4H, m), 3.43-3.57 (2H, m), 3.73-3.83 (4H, m), 3.87 (1H, d, J = 9.7 Hz), 3.97 (1H, t, J = 6.1 Hz), 4.12 (1H, d, J = 10.3 Hz), 4.76-4.84 (1H, m), 5.50-5.58 (1H, m), 7.03 (2H, d, J = 8.3 Hz), 7.55 (2H, d, J = 7.8 Hz), 7.76 (1H, s), 12.61 (1H, br s). | 1.72 | 455 | C |
| I-1-47 | 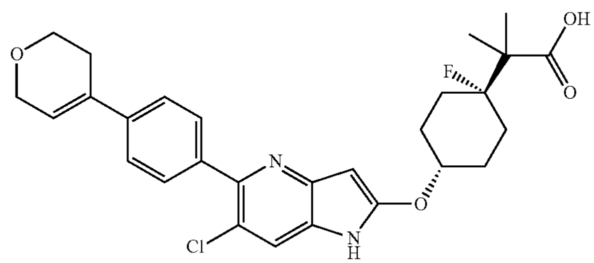 [SMILES: CC(C)(C(=O)O)[C@]1(F)CC[C@@H](Oc2cc3nc(-c4ccc(C5=CCOCC5)cc4)c(Cl)cc3[nH]2)CC1] | | 1.8 | 513.15 | C |
| I-1-48 | 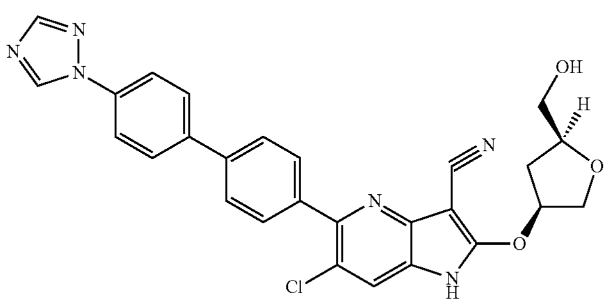 [SMILES: N#Cc1c(O[C@@H]2CO[C@H](CO)C2)[nH]c2cc(Cl)c(-c3ccc(-c4ccc(-n5cncn5)cc4)cc3)nc12] | 1H-NMR (DMSO-D6) δ: 2.00 (1H, dd, J = 14.1, 5.5 Hz), 3.42-3.59 (2H, m), 3.88 (1H, dd, J = 11.0, 3.8 Hz), 3.94-4.05 (1H, m), 4.15 (1H, d, J = 11.0 Hz), 4.81 (1H, t, J = 5.3 Hz), 5.57 (1H, t, J = 4.1 Hz), 7.77 (2H, d, J = 8.3 Hz), 7.83-7.91 (3H, m), 7.98 (4H, q, J = 9.0 Hz), 8.28 (1H, s), 9.38 (1H, s), 12.70 (1H, br s). | 1.87 | 513.1 | C |

TABLE 9

| ID | Structure | NMR | a | b | c |
|---|---|---|---|---|---|
| I-1-49 | 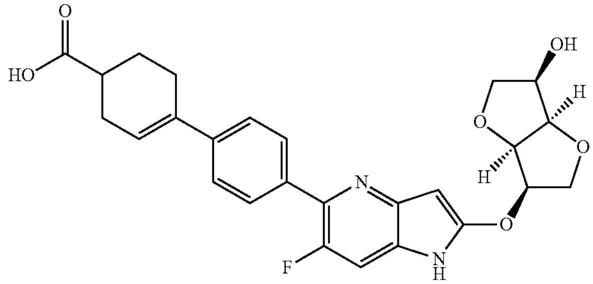 [SMILES: O=C(O)C1CC=C(c2ccc(-c3nc4cc(O[C@@H]5CO[C@H]6[C@@H]5OC[C@H]6O)[nH]c4cc3F)cc2)CC1] | 1H-NMR (DMSO-D6) δ: 1.70-1.75 (m, 1H), 2.10-2.11 (m, 1H), 2.33-2.43 (m, 5H), 3.44 (t, J = 8.4 Hz, 1H), 3.80-3.83 (m, 2H), 4.15-4.18 (m, 2H), 4.39 (t, J = 4.8 Hz, 1H), 4.83 (t, J = 5.0 Hz, 1H), 4.97-5.02 (m, 2H), 5.96 (s, 1H), 6.25 (s, 1H), 7.41-7.44 (m, 1H), 7.50-7.52 (m, 2H), 7.83-7.85 (m, 2H). | 1.37 | 481.1 | C |

TABLE 9-continued

| ID | Structure | 1H-NMR | | | |
|---|---|---|---|---|---|
| I-1-50 | 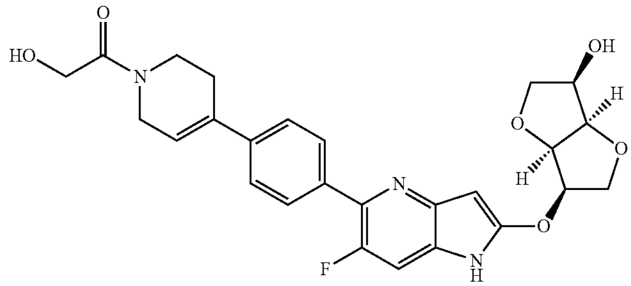 [SMILES: O=C(CO)N1CC=C(c2ccc(-c3nc4cc(O[C@@H]5CO[C@H]6[C@@H]5OC[C@H]6O)[nH]c4cc3F)cc2)CC1] | 1H-NMR (DMSO-D6) δ: 2.60 (s, 2H), 3.43-3.45 (m, 1H), 3.57-3.58 (m, 1H), 3.76-3.81 (m, 3H), 4.12-4.16 (m, 6H), 4.39 (t, J = 4.9 Hz, 1H), 4.56-4.62 (m, 1H), 4.83 (t, J = 4.9 Hz, 1H), 4.97-5.03 (m, 2H), 5.95 (s, 1H), 6.25-6.29 (m, 1H), 7.41-7.44 (m, 1H), 7.54-7.56 (m, 2H), 7.86-7.88 (m, 2H). | 1.21 | 496.05 | C |
| I-1-51 | 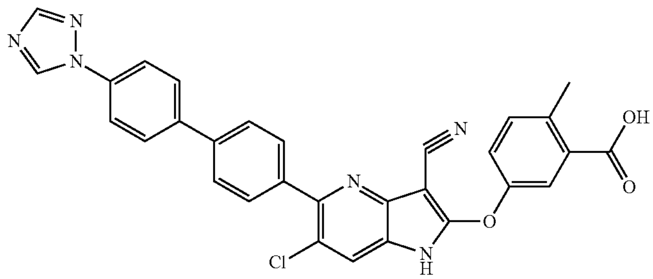 [SMILES: Cc1ccc(Oc2[nH]c3cc(Cl)c(-c4ccc(-c5ccc(-n6cncn6)cc5)cc4)nc3c2C#N)cc1C(=O)O] | 1H-NMR (DMSO-D6) δ: 2.57 (3H, s), 7.47 (1H, d, J = 8.5 Hz), 7.56 (1H, dd, J = 8.5, 2.8 Hz), 7.74-7.81 (3H, m), 7.87 (2H, d, J = 8.3 Hz), 7.98 (5H, q, J = 9.0 Hz), 8.27 (1H, s), 9.38 (1H, s), 13.04 (1H, br s). | 2.16 | 547 | C |
| I-1-52 | 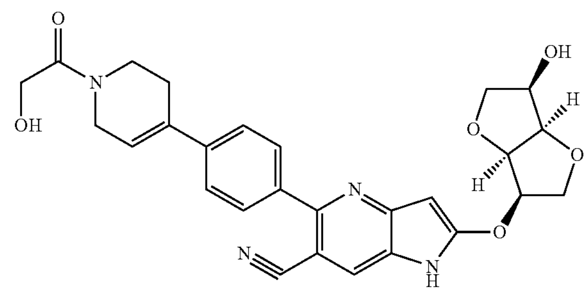 [SMILES: N#Cc1cc2[nH]c(O[C@@H]3CO[C@H]4[C@@H]3OC[C@H]4O)cc2nc1-c1ccc(C2=CCN(C(=O)CO)CC2)cc1] | | 1.01 | 503.2 | B |
| I-1-53 | 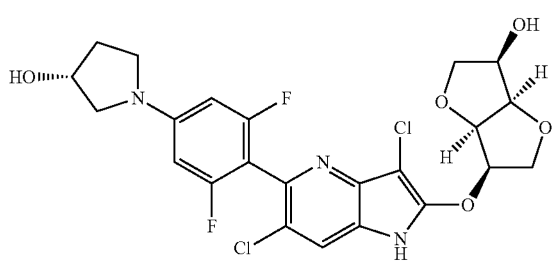 [SMILES: O[C@@H]1CCN(c2cc(F)c(-c3nc4c(Cl)c(O[C@@H]5CO[C@H]6[C@@H]5OC[C@H]6O)[nH]c4cc3Cl)c(F)c2)C1] | | 1.48 | 528.25 | B |

TABLE 10

| ID | Structure | 1H-NMR | | | |
|---|---|---|---|---|---|
| I-1-54 | 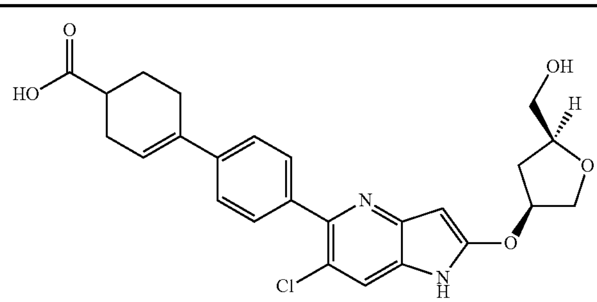 | 1H-NMR (MeOD) δ: 1.85-1.88 (m, 1H), 1.98-2.05 (m, 1H), 2.19-2.23 (m, 1H), 2.45-2.65 (m, 6H), 3.64-3.68 (m, 2H), 3.94-3.97 (m, 1H), 4.05-4.11 (m, 1H), 4.19-4.21 (m, 1H), 4.60 (s, 1H), 5.13 (s, 1H), 5.71 (s, 1H), 6.22-6.22 (m, 1H), 7.47-7.54 (m, 4H), 7.63-7.63 (m, 1H). | 1.38 | 469.1 | C |

TABLE 10-continued

| ID | Structure | 1H-NMR | RT | MS | Cat |
|---|---|---|---|---|---|
| I-1-55 | 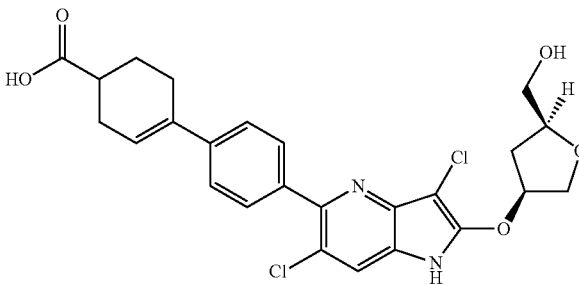 | 1H-NMR (MeOD) δ: 1.87-1.91 (m, 1H), 2.04-2.07 (m, 1H), 2.20-2.23 (m, 1H), 2.45-2.60 (m, 6H), 3.66-3.73 (m, 2H), 3.91-3.94 (m, 1H), 4.08-4.11 (m, 1H), 4.19-4.22 (m, 1H), 4.57 (s, 1H), 5.48 (s, 1H), 6.23 (s, 1H), 7.50-7.56 (m, 4H), 7.73-7.75 (m, 1H). | 1.7 | 503.15 | B |
| I-1-56 | 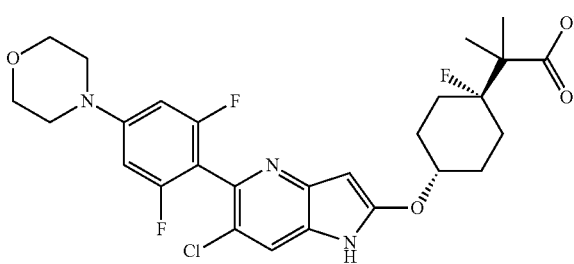 | | 1.88 | 552 | B |
| I-1-57 | 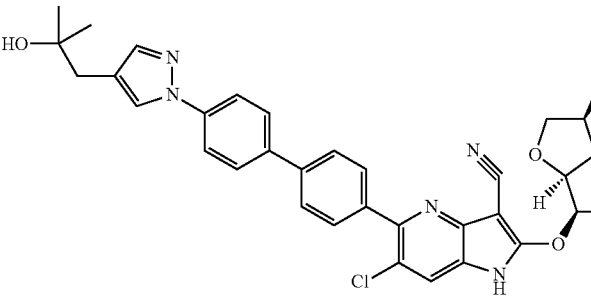 | 1H-NMR (DMSO-D6) δ: 1.1 (6H, s), 2.6 (2H, s), 3.4 (1H, t, J = 9.0 Hz), 3.8 (1H, t, J = 7.3 Hz), 4.0 (1H, dd, J = 10.7, 4.6 Hz), 4.1-4.2 (2H, m), 4.3 (1H, t, J = 5.0 Hz), 4.4 (1H, s), 4.9 (1H, t, J = 5.3 Hz), 5.1 (1H, d, J = 6.3 Hz), 5.4-5.4 (1H, m), 7.6 (1H, s), 7.7 (2H, d, J = 8.3 Hz), 7.8-7.9 (5H, m), 7.8 (2H, d, J = 8.8 Hz), 8.3 (1H, s). | 1.95 | 612.1 | C |
| I-1-58 | 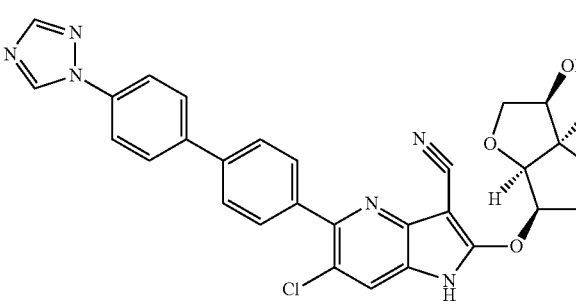 | 1H-NMR (DMSO-D6) δ: 3.43 (1H, t, J = 8.8 Hz), 3.78 (1H, t, J = 7.3 Hz), 3.96-4.05 (1H, m), 4.06-4.18 (2H, m), 4.33 (1H, t, J = 5.0 Hz), 4.91 (1H, t, J = 5.3 Hz), 5.07 (1H, d, J = 6.8 Hz), 5.42 (1H, dd, J = 8.3. 5.0 Hz), 7.77 (2H, d, J = 8.3 Hz), 7.83-7.89 (3H, m), 7.98 (4H, dd, J = 18.6, 8.8 Hz), 8.28 (1H, s), 9.38 (1H, s), 12.73 (1H, br s). | 1.79 | 541.1 | C |

TABLE 11

| ID | Structure | 1H-NMR | RT | MS | Cat |
|---|---|---|---|---|---|
| I-1-59 | 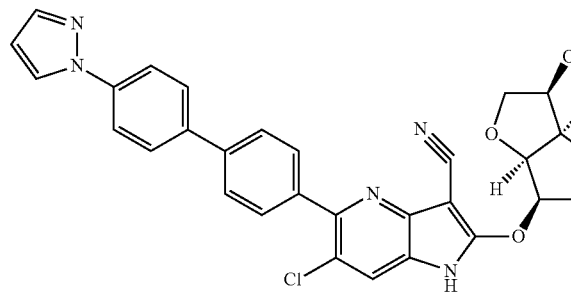 | 1H-NMR (DMSO-D6) δ: 3.4 (1H, t, J = 8.8 Hz), 3.8 (1H, t, J = 7.3 Hz), 4.0 (1H, dd, J = 10.7, 4.9 Hz), 4.1-4.2 (2H, m), 4.3 (1H, t, J = 5.0 Hz), 4.9 (1H, t, J = 5.1 Hz), 5.1 (1H, d, J = 6.8 Hz), 5.4 (1H, dd, J = 8.5, 4.8 Hz), 6.6 (1H, t, J = 2.1 Hz), 7.7-7.8 (3H, m), 7.8-7.9 (5H, m), 8.0 (2H, d, J = 8.8 Hz), 8.6 (1H, d, J = 2.5 Hz), 12.7 (1H, br s). | 2.08 | 540.1 | C |

TABLE 11-continued

| ID | Structure | NMR | RT | MS | Grade |
|---|---|---|---|---|---|
| I-1-60 | (structure) | | 1.65 | 495.4 | B |
| I-1-61 | (structure) | 1H-NMR (DMSO-D6) δ: 1.87-1.97 (1H, m), 2.01-2.12 (1H, m), 3.14 (1H, d, J = 9.4 Hz), 3.39-3.51 (2H, m), 3.77 (1H, t, J = 7.4 Hz), 3.96-4.17 (3H, m), 4.29-4.37 (1H, m), 4.38-4.47 (1H, m), 4.84-4.92 (1H, m), 4.96-5.01 (1H, m), 5.05 (1H, d, J = 6.7 Hz), 5.34-5.44 (1H, m), 6.59 (2H, d, J = 7.9 Hz), 7.51 (2H, d, J = 8.2 Hz), 7.72 (1H, s), 12.53 (1H, br s). | 1.56 | 483.1 | C |
| I-1-62 | (structure) | | 1.77 | 477 | C |
| I-1-63 | (structure) | | 1.34 | 534.3 | C |

TABLE 12

| ID | Structure | NMR | RT | MS | Grade |
|---|---|---|---|---|---|
| I-1-64 | (structure) | 1H-NMR (DMSO-D6) δ: 1.05 (s, 6H), 1.24-1.27 (m, 2H), 1.38-1.44 (m, 2H), 1.56-1.70 (m, 3H), 2.25-2.27 (m, 2H), 3.17-3.18 (m, 4H), 3.76-3.77 (m, 4H), 4.29-4.34 (m, 1H), 5.80 (s, 1H), 7.01-7.03 (m, 2H), 7.33-7.36 (m, 1H), 7.76-7.78 (m, 2H). | 1.6 | 482.15 | C |

TABLE 12-continued
| No. | Structure | | Retention time | Mass (M+H) | Method |
|---|---|---|---|---|---|
| I-1-65 | (structure) | 1H-NMR (DMSO-D6) δ: 1.06 (s, 6H), 1.24-1.27 (m, 2H), 1.38-1.44 (m, 2H), 1.56-1.70 (m, 3H), 2.24-2.27 (m, 2H), 3.23-3.24 (m, 4H), 3.73-3.74 (m, 4H), 4.30-4.36 (m, 1H), 5.81 (s, 1H), 6.73-6.76 (m, 2H), 7.39-7.42 (m, 1H). | 1.75 | 518.1 | C |
| I-1-66 | (structure) | 1H-NMR (DMSO-D6) δ: 1.71-1.74 (m, 1H), 1.87-1.90 (m, 1H), 2.10-2.11 (m, 1H), 2.32-2.47 (m, 6H), 3.48-3.49 (m, 2H), 3.87-3.92 (m, 2H), 4.03-4.05 (m, 1H), 4.77 (s, 1H), 5.10 (s, 1H), 5.80 (s, 1H), 6.26 (s, 1H), 7.41-7.45 (m, 1H), 7.50-7.52 (m, 2H), 7.83-7.85 (m, 2H). | 1.35 | 453.05 | C |
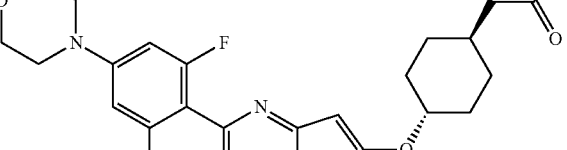
TABLE 13
| No. | Structure | retention time | Mass (M + H) | method |
|---|---|---|---|---|
| I-2-17 | (structure) | 0.88 | 459.15 | B |
| I-2-18 | (structure) | 1.01 | 503.2 | B |
| I-2-19 | (structure) | 1.27 | 446.5 | B |
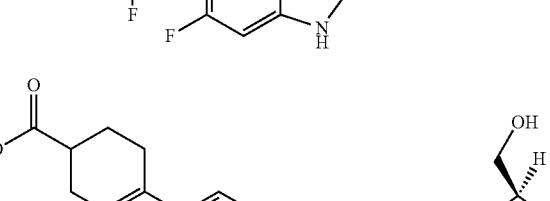

TABLE 13-continued

| No. | Structure | retention time | Mass (M + H) | method |
|---|---|---|---|---|
| I-2-20 | 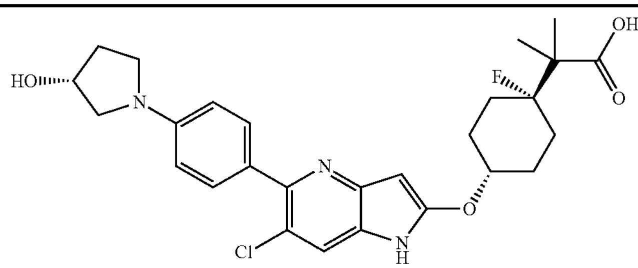 | 1.63 | 516 | A |

TABLE 14

| No. | Structure | retention time | Mass (M + H) | method |
|---|---|---|---|---|
| I-2-21 | 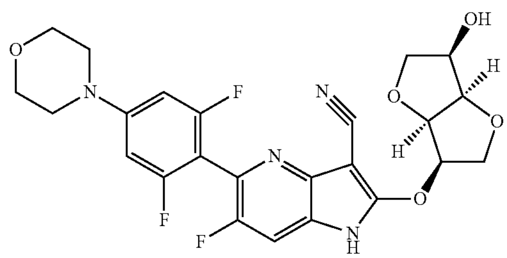 [SMILES: N#Cc1c(O[C@@H]2CO[C@H]3[C@@H]2OC[C@H]3O)[nH]c2cc(F)c(-c3c(F)cc(N4CCOCC4)cc3F)nc12] | 1.56 | 503.1 | B |
| I-2-22 | 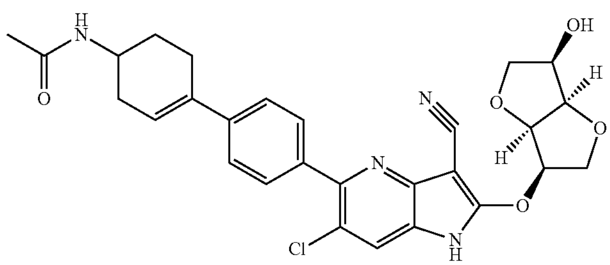 [SMILES: CC(=O)NC1CC=C(c2ccc(-c3nc4c(C#N)c(O[C@@H]5CO[C@H]6[C@@H]5OC[C@H]6O)[nH]c4cc3Cl)cc2)CC1] | 1.63 | 535 | C |
| I-2-23 | 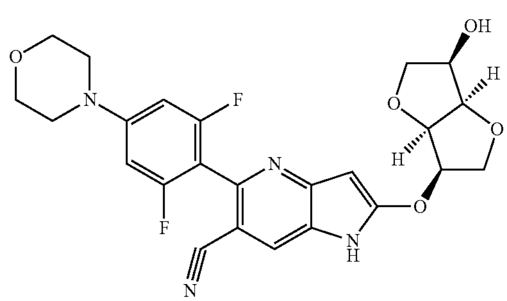 [SMILES: N#Cc1cc2[nH]c(O[C@@H]3CO[C@H]4[C@@H]3OC[C@H]4O)cc2nc1-c1c(F)cc(N2CCOCC2)cc1F] | 1.31 | 485.2 | B |
| I-2-24 | 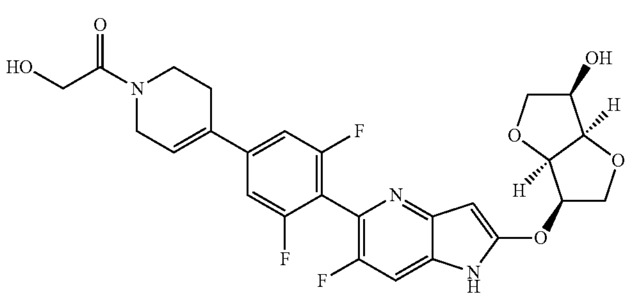 [SMILES: O=C(CO)N1CC=C(c2cc(F)c(-c3nc4cc(O[C@@H]5CO[C@H]6[C@@H]5OC[C@H]6O)[nH]c4cc3F)c(F)c2)CC1] | 1.31 | 532 | C |

TABLE 15

| | | | | |
|---|---|---|---|---|
| I-2-25 | | 1.61 | 521 | C |
| I-2-26 | | 1.07 | 463.95 | C |
| I-2-27 | | 1.79 | 480.95 | C |
| I-2-28 | | 1.80 | 451 | C |

TABLE 16

| | | | | |
|---|---|---|---|---|
| I-2-29 | | 1.75 | 463.95 | C |

TABLE 16-continued
| | | | | |
|---|---|---|---|---|
| I-2-30 | 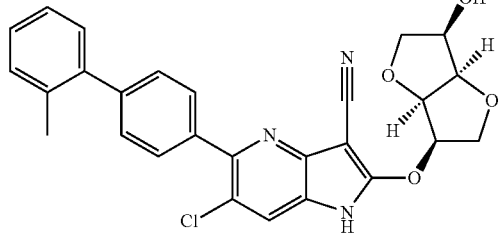 | 2.32 | 488 | C |
| I-2-31 | 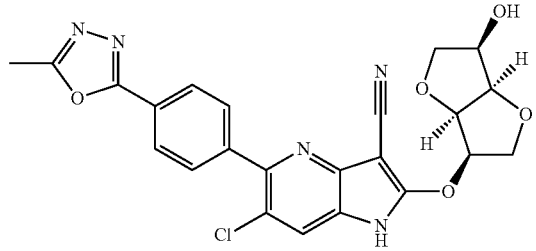 [SMILES: Cc1nnc(-c2ccc(-c3nc4c(C#N)c(O[C@@H]5CO[C@H]6[C@@H]5OC[C@H]6O)[nH]c4cc3Cl)cc2)o1] | 1.56 | 479.95 | C |
| I-2-32 | 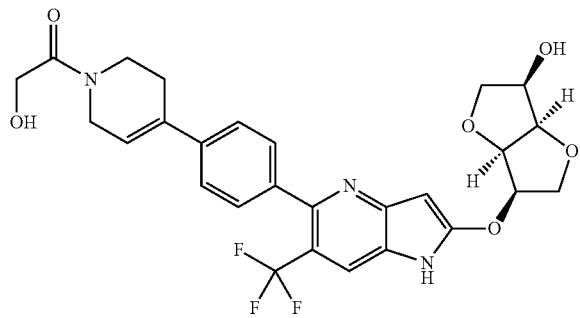 [SMILES: O=C(CO)N1CC=C(c2ccc(-c3nc4cc(O[C@@H]5CO[C@H]6[C@@H]5OC[C@H]6O)[nH]c4cc3C(F)(F)F)cc2)CC1] | 1.13 | 546.1 | B |
TABLE 17
| | | | | |
|---|---|---|---|---|
| I-2-33 | 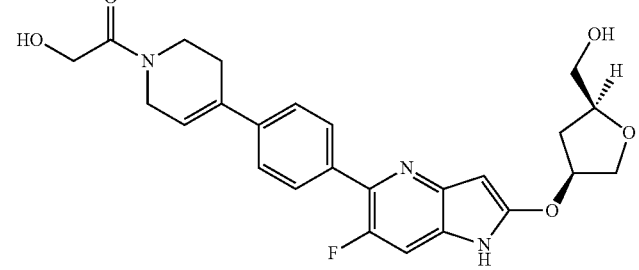 | 1.18 | 468.05 | C |
| I-2-34 | 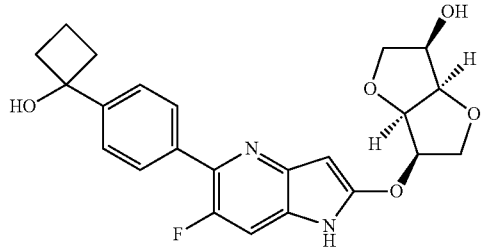 [SMILES: O[C@@H]1CO[C@H]2[C@@H]1OC[C@H]2Oc1cc2nc(-c3ccc(C4(O)CCC4)cc3)c(F)cc2[nH]1] | 1.25 | 427 | C |

TABLE 17-continued
| | | | | |
|---|---|---|---|---|
| I-2-35 | 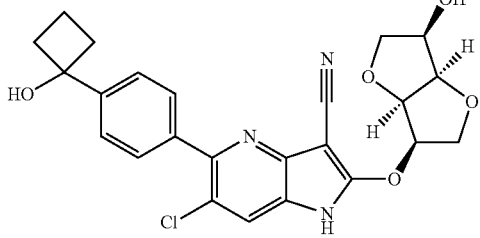 | 1.66 | 468 | C |
| I-2-36 | 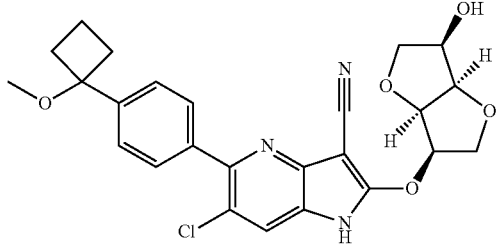 [SMILES: COC1(c2ccc(-c3nc4c(C#N)c(O[C@@H]5CO[C@H]6[C@@H]5OC[C@H]6O)[nH]c4cc3Cl)cc2)CCC1] | 2.03 | 482 | C |
TABLE 18
| | | | | |
|---|---|---|---|---|
| I-2-37 | 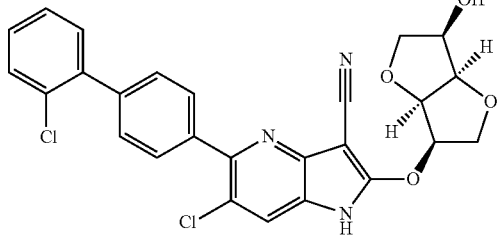 | 2.23 | 508.1 | B |
| I-2-38 | 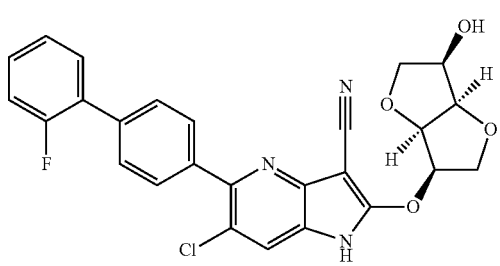 | 2.18 | 491.95 | C |
| I-2-39 | 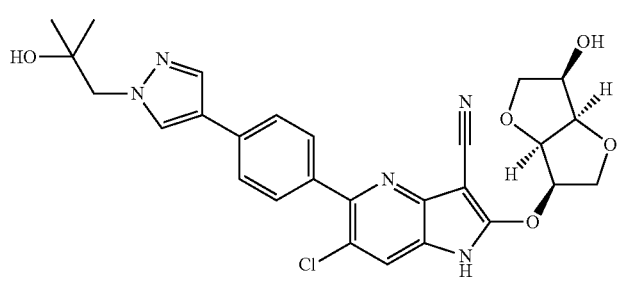 [SMILES: CC(C)(O)Cn1cc(-c2ccc(-c3nc4c(C#N)c(O[C@@H]5CO[C@H]6[C@@H]5OC[C@H]6O)[nH]c4cc3Cl)cc2)cn1] | 1.61 | 536.05 | C |

TABLE 18-continued
| | | | | |
|---|---|---|---|---|
| I-2-40 | 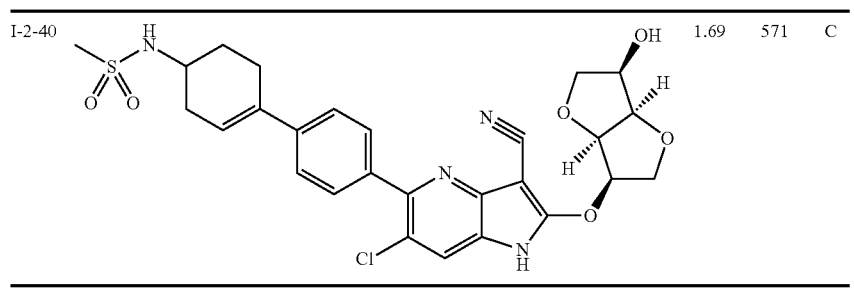 | 1.69 | 571 | C |
TABLE 19
| | | | | |
|---|---|---|---|---|
| I-2-41 | 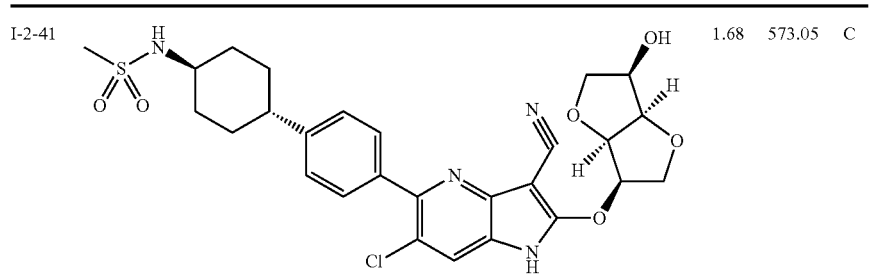 | 1.68 | 573.05 | C |
| I-2-42 | 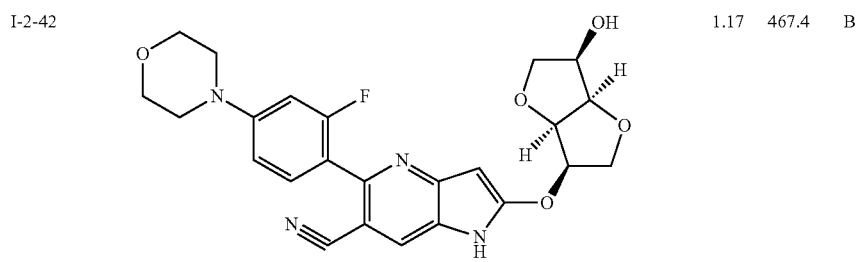 | 1.17 | 467.4 | B |
| I-2-43 | 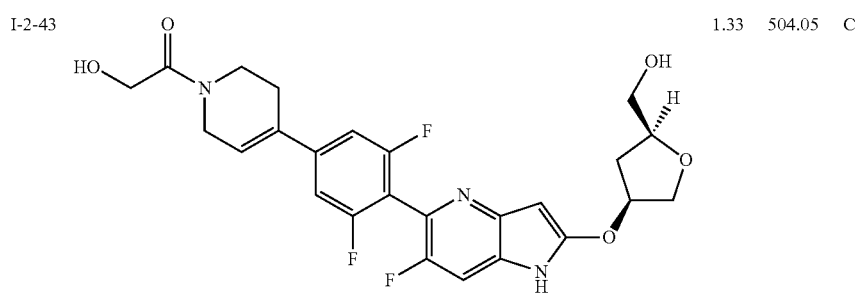 | 1.33 | 504.05 | C |
| I-2-44 | 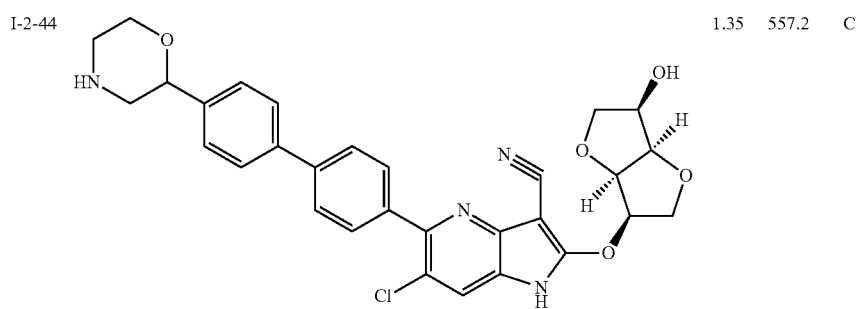 | 1.35 | 557.2 | C |

TABLE 20
| | | | | |
|---|---|---|---|---|
| I-2-45 | 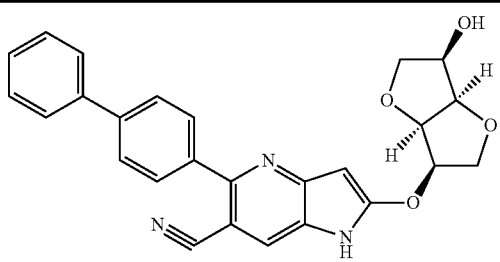 | 1.72 | 440.2 | B |
| I-2-46 | 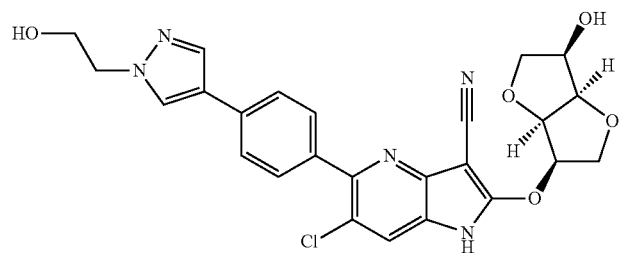 [SMILES: N#Cc1c(O[C@@H]2CO[C@H]3[C@@H]2OC[C@H]3O)[nH]c2cc(Cl)c(-c3ccc(-c4cnn(CCO)c4)cc3)nc12] | 1.43 | 508 | C |
| I-2-47 | 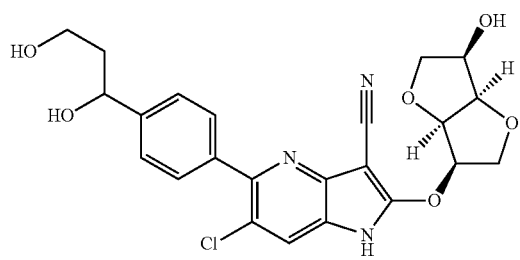 [SMILES: N#Cc1c(O[C@@H]2CO[C@H]3[C@@H]2OC[C@H]3O)[nH]c2cc(Cl)c(-c3ccc(C(O)CCO)cc3)nc12] | 1.26 | 472 | C |
| I-2-48 | 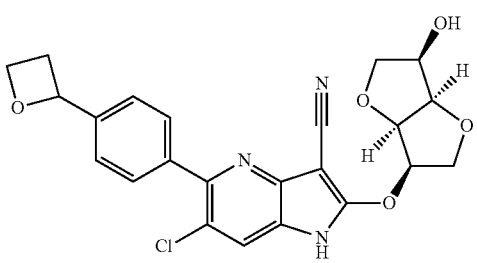 [SMILES: N#Cc1c(O[C@@H]2CO[C@H]3[C@@H]2OC[C@H]3O)[nH]c2cc(Cl)c(-c3ccc(C4CCO4)cc3)nc12] | 1.56 | 454.1 | B |
TABLE 21
| | | | | |
|---|---|---|---|---|
| I-2-49 | 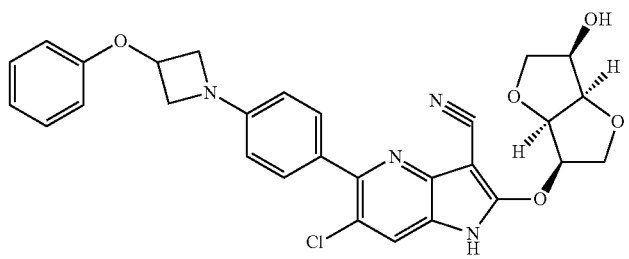 [SMILES: N#Cc1c(O[C@@H]2CO[C@H]3[C@@H]2OC[C@H]3O)[nH]c2cc(Cl)c(-c3ccc(N4CC(Oc5ccccc5)C4)cc3)nc12] | 2.23 | 545.1 | C |

TABLE 21-continued

| ID | Structure | a | b | c |
|---|---|---|---|---|
| I-2-50 | 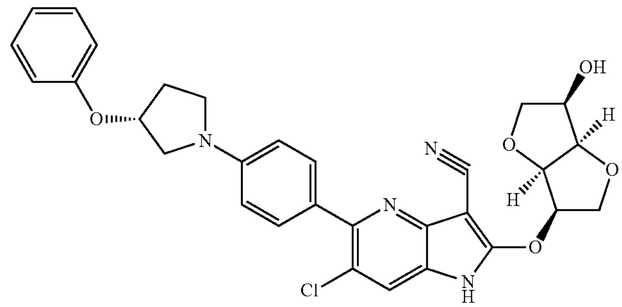 [SMILES: N#Cc1c(O[C@@H]2CO[C@H]3[C@@H]2OC[C@H]3O)[nH]c2cc(Cl)c(-c3ccc(N4CC[C@@H](Oc5ccccc5)C4)cc3)nc12] | 2.29 | 559.1 | C |
| I-2-51 | 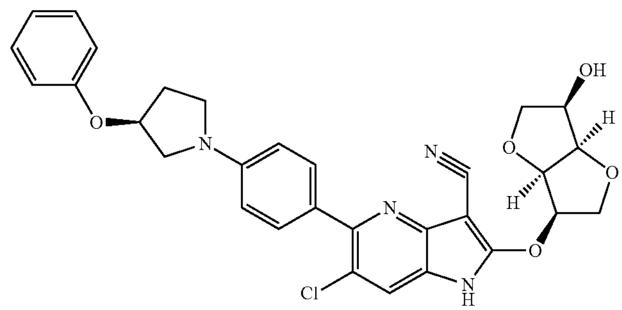 [SMILES: N#Cc1c(O[C@@H]2CO[C@H]3[C@@H]2OC[C@H]3O)[nH]c2cc(Cl)c(-c3ccc(N4CC[C@H](Oc5ccccc5)C4)cc3)nc12] | 2.28 | 559.1 | C |
| I-2-52 | 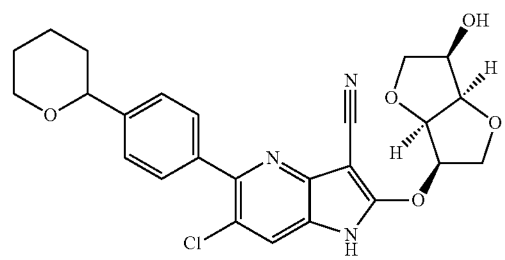 [SMILES: N#Cc1c(O[C@@H]2CO[C@H]3[C@@H]2OC[C@H]3O)[nH]c2cc(Cl)c(-c3ccc(C4CCCCO4)cc3)nc12] | 2.03 | 482 | C |

TABLE 22

| ID | Structure | a | b | c |
|---|---|---|---|---|
| I-2-53 | 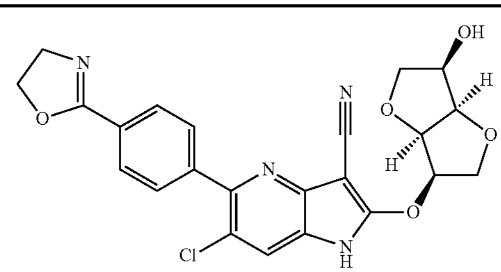 | 1.31 | 466.95 | C |
| I-2-54 | 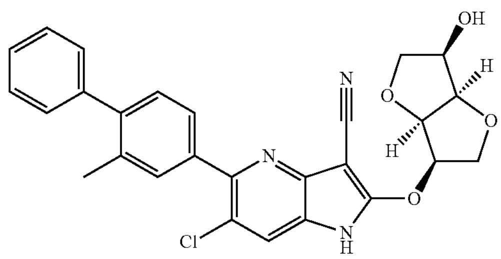 [SMILES: Cc1cc(-c2nc3c(C#N)c(O[C@@H]4CO[C@H]5[C@@H]4OC[C@H]5O)[nH]c3cc2Cl)ccc1-c1ccccc1] | 2.29 | 488 | C |

TABLE 22-continued
| I-2-55 | 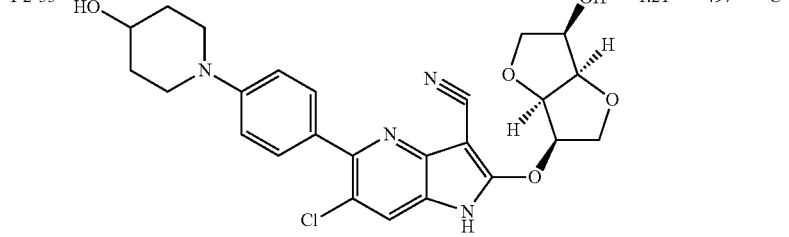 | 1.21 | 497 | C |
| I-2-56 | 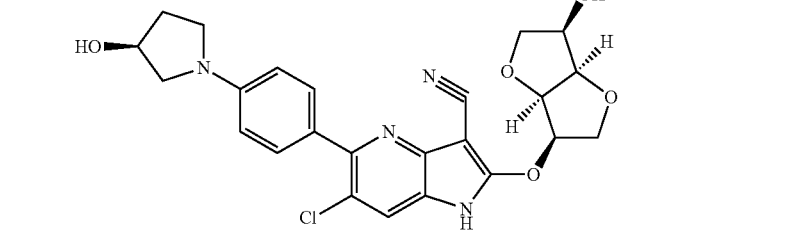 | 1.52 | 483 | C |
TABLE 23
| I-2-57 | 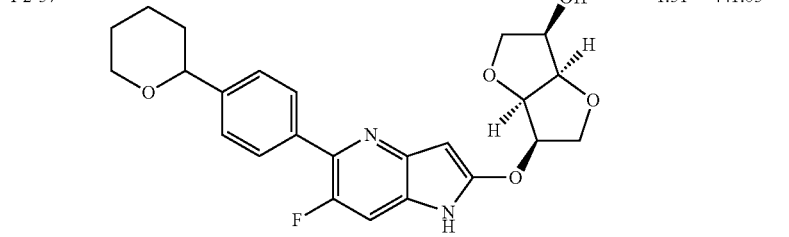 | 1.51 | 441.05 | C |
| I-2-58 | 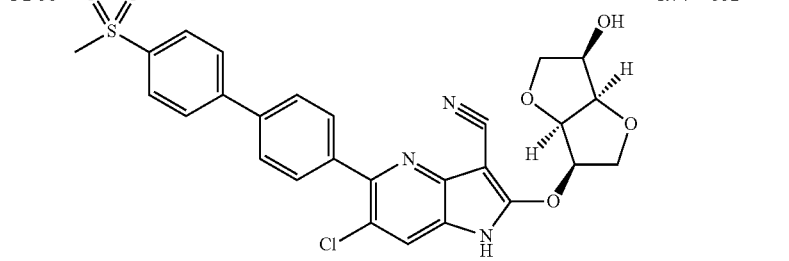 | 1.74 | 552 | C |
| I-2-59 | 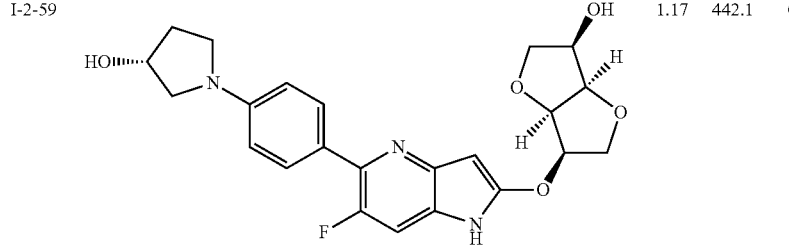 | 1.17 | 442.1 | C |

TABLE 23-continued
| I-2-60 | 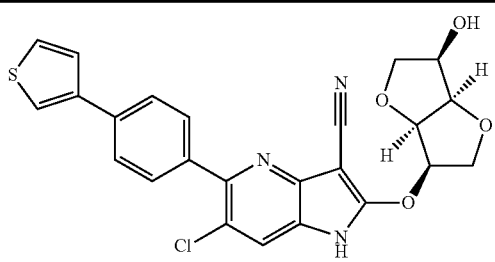 | 2.12 | 479.95 | C |
TABLE 24
| I-2-61-a | 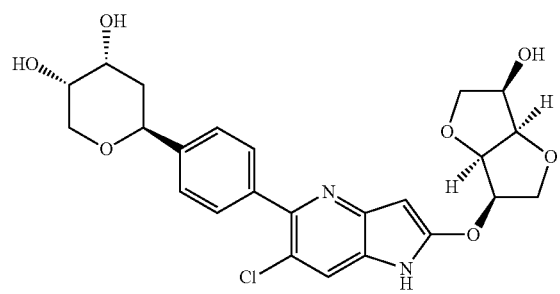 [SMILES: O[C@@H]1CO[C@H]2[C@@H]1OC[C@H]2Oc1cc2nc(-c3ccc([C@@H]4C[C@@H](O)[C@@H](O)CO4)cc3)c(Cl)cc2[nH]1] | 1.00 | 473 | C |
| I-2-61-b | | | | |
| I-2-62-a | 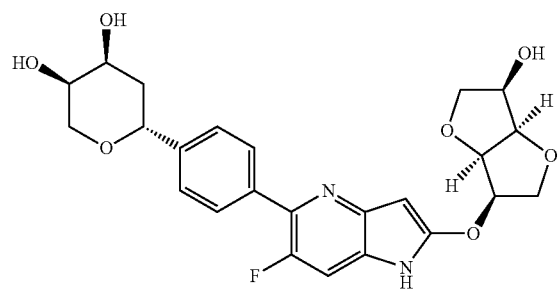 [SMILES: O[C@@H]1CO[C@H]2[C@@H]1OC[C@H]2Oc1cc2nc(-c3ccc([C@H]4C[C@H](O)[C@H](O)CO4)cc3)c(F)cc2[nH]1] | 0.98 | 473.05 | C |
| | 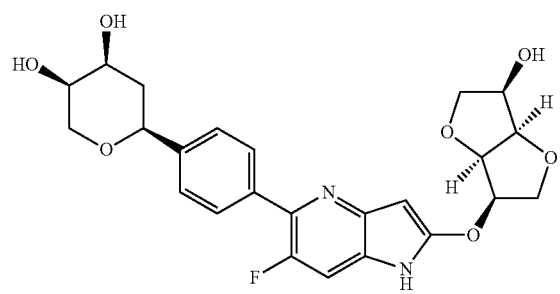 [SMILES: O[C@@H]1CO[C@H]2[C@@H]1OC[C@H]2Oc1cc2nc(-c3ccc([C@@H]4C[C@H](O)[C@H](O)CO4)cc3)c(F)cc2[nH]1] | | | |
| I-2-62-b | 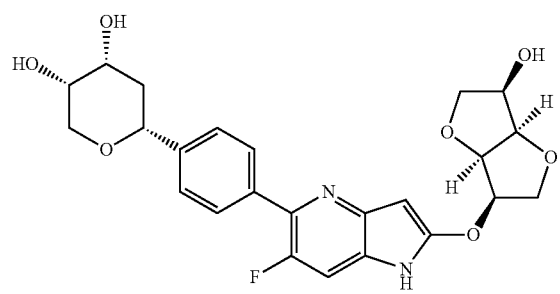 [SMILES: O[C@@H]1CO[C@H]2[C@@H]1OC[C@H]2Oc1cc2nc(-c3ccc([C@H]4C[C@@H](O)[C@@H](O)CO4)cc3)c(F)cc2[nH]1] | | | |

TABLE 25
I-2-63 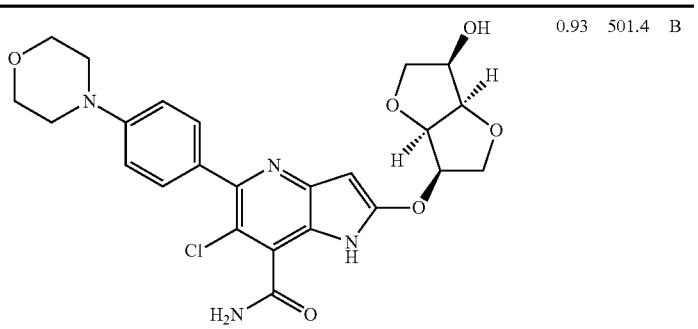 0.93 501.4 B
I-2-64 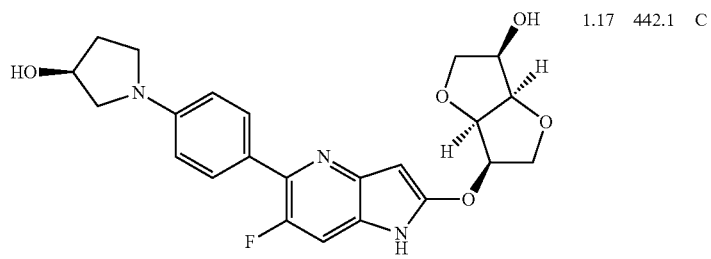 1.17 442.1 C
I-2-65 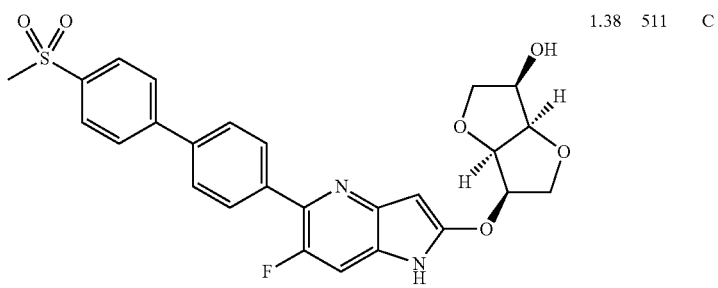 1.38 511 C
I-2-66 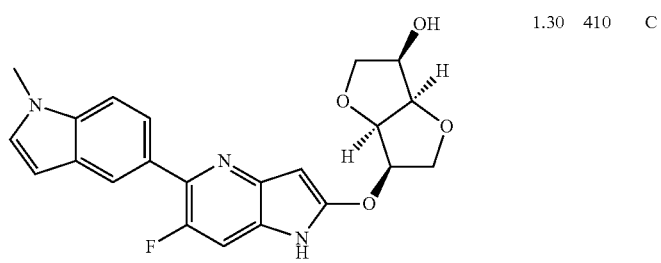 1.30 410 C
TABLE 26
I-2-67 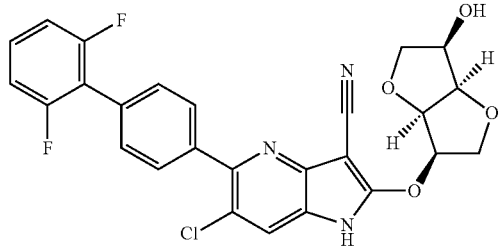 [SMILES: N#Cc1c(O[C@@H]2CO[C@H]3[C@@H]2OC[C@H]3O)[nH]c2cc(Cl)c(-c3ccc(-c4c(F)cccc4F)cc3)nc12] 2.16 510 C TABLE 26-continued
| | | | | |
|---|---|---|---|---|
| I-2-68 | 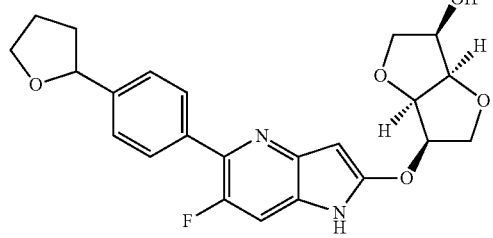 | 1.36 | 427 | C |
| I-2-69 | 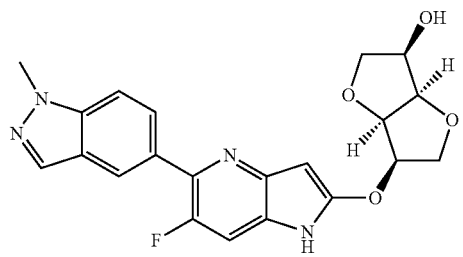 [SMILES: Cn1ncc2cc(-c3nc4cc(O[C@@H]5CO[C@H]6[C@@H]5OC[C@H]6O)[nH]c4cc3F)ccc21] | 1.16 | 411 | C |
| I-2-70 | 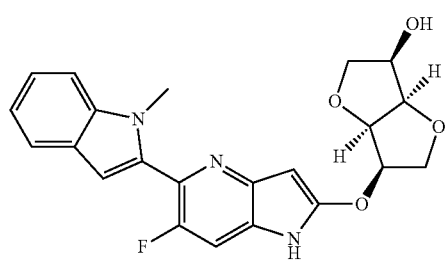 [SMILES: Cn1c(-c2nc3cc(O[C@@H]4CO[C@H]5[C@@H]4OC[C@H]5O)[nH]c3cc2F)cc2ccccc21] | 1.58 | 410 | C |
TABLE 27
| | | | | |
|---|---|---|---|---|
| I-2-71 | 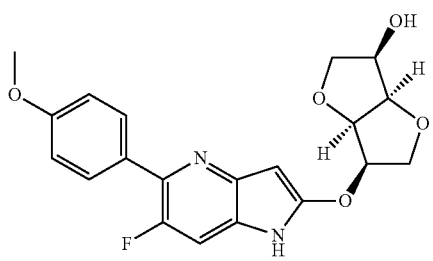 [SMILES: COc1ccc(-c2nc3cc(O[C@@H]4CO[C@H]5[C@@H]4OC[C@H]5O)[nH]c3cc2F)cc1] | 1.23 | 386.95 | C |
| I-2-72 | 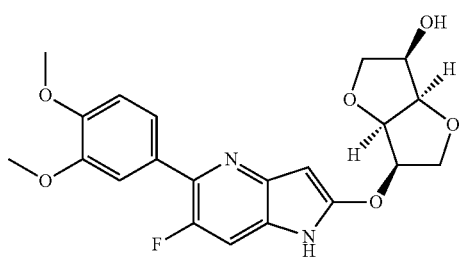 [SMILES: COc1ccc(-c2nc3cc(O[C@@H]4CO[C@H]5[C@@H]4OC[C@H]5O)[nH]c3cc2F)cc1OC] | 1.68 | 416.95 | C |

TABLE 27-continued
| | | | | |
|---|---|---|---|---|
| I-2-73 | 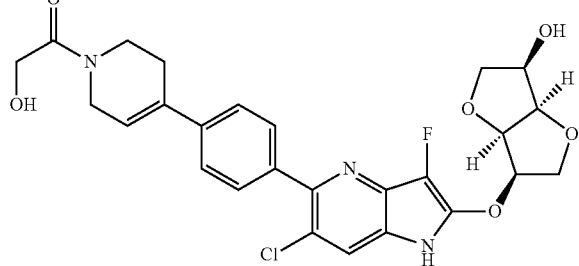 | 1.34 | 530.3 | B |
| I-2-74 | 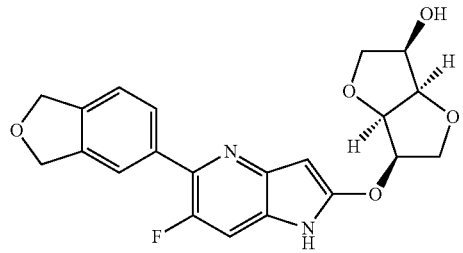 [SMILES: O[C@@H]1CO[C@H]2[C@@H]1OC[C@H]2Oc1cc2nc(-c3ccc4c(c3)COC4)c(F)cc2[nH]1] | 1.15 | 398.9 | C |
TABLE 28
| | | | | |
|---|---|---|---|---|
| I-2-75 | 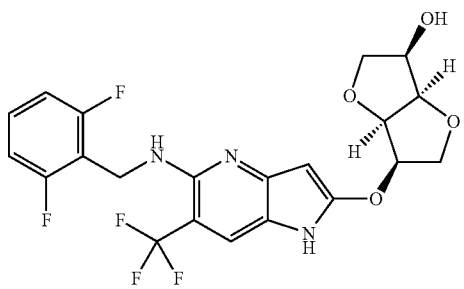 [SMILES: O[C@@H]1CO[C@H]2[C@@H]1OC[C@H]2Oc1cc2nc(NCc3c(F)cccc3F)c(C(F)(F)F)cc2[nH]1] | 1.51 | 472.15 | B |
| I-2-76 | 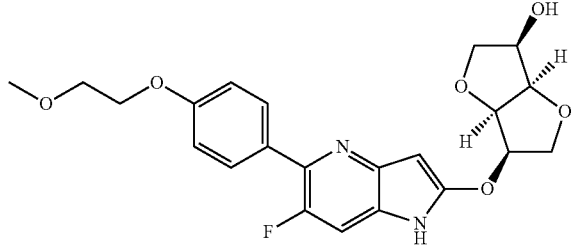 [SMILES: COCCOc1ccc(-c2nc3cc(O[C@@H]4CO[C@H]5[C@@H]4OC[C@H]5O)[nH]c3cc2F)cc1] | 1.24 | 431 | C |
| I-2-77 | 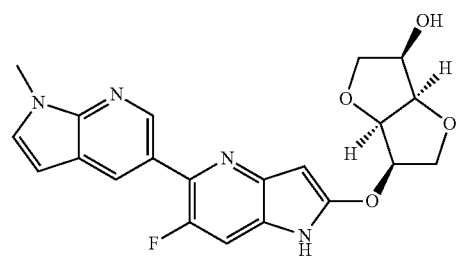 [SMILES: Cn1ccc2cc(-c3nc4cc(O[C@@H]5CO[C@H]6[C@@H]5OC[C@H]6O)[nH]c4cc3F)cnc21] | 1.20 | 411 | C |

TABLE 28-continued
| No. | Structure | retention time | Mass (M + H) | method |
|---|---|---|---|---|
| I-2-78 | 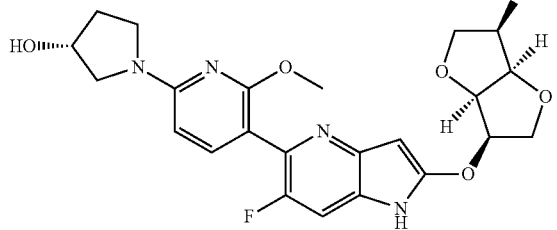 | 1.04 | 473.15 | B |
TABLE 29
| No. | Structure | retention time | Mass (M + H) | method |
|---|---|---|---|---|
| I-3-13 | 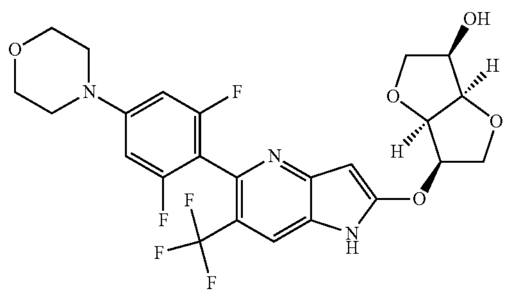 [SMILES: O[C@@H]1CO[C@H]2[C@@H]1OC[C@H]2Oc1cc2nc(-c3c(F)cc(N4CCOCC4)cc3F)c(C(F)(F)F)cc2[nH]1] | 1.51 | 528.35 | B |
| I-3-14 | 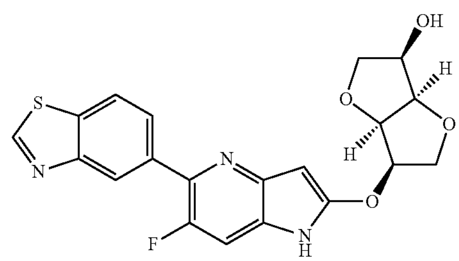 [SMILES: O[C@@H]1CO[C@H]2[C@@H]1OC[C@H]2Oc1cc2nc(-c3ccc4scnc4c3)c(F)cc2[nH]1] | 1.23 | 414 | C |
| I-3-15 | 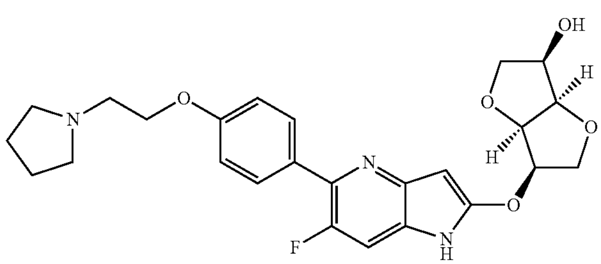 [SMILES: O[C@@H]1CO[C@H]2[C@@H]1OC[C@H]2Oc1cc2nc(-c3ccc(OCCN4CCCC4)cc3)c(F)cc2[nH]1] | 0.85 | 470 | C |
| I-3-16 | 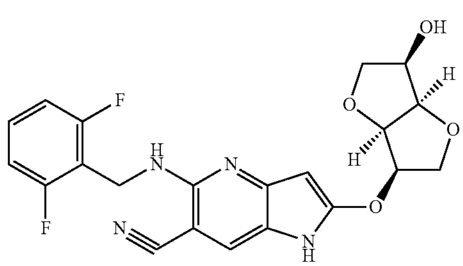 [SMILES: N#Cc1cc2[nH]c(O[C@@H]3CO[C@H]4[C@@H]3OC[C@H]4O)cc2nc1NCc1c(F)cccc1F] | 1.50 | 429 | C |

TABLE 29-continued

| No. | Structure | retention time | Mass (M + H) | method |
|---|---|---|---|---|
| I-3-17 | 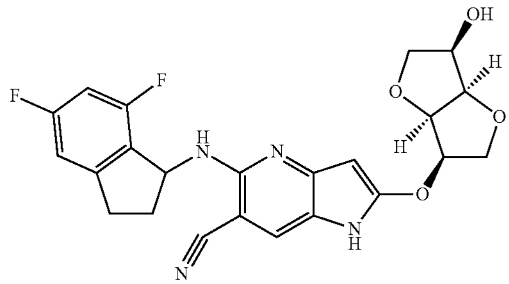 [SMILES: N#Cc1cc2[nH]c(O[C@@H]3CO[C@H]4[C@@H]3OC[C@H]4O)cc2nc1NC1CCc2cc(F)cc(F)c21] | 1.61 | 455.05 | C |

TABLE 30

| | | | | |
|---|---|---|---|---|
| I-3-18 | | 1.13 | 473.15 | B |
| I-3-19 | | 1.65 | 498.15 | B |
| I-3-20 | | 0.88 | 443.15 | B |
| I-3-21 | | 1.05 | 422.1 | B |
| I-3-22 | | 1.32 | 482.1 | C |

TABLE 31

| | | | | |
|---|---|---|---|---|
| I-3-23 | | 1.63 | 439 | C |
| I-3-24 | | 1.20 | 362.95 | C |
| I-3-25 | | 1.22 | 437.05 | C |
| I-3-26 | | 0.88 | 457.2 | B |
| I-3-27 | | 1.43 | 457.15 | B |

TABLE 32
| | | | | |
|---|---|---|---|---|
| I-3-28 | 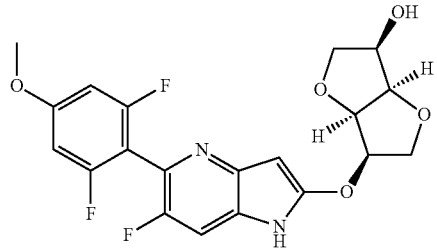 [SMILES: COc1cc(F)c(-c2nc3cc(O[C@@H]4CO[C@H]5[C@@H]4OC[C@H]5O)[nH]c3cc2F)c(F)c1] | 1.44 | 423 | C |
| I-3-29 | 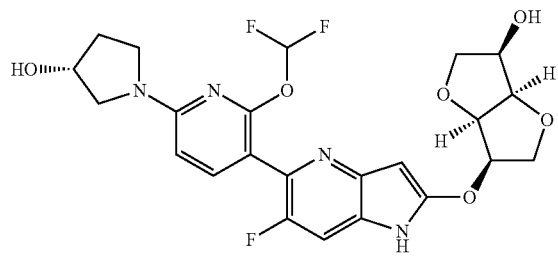 [SMILES: O[C@@H]1CCN(c2ccc(-c3nc4cc(O[C@@H]5CO[C@H]6[C@@H]5OC[C@H]6O)[nH]c4cc3F)c(OC(F)F)n2)C1] | 1.10 | 509.4 | B |
| I-3-30 | 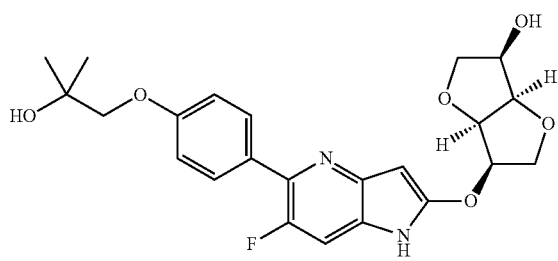 [SMILES: CC(C)(O)COc1ccc(-c2nc3cc(O[C@@H]4CO[C@H]5[C@@H]4OC[C@H]5O)[nH]c3cc2F)cc1] | 1.24 | 445.05 | C |
| I-3-31 | 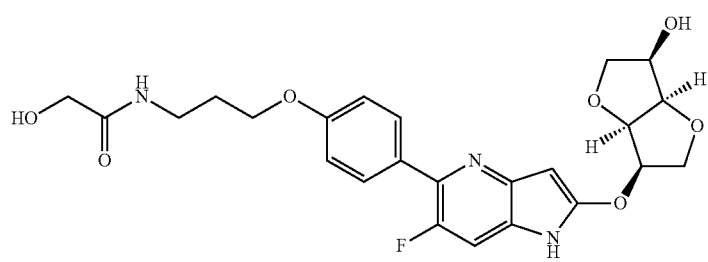 [SMILES: O=C(CO)NCCCOc1ccc(-c2nc3cc(O[C@@H]4CO[C@H]5[C@@H]4OC[C@H]5O)[nH]c3cc2F)cc1] | 1.09 | 448.05 | C |
| I-3-32 | 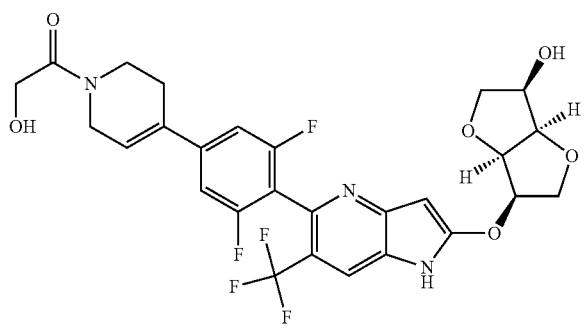 [SMILES: O=C(CO)N1CC=C(c2cc(F)c(-c3nc4cc(O[C@@H]5CO[C@H]6[C@@H]5OC[C@H]6O)[nH]c4cc3C(F)(F)F)c(F)c2)CC1] | 1.40 | 582.1 | B |

TABLE 33
| | | | | |
|---|---|---|---|---|
| I-3-33 | 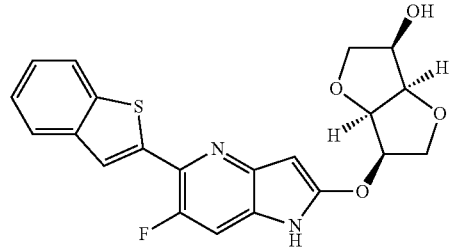 | 1.97 | 413 | C |
| I-3-34 | 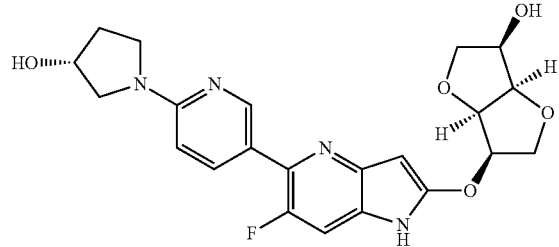 | 0.73 | 443.15 | B |
| I-3-35 | 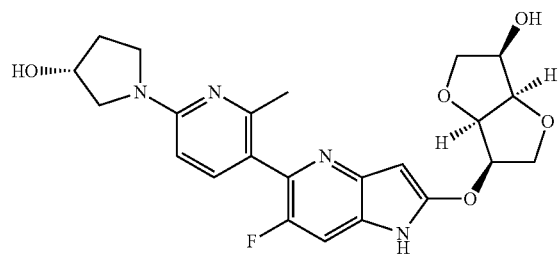 [SMILES: Cc1nc(N2CC[C@@H](O)C2)ccc1-c1nc2cc(O[C@@H]3CO[C@H]4[C@@H]3OC[C@H]4O)[nH]c2cc1F] | 0.66 | 457.15 | B |
| I-3-36 | 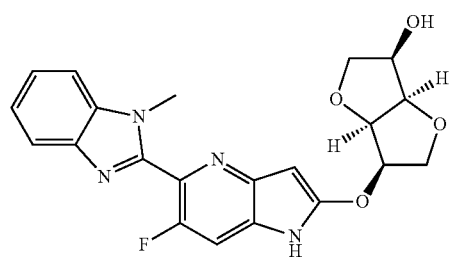 [SMILES: Cn1c(-c2nc3cc(O[C@@H]4CO[C@H]5[C@@H]4OC[C@H]5O)[nH]c3cc2F)nc2ccccc21] | 1.11 | 411 | C |
| I-3-37 | 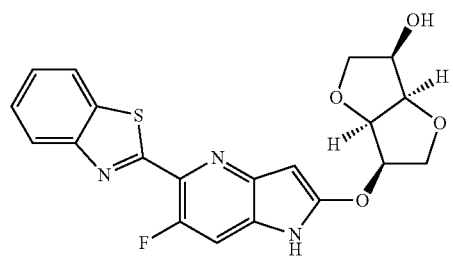 | 1.69 | 414 | C |

TABLE 34
| | | | | |
|---|---|---|---|---|
| I-3-38 | 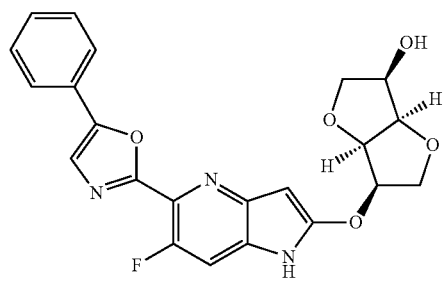 [SMILES: O[C@@H]1CO[C@H]2[C@@H]1OC[C@H]2Oc1cc2nc(-c3ncc(-c4ccccc4)o3)c(F)cc2[nH]1] | 1.63 | 424 | C |
| I-3-39 | 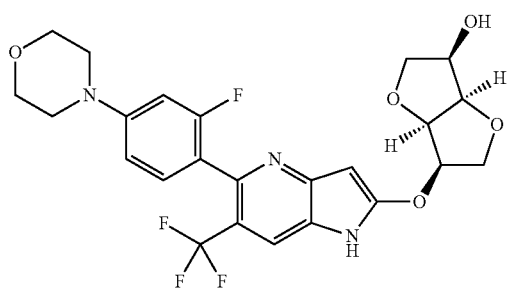 [SMILES: O[C@@H]1CO[C@H]2[C@@H]1OC[C@H]2Oc1cc2nc(-c3ccc(N4CCOCC4)cc3F)c(C(F)(F)F)cc2[nH]1] | 1.30 | 510.15 | B |
| I-3-40 | 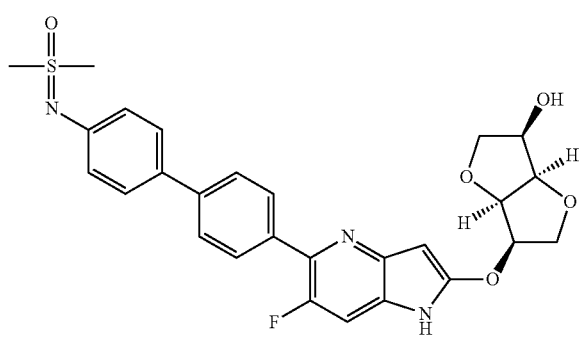 [SMILES: CS(C)(=O)=Nc1ccc(-c2ccc(-c3nc4cc(O[C@@H]5CO[C@H]6[C@@H]5OC[C@H]6O)[nH]c4cc3F)cc2)cc1] | 1.25 | 524.05 | C |
| I-3-41 | 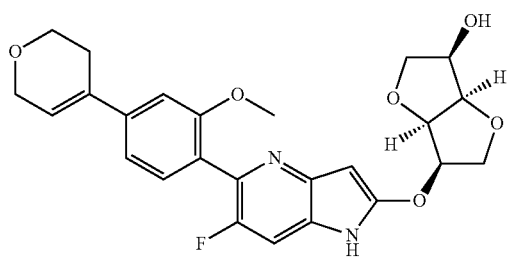 [SMILES: COc1cc(C2=CCOCC2)ccc1-c1nc2cc(O[C@@H]3CO[C@H]4[C@@H]3OC[C@H]4O)[nH]c2cc1F] | 1.16 | 469.2 | B |
| I-3-42 | 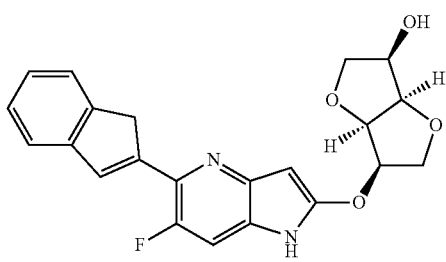 [SMILES: O[C@@H]1CO[C@H]2[C@@H]1OC[C@H]2Oc1cc2nc(C3=Cc4ccccc4C3)c(F)cc2[nH]1] | 1.47 | 395 | C |

TABLE 35

| No. | Structure | retention time | Mass (M + H) | method |
|---|---|---|---|---|
| I-3-43 | 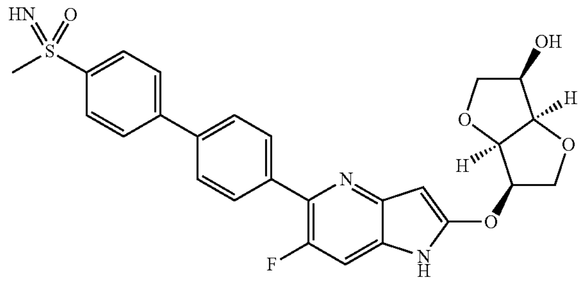 [SMILES: CS(=N)(=O)c1ccc(-c2ccc(-c3nc4cc(O[C@@H]5CO[C@H]6[C@@H]5OC[C@H]6O)[nH]c4cc3F)cc2)cc1] | 0.99 | 510.15 | B |
| I-3-44 | 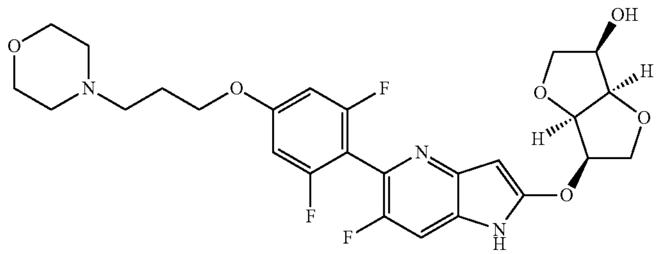 [SMILES: O[C@@H]1CO[C@H]2[C@@H]1OC[C@H]2Oc1cc2nc(-c3c(F)cc(OCCCN4CCOCC4)cc3F)c(F)cc2[nH]1] | 1.02 | 536.1 | C |

TABLE 36

| No. | Structure | retention time | Mass (M + H) | method |
|---|---|---|---|---|
| I-4-12 | 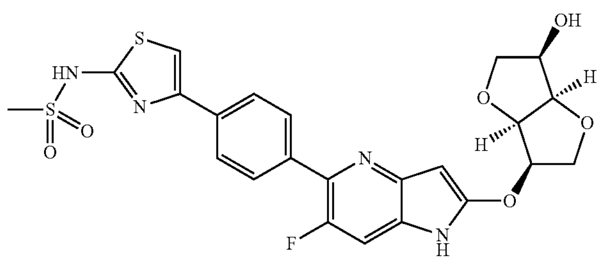 [SMILES: CS(=O)(=O)Nc1nc(-c2ccc(-c3nc4cc(O[C@@H]5CO[C@H]6[C@@H]5OC[C@H]6O)[nH]c4cc3F)cc2)cs1] | 1.19 | 533 | C |
| I-4-13 | 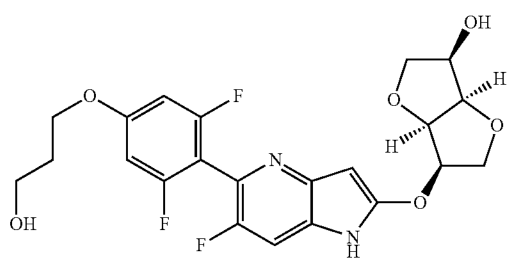 [SMILES: OCCCOc1cc(F)c(-c2nc3cc(O[C@@H]4CO[C@H]5[C@@H]4OC[C@H]5O)[nH]c3cc2F)c(F)c1] | 1.26 | 467.1 | C |
| I-4-14 | 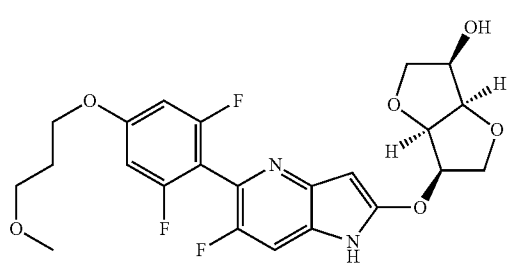 [SMILES: COCCCOc1cc(F)c(-c2nc3cc(O[C@@H]4CO[C@H]5[C@@H]4OC[C@H]5O)[nH]c3cc2F)c(F)c1] | 1.57 | 481.1 | C |

TABLE 36-continued

| No. | Structure | retention time | Mass (M + H) | method |
|---|---|---|---|---|
| I-4-15 | 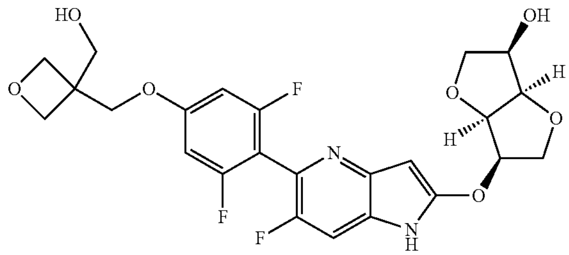 [SMILES: OCC1(COc2cc(F)c(-c3nc4cc(O[C@@H]5CO[C@H]6[C@@H]5OC[C@H]6O)[nH]c4cc3F)c(F)c2)COC1] | 1.21 | 509.1 | C |
| I-4-16 | 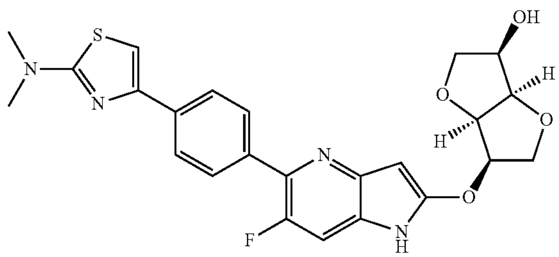 [SMILES: CN(C)c1nc(-c2ccc(-c3nc4cc(O[C@@H]5CO[C@H]6[C@@H]5OC[C@H]6O)[nH]c4cc3F)cc2)cs1] | 1.51 | 483.1 | C |

TABLE 37

| No. | Structure | retention time | Mass (M + H) | method |
|---|---|---|---|---|
| I-4-17 | 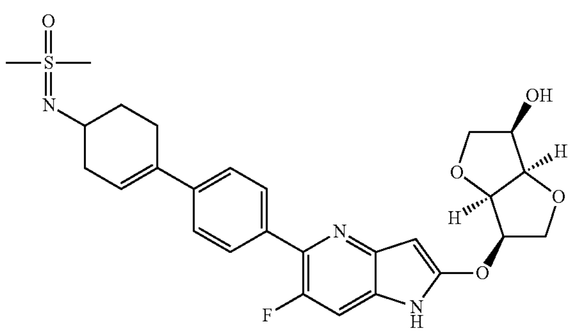 [SMILES: CS(C)(=O)=NC1CC=C(c2ccc(-c3nc4cc(O[C@@H]5CO[C@H]6[C@@H]5OC[C@H]6O)[nH]c4cc3F)cc2)CC1] | 1.11 | 528.1 | C |
| I-4-18 | 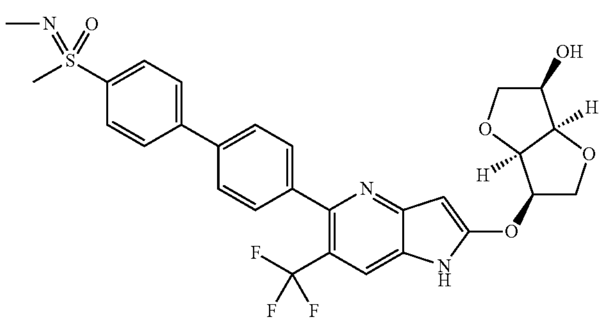 [SMILES: CN=S(C)(=O)c1ccc(-c2ccc(-c3nc4cc(O[C@@H]5CO[C@H]6[C@@H]5OC[C@H]6O)[nH]c4cc3C(F)(F)F)cc2)cc1] | 1.19 | 574.3 | B |
| I-4-19 | 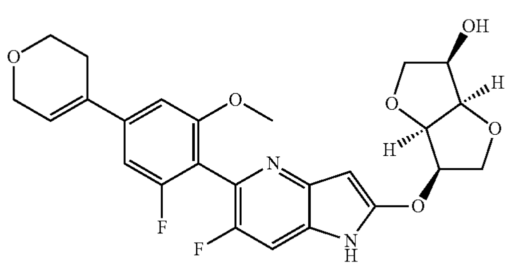 | 1.2 | 487.3 | B |

TABLE 37-continued
| | | | | |
|---|---|---|---|---|
| I-4-20 | 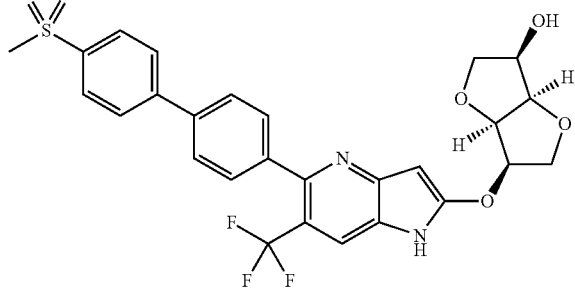 | 1.11 | 560.3 | B |
| I-4-21 | 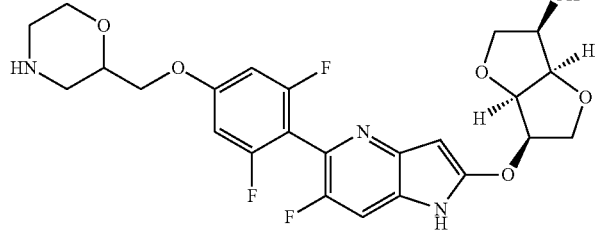 | 0.74 | 508 | B |
| I-4-22 | 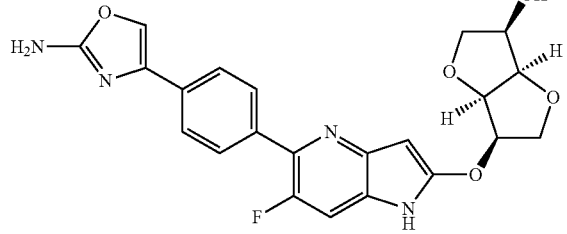 | 1.08 | 439.1 | C |
TABLE 38
| | | | | |
|---|---|---|---|---|
| I-4-23 | 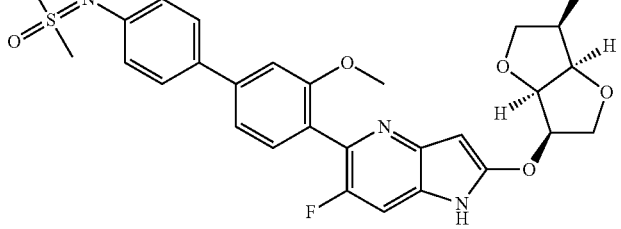 | 1.06 | 554.3 | B |
| I-4-24 | 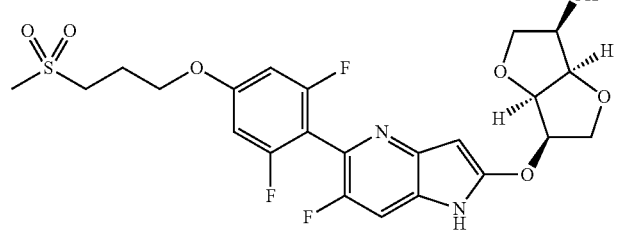 | 1.15 | 529 | A |

TABLE 38-continued

| ID | Structure | | | |
|---|---|---|---|---|
| I-4-25 | 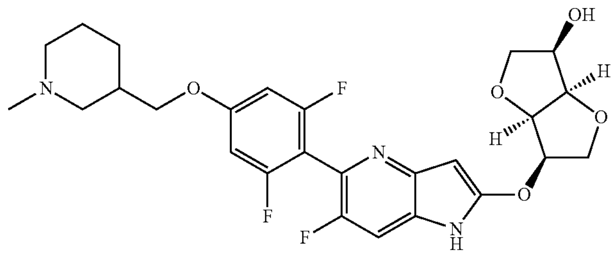 [SMILES: CN1CCCC(COc2cc(F)c(-c3nc4cc(O[C@@H]5CO[C@H]6[C@@H]5OC[C@H]6O)[nH]c4cc3F)c(F)c2)C1] | 0.91 | 520 | A |
| I-4-26 | 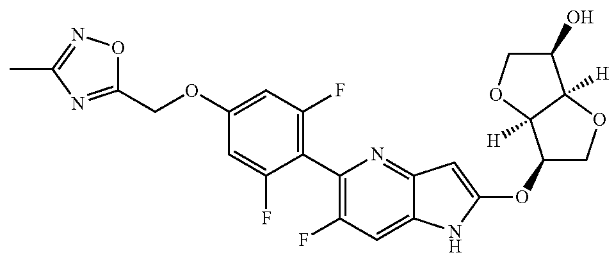 [SMILES: Cc1noc(COc2cc(F)c(-c3nc4cc(O[C@@H]5CO[C@H]6[C@@H]5OC[C@H]6O)[nH]c4cc3F)c(F)c2)n1] | 1.34 | 505 | A |
| I-4-27 | 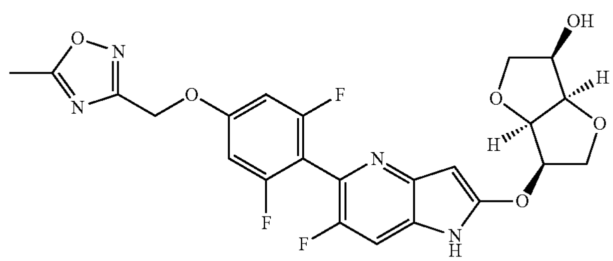 [SMILES: Cc1nc(COc2cc(F)c(-c3nc4cc(O[C@@H]5CO[C@H]6[C@@H]5OC[C@H]6O)[nH]c4cc3F)c(F)c2)no1] | 1.32 | 505 | A |
| I-4-28 | 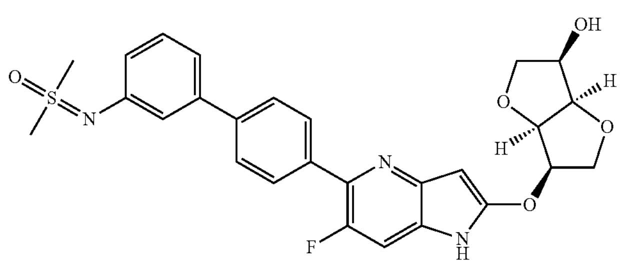 [SMILES: CS(C)(=O)=Nc1cccc(-c2ccc(-c3nc4cc(O[C@@H]5CO[C@H]6[C@@H]5OC[C@H]6O)[nH]c4cc3F)cc2)c1] | 1.29 | 524 | A |

TABLE 39

| ID | Structure | | | |
|---|---|---|---|---|
| I-4-29 | 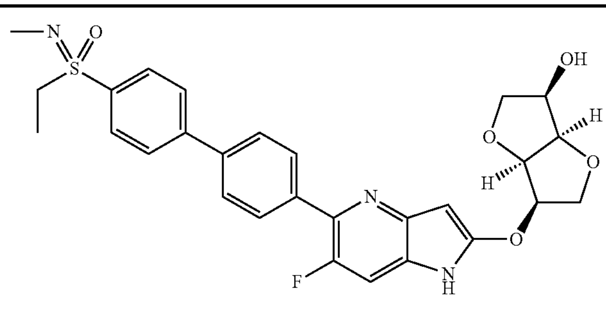 | 1.09 | 538.3 | B |

TABLE 39-continued

| | | | |
|---|---|---|---|
| I-4-30 | [structure] | 1.17 552.3 | B |
| I-4-31 | [structure] | 0.96 554.3 | B |
| I-4-32 | [structure] | 1.08 531.2 | B |
| I-4-33 | [structure] | 0.82 523.3 | B |
| I-4-34 | [structure] | 1.13 541.3 | B |

TABLE 40
| | | | | |
|---|---|---|---|---|
| I-4-35 | 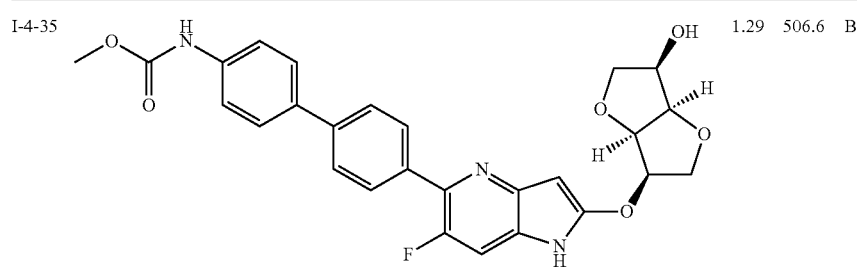 | 1.29 | 506.6 | B |
| I-4-36 | 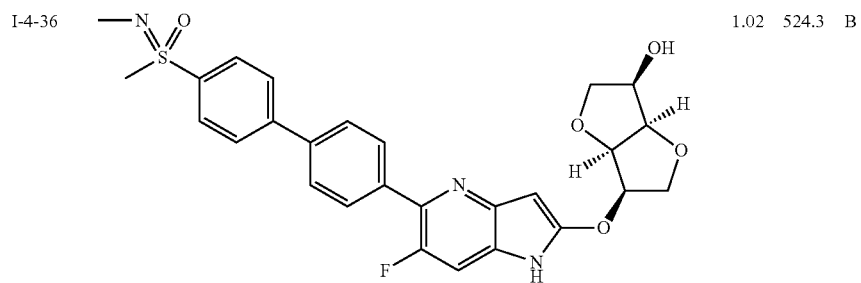 | 1.02 | 524.3 | B |
| I-4-37 | 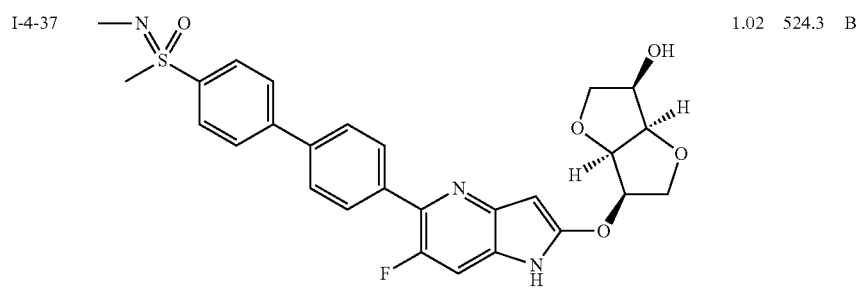 | 1.02 | 524.3 | B |
| I-4-38 | 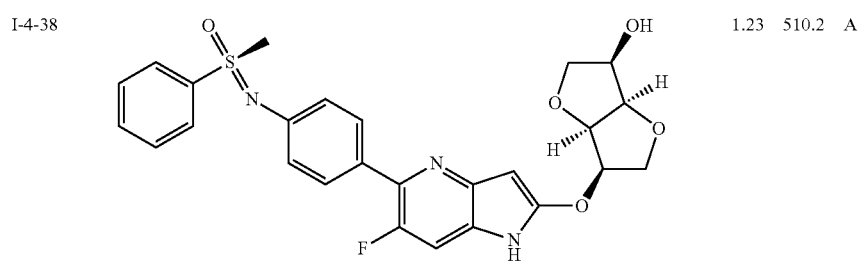 | 1.23 | 510.2 | A |
| I-4-39 | 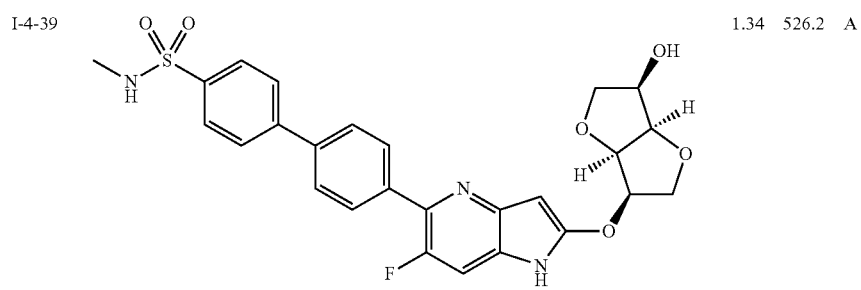 | 1.34 | 526.2 | A |

TABLE 40-continued
| | | | | |
|---|---|---|---|---|
| I-4-40 | 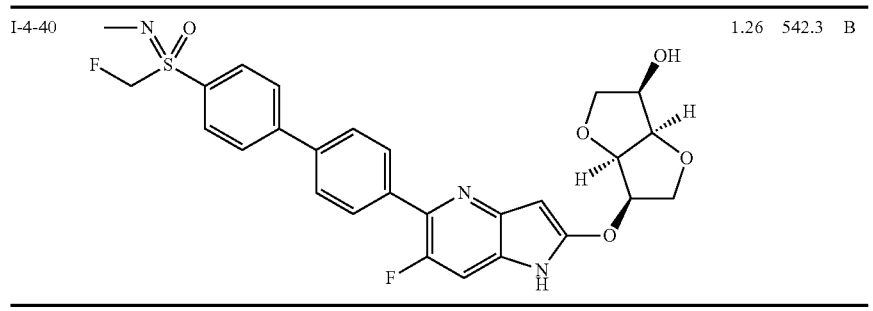 | 1.26 | 542.3 | B |
TABLE 41
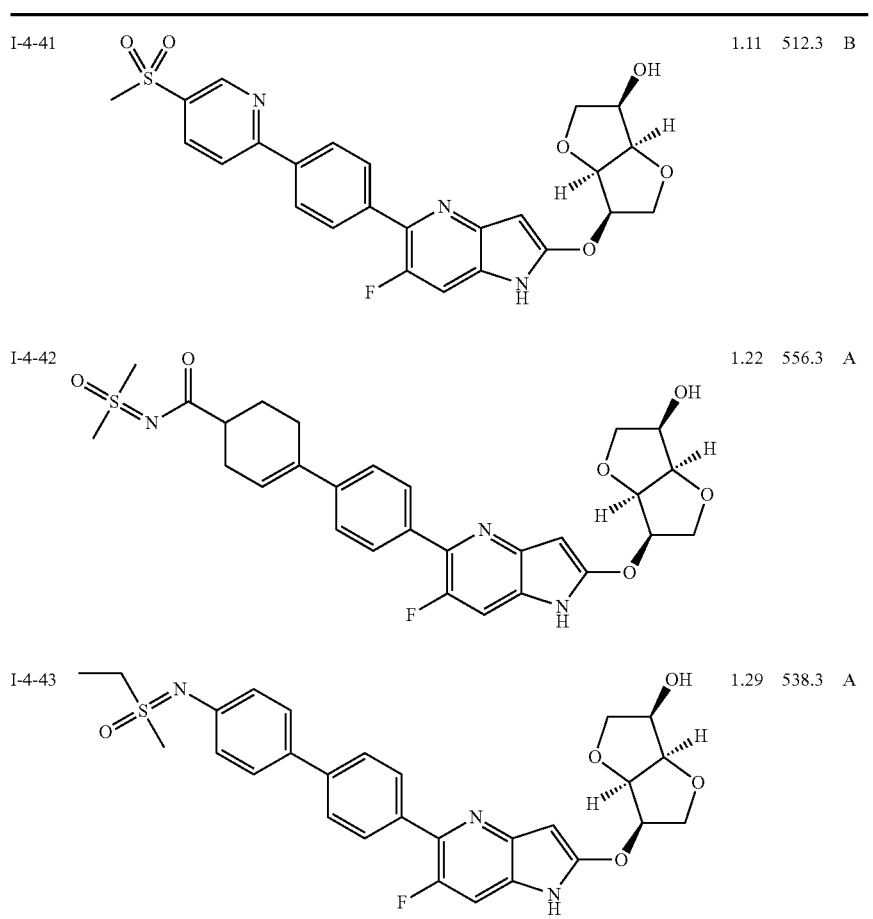
| | | | | |
|---|---|---|---|---|
| I-4-41 | | 1.11 | 512.3 | B |
| I-4-42 | | 1.22 | 556.3 | A |
| I-4-43 | | 1.29 | 538.3 | A |
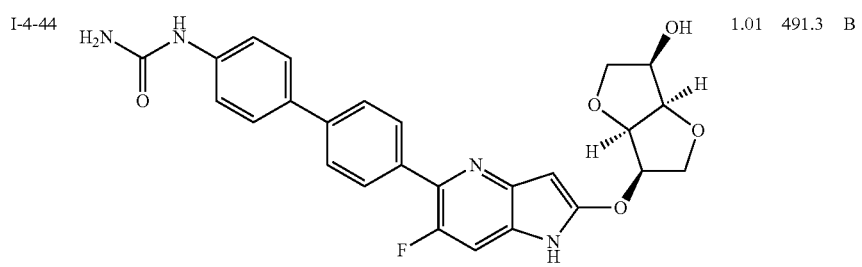
| | | | | |
|---|---|---|---|---|
| I-4-44 | | 1.01 | 491.3 | B |

TABLE 41-continued
| | | | | |
|---|---|---|---|---|
| I-4-45 | 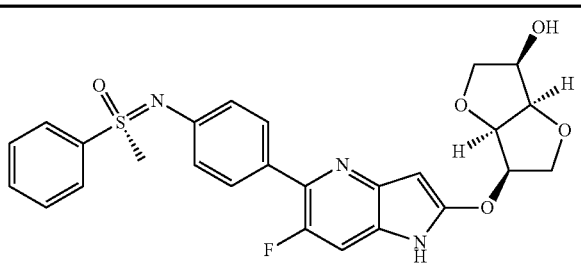 | 1.23 | 510.2 | A |
| I-4-46 | 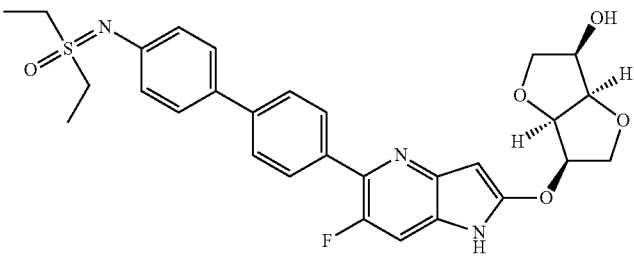 [SMILES: CCS(=O)(CC)=Nc1ccc(-c2ccc(-c3nc4cc(O[C@@H]5CO[C@H]6[C@@H]5OC[C@H]6O)[nH]c4cc3F)cc2)cc1] | 1.40 | 552.3 | A |
TABLE 42
| | | | | |
|---|---|---|---|---|
| I-4-47 | 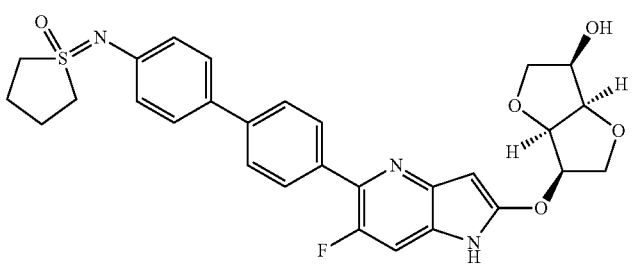 [SMILES: O=S1(=Nc2ccc(-c3ccc(-c4nc5cc(O[C@@H]6CO[C@H]7[C@@H]6OC[C@H]7O)[nH]c5cc4F)cc3)cc2)CCCC1] | 1.34 | 550.2 | A |
| I-4-48 | 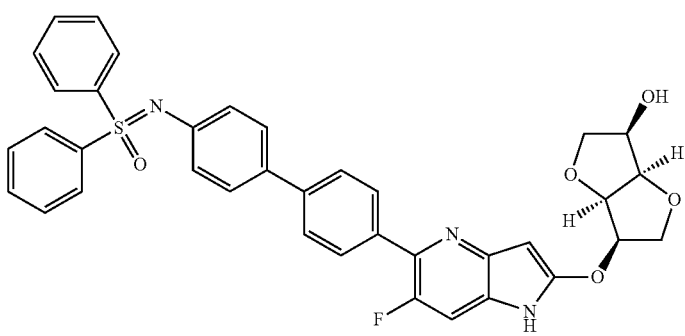 [SMILES: O=S(=Nc1ccc(-c2ccc(-c3nc4cc(O[C@@H]5CO[C@H]6[C@@H]5OC[C@H]6O)[nH]c4cc3F)cc2)cc1)(c1ccccc1)c1ccccc1] | 2.09 | 646.3 | A |
| I-4-49 | 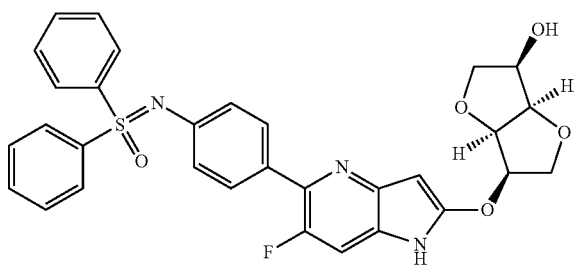 [SMILES: O=S(=Nc1ccc(-c2nc3cc(O[C@@H]4CO[C@H]5[C@@H]4OC[C@H]5O)[nH]c3cc2F)cc1)(c1ccccc1)c1ccccc1] | 1.77 | 572.2 | A |

TABLE 42-continued
| | | | | |
|---|---|---|---|---|
| I-4-50 | 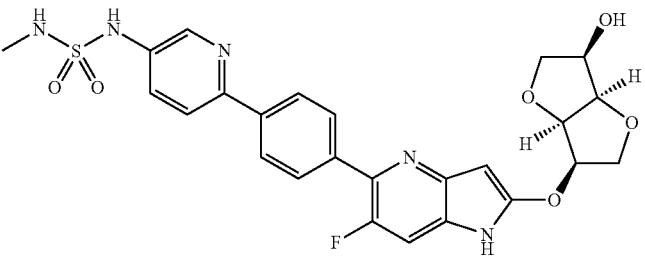 [SMILES: CNS(=O)(=O)Nc1ccc(-c2ccc(-c3nc4cc(O[C@@H]5CO[C@H]6[C@@H]5OC[C@H]6O)[nH]c4cc3F)cc2)nc1] | 1.09 | 542.2 | A |
| I-4-51 | 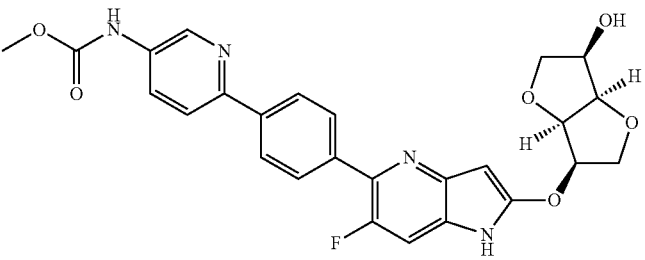 [SMILES: COC(=O)Nc1ccc(-c2ccc(-c3nc4cc(O[C@@H]5CO[C@H]6[C@@H]5OC[C@H]6O)[nH]c4cc3F)cc2)nc1] | 1.19 | 507.2 | A |
| I-4-52 | 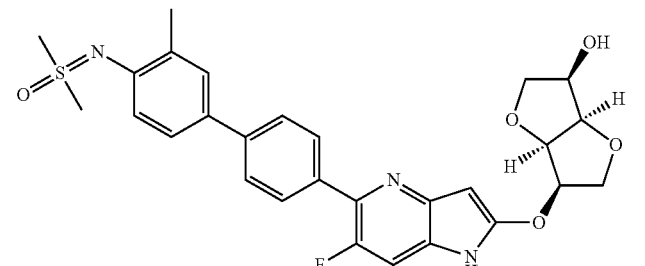 | 1.31 | 538.2 | A |
TABLE 43
| | | | | |
|---|---|---|---|---|
| I-4-53 | 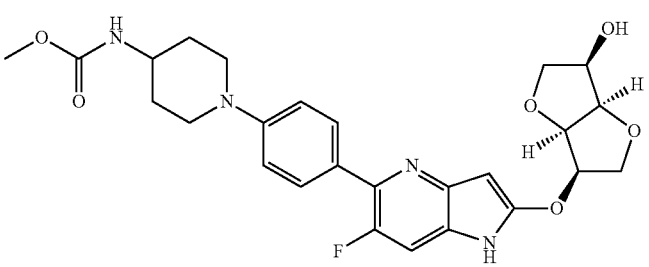 [SMILES: COC(=O)NC1CCN(c2ccc(-c3nc4cc(O[C@@H]5CO[C@H]6[C@@H]5OC[C@H]6O)[nH]c4cc3F)cc2)CC1] | 1.07 | 513.4 | B |
| I-4-54 | 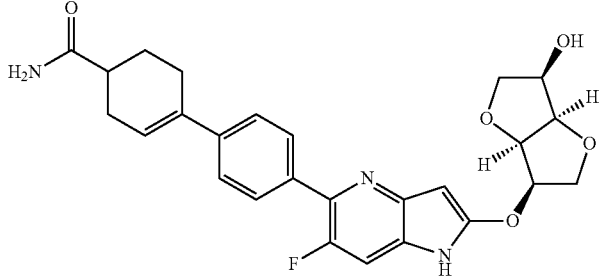 [SMILES: NC(=O)C1CC=C(c2ccc(-c3nc4cc(O[C@@H]5CO[C@H]6[C@@H]5OC[C@H]6O)[nH]c4cc3F)cc2)CC1] | 0.99 | 480.3 | B |

TABLE 43-continued

| ID | Structure | Col3 | Col4 | Col5 |
|---|---|---|---|---|
| I-4-55 | 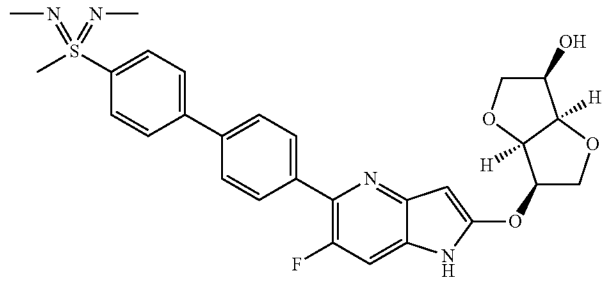 [SMILES: CN=S(C)(=NC)c1ccc(-c2ccc(-c3nc4cc(O[C@@H]5CO[C@H]6[C@@H]5OC[C@H]6O)[nH]c4cc3F)cc2)cc1] | 0.94 | 537.6 | B |
| I-4-56 | 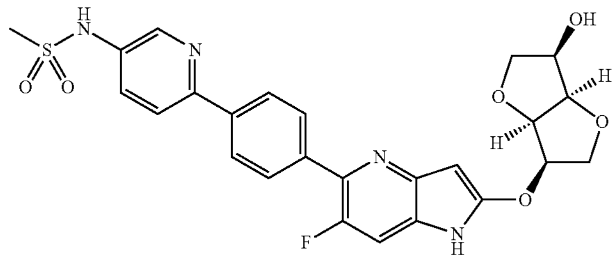 [SMILES: CS(=O)(=O)Nc1ccc(-c2ccc(-c3nc4cc(O[C@@H]5CO[C@H]6[C@@H]5OC[C@H]6O)[nH]c4cc3F)cc2)nc1] | 1.14 | 527.2 | A |
| I-4-57 | 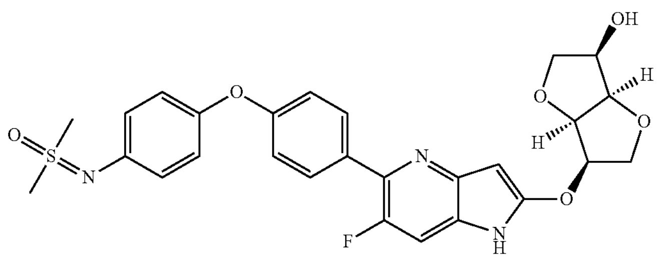 [SMILES: CS(C)(=O)=Nc1ccc(Oc2ccc(-c3nc4cc(O[C@@H]5CO[C@H]6[C@@H]5OC[C@H]6O)[nH]c4cc3F)cc2)cc1] | 1.26 | 540.2 | A |
| I-4-58 | 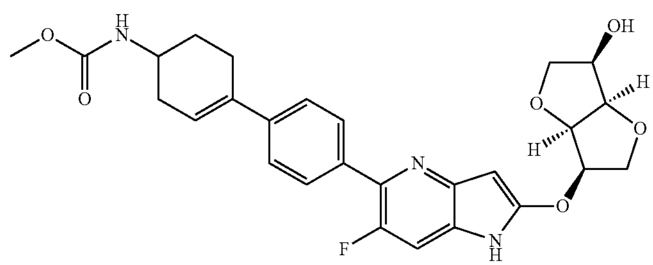 [SMILES: COC(=O)NC1CC=C(c2ccc(-c3nc4cc(O[C@@H]5CO[C@H]6[C@@H]5OC[C@H]6O)[nH]c4cc3F)cc2)CC1] | 1.39 | 510.3 | A |

Evaluation Method of an Activator for AMP-Activated Protein Kinase (AMPK)

Test Example 1

To a buffer solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl tetraacetic acid (EGTA), 5 mM disodium β-glycerophosphate and 2 mM dithiothreitol, a human AMPK α1β1γ1 enzyme (manufactured by Carna Biosciences, Inc.) was added in an amount to give a conversion rate of approximately 10% by reaction for 2 hours, and a compound dissolved in DMSO was added thereto so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophosphate, 2 mM dithiothreitol, 0.4 mM ATP and 3 μM FL-Peptide 7 (manufactured by Caliper Life Sciences, Inc.) was added in equal amount (10 μl in total). The obtained liquid was allowed to react at 25° C. for 2 hours, and 10 μl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

Preparation Method of Human AMPK α2β2γ1

The full length cDNAs of human AMPK β2 (NM_005399.3) and human AMPK α2 (NM_006252.3) were inserted into the MCS1 and MCS2 of the pETDuet-1 vector to prepare a human AMPK β2 and human AMPK α2 (6× His tag at the 5' terminus) expressing plasmid. The plasmid was cotransfected with an expression plasmid, in which the full length cDNA of human AMPK γ1 (NM_002733.3) had been inserted into pET28b(+), into BL21 CodonPlus (DE3)-RTL to obtain an expression strain. The expression strain was cultured in TB medium, followed by induction with 0.5 mM IPTG, and cultured at 25° C. for 3 hours and then harvested. After ultrasonication, supernatant was collected and applied to Histrap FF column (GE) and RESOUECE Q column (GE) to prepare 12.5 mg of purified sample containing three types of subunit from 1.8 L of broth.

Preparation Method of Human CaMKK2 Used to Impart Activity to AMPK

An expression vector, in which the full length cDNA of human CAMKK β (NM_172226.1) had been inserted into pGEX-6P-3, was transfected into BL21 Star (DE3). The expression strain was cultured in TB medium, followed by induction with 0.5 mM IPTG, and cultured at 25° C. for 3 hours and then harvested. After ultrasonication, supernatant was collected and applied to GSTrap FF column (GE) to prepare 14 mg of GST-fused CAMKK β from 720 ml of broth.

Evaluation Method of an Activator for AMP-Activated Protein Kinase (AMPK)

Test Example 2

Human AMPK α2β2γ1 prepared in *Escherichia coli* was not phosphorylated and did not exhibit activity. Thus, phosphorylation treatment was carried out as pretreatment.

Human AMPK α2β2γ1 in an amount to give a conversion rate of approximately 10% by reaction for 2 hours, and CaMKK2 in an amount capable of sufficiently imparting activity to AMPK for one hour were mixed in a buffer solution consisting of a 50 mM HEPES-NaOH buffer solution (pH 7.0), 100 mM NaCl, 5 mM magnesium chloride, 0.1% bovine serum albumin, 0.2 mM sodium orthovanadate (V), 1 mM ethylene glycol-bis(2-aminoethyl ether)-N,N,N',N'-tetraacetic acid (EGTA), 5 mM disodium β-glycerophosphate, 1 mM dithiothreitol and 0.2 mM ATP, and the obtained liquid was left to stand at 25° C. for 1 to 1.5 hours to sufficiently phosphorylate AMPK.

After that, to the enzyme liquid, which had been subjected to phosphorylation treatment, a compound dissolved in DMSO was added so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophosphate, 2 mM dithiothreitol, 0.4 mM ATP and 3 μM FL-Peptide 7 (manufactured by Caliper Life Sciences, Inc.) was added in equal amount (10 μl in total). The obtained liquid was allowed to react at 25° C. for 2 hours, and 10 μl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement, range was used as Emax.

The results of Test Example 2 are shown below.
Compound (I-1-1); EC150=330 nM, Emax=660%
Compound (I-1-4); EC150=8.3 nM, Emax=849%
Compound (I-1-6); EC150=2 nM, Emax=647%
Compound (I-1-7); EC150=59 nM, Emax=805%
Compound (I-1-8); EC150=4.1 nM, Emax=338%
Compound (I-1-10); EC150=1.8 nM, Emax=751%
Compound (I-1-11); EC150=3.9 nM, Emax=770%
Compound (I-1-12); EC150=23 nM, Emax=779%
Compound (I-1-15); EC150=53 nM, Emax=680%
Compound (I-1-16); EC150=810 nM, Emax=204%
Compound (I-1-18): EC150=22 nM, Emax=776%
Compound (I-1-20); EC150=2.9 nM, Emax=746%
Compound (I-1-23); EC150=11 nM, Emax=341%
Compound (I-1-25): EC150=11 nM, Emax=768%
Compound (I-1-37); EC150=6 nM, Emax=859%
Compound (I-1-38); EC150=1.5 nM, Emax=841%
Compound (I-1-39); EC150=5.3 nM, Emax=788%
Compound (I-1-43); EC150=98 nM, Emax=302%
Compound (I-1-45); EC150=13 nM, Emax=718%
Compound (I-1-50): EC150=2.4 nM, Emax=827%
Compound (I-1-55): EC150=54 nM, Emax=689%
Compound (I-1-58): EC150=3.8 nM, Emax=836%
Compound (I-1-62): EC150=5.7 nM, Emax=851%
Compound (I-1-63): EC150=6.3 nM, Emax=791%
Compound (I-2-2): EC150=38 nM, Emax=511%
Compound (I-2-3): EC150=6.9 nM, Emax=508%
Compound (I-2-6): EC150=3.7 nM, Emax=578%
Compound (I-2-7): EC150=36 nM, Emax=322%
Compound (I-2-8): EC150=8.9 nM, Emax=447%
Compound (I-2-9): EC150=66 nM, Emax=395%
Compound (I-2-10): EC150=49 nM, Emax=506%
Compound (I-2-11): EC150=40 nM, Emax=867%
Compound (I-2-19): EC150=1.6 nM, Emax=916%
Compound (I-2-28): EC150=57 nM, Emax=446%
Compound (I-2-33): EC150=2.5 nM, Emax=511%
Compound (I-2-34): EC150=20 nM, Emax=495%
Compound (I-2-42): EC150=48 nM, Emax=481%
Compound (I-2-45): EC150=19 nM, Emax=492%
Compound (I-2-46): EC150=77 nM, Emax=510%
Compound (I-2-57): EC150=10 nM, Emax=484%
Compound (I-2-61-a): EC150=6.4 nM, Emax=442%
Compound (I-2-61-b): EC150=6.4 nM, Emax=442%
Compound (I-2-68): EC150=26 nM, Emax=382%
Compound (I-2-69): EC150=58 nM, Emax=521%
Compound (I-2-70): EC150=38 nM, Emax=511%
Compound (I-2-71): EC150=89 nM, Emax=446%
Compound (I-2-78): EC150=7.1 nM, Emax=490%
Compound (I-3-4): EC150=30 nM, Emax=568%

Compound (I-3-6): EC150=74 nM, Emax=475%
Compound (I-3-10): EC150=7.9 nM, Emax=391%
Compound (I-3-12): EC150=4.2 nM, Emax=396%
Compound (I-3-14): EC150=150 nM, Emax=430%
Compound (I-3-17): EC150=40 nM, Emax=492%
Compound (I-3-19): EC150=120 nM, Emax=543%
Compound (I-3-23): EC150=5 nM, Emax=510%
Compound (I-3-24): EC150=340 nM, Emax=315%
Compound (I-3-25): EC150=6.6 nM, Emax=493%
Compound (I-3-27): EC150=12 nM, Emax=633%
Compound (I-3-28): EC150=87 nM, Emax=430%
Compound (I-3-31): EC150=55 nM, Emax=505%
Compound (I-3-39): EC150=200 nM, Emax=491%
Compound (I-3-40): EC150=0.91 nM, Emax=491%
Compound (I-3-41): EC150=31 nM, Emax=500%
Compound (I-3-43): EC150=0.84 nM, Emax=538%
Compound (I-4-1): EC150=1.4 nM, Emax=496%
Compound (I-4-5): EC150=3.2 nM, Emax=510%
Compound (I-4-6): EC150=1.1 nM, Emax=464%
Compound (I-4-8): EC150=1.8 nM, Emax=577%
Compound (I-4-10): EC150=21 nM, Emax=428%
Compound (I-4-11): EC150=3.5 nM, Emax=440%
Compound (I-4-17): EC150=2.9 nM, Emax=511%
Compound (I-4-18): EC150=9.5 nM, Emax=598%
Compound (I-4-31): EC150=3.1 nM, Emax=674%
Compound (I-4-34): EC150=4 nM, Emax=431%
Compound (I-4-35): EC150=10 nM, Emax=447%
Compound (I-4-36): EC150=2.3 nM, Emax=510%
Compound (I-4-37): EC150=1.5 nM, Emax=502%
Compound (I-4-39): EC150=1.9 nM, Emax=479%
Compound (I-4-41): EC150=1.4 nM, Emax=441%
Compound (I-4-43): EC150=1.3 nM, Emax=453%
Compound (I-4-44): EC150=1.6 nM, Emax=518%
Compound (I-4-53): EC150=10 nM, Emax=509%
Compound (I-4-56): EC150=5.8 nM, Emax=396%
Compound (I-4-58): EC150=4.3 nM, Emax=486%

The compounds of the present invention have an excellent activating effect on an AMPK α1 trimer and/or an AMPK α2 trimer.

Usefulness as a medicament can be examined by the following tests, etc. CYP3A4 fluorescent MBI test The CYP3A4 fluorescent MBI test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylcoumarin (7-BFC) is debenzylated by the CYP3A4 enzyme to produce a metabolite, 7-hydroxytrifluoromethylcoumarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (enzyme expressed in *Escherichia coli*), at pre-reaction 62.5 pmol/mL, at reaction 6.25 pmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted with a substrate and a K-Pi buffer, NADPH as a coenzyme was added to initiate a reaction as an index (without pre-reaction) and, after a predetermined time of a reaction, acetonitrile/0.5 mol/L Tris (trishydroxyaminomethane)=4/1 was added to stop the reaction. In addition, NADPH was added to a remaining pre-reaction solution to initiate a pre-reaction (with pre-reaction) and, after a pre-determined time of a pre-reaction, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate. When a difference between $IC_{50}$ values is 5 μM or more, this was defined as (+) and, when the difference is 3 μM or less, this was defined as (−).

CVP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenadine (CYP3A4) reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, or a test drug in 50 mM Hepes buffer as a reaction solution was added to a 96-well plate at the composition as described above, NADPH, as a coenzyme was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the centrifuge supernatant was quantified by a fluorescent multilabel counter and tolbutamide hydroxide (CYP2C9 metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

FAT Test

Each 20 μL of freeze-stored *Salmonella typhimurium* (strains TA98 and TA100) is inoculated in 10 mL of liquid nutrient medium (2.5% Oxoid nutrient broth No. 2), and the cultures are preincubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), and the suspension is added to 110 mL of Exposure medium (Micro F buffer containing Biotin:

8 µg/mL, histidine: 0.2 µg/mL, glucose: 8 mg/mL). 3.16 mL of TA100 culture is added to 120 mL of Exposure medium to prepare the test bacterial solution. 588 µL of the test bacterial solution (or mixed solution of 498 µL of the test bacterial solution and 90 µL of the S9 mix in the case with metabolic activation conditions) is mixed with each 12 µL of the following solution: DMSO solution of the test substance (eight dose levels from maximum dose 50 mg/mL at 2-fold ratio); DMSO as negative control; 50 µg/mL of 4-nitroquinoline-1-oxide DMSO solution as positive control for strain TA98 without metabolic activation conditions; 0.25 µg/mL of 2-(2-furyl)-3-(5-nitro-2-furyl)acrylamide DMSO solution as positive control for strain TA100 without metabolic activation conditions; 40 µg/mL of 2-aminoanthracene DMSO solution as positive control for strain TA98 with metabolic activation conditions; or 20 µg/mL of 2-aminoanthracene DMSO solution as positive control for strain TA100 with metabolic activation conditions. 12 µL of the solution and 588 µL of the test bacterial solution (a mixed solution of 498 µL of the test bacterial solution and 90 µL of S9 mix with metabolic activation conditions) are mixed and incubated at 37° C. under shaking for 90 minutes. 460 µL of the culture exposed to the test substance is mixed with 2300 µL of Indicator medium (Micro F buffer containing biotin: 8 µg/mL, histidine: 0.2 µg/mL, glucose: 8 mg/mL, Bromo Cresol Purple: 37.5 µg/mL), each 50 µL is dispensed into 48 wells per dose in the microwell plates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. Then, the number of the yellow wells among the 48 total wells per dose is counted to evaluate the mutagenicity by comparing with the negative control group.

Solubility Test

The solubility of a compound was determined under a condition in which 1% DMSO was added. 10 mM compound solution was prepared using DMSO, and then 6 µL of the compound solution was added to 594 µL of artificial intestinal juice in pH 6.8 (to 250 mL of a 0.2 mol/L potassium dihydrogen phosphate reagent solution were added 118 mL of a 0.2 mol/L NaOH reagent solution and water to provide a final volume of 1000 mL). After standing at 25° C. for 16 hours, the mixed solution was filtrated with suction. The filtrate was diluted twice with methanol/water (1/1), and then a concentration in the filtration was measured with HPLC or LC/MS/MS by the absolute calibration method.

Metabolic Stability Test

Using commercially available pooled human hepatic microsomes, an object compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), and the mixture was mixed and centrifuged at 3000 rpm for 15 minutes. The test compound in the centrifuge supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier $K^+$ current ($I_{Kr}$), which plays an important role in the ventricular repolarization process, is studied using HEK293 cells expressing human ether-a-go-go related gene (hERG) channel.

After a cell is retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds is recorded. After the generated current is stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test compound has been dissolved at an objective concentration is applied to the cell under the room temperature condition for 10 minutes. From the recording $I_{Kr}$, an absolute value of the tail peak current is measured based on the current value at the resting membrane potential using an analysis software (DataXpress ver. 1, Molecular Devices Corporation). Further, the % inhibition relative to the tail peak current before application of the test substance is calculated, and compared with the vehicle-applied group (0.1% dimethyl sulfoxide solution) to assess influence of the test substance on $I_{Kr}$.

Powder Solubility Test

Appropriate amounts of the test substances are put into appropriate containers. To the respective containers are added 200 µL of JP-1 fluid (sodium chloride 2.0 g, hydrochloric acid 7.0 mL and water to reach 1000 mL), 200 µL of JP-2 fluid (phosphate buffer (pH 6.8) 500 mL and water 500 mL), and 200 µL of 20 mmol/L TCA (sodium taurocholate)/JP-2 fluid (TCA 1.08 g and water to reach 100 mL). In the case that the test liquid is dissolved after the addition of the test fluid, the bulk powder is added as appropriate. The containers are sealed, and shaken for 1 hour at 37° C. The mixtures are filtered, and 100 µL of methanol is added to each of the filtrate (100 µL) so that the filtrates are two-fold diluted. The dilution ratio is changed if necessary. After confirmation of no bubbles and precipitates, the containers are sealed and shaken. Quantification is performed by HPLC with an absolute calibration method.

BA Test

Materials and Methods for Studies on Oral Absorption
(1) Animals: mice or rats
(2) Animal husbandry: Mice and rats had free access to solid food and sterilized bottled tap water.
(3) Setting of Dose and group compositions: orally or intravenously administered at a predetermined dose; Group compositions were as shown below (Dose depends on the compound)
   Oral: 1 to 30 mg/kg (n=2 to 3)
   Intravenous: 0.5 to 10 mg/kg (n=2 to 3)
(4) Preparation for dosing formulation: for oral administration, in a solution or a suspension state; for intravenous administration, in a solubilized state
(5) Dosing procedure: In oral administration study, the test substance was forcibly administered to the stomach of rats by using a gavage tube. In intravenous administration study, the test substance was administered to rats via tail vein using a syringe with a needle.

(6) Evaluation items: Blood was collected at each time point, and plasma concentration of the drug was determined by LC/MS/MS.
(7) Data analysis: Regarding the transition of the plasma concentration, area under the plasma concentration-time curve (AUC) was calculated by means of WinNonlin® program, respectively. Bioavailability (BA) was calculated from AUCs of the oral administration group and intravenous administration group.

Formulation Examples are shown below.

Formulation Example 1

Tablets

The compound of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2

Capsules

The compound of the present invention, lactose and calcium stearate are mixed uniformly to obtain powder medicines in the form of powders or fine granules. The powder medicines are filled into capsule containers to give capsules.

Formulation Example 3

Granules

The compound of the present invention, lactose and calcium stearate are mixed uniformly and the mixture is compressed and molded. Then, it is crushed, granulated and sieved to give suitable sizes of granules.

Formulation Example 4

Orally Disintegrating Tablets

The compound of the present invention and crystalline cellulose are mixed and granulated, then tableted to give orally disintegrating tablets.

Formulation Example 5

Dry Syrups

The compound of the present invention and lactose are mixed, crushed, granulated and sieved to give suitable sizes of dry syrups.

Formulation Example 6

Injections

The compound of the present invention and phosphate buffer are mixed to give injection.

Formulation Example 7

Infusions

The compound of the present invention and phosphate buffer are mixed to give injection.

Formulation Example 8

Inhalations

The compound of the present invention and lactose are mixed and crushed finely to give inhalations.

Formulation Example 9

Ointments

The compound of the present invention and petrolatum are mixed to give ointments.

Formulation Example 10

Patches

The compound of the present invention and base such as adhesive plaster or the like are mixed to give patches.

INDUSTRIAL APPLICABILITY

As is apparent from the above test examples, the compounds of the present invention show an AMPK activating effect. Therefore, the compounds of the present invention are very useful as a therapeutic agent for type II diabetes, hyperglycemia, metabolic syndrome, obesity, hypercholesterolemia and hypertension.

The invention claimed is:
1. A compound represented by formula (I),

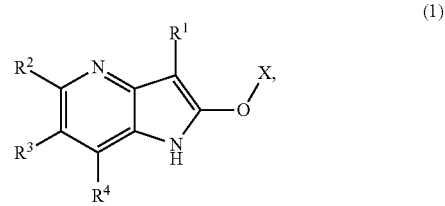

or a pharmaceutically acceptable salt thereof,
wherein
X is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;
$R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl;
$R^2$ is halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^3$ is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^4$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that excluded are

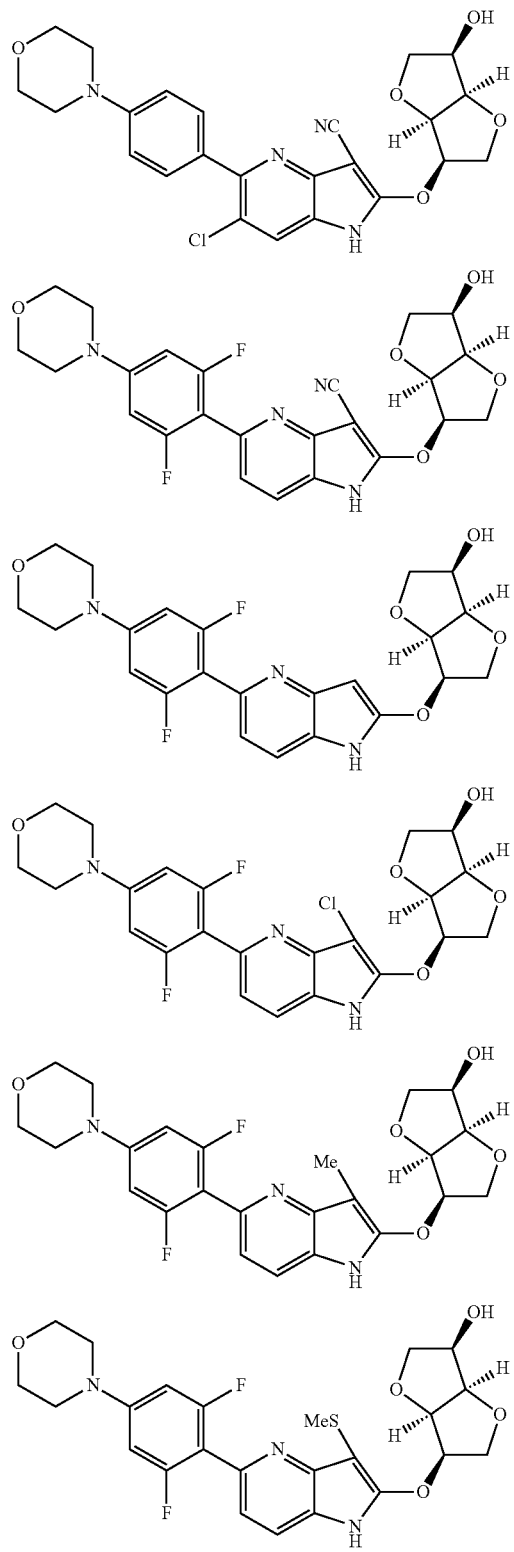

317
-continued
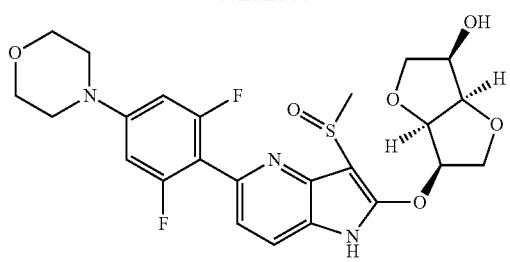
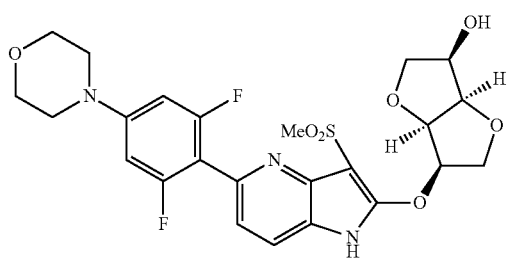
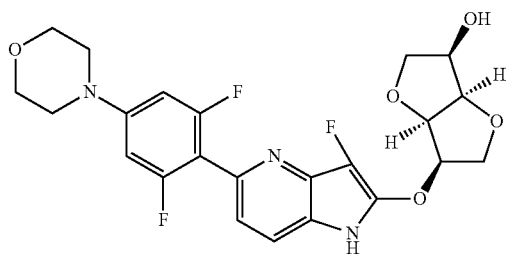
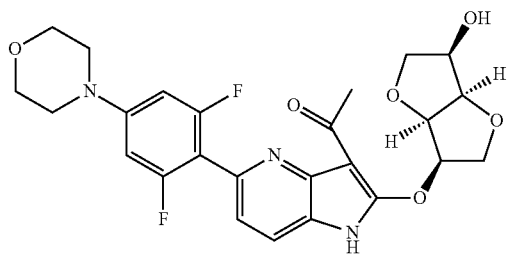
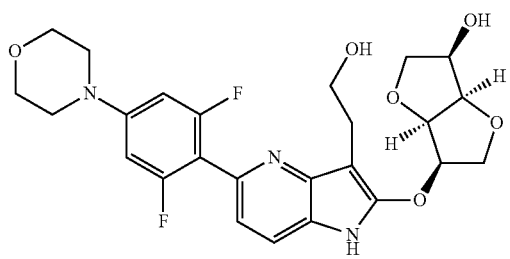
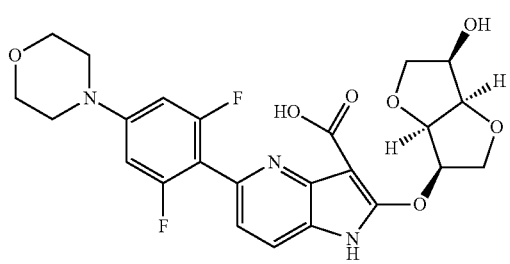
318
-continued
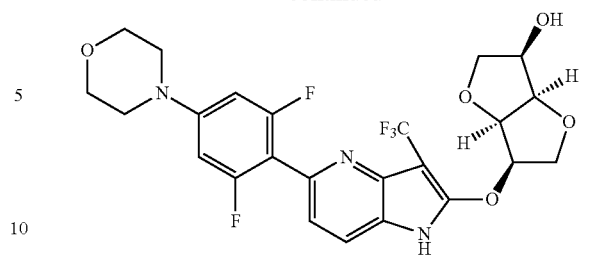
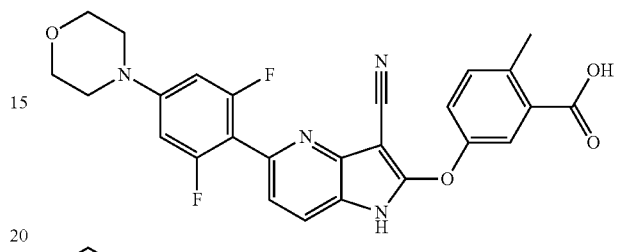
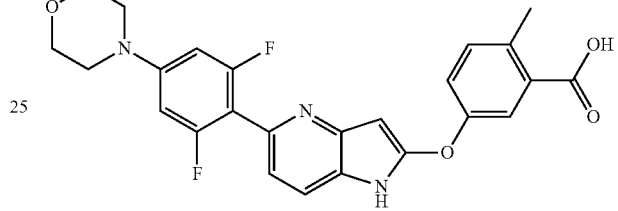
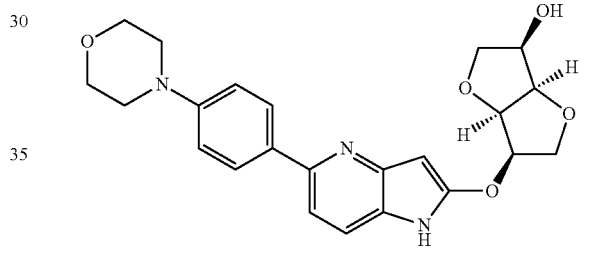
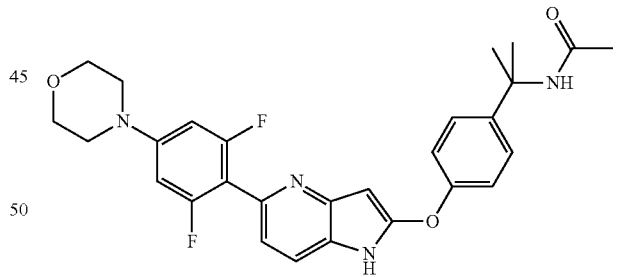
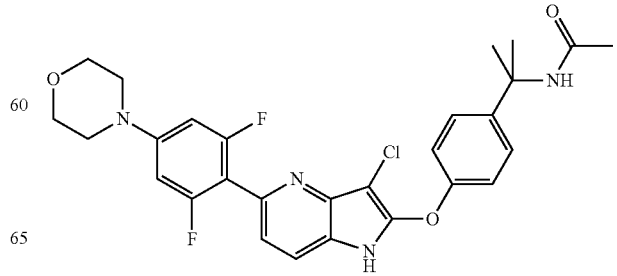

319
-continued
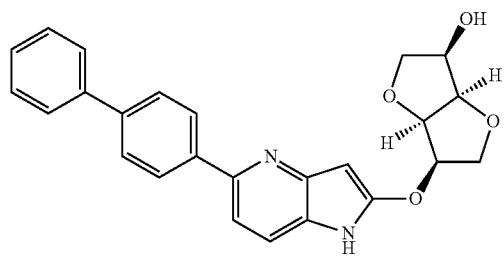
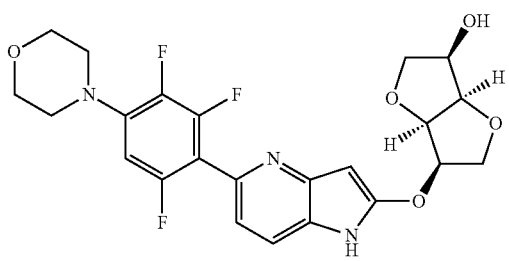
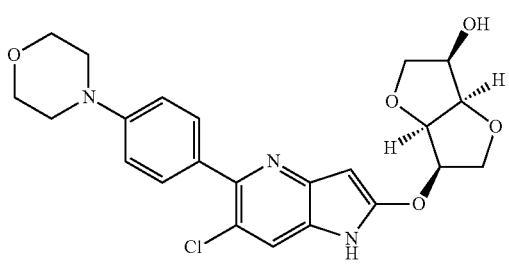
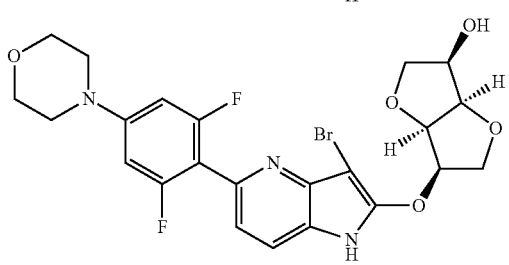
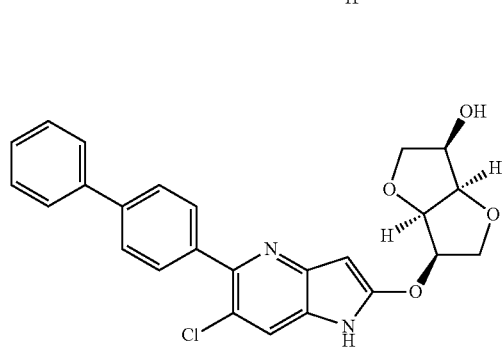
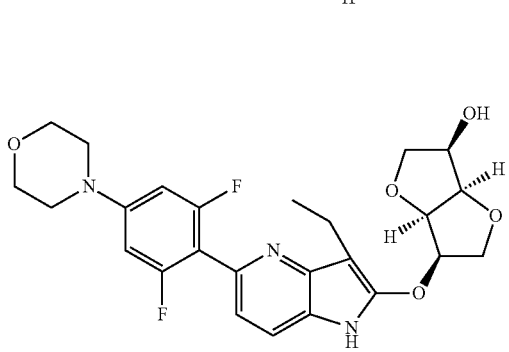
320
-continued
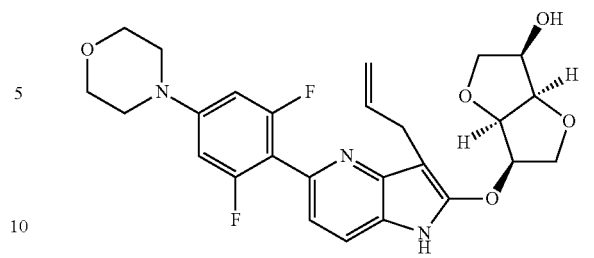
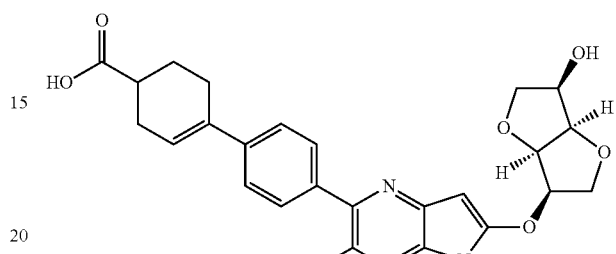
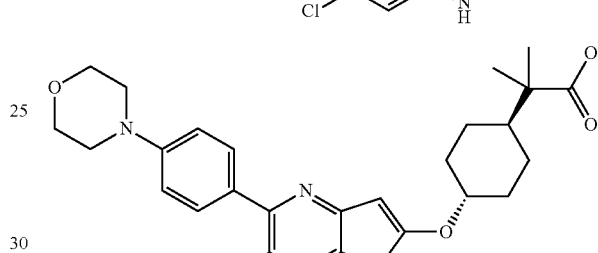
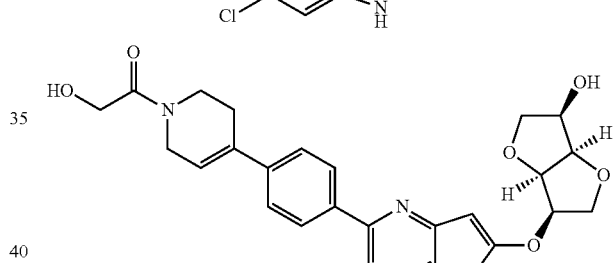
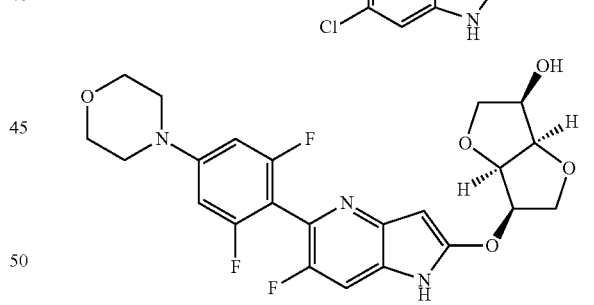
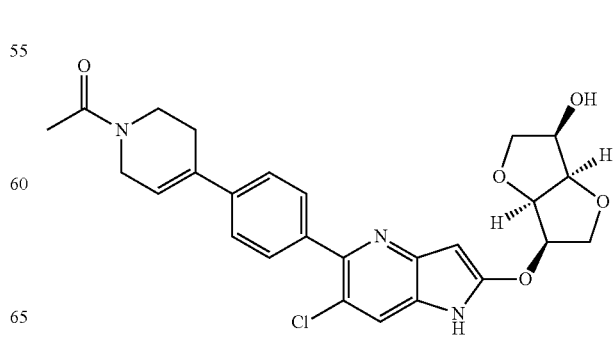

321
-continued
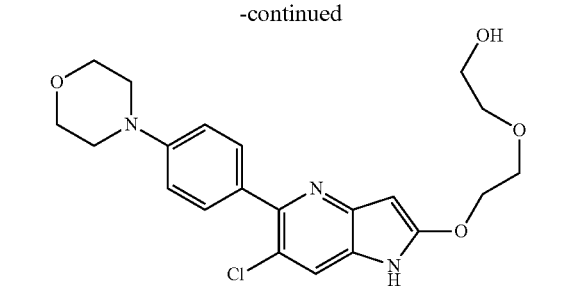
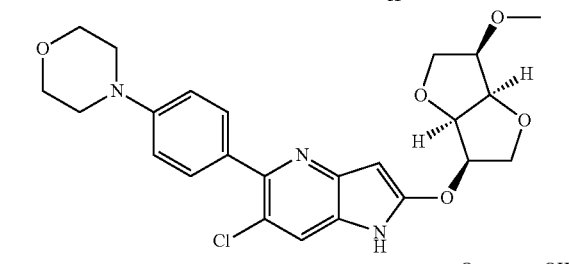
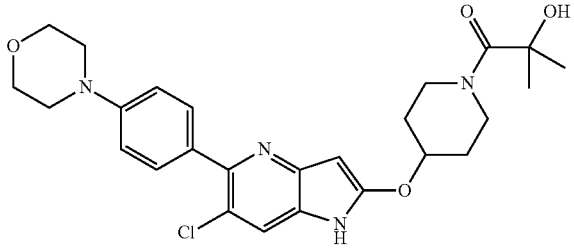
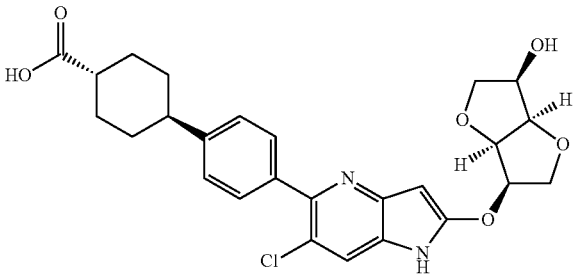
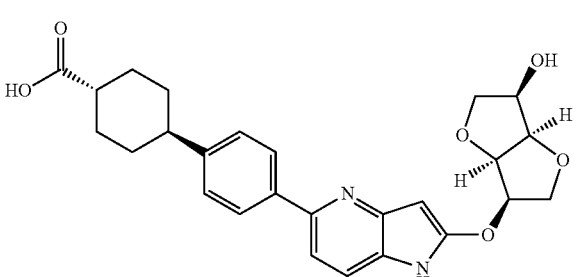
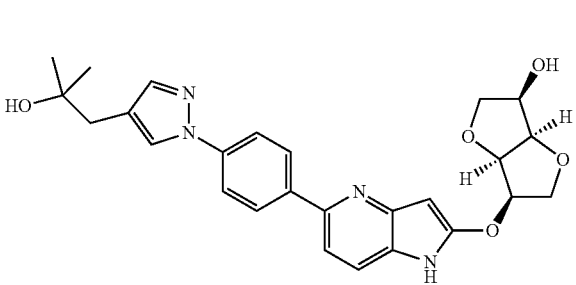
322
-continued
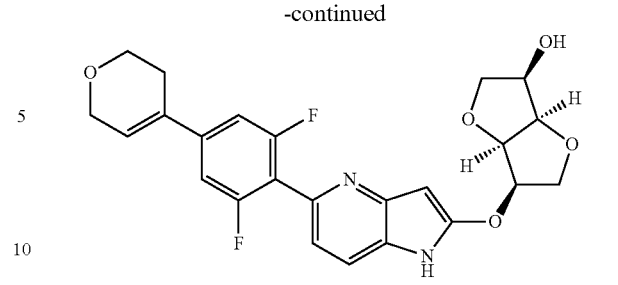
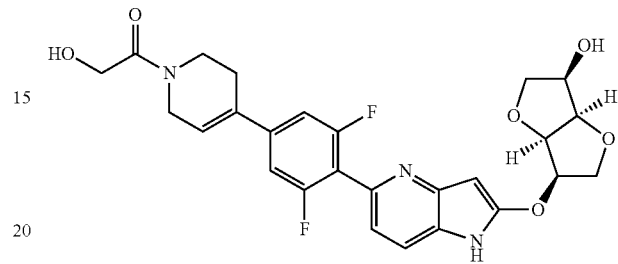
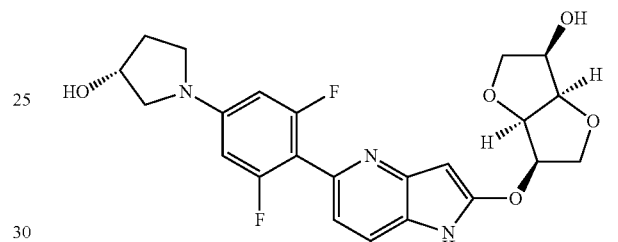
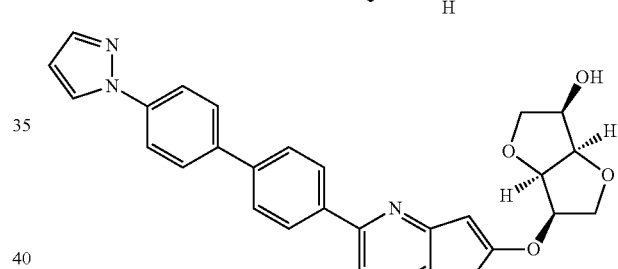
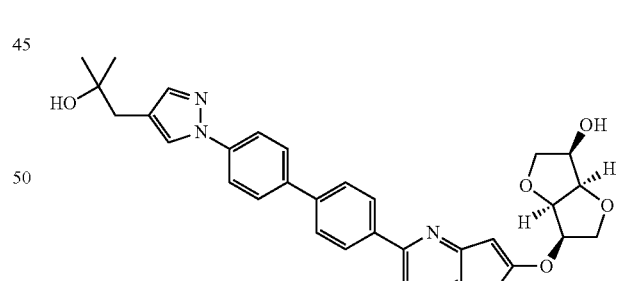
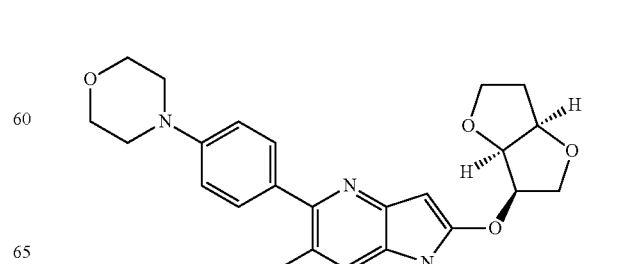

323
-continued
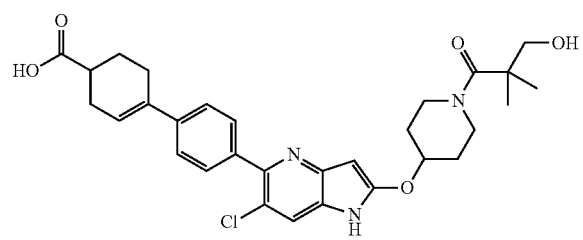
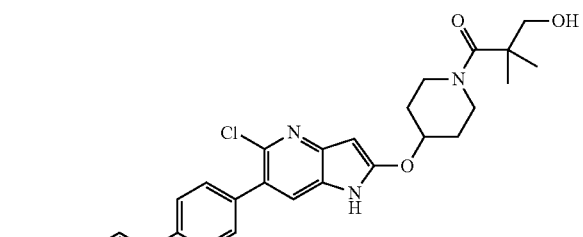
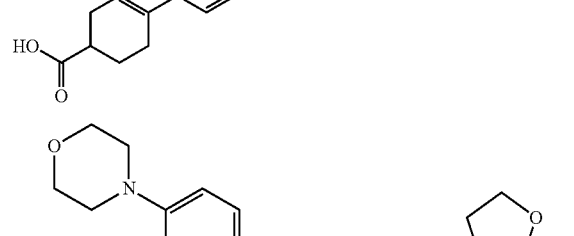
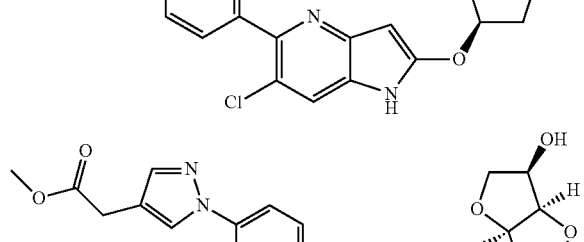
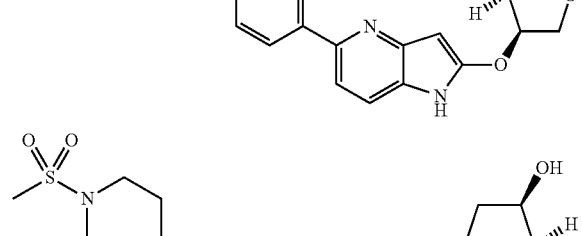
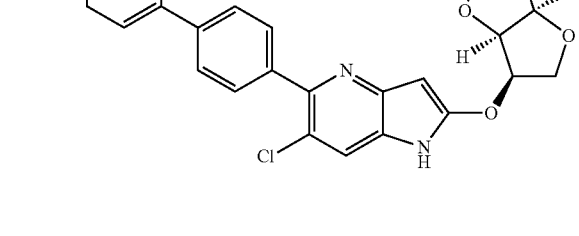
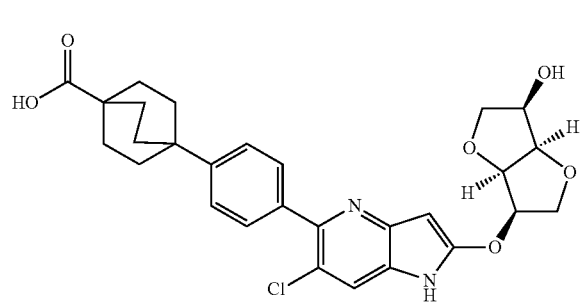
324
-continued
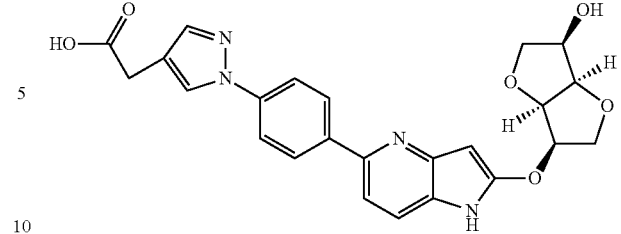
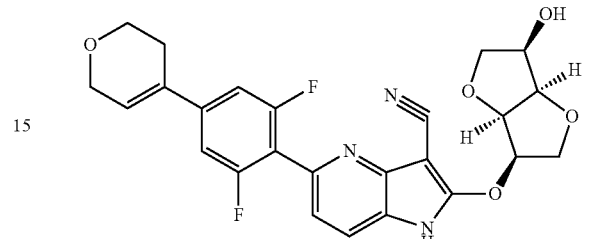
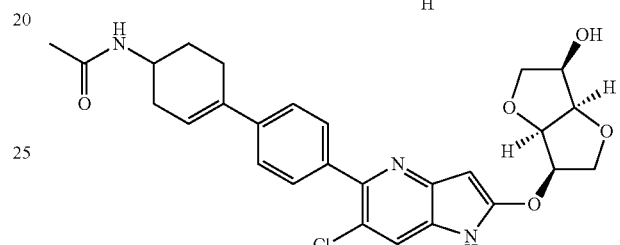
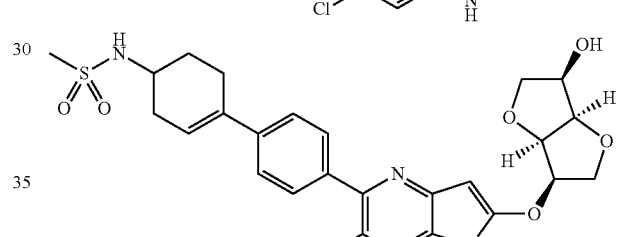
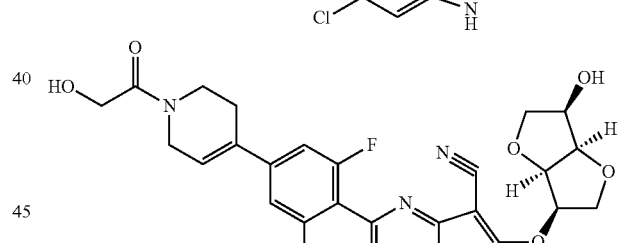
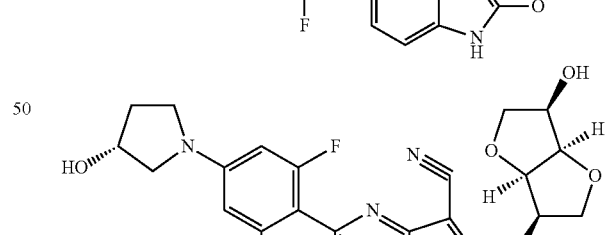
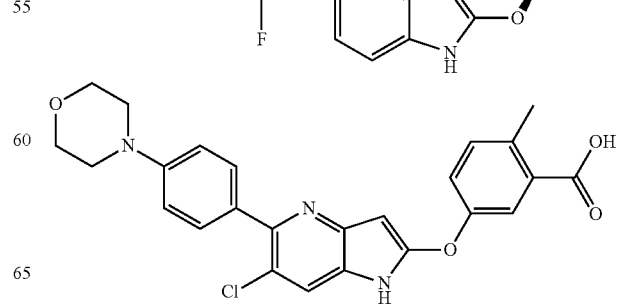

325
-continued
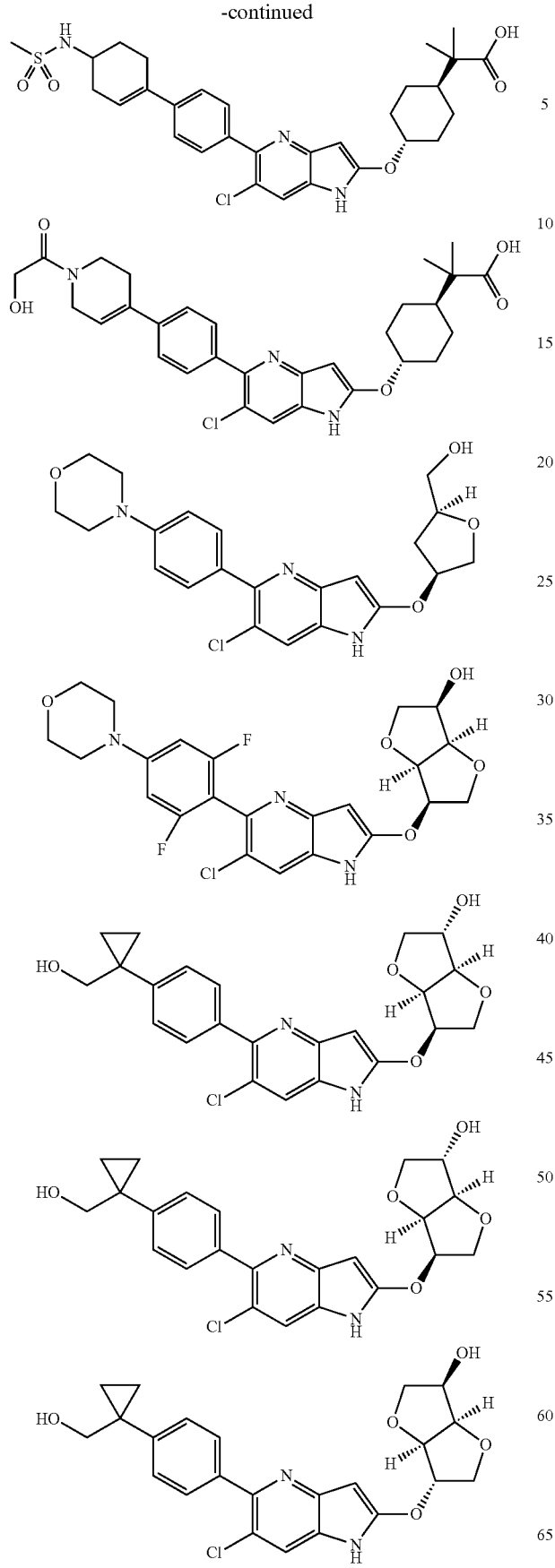
326
-continued
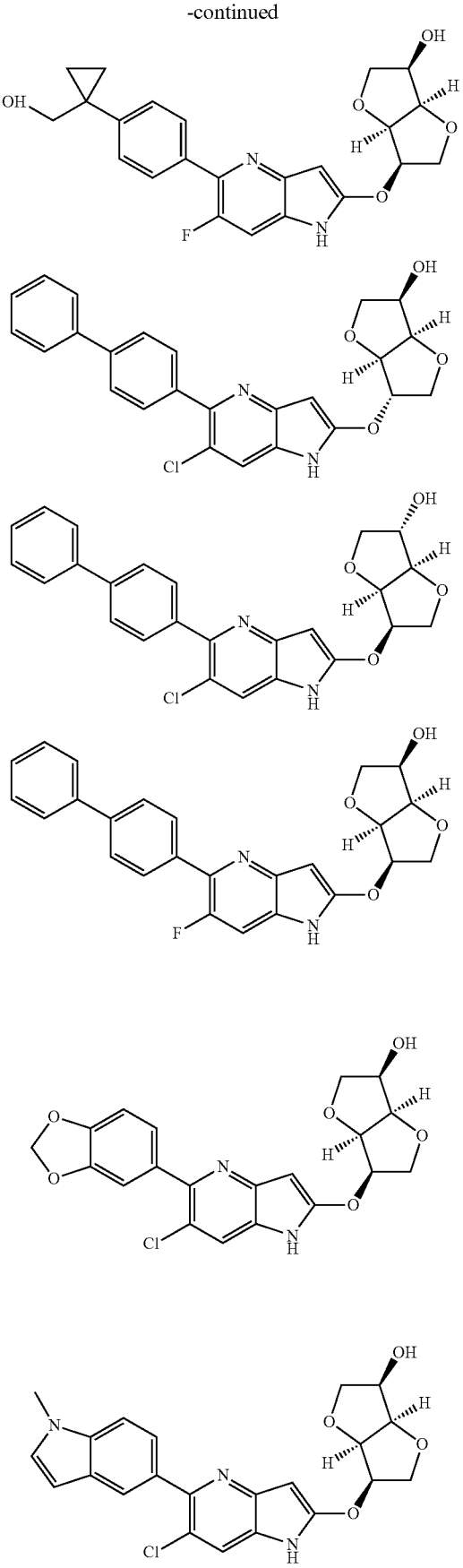

327
-continued
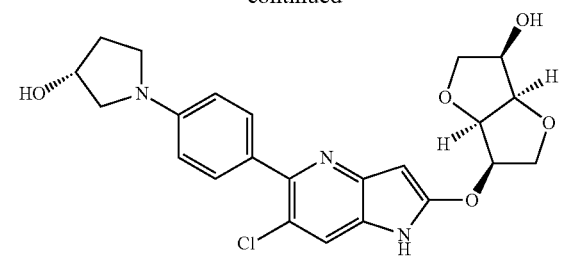
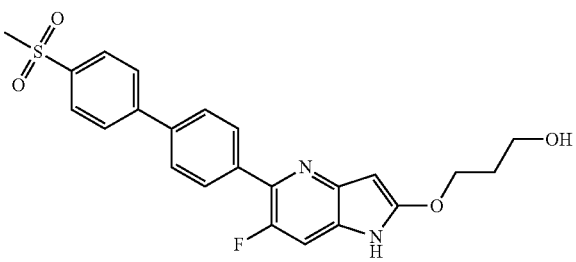
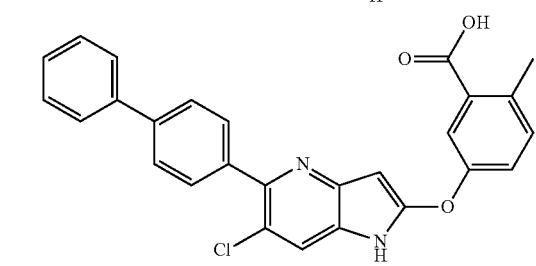
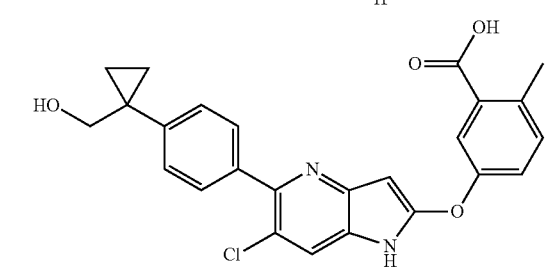
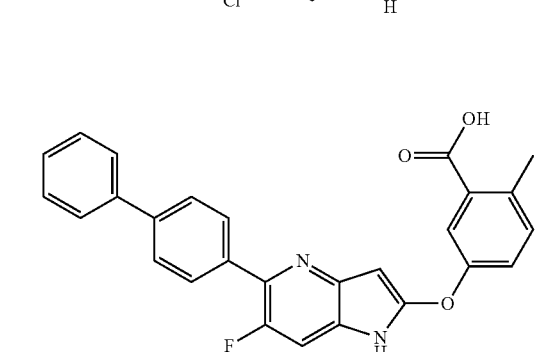
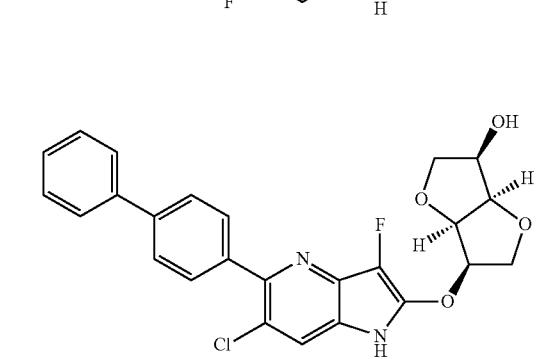
328
-continued
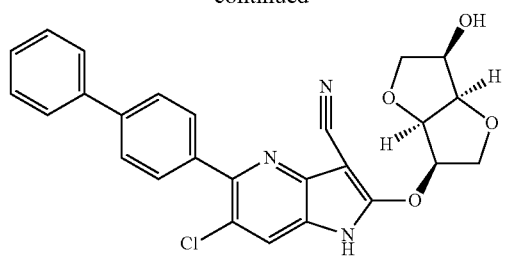
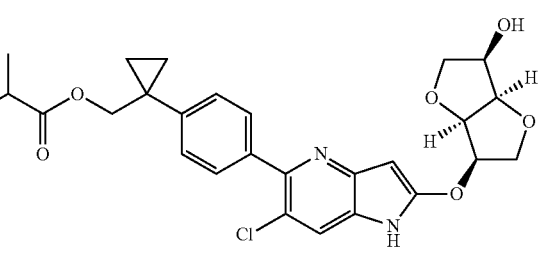
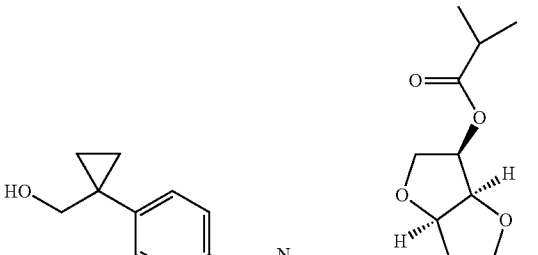
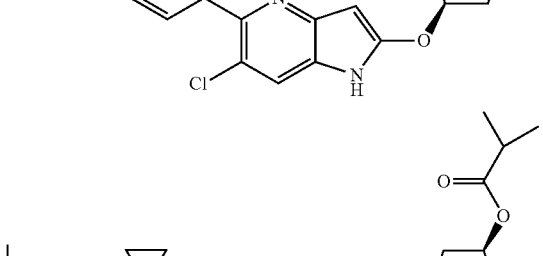
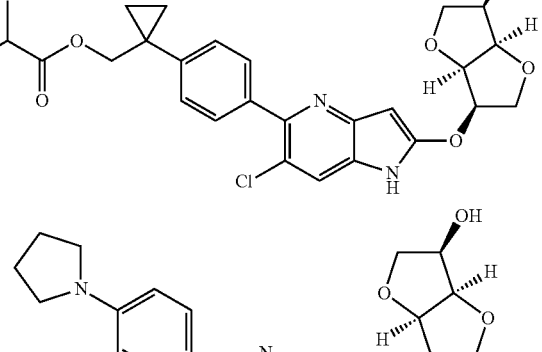
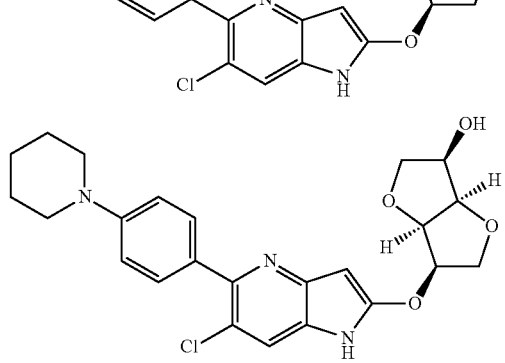

329
-continued
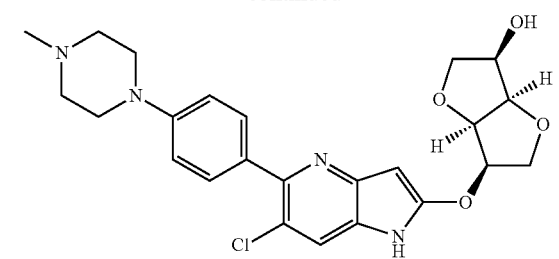
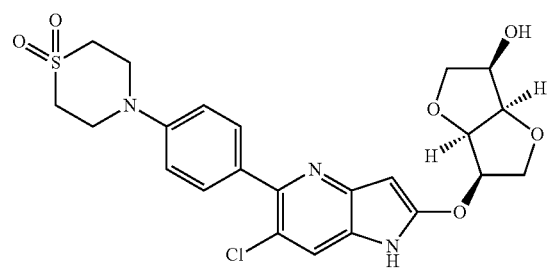
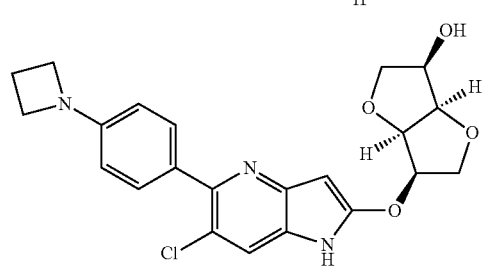
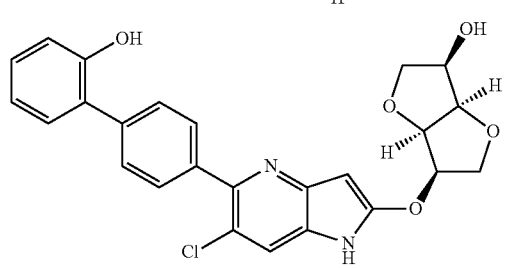
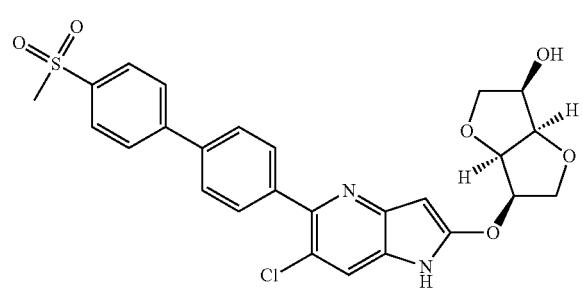
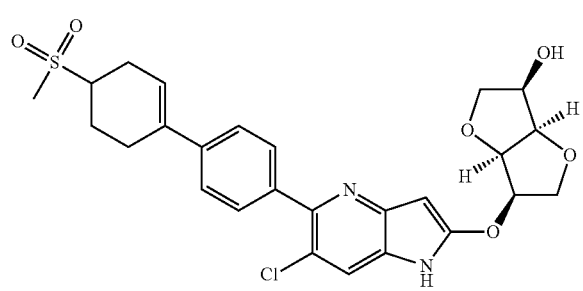
330
-continued
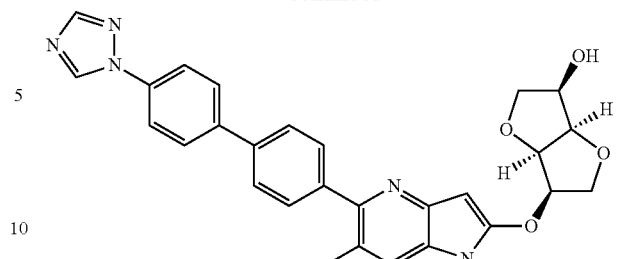
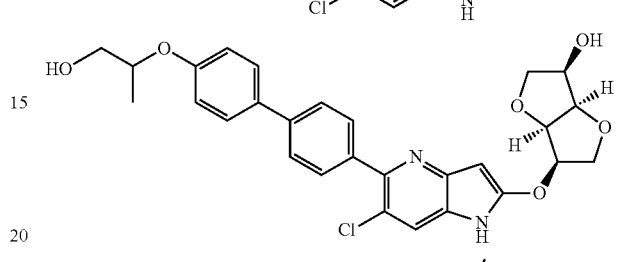
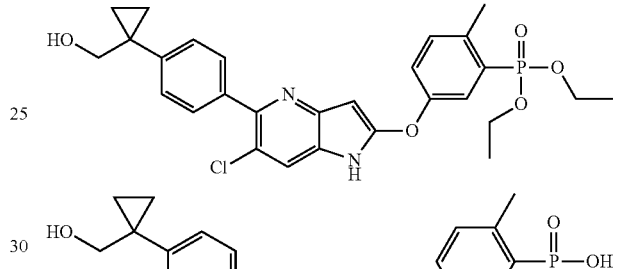
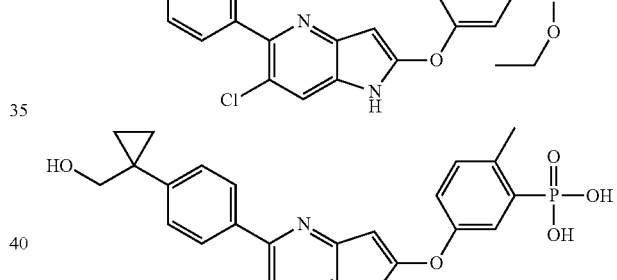
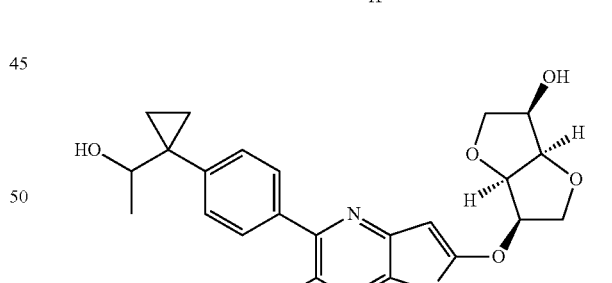
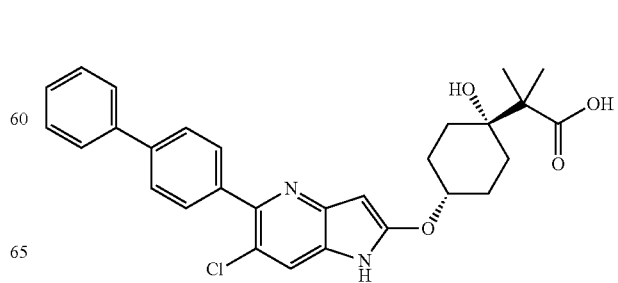

331
-continued
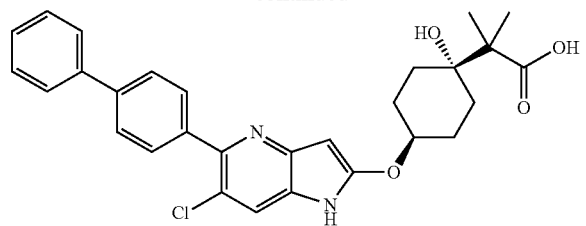
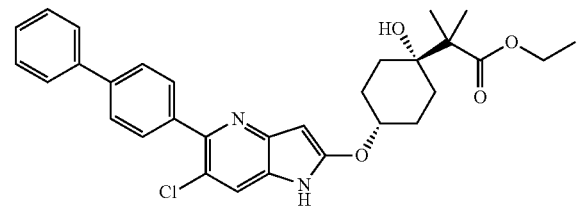
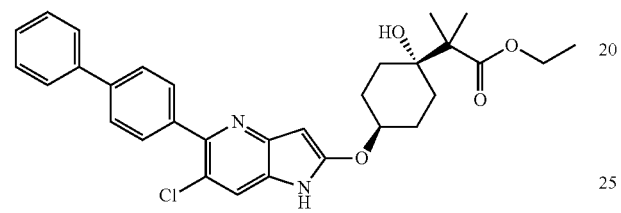
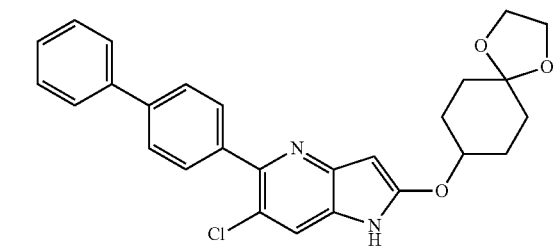
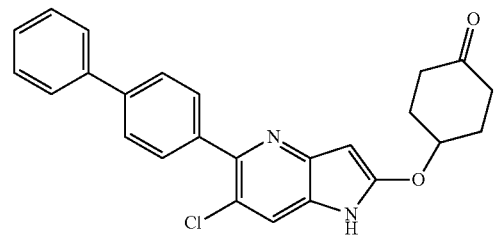
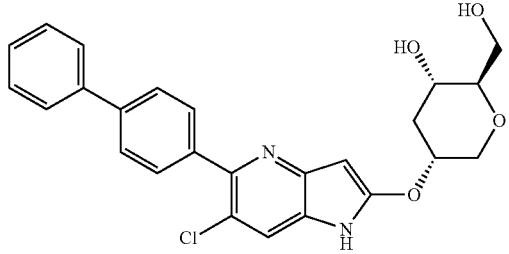
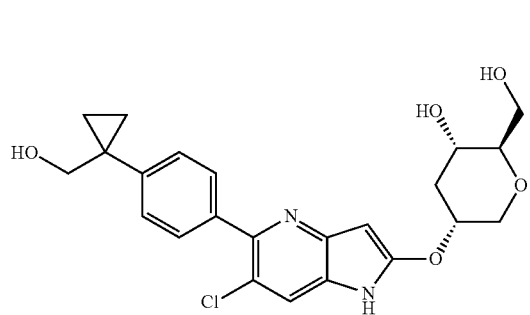
332
-continued
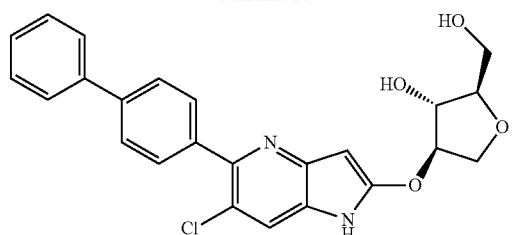
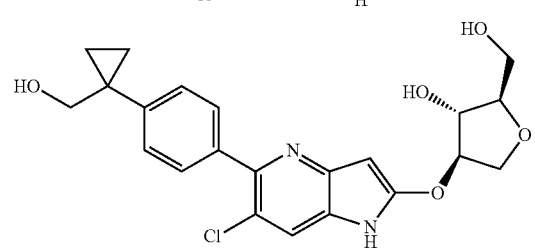
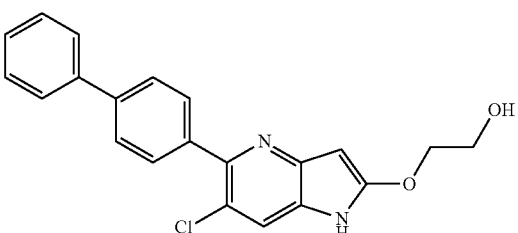
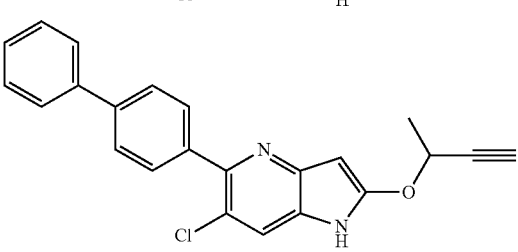
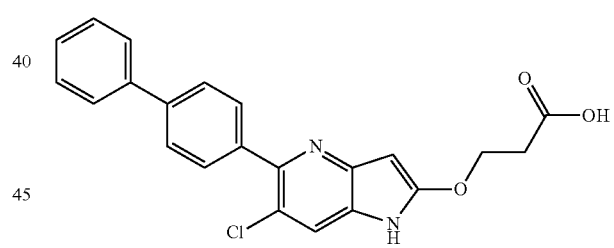
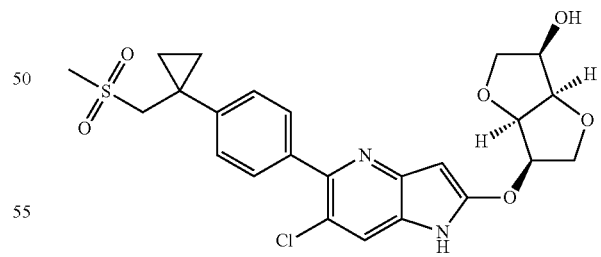
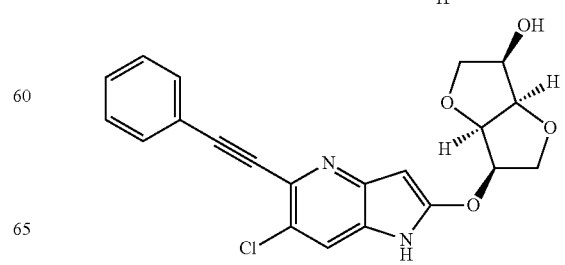

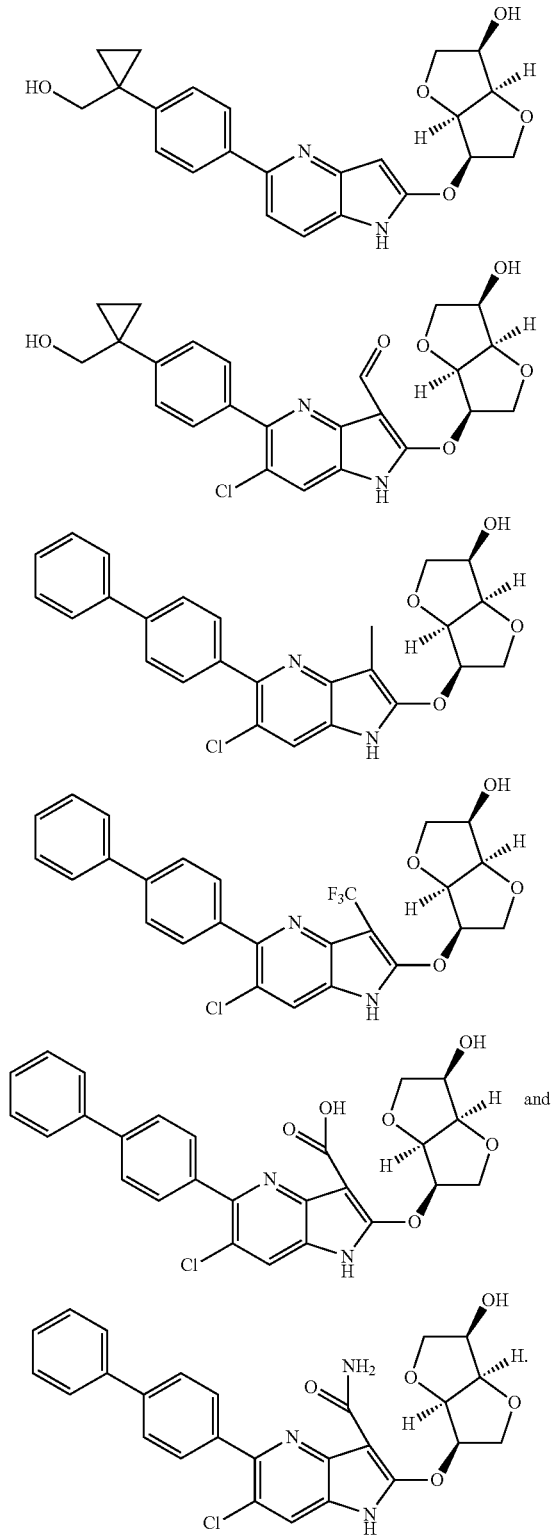

2. The compound according to claim 1 or pharmaceutically acceptable salt, wherein $R^1$ is hydrogen, halogen, cyano, nitro, carboxy, substituted or unsubstituted alkyl, substituted or unsubstituted alkenyl, substituted or unsubstituted acyl, substituted or unsubstituted carbamoyl, substituted or unsubstituted alkylthio, substituted or unsubstituted alkylsulfinyl, substituted or unsubstituted alkylsulfonyl, or substituted or unsubstituted alkyloxycarbonyl.

3. The compound according to claim 1 or pharmaceutically acceptable salt, wherein $R^1$ is hydrogen, halogen, or cyano.

4. The compound according to claim 1 or pharmaceutically acceptable salt, wherein $R^1$ is hydrogen and $R^3$ is fluoro, cyano, or substituted or unsubstituted alkyl.

5. The compound according to claim 1 or pharmaceutically acceptable salt, wherein $R^1$ is fluoro and $R^3$ is chloro, or $R^1$ is bromo and $R^3$ is chloro.

6. The compound according to claim 1 or pharmaceutically acceptable salt, wherein $R^2$ is substituted or unsubstituted aryl, substituted or unsubstituted heteroaryl, substituted or unsubstituted cycloalkyl, substituted or unsubstituted cycloalkenyl, or substituted or unsubstituted heterocyclyl.

7. The compound according to claim 6 or pharmaceutically acceptable salt, wherein $R^2$ is substituted or unsubstituted aryl.

8. The compound according to claim 7 or pharmaceutically acceptable salt, wherein $R^2$ is

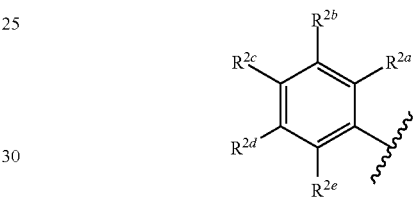

wherein $R^{2a}$, $R^{2b}$, $R^{2d}$ and $R^{2e}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^{2c}$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

9. The compound according to claim 8 or pharmaceutically acceptable salt, wherein at least one of $R^{2a}$ or $R^{2c}$ is halogen.

10. The compound according to claim 6 or pharmaceutically acceptable salt, wherein $R^2$ is substituted aryl, substituted heteroaryl, substituted cycloalkyl, substituted cycloalkenyl, or substituted heterocyclyl.

11. The compound according to claim 10 or pharmaceutically acceptable salt, wherein $R^2$ is

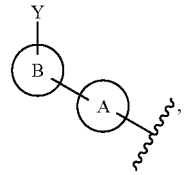

wherein
ring A is substituted aryl, substituted heteroaryl, substituted cycloalkyl, substituted cycloalkenyl, or substituted heterocyclyl, the ring A may further have (a) substituent(s) at arbitrary position(s) other than the position that is substituted with ring B;
ring B is substituted aryl, substituted heteroaryl, substituted cycloalkyl, substituted cycloalkenyl, or substituted heterocyclyl, the ring B may further have (a) substituent(s) at arbitrary position(s) other than the position that is substituted with Y and ring A;
Y is $R^S R^{St}(O=)S=N-$, $R^S R^{St}(O=)S=N-R^{2f}-$, $R^S R^{St}(O=)S=N-C(=O)-$, $(R^N)N=S(=O)(R^S)-$, $(R^N)N=S(=O)(R^S)-R^{2f}-$, $R^S R^{St}(R^M-N=)S=N-$, $((R^N)N=)_2 S(R^S)-$, $(R^N R^M)N-C(=O)-O-$, $R^O O-C(=O)-N(R^N)-$, or $R^O O-C(=O)-O-$;
$R^S$ and $R^{St}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;
$R^S$ and $R^{St}$ bound to the same sulfur atom may form a substituted or unsubstituted ring together with the sulfur atom;
$R^{2f}$ is substituted or unsubstituted alkylene;
$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;
$R^N$ together with the adjacent nitrogen atom may form a substituted or unsubstituted ring when Y is $((R^N)N=)_2 S(R^S)-$;
$R^M$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;
$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

12. The compound according to claim 11 or pharmaceutically acceptable salt, wherein ring A is substituted aryl, or substituted heteroaryl.

13. The compound according to claim 11 or pharmaceutically acceptable salt, wherein ring B is substituted aryl, or substituted heteroaryl.

14. The compound according to claim 10 or pharmaceutically acceptable salt, wherein Y is $R^S R^{St}(O=)S=N-$, $(R^N)N=S(=O)(R^S)-$, or $R^O O-C(=O)-N(R^N)-$.

15. The compound according to claim 10 or pharmaceutically acceptable salt, wherein $R^2$ is

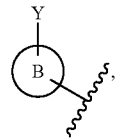

wherein
ring B is substituted aryl, substituted heteroaryl, substituted cycloalkyl, substituted cycloalkenyl, or substituted heterocyclyl, the ring B may further have (a) substituent(s) other than Y;
Y is $R^S R^{St}(O=)S=N-$, $R^S R^{St}(O=)S=N-R^{2f}-$, $R^S R^{St}(O=)S=N-C(=O)-$, $(R^N)N=S(=O)(R^S)-$, $(R^N)N=S(=O)(R^S)-R^{2f}-$, $R^S R^{St}(R^M-N=)S=N-$, $((R^N)N=)_2 S(R^S)-$, $(R^N R^M)N-C(=O)-O-$, $R^O O-C(=O)-N(R^N)-$, or $R^O O-C(=O)-O-$;
$R^S$ and $R^{St}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;
$R^S$ and $R^{St}$ bound to the same sulfur atom may form a substituted or unsubstituted ring together with the sulfur atom;
$R^{2f}$ is substituted or unsubstituted alkylene;
$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;
$R^N$ together with the adjacent nitrogen atom may form a substituted or unsubstituted ring when Y is $((R^N)N=)_2 S(R^S)-$;
$R^M$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;
$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

16. The compound according to claim 15 or pharmaceutically acceptable salt, wherein ring B is substituted aryl, substituted heteroaryl, substituted cycloalkenyl, or substituted heterocyclyl.

17. The compound according to claim 15 or pharmaceutically acceptable salt, wherein Y is $R^SR^S(O=)S=N-$, $(R^N)N=S(=O)(R^S)-$, or $R^OO-C(=O)-N(R^N)-$.

18. The compound according to claim 1 or pharmaceutically acceptable salt, wherein $R^3$ is halogen, cyano, carboxy, substituted or unsubstituted alkyl, substituted or unsubstituted alkylsulfonyl, or substituted or unsubstituted carbamoyl.

19. The compound according to claim 18 or pharmaceutically acceptable salt, wherein $R^3$ is fluoro, cyano, or substituted alkyl, wherein the substituent of the substituted alkyl is halogen.

20. The compound according to claim 1 or pharmaceutically acceptable salt,
wherein X is

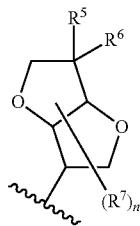

wherein $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^7$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; and a is an integer from 0 to 7.

21. The compound according to claim 1 or pharmaceutically acceptable salt, wherein $R^4$ is hydrogen.

22. The compound according to claim 1 or pharmaceutically acceptable salt, wherein $R^4$ is halogen.

23. A pharmaceutical composition comprising the compound according to claim 1, or pharmaceutically acceptable salt.

24. The pharmaceutical composition according to claim 23, which has an activating effect on adenosine monophosphate-activated protein kinase.

25. A method for treating diabetes, comprising:
administering the compound according to claim 1 or pharmaceutically acceptable salt to a subject in need thereof.

* * * * *